(12) United States Patent
Dahmann et al.

(10) Patent No.: US 9,096,579 B2
(45) Date of Patent: Aug. 4, 2015

(54) AMINO-INDOLYL-SUBSTITUTED IMIDAZOLYL-PYRIMIDINES AND THEIR USE AS MEDICAMENTS

(71) Applicants: Georg Dahmann, Warthausen-Birkenhard (DE); Horst Dollinger, Schemmerhofen (DE); Christian Gnamm, Biberach an der Riss (DE); Dennis Fiegen, Biberach an der Riss (DE); Matthias Hoffmann, Mittelbiberach (DE); Jasna Klicic, Biberach an der Riss (DE); David James Lamb, Mittelbiberach (DE); Andreas Schnapp, Biberach an der Riss (DE)

(72) Inventors: Georg Dahmann, Warthausen-Birkenhard (DE); Horst Dollinger, Schemmerhofen (DE); Christian Gnamm, Biberach an der Riss (DE); Dennis Fiegen, Biberach an der Riss (DE); Matthias Hoffmann, Mittelbiberach (DE); Jasna Klicic, Biberach an der Riss (DE); David James Lamb, Mittelbiberach (DE); Andreas Schnapp, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 169 days.

(21) Appl. No.: 13/864,394

(22) Filed: Apr. 17, 2013

(65) Prior Publication Data
US 2013/0281430 A1    Oct. 24, 2013

(30) Foreign Application Priority Data
Apr. 20, 2012 (EP) .................................... 12164861

(51) Int. Cl.
*A61K 31/506* (2006.01)
(Continued)

(52) U.S. Cl.
CPC ............ *C07D 403/14* (2013.01); *A61K 31/506* (2013.01); *A61K 31/5377* (2013.01); *A61K 31/5386* (2013.01); *A61K 31/541* (2013.01); *A61K 31/55* (2013.01); *A61K 31/551* (2013.01); *A61K 31/553* (2013.01); *A61K 45/06* (2013.01); *C07D 209/42* (2013.01); *C07D 401/14* (2013.01); *C07D 403/06* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 487/10* (2013.01); *C07D 498/04* (2013.01); *C07D 498/10* (2013.01); *C07D 513/04* (2013.01)

(58) Field of Classification Search
CPC . A61K 31/506; A61K 31/551; A61K 31/553; A61K 31/5386; A61K 31/5377; A61K 31/541; A61K 31/55; C07D 403/14; C07D 209/42; C07D 403/06; C07D 487/04; C07D 409/14; C07D 405/14; C07D 498/10; C07D 401/14; C07D 413/14
USPC ............... 514/210.18, 275, 252.19, 249, 218, 514/211.15, 230.8; 540/544, 575; 544/331, 544/295, 71, 122, 58.2, 373; 548/492
See application file for complete search history.

(56) References Cited

FOREIGN PATENT DOCUMENTS

WO        9818782 A1    5/1998
WO     2004087698 A2   10/2004
(Continued)

OTHER PUBLICATIONS

Bingham A.H., et al. "A novel series of potent and selective IKK2 inhibitors", Bioorganic and medicinal chemistry letters, Apr. 2004, pp. 409-412, vol. 14, 01.

(Continued)

*Primary Examiner* — James O Wilson
*Assistant Examiner* — Ebenezer O Sackey
(74) *Attorney, Agent, or Firm* — Michael P. Morris; Wendy A. Petka; Usha R. Patel

(57) ABSTRACT

The invention relates to new amino-indole-substituted imidazolyl-pyrimidines of formula 1

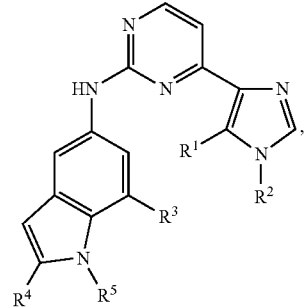

wherein
$R^1$, $R^2$, $R^3$, $R^4$ and $R^5$ are defined as in claim 1 and pharmaceutically acceptable salts thereof and the use of these compounds for the preparation of a medicament for treating a disease selected from asthma, COPD, rheumatoid arthritis, specific lymphomas and specific diseases of the nervous system.

25 Claims, No Drawings

(51) Int. Cl.

| | | |
|---|---|---|
| *A61K 31/551* | (2006.01) | |
| *A61K 31/553* | (2006.01) | |
| *A61K 31/5386* | (2006.01) | |
| *A61K 31/5377* | (2006.01) | |
| *A61K 31/541* | (2006.01) | |
| *A61K 31/55* | (2006.01) | |
| *C07D 498/10* | (2006.01) | |
| *C07D 209/42* | (2006.01) | |
| *C07D 403/06* | (2006.01) | |
| *C07D 487/04* | (2006.01) | |
| *C07D 409/14* | (2006.01) | |
| *C07D 403/14* | (2006.01) | |
| *C07D 405/14* | (2006.01) | |
| *C07D 401/14* | (2006.01) | |
| *C07D 413/14* | (2006.01) | |
| *A61K 45/06* | (2006.01) | |
| *C07D 417/14* | (2006.01) | |
| *C07D 471/04* | (2006.01) | |
| *C07D 487/10* | (2006.01) | |
| *C07D 498/04* | (2006.01) | |
| *C07D 513/04* | (2006.01) | |

(56) References Cited

FOREIGN PATENT DOCUMENTS

| WO | 2007085540 A1 | 8/2007 |
|---|---|---|
| WO | 2011052923 A2 | 5/2011 |
| WO | 2011060295 A1 | 5/2011 |
| WO | 2011086085 A1 | 7/2011 |

OTHER PUBLICATIONS

International Search Report, Form PCT/ISA 220, for PCT/EP2013/058203, mailed Apr. 20, 2012.

AMINO-INDOLYL-SUBSTITUTED IMIDAZOLYL-PYRIMIDINES AND THEIR USE AS MEDICAMENTS

The invention relates to new amino-indolyl-substituted imidazolyl-pyrimidines of formula 1

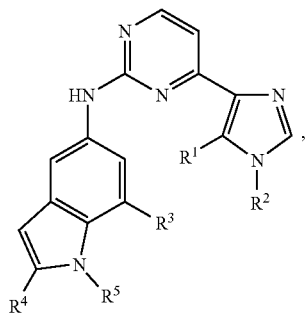

wherein
$R^1$, $R^2$, $R^3$, $R^4$ and $R^5$ are defined as in claim 1 and pharmaceutically acceptable salts thereof and the use of these compounds for the preparation of a medicament for treating a disease selected from asthma, COPD, rheumatoid arthritis, specific lymphomas and specific diseases of the nervous system.

1. BACKGROUND TO THE INVENTION

1.1 Syk-Inhibitors

The present invention describes new substituted quinolines that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; Leib and Gut-Landmann et al.; Nature Immunology (2007) 8, 630-638; Slack et al., European J. Immunol. (2007) 37, 1600-1612). The molecular processes are described best for the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in many of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (βHA), as well as for the synthesis of lipid mediators, such as e.g. prostaglandins and leukotrienes.

In view of its central function in different signal transduction pathways Syk has been discussed as a therapeutic target for different diseases such as e.g. allergic rhinitis, asthma, autoimmune diseases, rheumatoid arthritis, atherosclerosis, osteopenia, osteoporosis, COPD and various leukaemias and lymphomas (Wong et al.; Expert Opin. Investig. Drugs (2004) 13(7), 743-762; Ulanova et al.; Expert Opion. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467; Riccaboni et al., Drug Discovery Today (2010) Vol 15 (13-14); 517-530; Efremov and Luarenti, Expert Opin Investig Drugs. (2011) 20(5):623-36); Hilgendorf et al. Arterioscler, Thromb, Vasc Res (2011) 31:1991-1999).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornell et al., PNAS (2000) 97(4), 1713-1718). An inhibitor of the Syk kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a si-RNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda, Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with peripheral T-cell lymphomas (PTCL). Moreover, constitutively active Syk was found in B-cell lymphoma cells of patients, especially in B-lineage acute lymphoblastic leukemia (B-ALL), follicular lymphoma (FL), diffuse large B-cell lymphoma (DLBCL), mantle cell lymphomas and B cell Non-Hodgkin Lymphomas (NHLs) as well as in acute myeloid leukemia (AML). On the basis of these data it seems that Syk is a protooncogene in haematopoietic cells and represents a potential target for the treatment of certain leukaemias and lymphomas.

Idiophathic thrombocytoenic purpura (ITP) is an autoimmune disease in which IgG autoantibodies against antigens present on platelets bind to and destroy platelets. Patients with ITP have an accelerated clearence of circulating IgG-coated platelets via macrophages in the spleen and the liver. In view of the pro-inflammatory FcγR-mediated function of Syk in macrophages an inhibitor of Syk is considered to have a therapeutic benefit in FcγR-mediated cytopenias like ITP. Indeed the Syk inhibitor R788 (R406) improved platelet counts in a single center, oben label study in patients with ITP (Podolanczuk et al; Blood (2009) 113, 3154-3169).

Atherosclerosis is a chronic inflammatory condition in which the wall of medium- and large-sized arteries thickens as a result of the accumulation of inflammatory cells (mainly macrophages), smooth muscle cells, extracellular matrix and cholesterol deposited by modified low density lipoproteins. The plaques grow over decades until either stenosis of the lumen occurs resulting in ischaemia, or they rupture, exposing thrombogenic material resulting in thrombus formation, and potentially thromboembolism. The Syk inhibitor R788 (R406) reduced atherosclerotic plaque size in a murine model of atherosclerosis (Hilgendorf et al. Arterioscler, Thromb, Vasc Res (2011) 31:1991-1999).

Bullous pemphigoid (Ujiie et al. Journal of Dermatology 2010; 37: 194-204) is a chronic, autoimmune, subepidermal, blistering skin disease that rarely involves mucous membranes. Bullous pemphigoid is characterized by the presence of immunoglobulin G (IgG) autoantibodies specific for the hemidesmosomal bullous pemphigoid antigens BP230 (BPAg1) and BP180 (BPAg2). Pemphigus vulgaris (Venugopal et al. Dermatol. Clin. 2011; 29:373-80) is a chronic blistering skin disease with skin lesions that are rarely pruritic, but which are often painful. Pemphigus vulgaris is an autoimmune disease caused by IgG autoantibodies directed against both desmoglein 1 and desmoglein 3 resulting in the loss of cohesion between keratinocytes in the epidermis. It is characterized by extensive flaccid blisters and mucocutaneous erosions. In both diseases IgG autoantibodies bind to Fc receptor gamma (FcRg) and activate FcRg and downstream signaling via Syk kinase. Thus, an inhibitor of the Syk kinase activity which blocks downstream signalling of the FcRg could be used therapeutically to treat patients with bullous pemphigoid and pemphigus vulgaris.

Systemic lupus erythematosus (SLE) is a chronic autoimmune disease which can affect basically any organ of the body. It is characterised by a multisystem inflammation of the microvascular and the presence of autoantibodies. FcγR-deficient mice are protected from several aspects of SLE in disease-related preclinical models, suggesting that an inhibitor of Syk can have a therapeutic benefit in SLE in view of the pro-inflammatory FcγR-mediated function of Syk in various cells.

1.2 Prior Art

WO 98/18782 discloses 2-pyridinyl-pyrimidines as Syk-inhibitors which—in contrast to the compounds of the instant invention—may not be substituted in 4-position by amino-indolyl and which do not carry an imidazolyl-residue at the 2-position.

WO 2004/058749 discloses 2,4-bisubstituted pyrimidines as Syk-inhibitors which are substituted in 4-position with a bicyclic heteroaryl containing at least one nitrogen-atom and one oxygen-atom for the treatment of for instance asthma. In contrast to that the compounds of the instant invention comprise in 4-position an imidazolyl-residue.

WO 02/096905, WO 2004/087698 and WO 2004/087699 disclose pyrimidines as inhibitors of certains protein kinases such as Syk which are in 4-position substituted by a thiazole-residue and which may be used for the treatment of asthma.

WO 2011/075515, WO 2011/075560 and WO 2011/075517 disclose pyrimidines which are substituted in the 2-position by amino-phenyl which may be used as Syk-inhibitors for the treatment of COPD and asthma, whereas the pyrimidines of the instant invention are substituted in the 2-position by aminoindolyl.

The unpublished application PCT/EP2012050672 discloses substituted 2-pyridinyl-pyrimidines as Syk-inhibitors and their use as medicaments for the treatment of for instance asthma.

However, surprisingly it has now been found that the (2-imidazolyl)-(4-amino-indolyl)-pyrimidines of formula 1 are particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis and COPD.

2. DESCRIPTION OF THE INVENTION

The instant invention refers to compound of formula 1

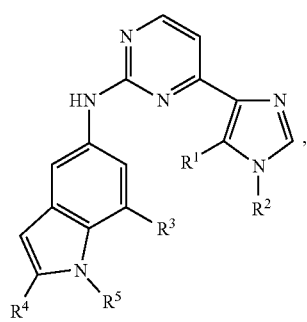

wherein
$R^1$ is selected from the group consisting of hydrogen, $C_{1-6}$-alkyl, $C_{1-6}$-haloalkyl,
$R^2$ is selected from the group consisting of hydrogen, $C_{1-6}$-alkyl, $C_{1-6}$-haloalkyl, —($C_{1-5}$-alkylene)-O—($C_{1-3}$-alkyl), three-, four-, five- or six-membered cycloalkyl, wherein this cycloalkyl may optionally be substituted by halogen $R^3$ is selected from the group consisting of hydrogen, $C_{1-6}$-alkyl, halogen, —O—$C_{1-6}$-alkyl, three-, four-, five- or six-membered cycloalkyl, —S—($C_{1-3}$-alkylene)-A, —S-A; -A, with A being a group selected from the group consisting of —CO—N($C_{1-3}$-alkyl)$_2$, —CO—NH($C_{1-3}$-alkyl), —CO—NH$_2$, five- or six-membered heteroaryl comprising 1, 2 or 3 heteroatoms each independently selected from the group of S, O and N; five-, six- or seven-membered heterocycle comprising 1, 2 or 3 heteroatoms each independently selected from the group of S, O and N, wherein A may optionally be further substituted by one, two or three groups each independently selected from —$C_{1-3}$-alkyl, halogen, -oxo, —OH and $C_{1-3}$-haloalkyl, $R^4$ is selected from the group consisting of hydrogen, -halogen, SH, —OH, —NH$_2$, —CO—Y, —CO—N(CH$_3$)—Y, —CO—N(CH$_3$)($C_{1-5}$-alkylene)-Y, —CO—N(ethyl)($C_{1-5}$-alkylene)-Y, —CO—N(ethyl)-Y, —CS—Y, —CS—N(CH$_3$)—Y, —CS—N(CH$_3$)—($C_{1-3}$-alkylene)-Y, —$C_{1-6}$-alkyl, —$C_{1-3}$-haloalkyl, —CO—NH—Y, —CO—NH—$C_{1-6}$-alkylene-Y, —CO—N(CH$_3$)—($C_{2-3}$-alkylene)-O—($C_{1-3}$-alkyl), —NH$_2$, —$C_{1-6}$-alkylene-L, —SO$_2$-phenyl, —SO$_2$—($C_{1-3}$-alkyl), —CO—N($C_{1-4}$-alkyl)$_2$ and —CO—N($C_{2-4}$-alkylene-O—$C_{1-3}$-alkyl)$_2$, or wherein $R^4$ is a five- or six-membered heteroaromatic group comprising 1, 2 or 3 heteroatoms each independently selected from the group N, S and O, wherein said heteroaromatic group on any atom available for substitution may optionally be further substituted by one, two or three groups each independently selected from among —$C_{1-3}$-alkyl, halogen, and $C_{1-3}$-haloalkyl, with Y being a group selected from the group consisting of —NH$_2$, —NH(CH$_3$), —N(CH$_3$)$_2$, —$C_{1-6}$-alkylene-N(CH$_3$)$_2$, —O—$C_{1-3}$-alkyl, —$C_{1-3}$-haloalkyl, —OH, —N(ethyl)$_2$ and —$C_{1-5}$-alkinyl, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —$C_{6-10}$-aryl and $C_{3-6}$-cycloalkyl, or with Y being a 8- to 11-membered bicyclic annellated fully saturated, partially unsaturated or aromatic heterocycle comprising 1, 2, 3 or 4 heteroatoms each independently from each other selected from the group N, S and O, or with Y being an 8- to 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional $C_{1-3}$-alkylene-unit, whereby each Y may optionally be substituted by one, two or three groups Z each independently from each other selected from the group consisting of halogen, -oxo, OH, —CN, —$C_{1-5}$-alkyl, —$C_{1-5}$-alkanol, —O—$C_{1-3}$-alkyl, a four-, five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO—($C_{1-3}$-alkyl), —CHO, —CO-L, —$C_{1-3}$-alkylene-CO-L, —$C_{1-4}$-alkylene-O—$C_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, —$C_{1-3}$-alkyl, —O—$C_{1-3}$-alkyl, —N(methyl)$_2$, —N(ethyl)$_2$, 5- to 6-membered fully saturated, partially unsaturated or aromatic heterocycle comprising 1 or 2 heteroatoms each independently selected from the group N, O and S, a $C_{3-6}$-cycloalkyl and —CN, wherein each group T may also optionally be substituted by a group selected from the group consisting of $C_{1-3}$-alkyl, halogen, OH, oxo and —O—$C_{1-3}$-alkyl, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, halogen, OH and -oxo, $R^5$ is selected from the group consisting of hydrogen, $C_{1-6}$-alkyl, $C_{1-3}$-haloalkyl and —($C_{1-4}$-alkylene)-O—($C_{1-3}$-alkyl), and the pharmaceutically acceptable salts of the aforementioned compounds.

In a preferred embodiment the instant invention refers to the above-mentioned compounds of formula 1, wherein $R^4$ is selected from the group consisting of —CO—Y, —CO—N(CH$_3$)—Y, —CO—N(CH$_3$)($C_{1-5}$-alkylene)-Y, —CO—N(ethyl)($C_{1-5}$-alkylene)-Y, —CO—NH—Y and —CO—NH—$C_{1-6}$-alkylene-Y, $R^4$ is a five- or six-membered heteroaromatic group comprising 1, 2 or 3 heteroatoms each independently selected from the group N, S and O, wherein said heteroaromatic group on any atom available for substitution may optionally be further substituted by one, two or three groups each independently selected from among —$C_{1-3}$-alkyl halogen, and $C_{1-3}$-haloalkyl, with Y being a group selected from the group consisting of —NH$_2$, —NH(CH$_3$), —N(CH$_3$)$_2$, —$C_{1-6}$-alkylene-N(CH$_3$)$_2$, —O—$C_{1-3}$-alkyl, —$C_{1-3}$-haloalkyl, —OH and —$C_{1-3}$-alkinyl, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —$C_{6-10}$-aryl and a $C_{3-6}$-cycloalkyl, or with Y being a 8-, 9-, 10- or 11-membered bicyclic annellated fully saturated, partially unsaturated or aromatic heterocycle comprising 1, 2, 3 or 4 heteroatoms each independently from each other selected from the group N, S and O, or with Y being an 8-, 9-, 10- or 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional $C_{1-3}$-alkylene-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, 5- to 6-membered fully saturated, partially unsaturated or aromatic heterocycle comprising 1 or 2 heteroatoms each independently selected from the group N, O and S, a $C_{3-6}$-cycloalkyl and —CN, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, halogen, OH and -oxo, and the pharmaceutically acceptable salts of the aforementioned compounds.

In a further preferred embodiment the invention concerns the aforementioned compounds of formula 1, wherein $R^1$ is selected from the group consisting of hydrogen or methyl, and the pharmaceutically acceptable salts of the aforementioned compounds.

Another preferred embodiment of the invention concerns the aforementioned compounds of formula 1, wherein $R^2$ is selected from the group consisting of methyl, ethyl, n-propyl, isopropyl, n-butyl, isobutyl, t-butyl, cyclopropyl, -methylene-O-methyl, -ethylene-O-methyl, and the pharmaceutically acceptable salts of the aforementioned compounds.

In another preferred embodiment the invention refers to the aforementioned compounds of formula 1, wherein $R^2$ is selected from the group consisting of methyl, isopropyl, isobutyl, cyclopropyl, -ethylene-O-methyl, and the pharmaceutically acceptable salts of the aforementioned compounds.

In a further particularly preferred embodiment the invention concerns the aforementioned compounds of formula 1, wherein $R^1$ is hydrogen, and the pharmaceutically acceptable salts of the aforementioned compounds.

In another preferred embodiment the invention refers to the aforementioned compounds of formula 1, wherein $R^2$ is methyl, isopropyl or cyclopropyl, and the pharmaceutically acceptable salts of the aforementioned compounds.

In another particularly preferred embodiment the invention concerns the aforementioned compounds of formula 1, wherein $R^2$ is methyl, and the pharmaceutically acceptable salts of the aforementioned compounds.

Additionally the invention preferably concerns the aforementioned compounds of formula 1, wherein $R^3$ is selected from the group consisting of hydrogen, methyl, ethyl, n-propyl, isopropyl, —F, —Cl, —Br, —O-methyl, —O-ethyl, —O-(n-propyl), —O-(isopropyl), cyclopropyl, —S-methylene-A, -A, with A being a group selected from the group consisting of —CO—$N(CH_3)_2$, —CO—$NH(CH_3)$, five- or six-membered heteroaryl comprising 1, 2 or 3 heteroatoms each independently selected from the group of S, O and N;

wherein A may optionally be further substituted by one, two or three groups each independently selected from methyl, ethyl, propyl or isopropyl, and the pharmaceutically acceptable salts of the aforementioned compounds.

The invention further preferably concerns the above-mentioned compounds of formula 1, wherein $R^3$ is selected from —Cl or methyl, and the pharmaceutically acceptable salts of the aforementioned compounds.

In another preferred embodiment the invention concerns the aforementioned compounds of formula 1, wherein $R^5$ is selected from the group consisting of hydrogen, methyl, ethyl, n-propyl, isopropyl, n-butyl, isobutyl, -methylene-O-methyl and -ethylene-O-methyl, and the pharmaceutically acceptable salts of the aforementioned compounds.

In another more preferred embodiment the invention concerns the aforementioned compounds of formula 1, wherein $R^5$ is selected from the group consisting of hydrogen, methyl, isobutyl and -ethylene-β-methyl, and the pharmaceutically acceptable salts of the aforementioned compounds.

In another particularly preferred embodiment the invention refers to the aforementioned compounds of formula 1, wherein $R^5$ is hydrogen, and the pharmaceutically acceptable salts of the aforementioned compounds.

In a further preferred embodiment the invention refers to the above-mentioned compounds of formula 1, wherein $R^4$ is selected from the group consisting of —CO—Y, —CO—$N(CH_3)$—Y, —CO—$N(CH_3)(C_{1-5}$-alkylene)-Y, —CO—$N(ethyl)(C_{1-5}$-alkylene)-Y, —CO—NH—Y and —CO—NH—$C_{1-6}$-alkylene-Y, $R^4$ is a five- or six-membered heteroaromatic group comprising 1, 2 or 3 heteroatoms each independently selected from the group N, S and O, wherein said heteroaromatic group on any atom available for substitution may optionally be further substituted by one, two or three groups each independently selected from among methyl, ethyl, n-propyl, isopropyl, F, CI, Br, and —$CF_3$, with Y being a group selected from the group consisting of —$NH_2$, —$NH(CH_3)$, —$N(CH_3)_2$, —$C_{1-6}$-alkylene-$N(CH_3)_2$, —O-methyl, —O-ethyl, —O-n-propyl, —O-isopropyl, methyl, ethyl, n-propyl, isopropyl, n-butyl, isobutyl, t-butyl, —$C_{1-3}$-haloalkyl, —OH and

—$CH_2$≡$CH_3$, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —$C_{6-10}$-aryl and a $C_{3-6}$-cycloalkyl, or with Y being a 8-, 9-, 10- or 11-membered bicyclic annellated fully saturated, partially unsaturated or aromatic heterocycle comprising 1, 2, 3 or 4 heteroatoms each independently from each other selected from the group N, S and O, or with Y being an 8-, 9-, 10- or 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional $C_{1-3}$-alkylene-unit, whereby each Y may optionally be substituted by one, two or three groups Z each independently from each other selected from the group consisting of —F, —Cl, —Br, —I, -oxo, OH, CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, $C_{3-6}$-cycloalkyl, —CN, 5- to 6-membered fully saturated, partially unsaturated or aromatic heterocycle comprising 1 or 2 heteroatoms each independently selected from the group N, O and S, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, —Cl, —Br, —F, —OH and -oxo, and the pharmaceutically acceptable salts of the aforementioned compounds.

In a particularly preferred embodiment the invention concerns the above-mentioned compounds of formula 1, wherein $R^4$ is selected from the group consisting of
—CO—N($CH_3$)—Y, —CO—N($CH_3$)($C_{1-5}$-alkylene)-Y, with Y being a group selected from the group consisting of —NH($CH_3$), —N($CH_3$)$_2$, —O-methyl, —$CF_3$, methyl, ethyl, OH, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —$C_{6-10}$-aryl, cyclopropyl, cyclobutyl, cyclopentyl and cyclohexyl, or with Y being a 8-, 9-, 10- or 11-membered bicyclic annellated fully saturated, partially unsaturated or aromatic heterocycle comprising 1, 2, 3 or 4 heteroatoms each independently from each other selected from the group N, S and O, or with Y being an 8-, 9-, 10- or 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional —$CH_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from the group N, S and O; a fully saturated or partially unsaturated $C_{3-6}$-cycloalkyl, a five- to six-membered heteroaromatic group comprising 1, 2 or 3 heteroatoms each independently selected from the group N, S and O; —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, $C_{3-6}$-cycloalkyl, —CN, 5- to 6-membered fully saturated, partially unsaturated or aromatic heterocycle comprising 1 or 2 heteroatoms each independently selected from the group N, O and S, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, —Cl, —Br, —F, —OH and -oxo, and the pharmaceutically acceptable salts of the aforementioned compounds.

In another particularly preferred embodiment the invention concerns the above-mentioned compounds of formula 1, wherein $R^4$ is selected from the group consisting of
—CO—NH—Y or —CO—NH—$C_{1-6}$-alkylene-Y, with Y being a group selected from the group consisting of —NH($CH_3$), —N($CH_3$)$_2$, —O-methyl, —$CF_3$, methyl, ethyl, —OH, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —$C_{6-10}$-aryl, cyclopropyl, cyclobutyl, cyclopentyl and cyclohexyl, or with Y being an 8-, 9-, 10- or 11-membered bicyclic annellated fully saturated, partially unsaturated or aromatic heterocycle comprising 1, 2, 3 or 4 heteroatoms each independently from each other selected from the group N, S and O, or with Y being an 8-, 9-, 10- or 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional —CH$_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —C$_{1-5}$-alkanol, —O—CH$_3$, —O-ethyl, —O-(n-propyl), —O-isopropyl, a four-, five-, six- or seven-membered fully saturated or partially unsaturated heterocycle comprising 1, 2 or 3 heteroatoms each independently selected from the group N, S and O; a fully saturated or partially unsaturated C$_{3-6}$-cycloalkyl, a five- to six-membered heteroaromatic group comprising 1, 2 or 3 heteroatoms each independently selected from the group N, S and O; —CO-methyl, —CO-ethyl, —CO-propyl, —CHO, —CO-L, —C$_{1-3}$-alkylene-CO-L, —C$_{1-4}$-alkylene-O—C$_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —N(methyl)$_2$, —N(ethyl)$_2$, C$_{3-6}$-cycloalkyl, —CN, 5- to 6-membered fully saturated, partially unsaturated or aromatic heterocycle comprising 1 or 2 heteroatoms each independently selected from the group N, O and S, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, —Cl, —Br, —F, —OH and -oxo, and the pharmaceutically acceptable salts of the aforementioned compounds.

In another particularly preferred embodiment the invention concerns the above-mentioned compounds of formula 1, wherein R$^4$ is selected from the group consisting of
—CO—Y, with Y being a group selected from the group consisting of —NH(CH$_3$), —N(CH$_3$)$_2$, —O-methyl, —CF$_3$, methyl, ethyl, —OH, or with Y being a group selected from the group consisting of a four-, five-, six- or seven-membered monocyclic fully saturated or partially unsaturated heterocycle comprising 1, 2 or 3 heteroatoms each independently selected from the group N, S and O; a five- or six-membered monocyclic heteroaromatic group comprising 1, 2 or 3 heteroatoms each independently selected from the group of N, S and O, —C$_{6-10}$-aryl, cyclopropyl, cyclobutyl, cyclopentyl and cyclohexyl, or with Y being a 8-, 9-, 10- or 11-membered bicyclic annellated fully saturated, partially unsaturated or aromatic heterocycle comprising 1, 2, 3 or 4 heteroatoms each independently from each other selected from the group N, S and O, or with Y being an 8-, 9-, 10- or 11-membered bicyclic fully saturated spiro-heterocycle comprising 1, 2 or 3 heteroatoms each independently selected from the group N, S and O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from the group N, S and O, which is bridged by an additional —CH$_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —C$_{1-5}$-alkanol, —O—CH$_3$, —O-ethyl, —O-(n-propyl), —O-isopropyl, a four-, five-, six- or seven-membered fully saturated or partially unsaturated heterocycle comprising 1, 2 or 3 heteroatoms each independently selected from the group N, S and O; a fully saturated or partially unsaturated C$_{3-6}$-cycloalkyl, a five- to six-membered heteroaromatic group comprising 1, 2 or 3 heteroatoms each independently selected from the group N, S and O; —CO-methyl, —CO-ethyl, —CO-propyl, —CHO, —CO-L, —C$_{1-3}$-alkylene-CO-L, —C$_{1-4}$-alkylene-O—C$_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —N(methyl)$_2$, —N(ethyl)$_2$, C$_{3-6}$-cycloalkyl, —CN, 5- to 6-membered fully saturated, partially unsaturated or aromatic heterocycle comprising 1 or 2 heteroatoms each independently selected from the group N, O and S, whereby L denotes a 5- or 6-membered fully saturated or partially unsaturated heterocycle comprising 1 or 2 heteroatoms each independently selected from the group N, O and S, which said heterocycle may optionally be substituted by one, two or three groups independently selected from among methyl, —Cl, —Br, —F, —OH and -oxo, and the pharmaceutically acceptable salts of the aforementioned compounds.

In another particularly preferred embodiment the invention concerns the above-mentioned compounds of formula 1, wherein R$^4$ is a five- or six-membered heteroaromatic group comprising 1, 2 or 3 heteroatoms each independently selected from the group N, S and O, wherein said heteroaromatic group on any atom available for substitution may optionally be further substituted by one, two or three groups each independently selected from among methyl, ethyl, F, Cl, Br, and —CF$_3$, and the pharmaceutically acceptable salts of the aforementioned compounds.

In a further particularly preferred embodiment the invention concerns the above-mentioned compounds of formula 1, wherein R$^4$ is an oxadiazole group that may optionally be substituted by one, two or three groups each independently selected from methyl, ethyl, F, Cl, and —CF$_3$ and the pharmaceutically acceptable salts of the aforementioned compounds.

In another particularly preferred embodiment the invention concerns the above-mentioned compounds of formula 1, selected from the group consisting of

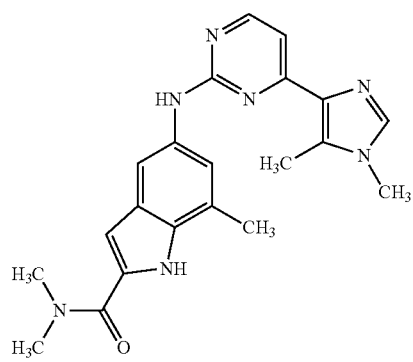

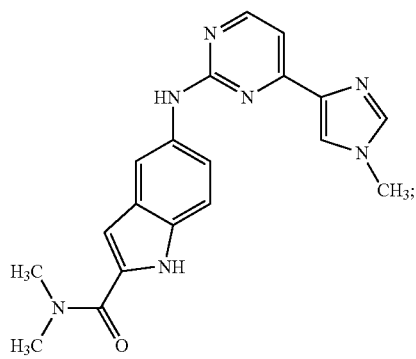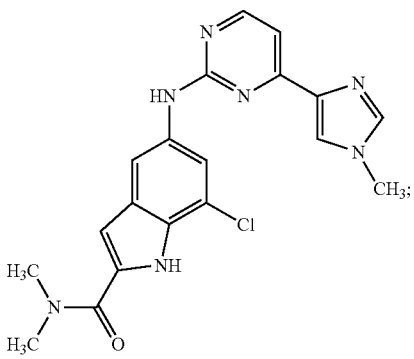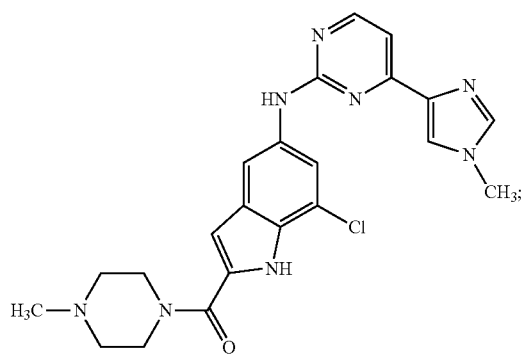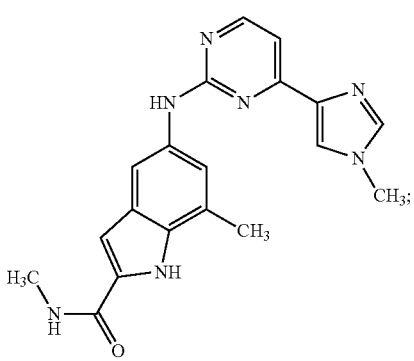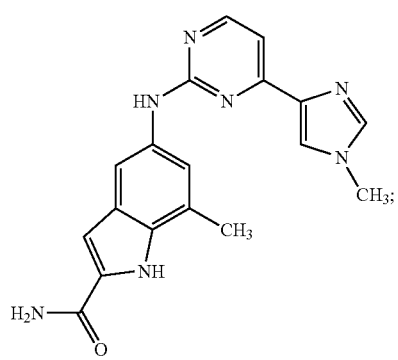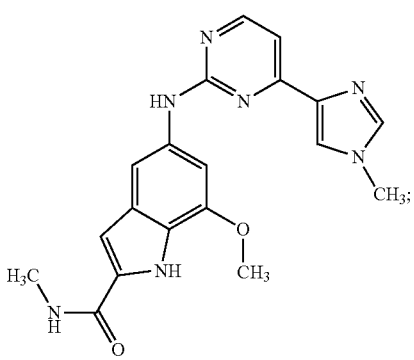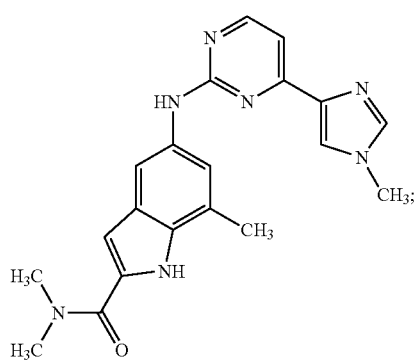

15
-continued
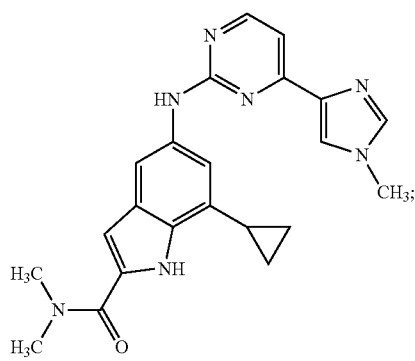
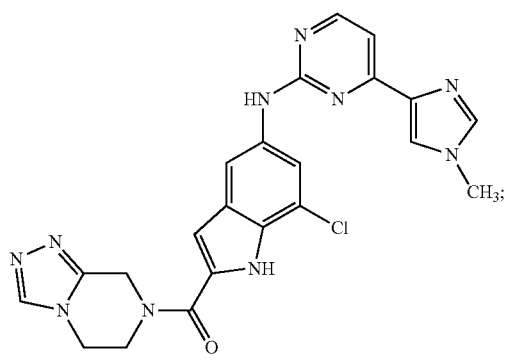
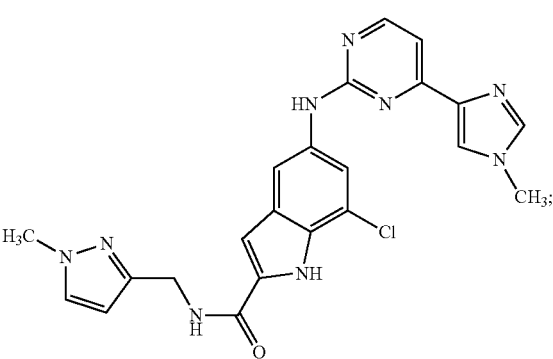
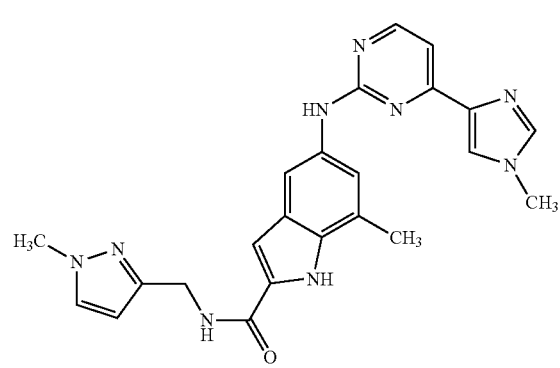
16
-continued
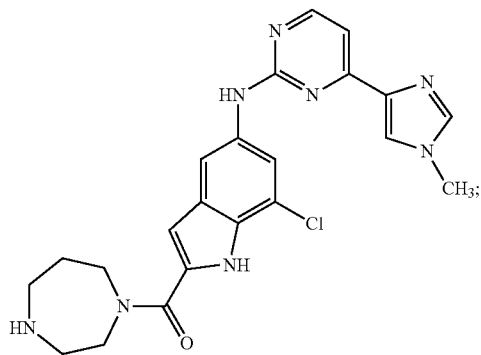
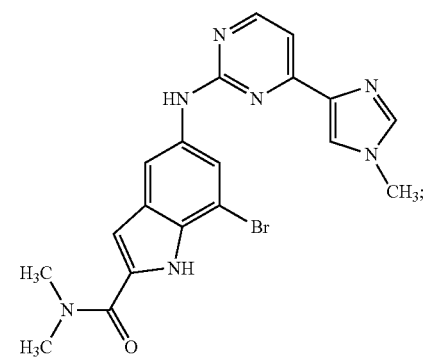
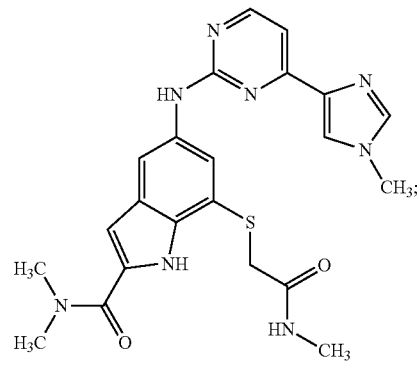
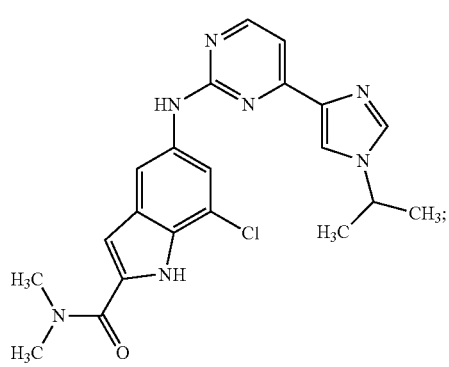

-continued

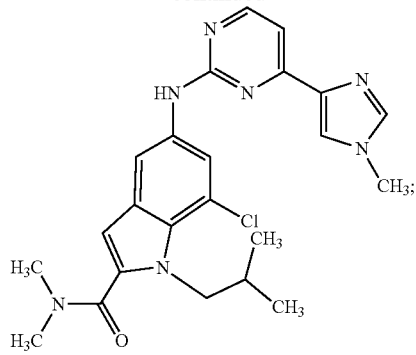
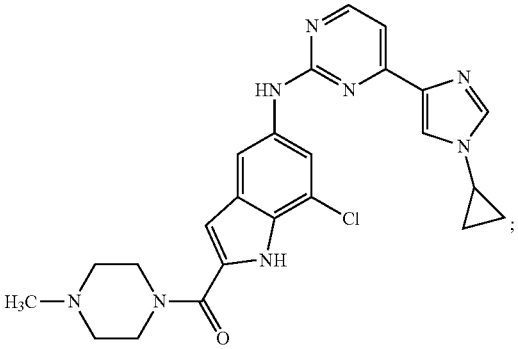

21
-continued
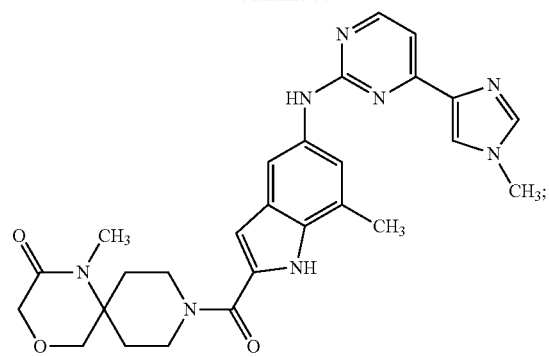
22
-continued
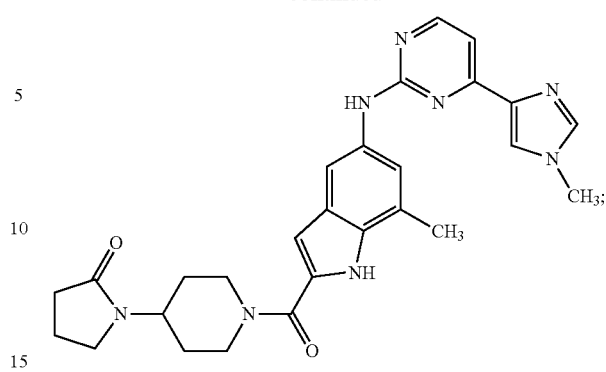
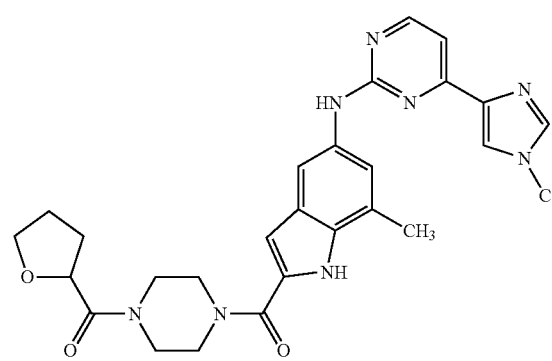
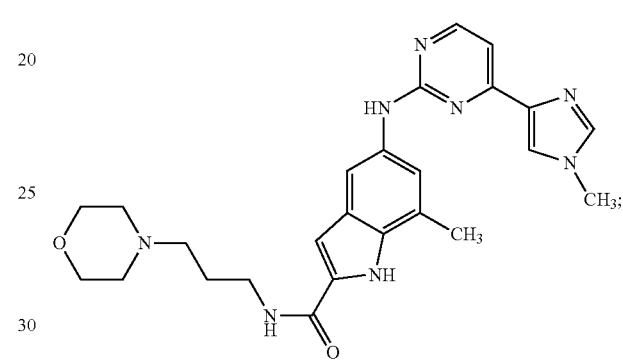
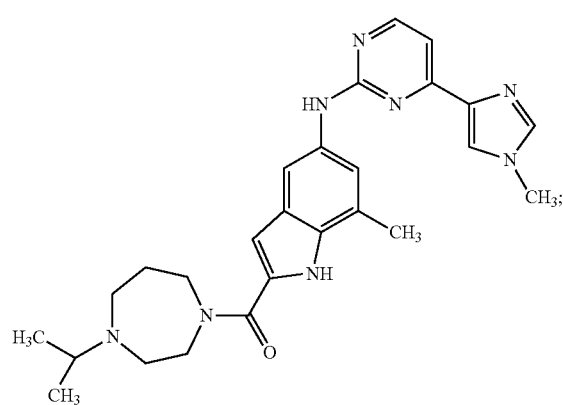
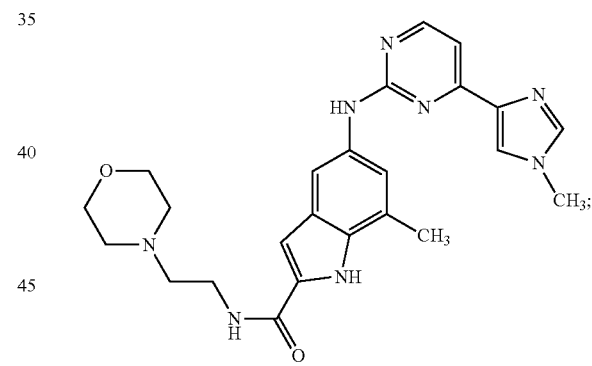
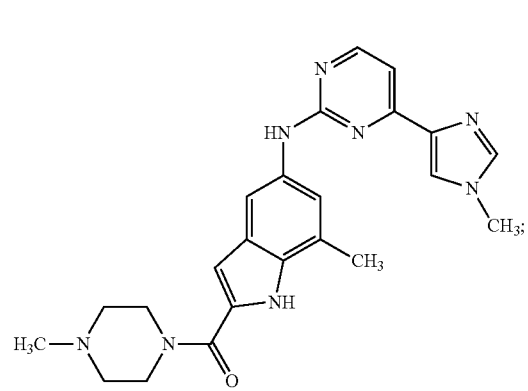
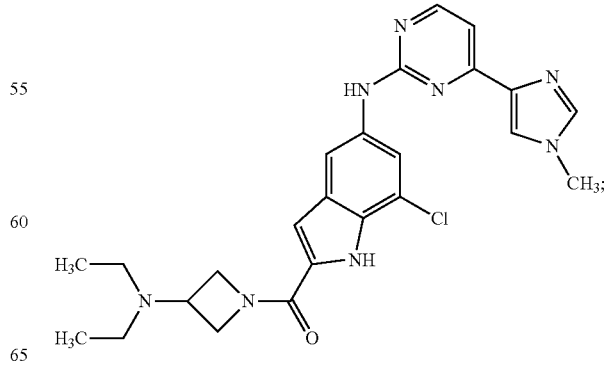

-continued
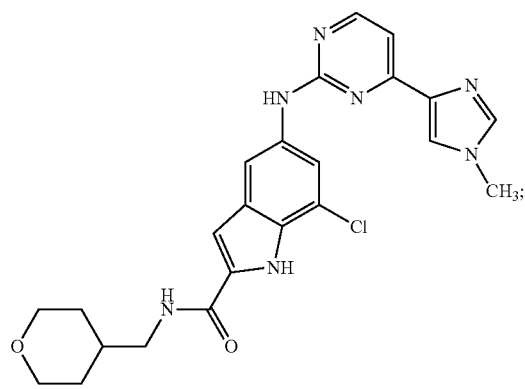
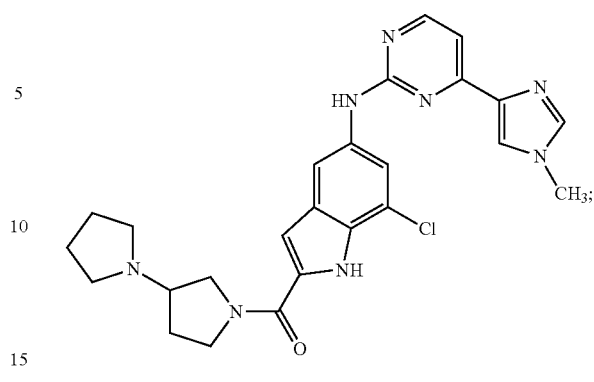
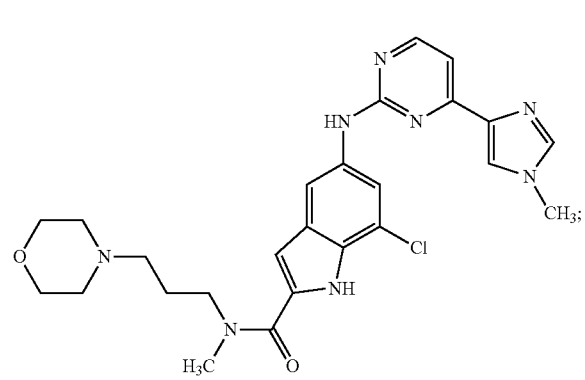
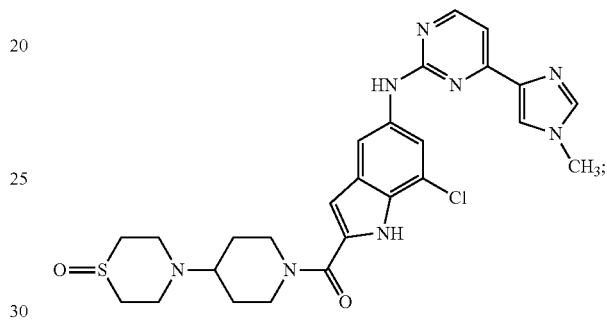
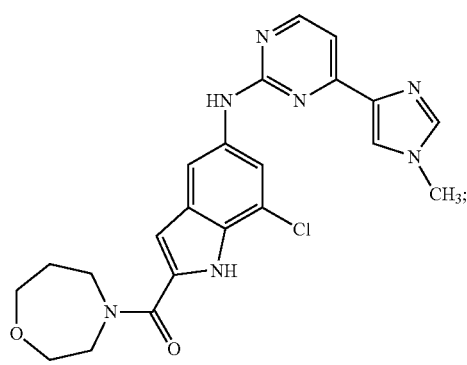
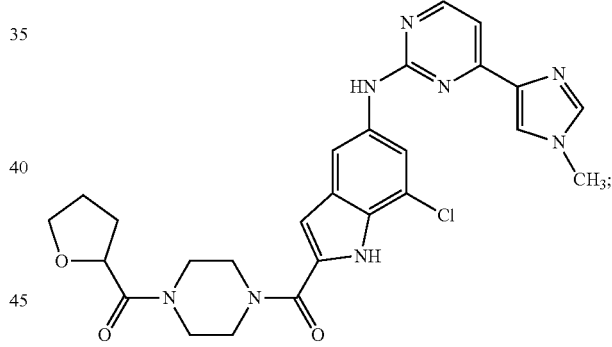
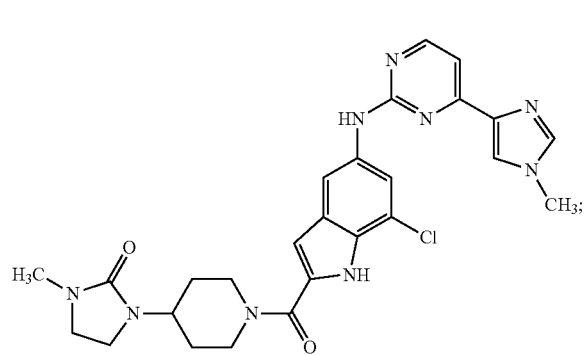
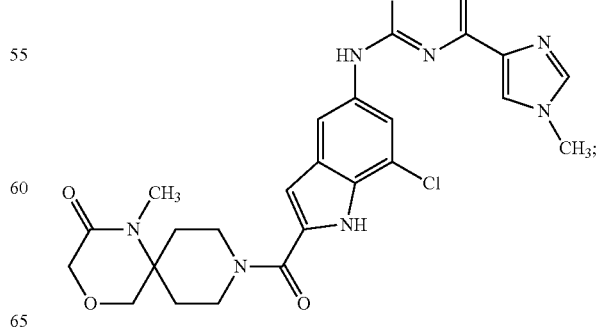

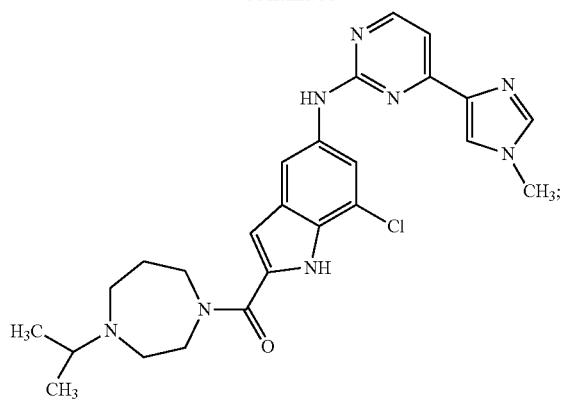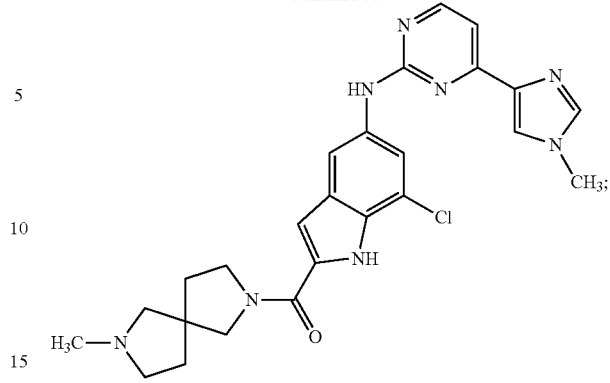

27
-continued
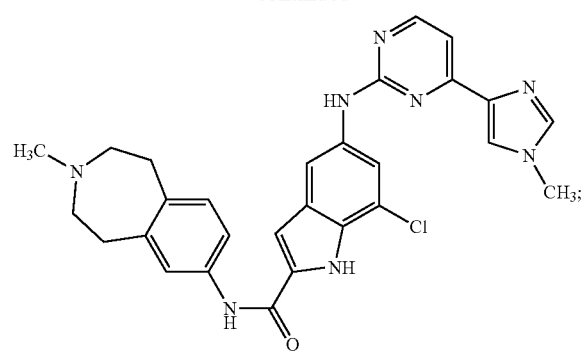
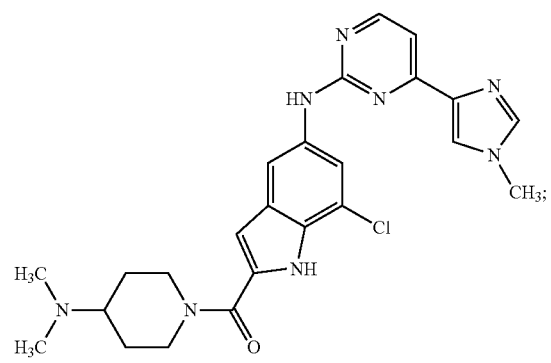
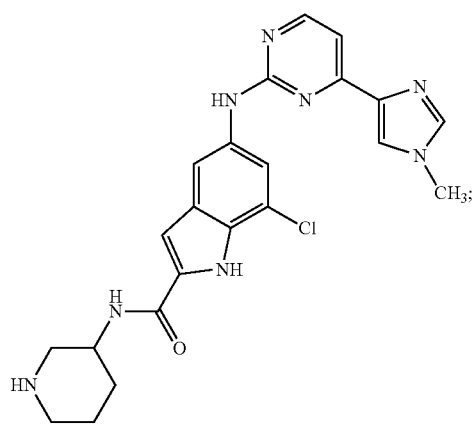
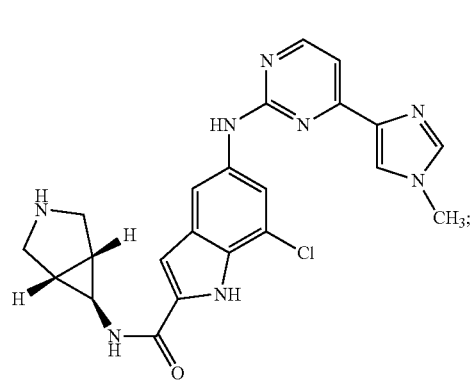
28
-continued
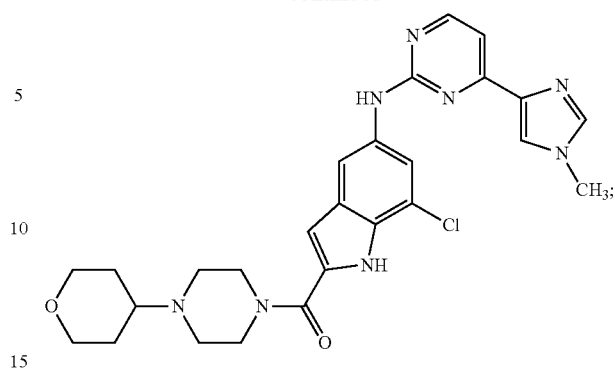
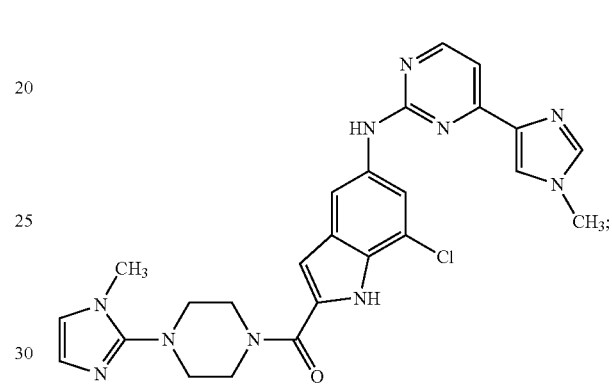
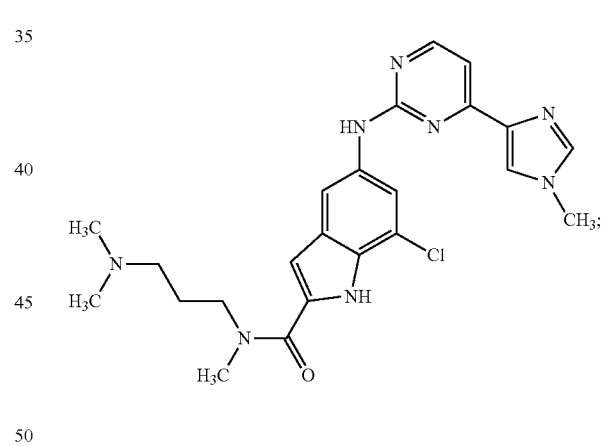
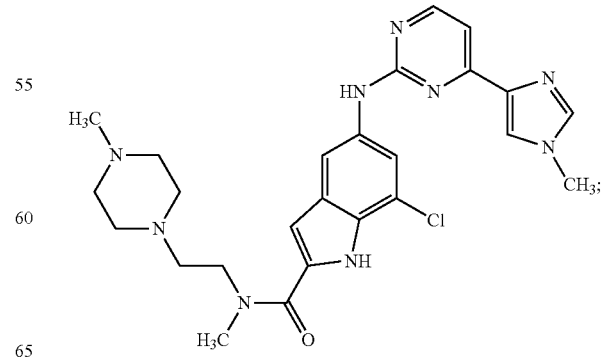

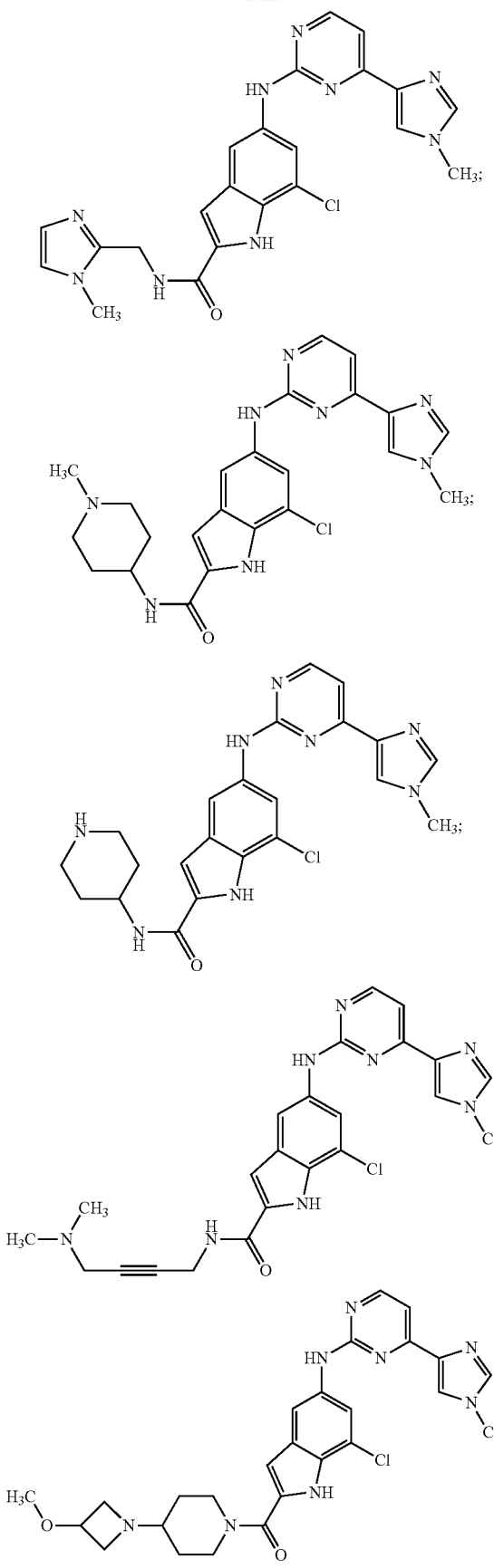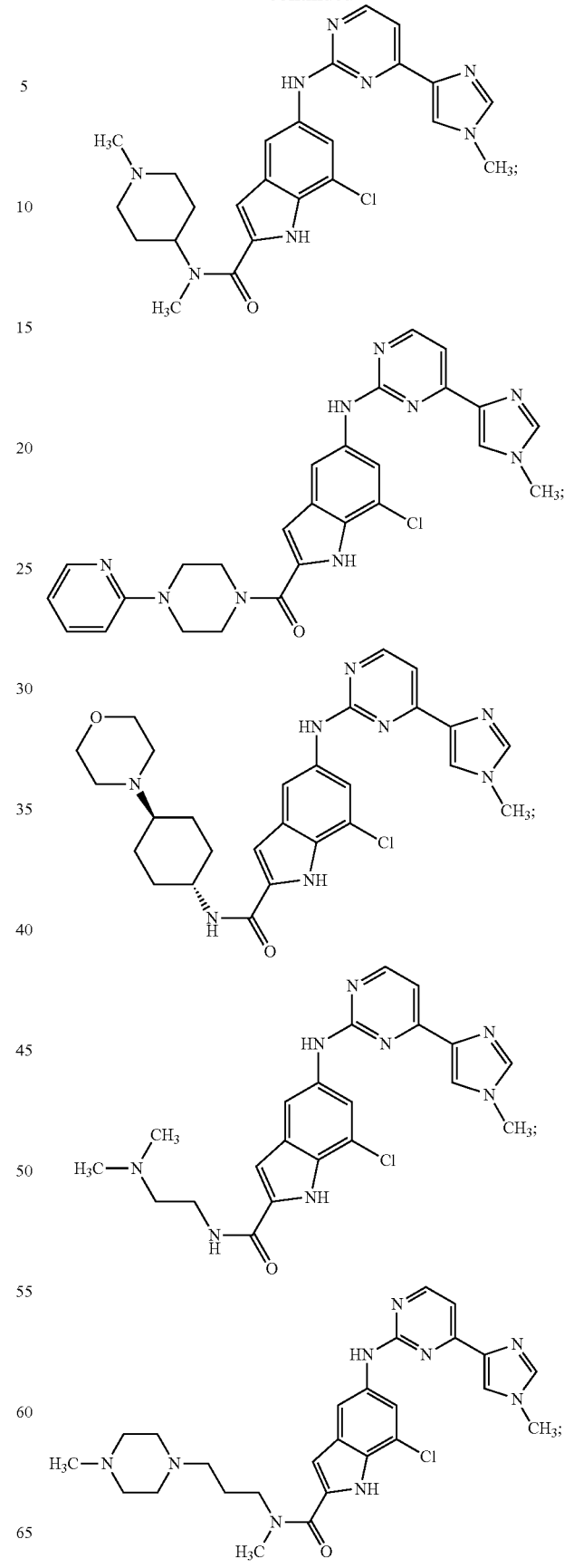

31
-continued
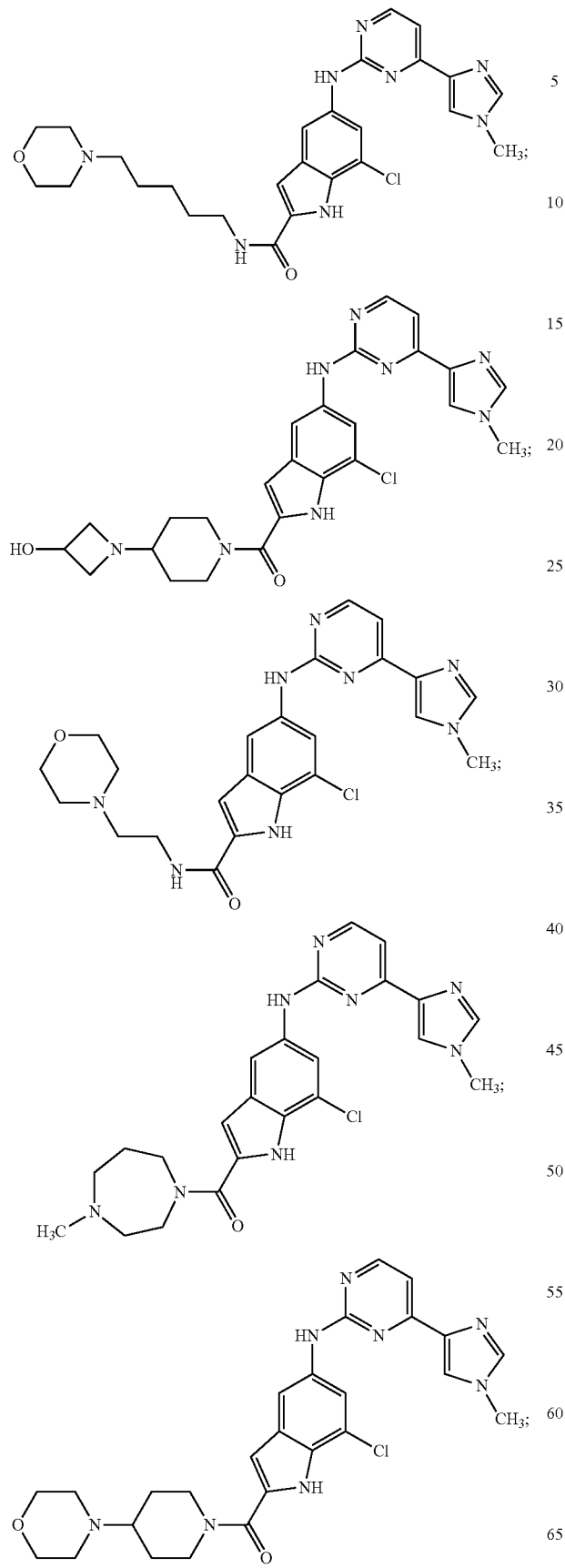
32
-continued
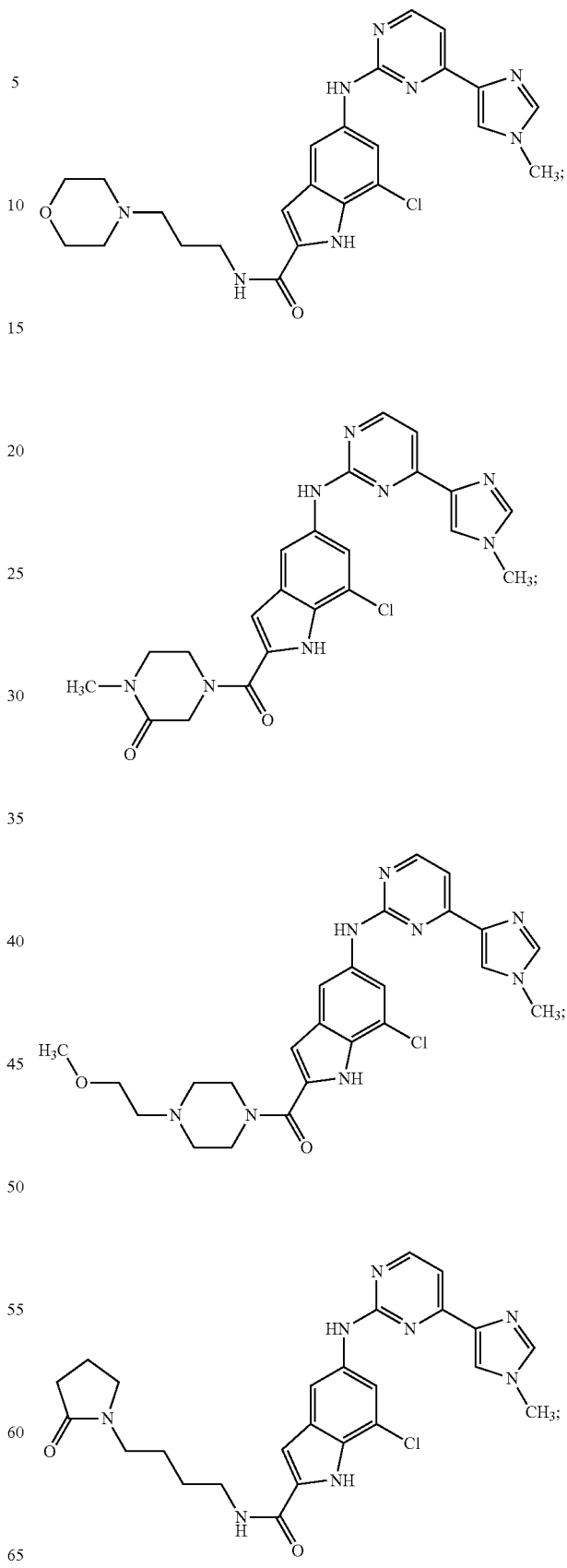

33
-continued
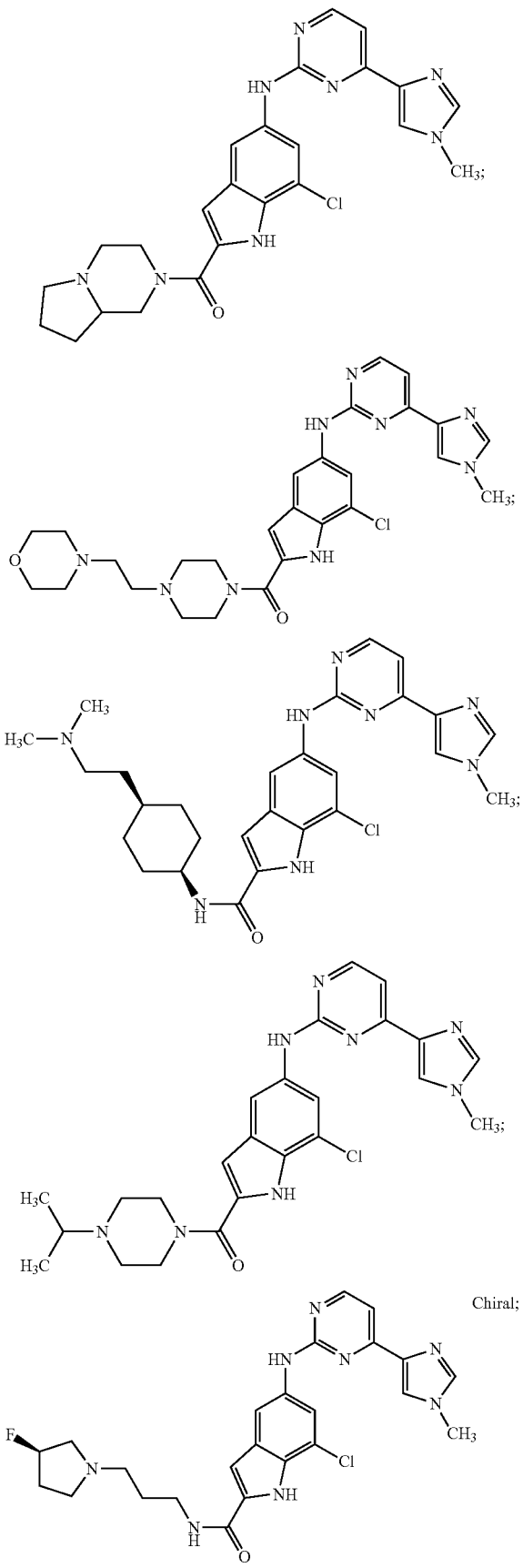
34
-continued
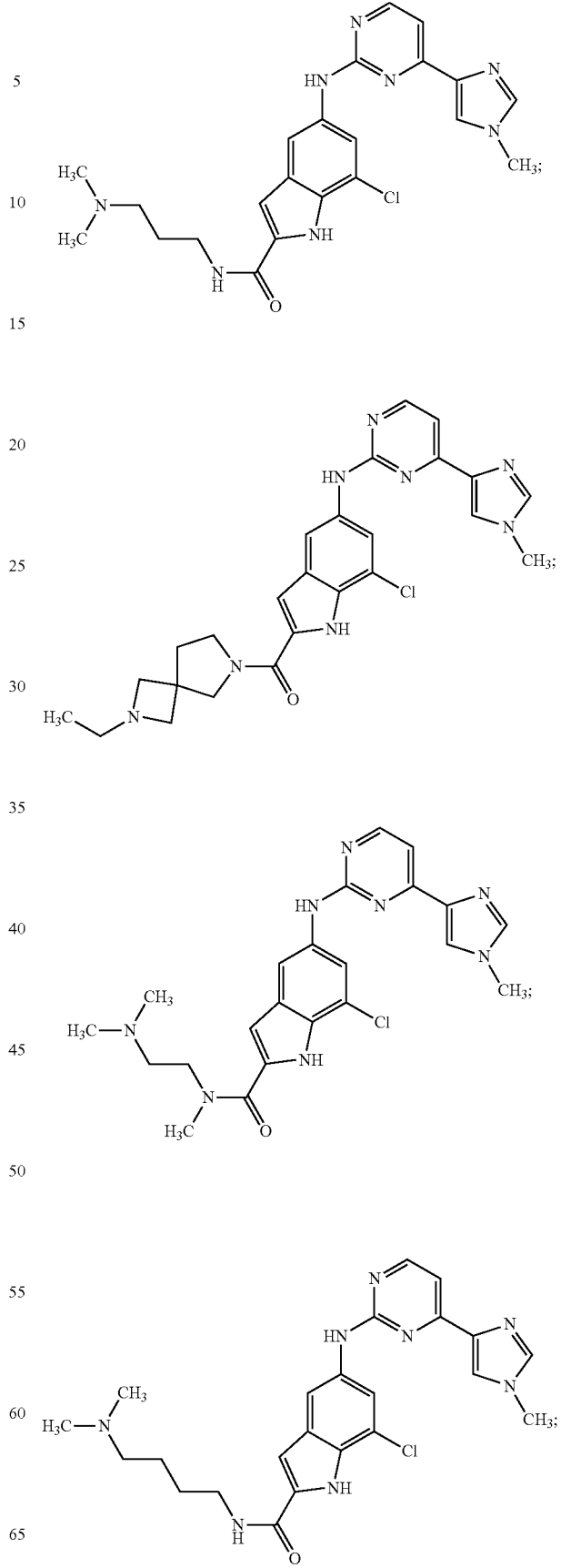

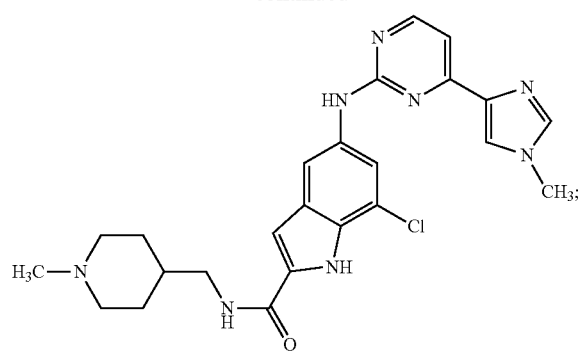
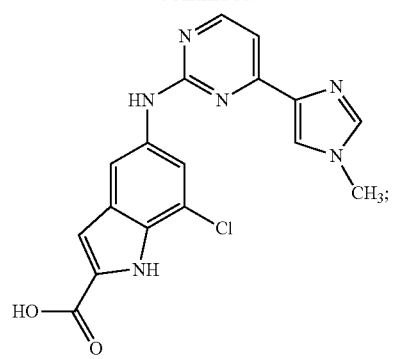
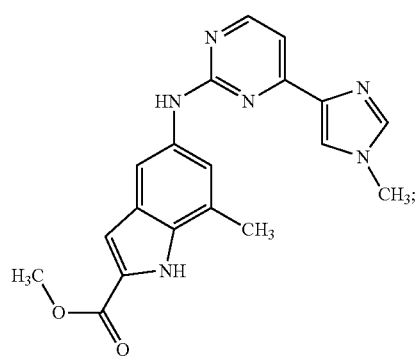
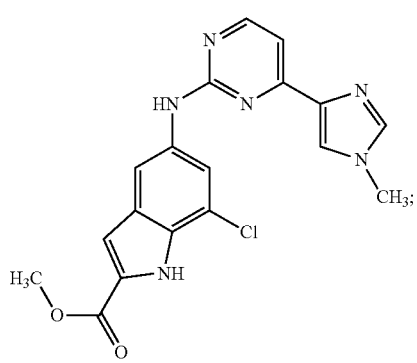
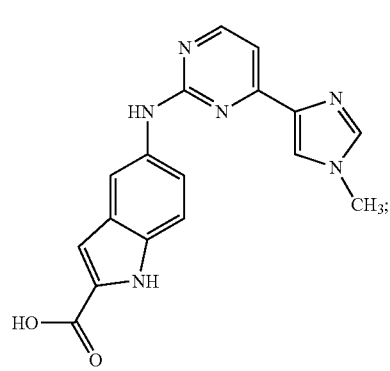
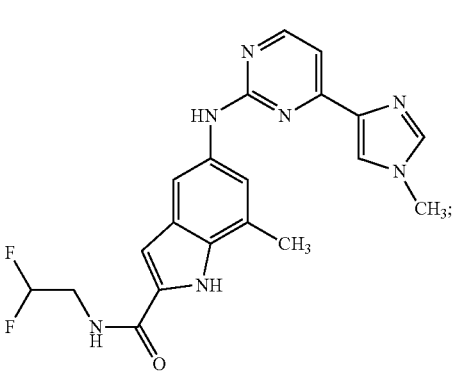
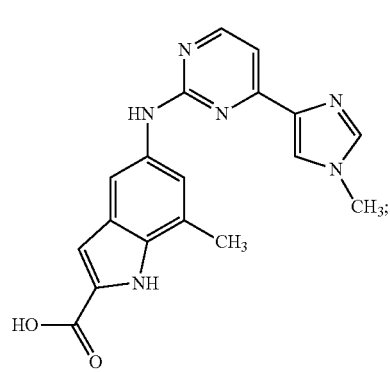
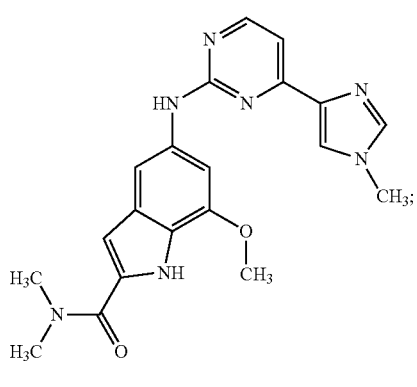

37
-continued
38
-continued
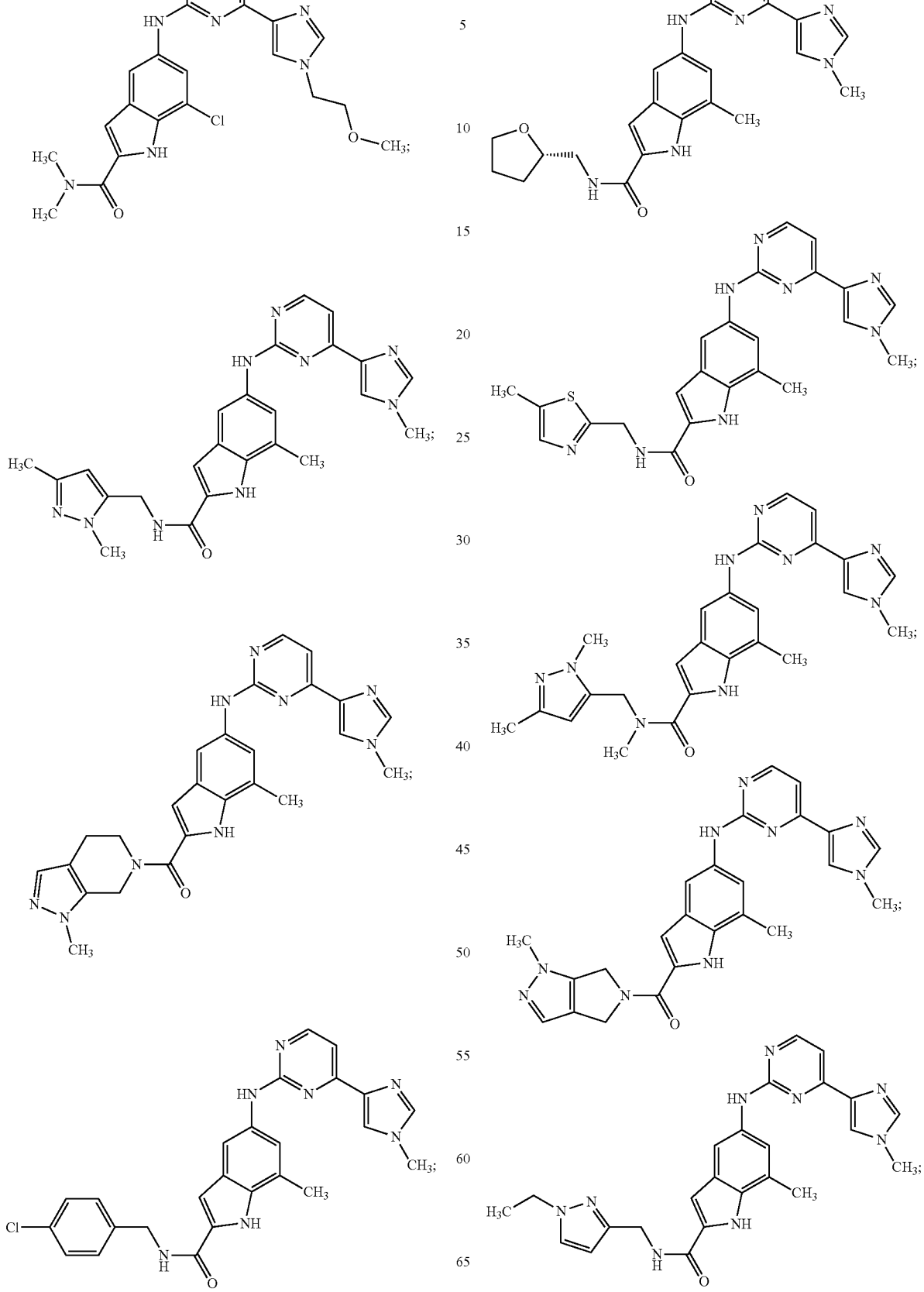

| 39 | 40 |
|---|---|
| -continued | -continued |
| 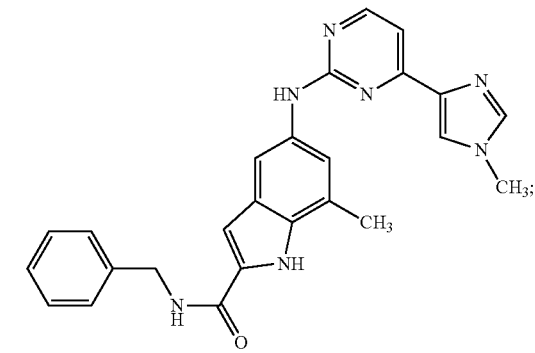 | 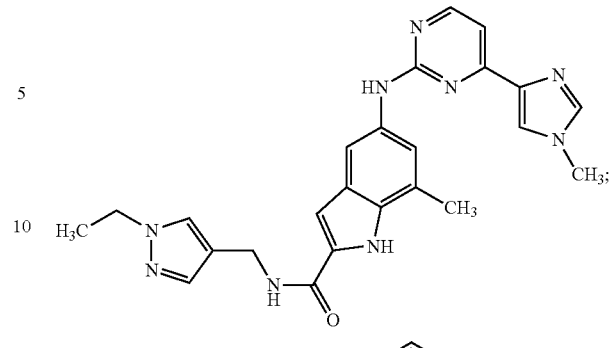 |
| 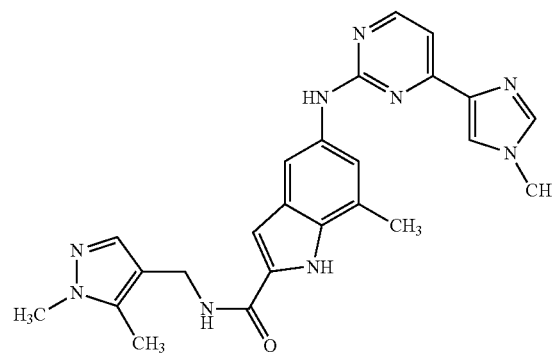 | 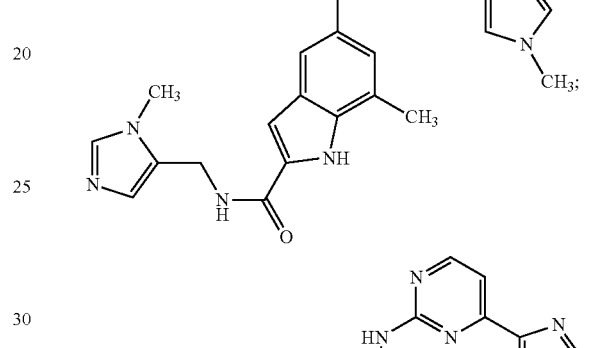 |
| 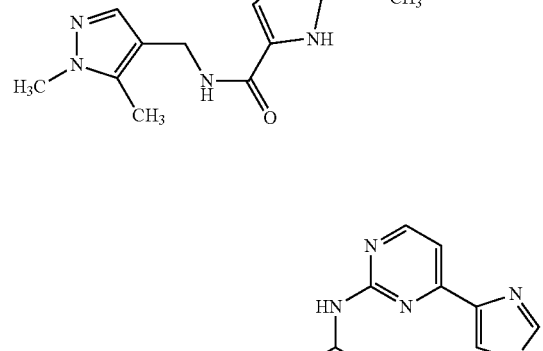 | 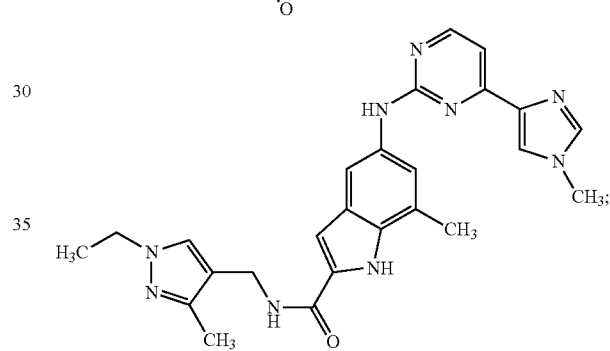 |
|  | 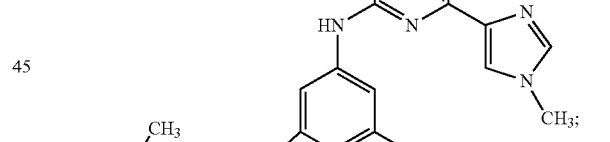 |
|  | 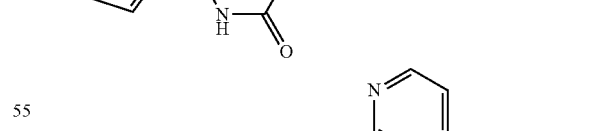 |

41
-continued
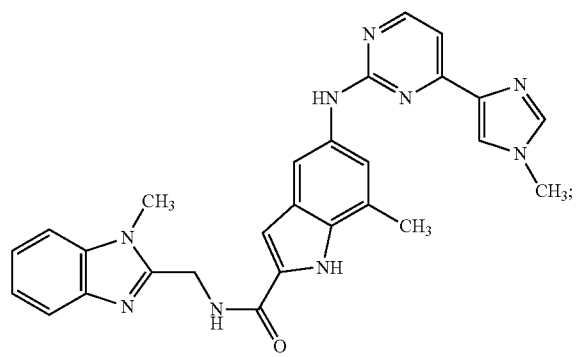
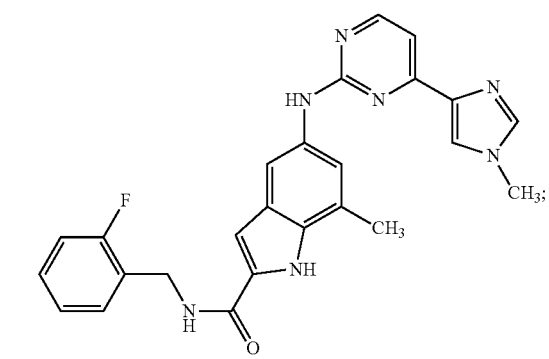
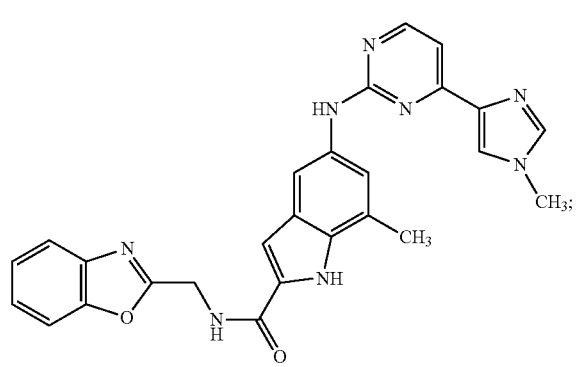
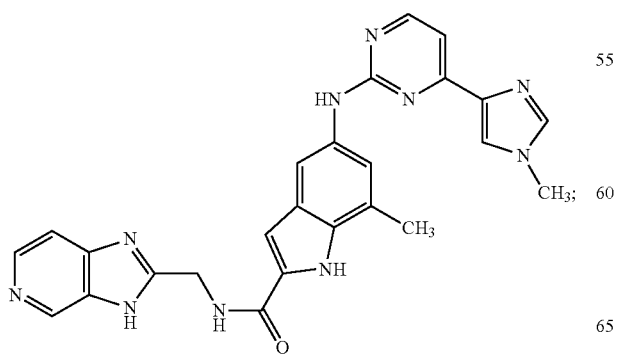
42
-continued
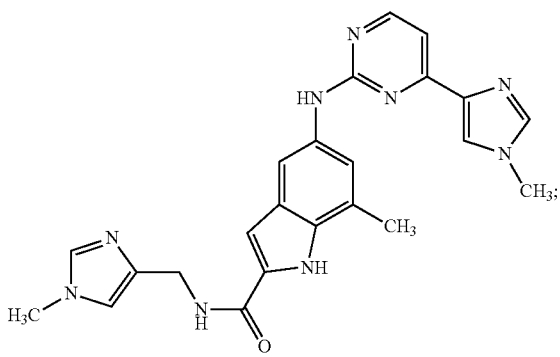
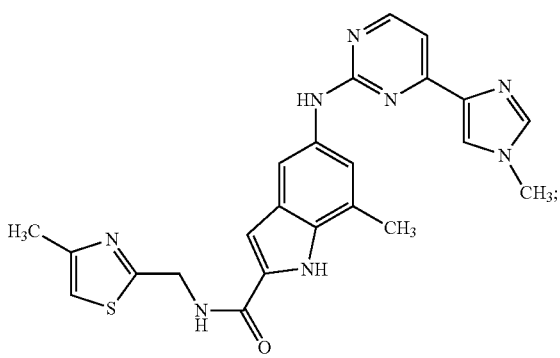
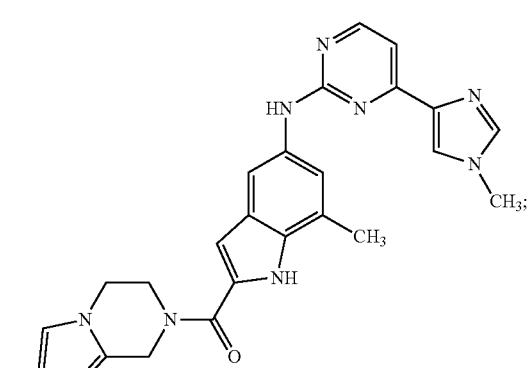
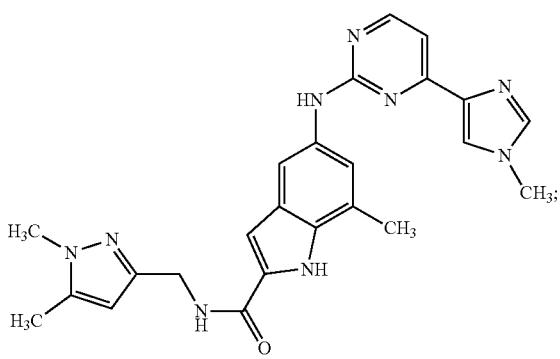

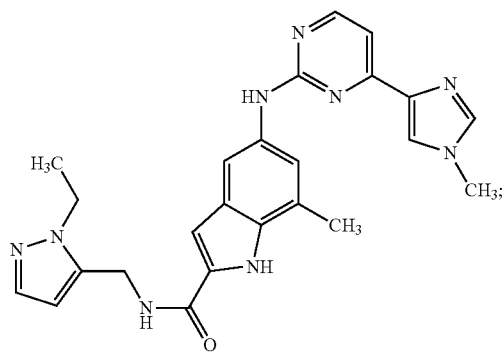
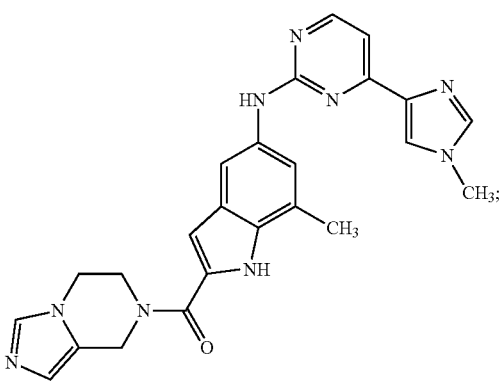
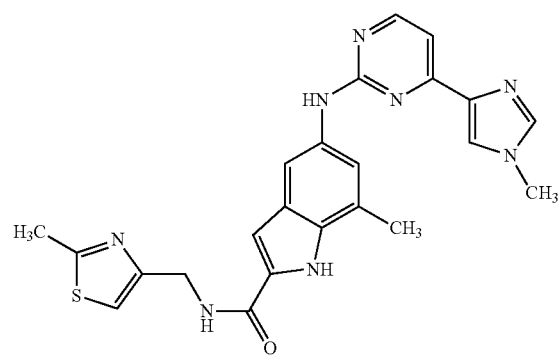
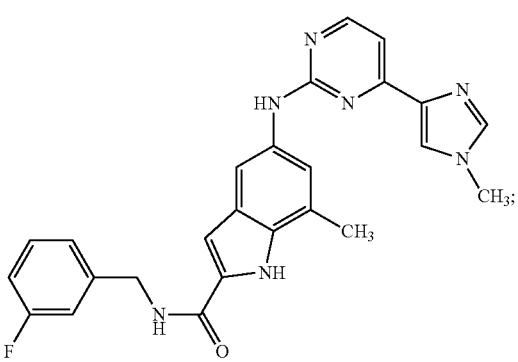
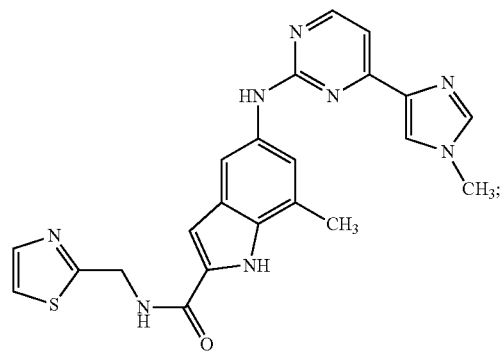
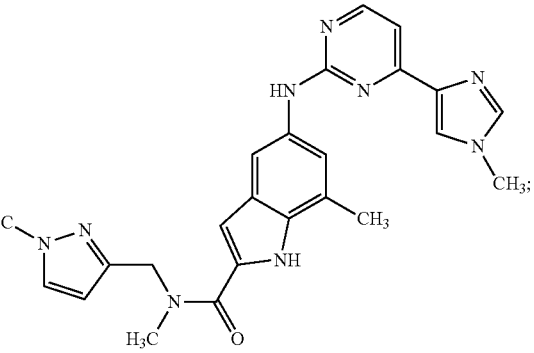
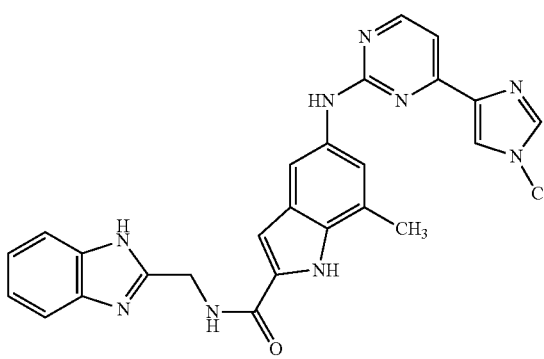
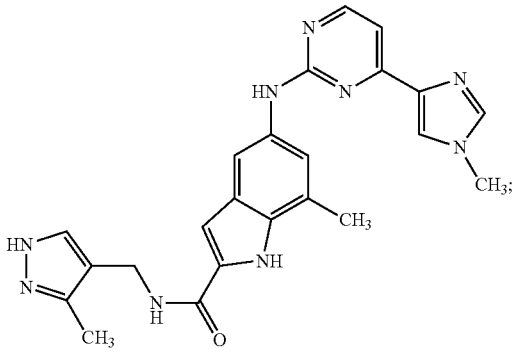

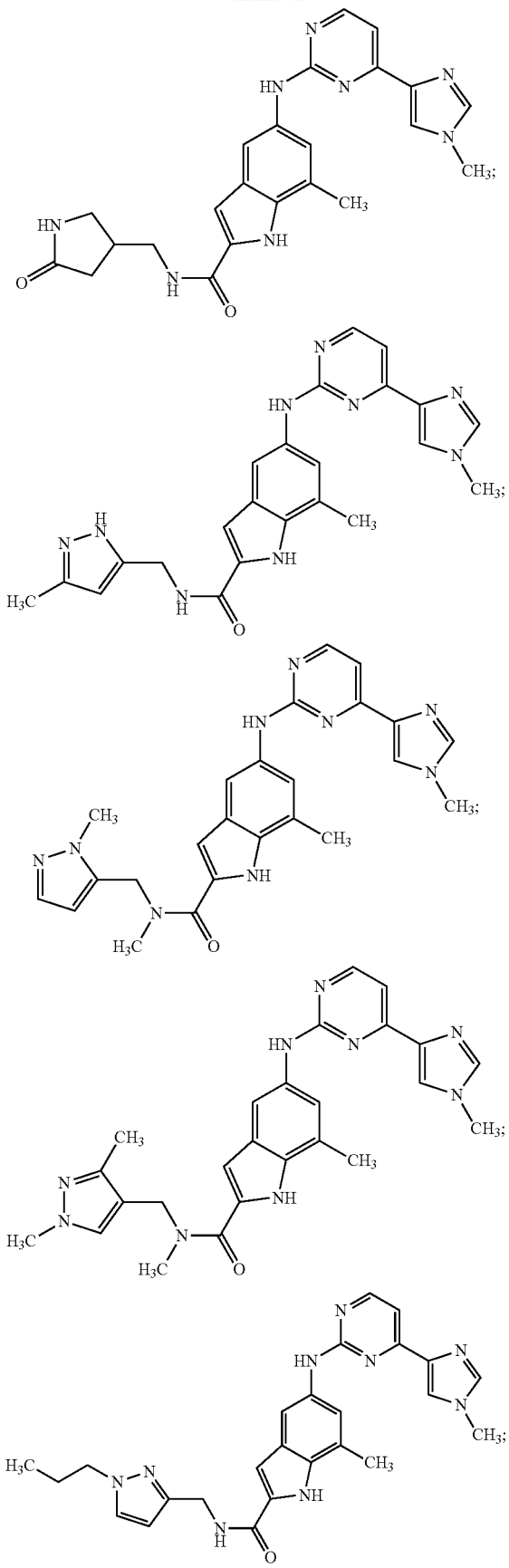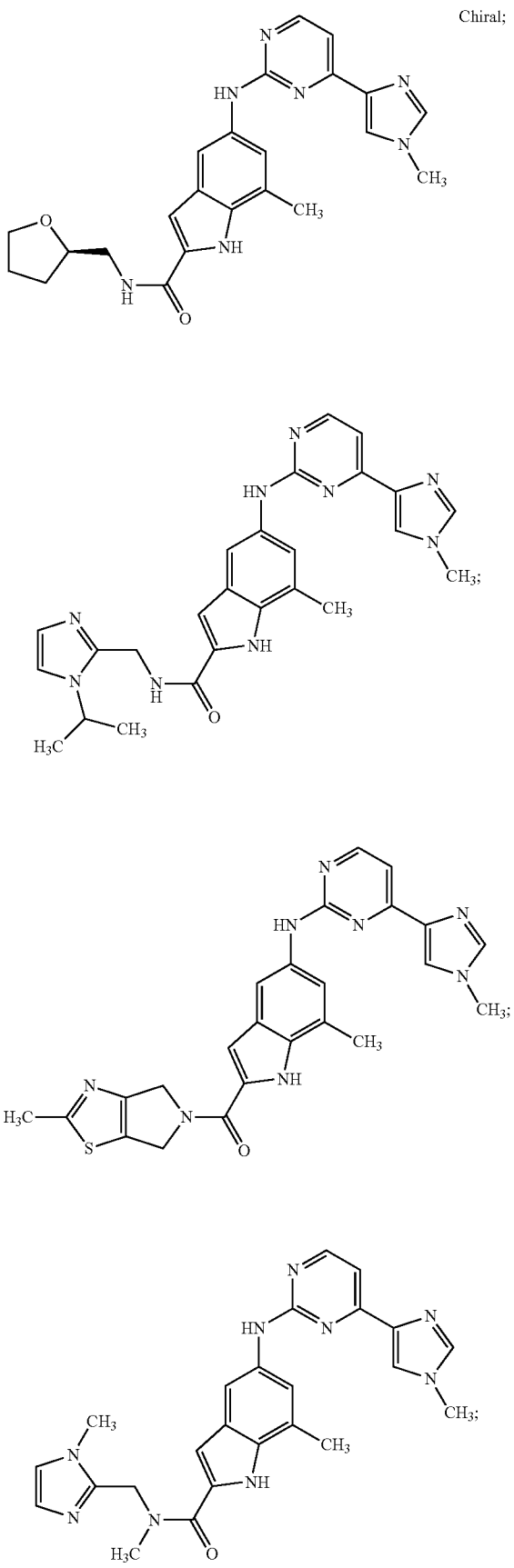

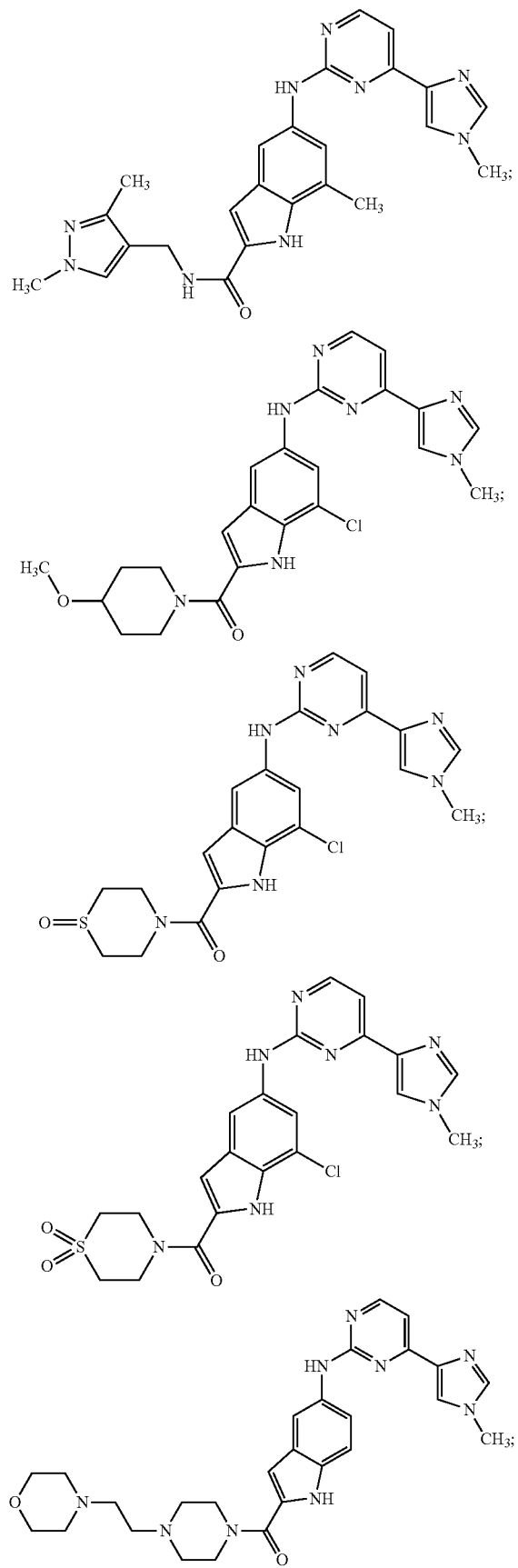
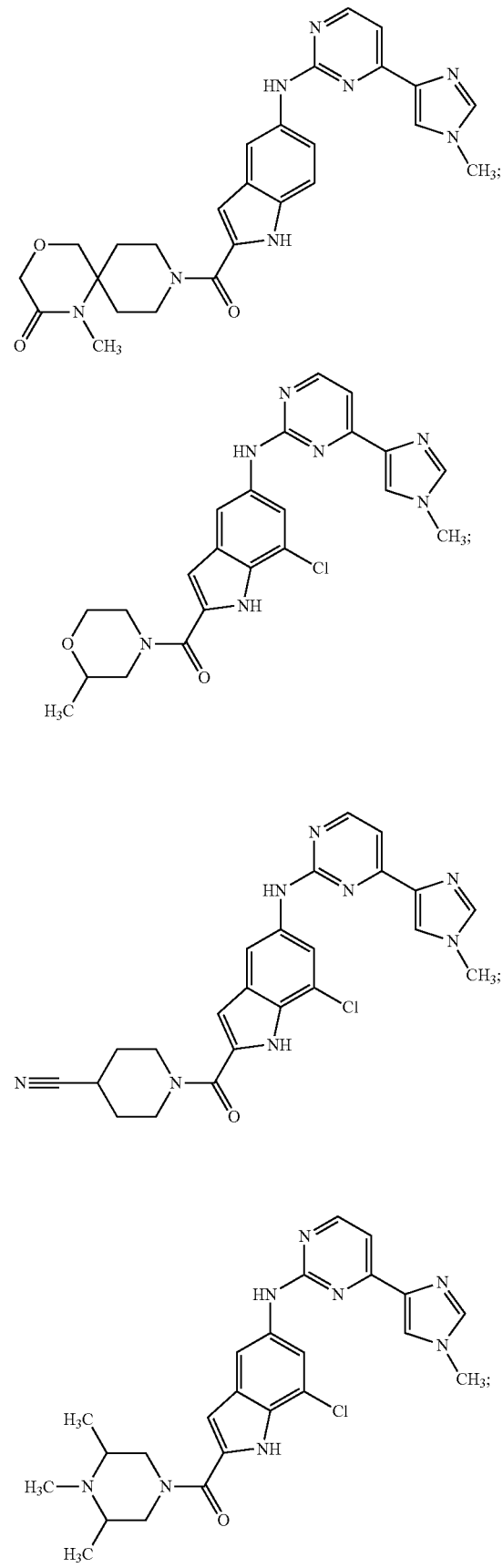

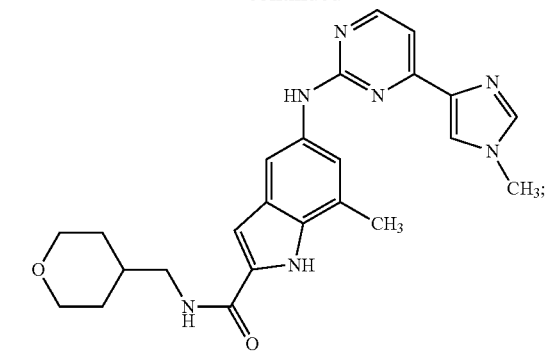
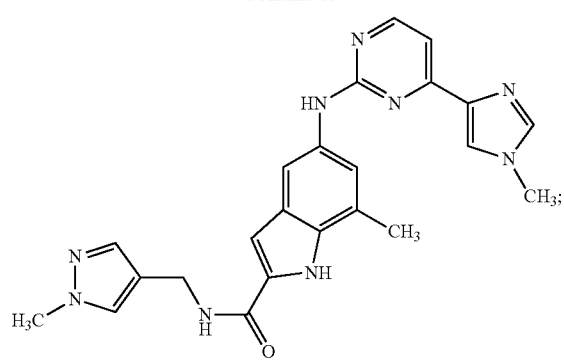

51
-continued
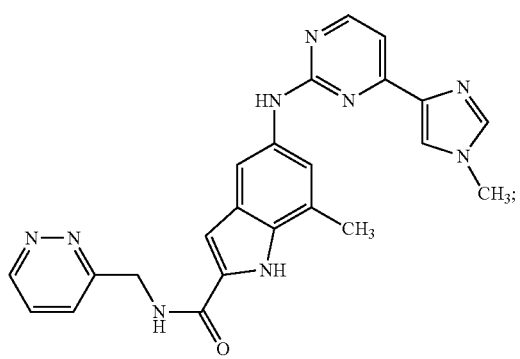
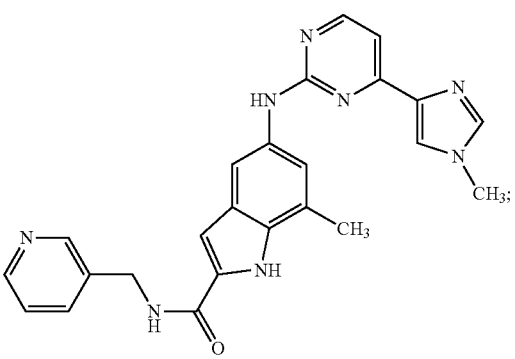
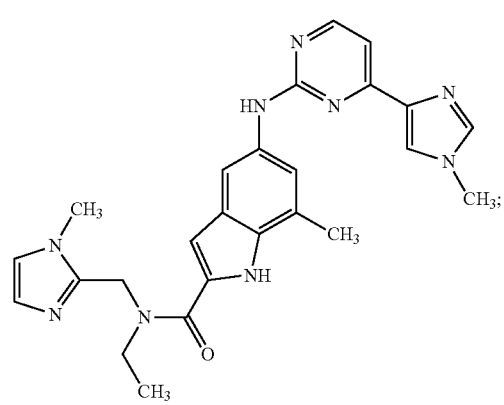
52
-continued
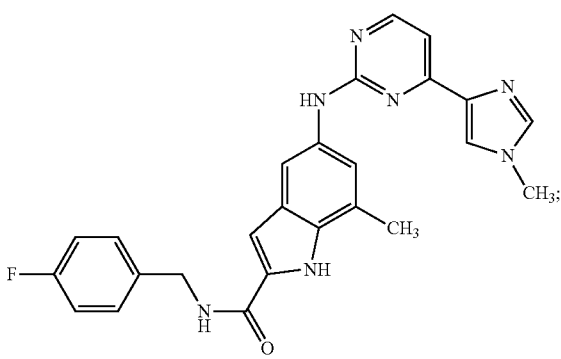
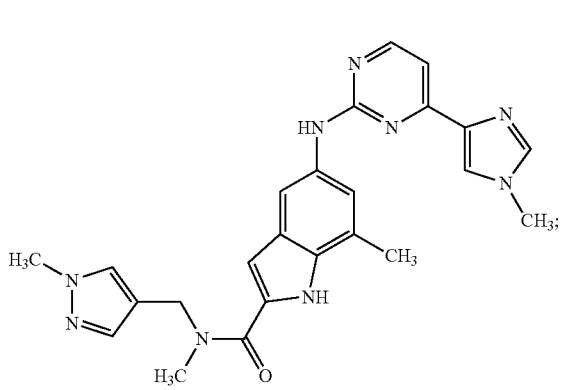

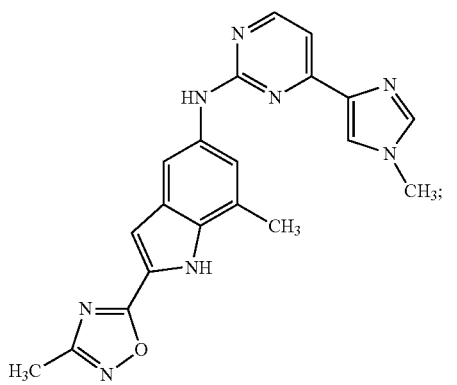

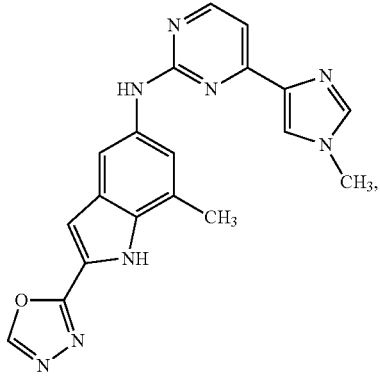 [SMILES: Cc1cc(Nc2nccc(-c3cn(C)cn3)n2)cc2cc(-c3nnco3)[nH]c12]

and the pharmaceutically acceptable salts of the aforementioned compounds.

In a further preferred embodiment the invention concerns the use of the aforementioned compounds of formula 1 for preparing a medicament for the treatment of diseases which can be treated by inhibition of the Syk enzyme.

In a further preferred embodiment the invention concerns the use of the aforementioned compounds of formula 1 for preparing a medicament for the treatment of diseases selected from among allergic rhinitis, asthma, COPD, adult respiratory distress syndrome, bronchitis, B-cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, capsule cell lymphoma, neutropenia, artheriosclerosis non-familial lateral sclerosis, Crohn's disease, multiple sclerosis, myasthenia gravis, osteoporosis, osteolytic diseases, osteopenia, psoriasis, Sjögren's syndrome, sclerodermy, T-cell lymphoma, urticaria/angiooedema, Wegener's granulomatosis and coeliac disease.

In another preferred embodiment the invention concerns the use of the aforementioned compounds of formula 1 for preparing a medicament for the treatment of diseases selected from among asthma, COPD, allergic rhinitis, adult respiratory distress syndrome, bronchitis, allergic dermatitis, contact dermatitis, idiopathic thrombocytopenic purpura, rheumatoid arthritis and allergic rhinoconjunctivitis.

In a further preferred embodiment the invention concerns the use of the aforementioned compounds of formula 1 for preparing a medicament for the treatment of diseases selected from among asthma, COPD, allergic rhinitis, allergic dermatitis and rheumatoid arthritis.

Another preferred embodiment of the invention concerns pharmaceutical formulations which contain one or more of the aforementioned compounds of formula 1.

A further preferred embodiment of the invention refers to pharmaceutical formulations which contain one or more compounds of formula 1 in combination with an active substance selected from among anticholinergics, betamimetics, corticosteroids, PDE4-inhibitors, EGFR-inhibitors, LTD4-antagonists, CCR3-inhibitors, iNOS-inhibitors, CRTH2-antagonists and HMG-CoA reductase inhibitors.

A further preferred embodiment of the invention refers to intermediate compounds according to formula 7

7 wherein R³, R⁴ and R⁵ are defined as above-mentioned, and the pharmaceutically acceptable salts of the aforementioned compounds.

A further preferred embodiment of the invention refers to intermediate compounds according to formula 8

8 wherein R¹, R², R³ and R⁵ are defined as above-mentioned, and the pharmaceutically acceptable salts of the aforementioned compounds.

A further preferred embodiment of the invention refers to intermediate compounds according to formula 10

10 wherein R¹, R², R⁴ and R⁵ are defined as above-mentioned, and the pharmaceutically acceptable salts of the aforementioned compounds.

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

I

II

III

IV

V

If there is no asterisk (*) in the structural formula of the substituent, each hydrogen atom may be removed at the substituent and the valency thus freed may serve as a binding site to the rest of a molecule. Thus, for example, VI

VI may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

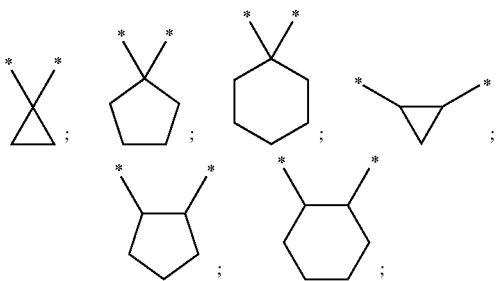

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"- branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

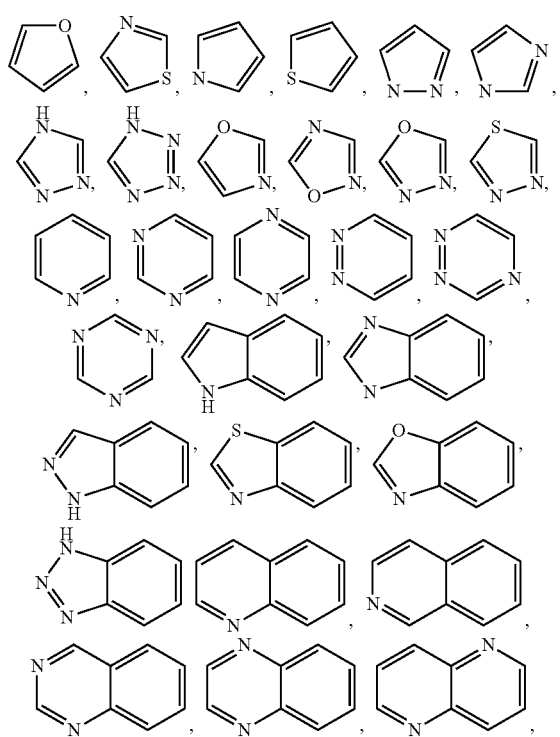

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

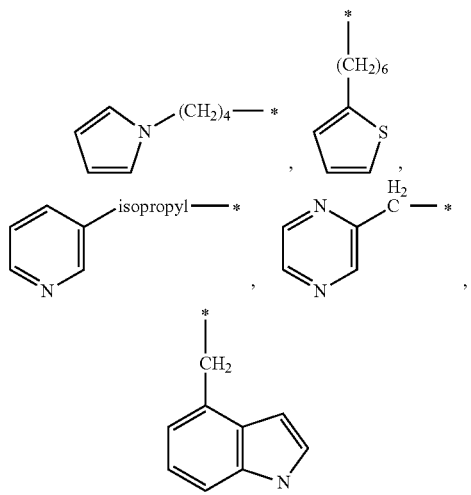

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

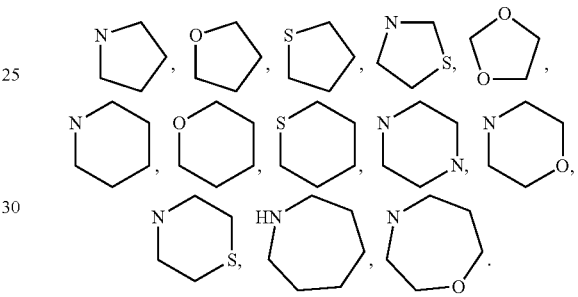

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed. Examples include:

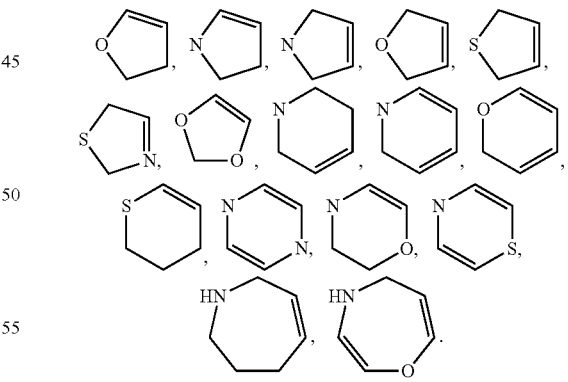

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

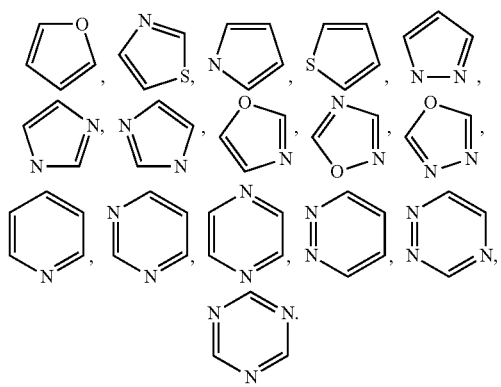

Unless otherwise mentioned, a heterocyclic ring (or heterocycle) may be provided with a keto group. Examples include:

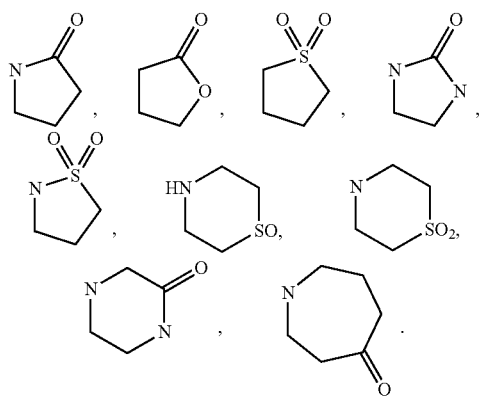

Although covered by the term "cycloalkyl", the term "bicyclic cycloalkyls" generally denotes eight-, nine- or ten-membered bicyclic carbon rings. Examples include

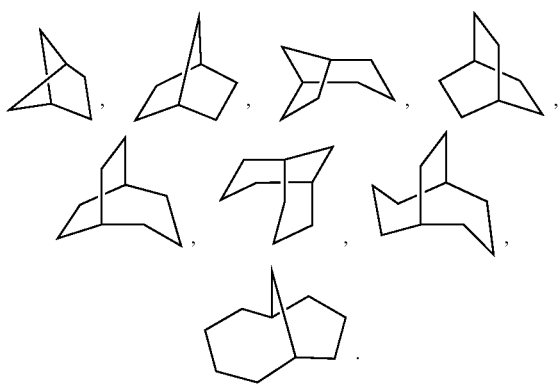

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

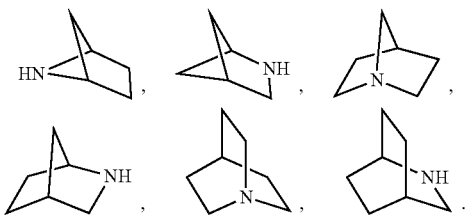

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

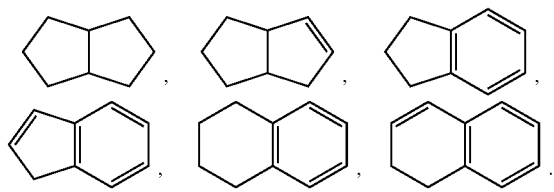

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

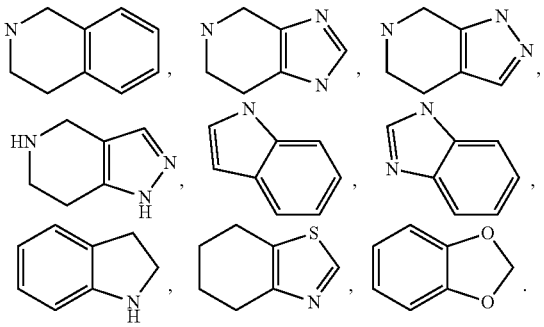

By the term "spiro group" (spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

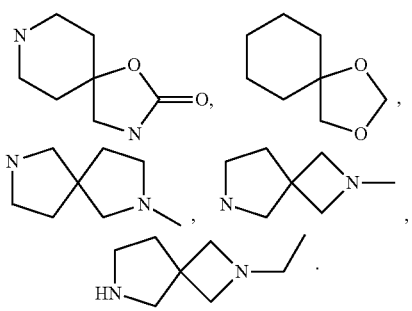

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. Amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. in the (R) or (S) form.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids— such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof. These pharmacologically acceptable salts of the compounds of formula 1 may also be present in the form of their respective hydrates (e.g. Monohydrates, dihydrates, etc.) as well as in the form of their respective solvates.

By a hydrate of the compound according to the formula 1 is meant, for the purposes of the invention, a crystalline salt of the compound according to formula 1, containing water of crystallisation.

By a solvate of the compound according to formula 1 is meant, for the purposes of the invention, a crystalline salt of the compound according to formula 1, which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The Examples 1 according to the invention were prepared according to Scheme 1a-1g.

Scheme 1a

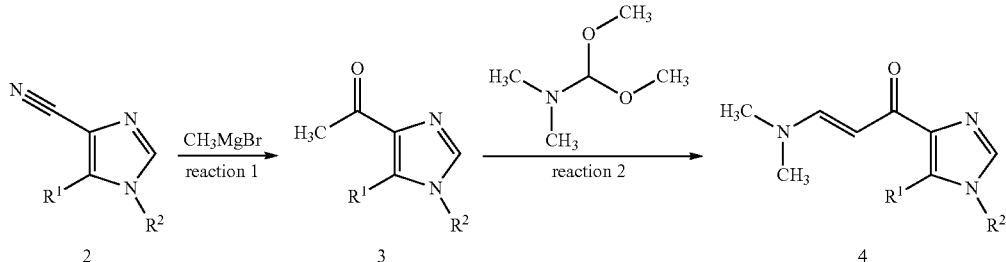

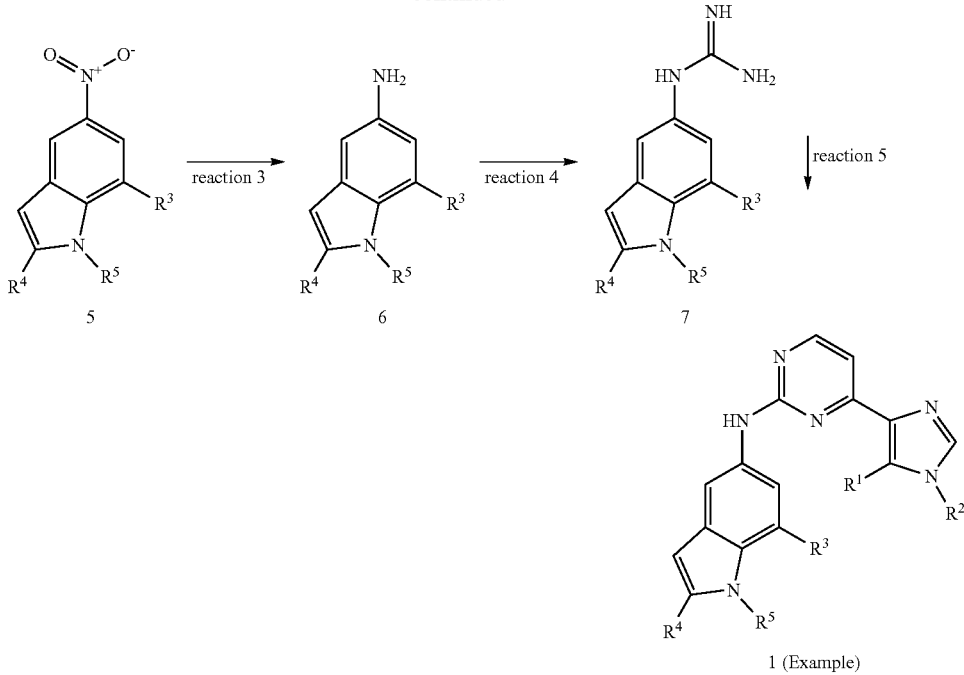
wherein R¹, R², R³, R⁴ and R⁵ are herein defined as aforementioned.
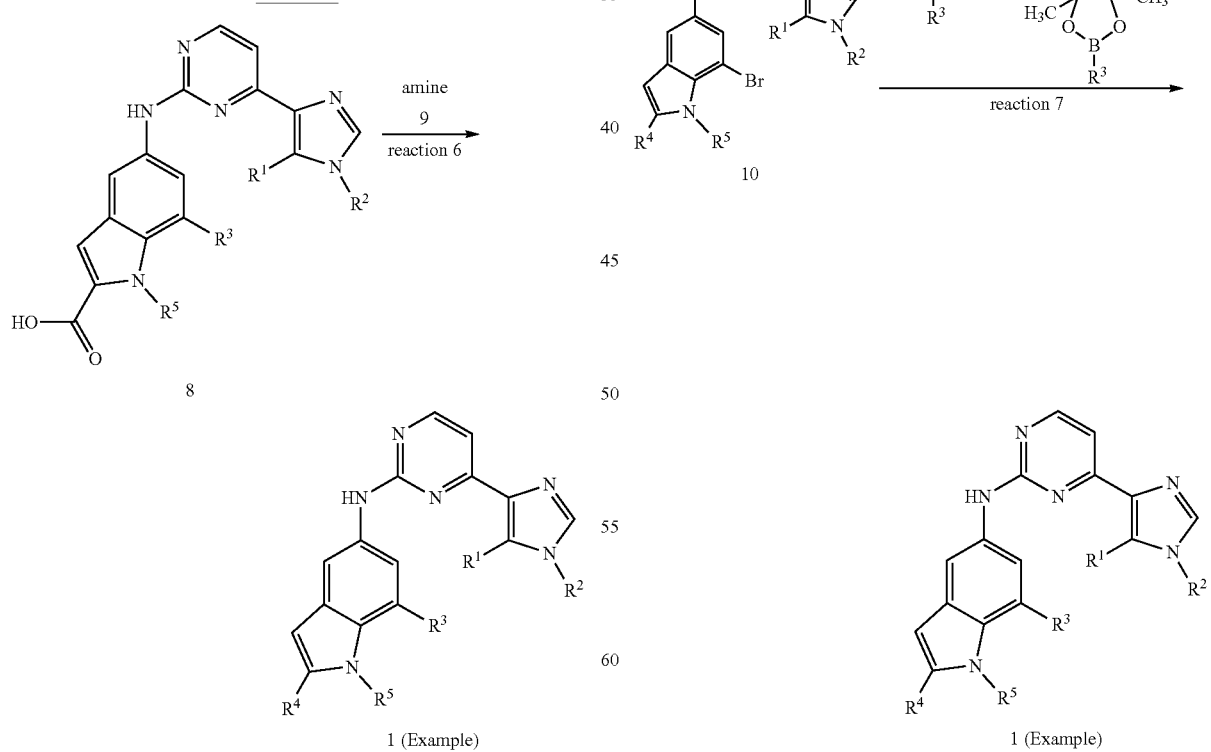
wherein R¹, R², R³, R⁴ and R⁵ are herein defined as aforementioned.
wherein R¹, R², R³, R⁴ and R⁵ are herein defined as aforementioned.

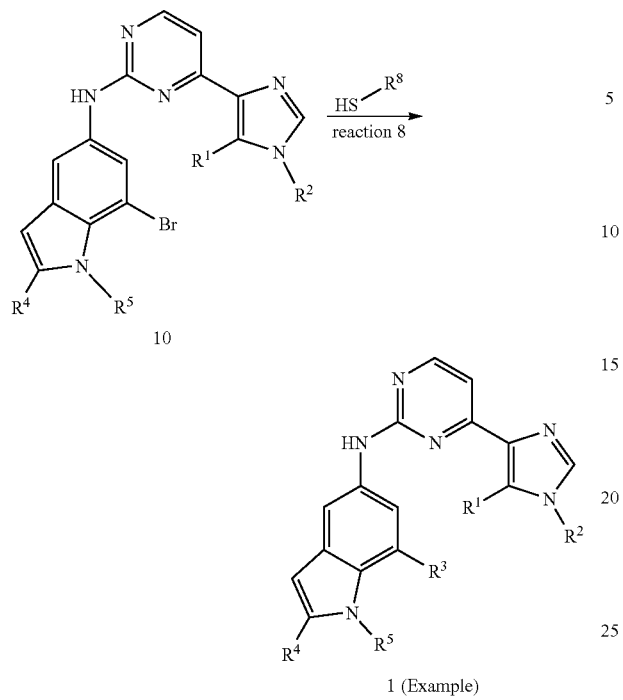

wherein $R^1$, $R^2$, $R^3$, $R^4$ and $R^5$ are herein defined as aforementioned and wherein $R^5$ is selected from —($C_{1-3}$-alkylene)-A and -A and wherein A is herein defined as aforementioned.

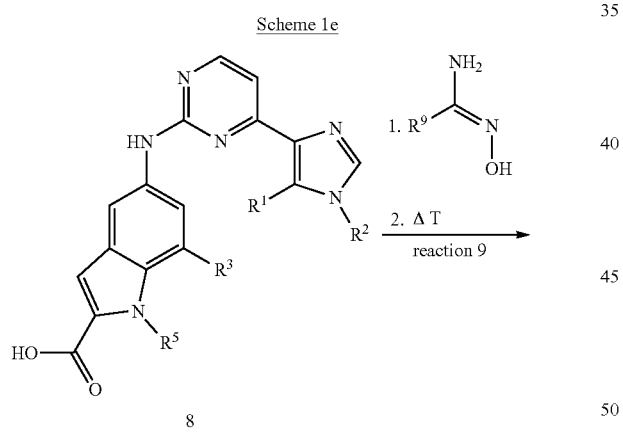

wherein $R^1$, $R^2$, $R^3$ and $R^5$ are herein defined as aforementioned and wherein $R^4$ is five- or six-membered heterocycle that may optionally be substituted by $R^9$ and wherein $R^9$ is selected from —$C_{1-6}$-alkyl and H, preferably from methyl and H.

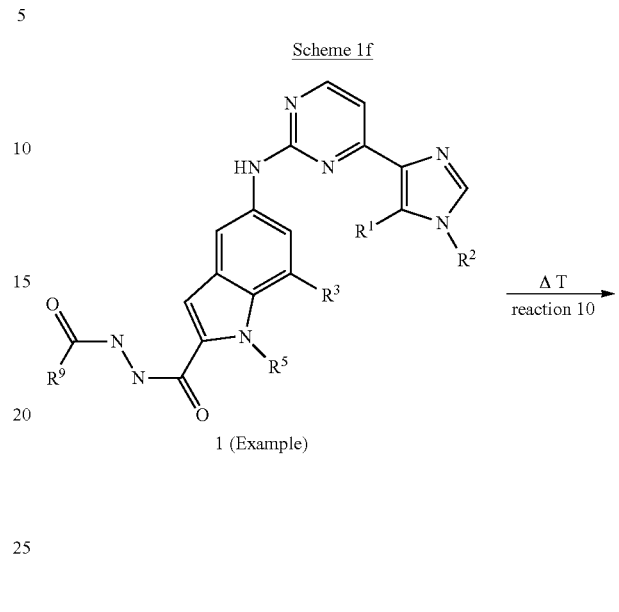

wherein $R^1$, $R^2$, $R^3$, $R^4$ and $R^5$ are herein defined as aforementioned and wherein $R^9$ is selected from —$C_{1-6}$-alkyl and H.

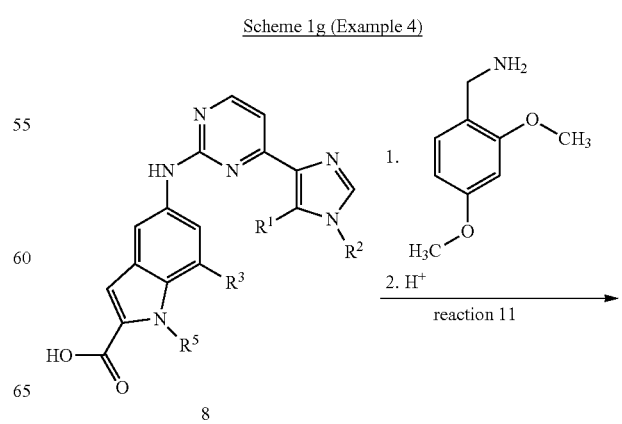

-continued

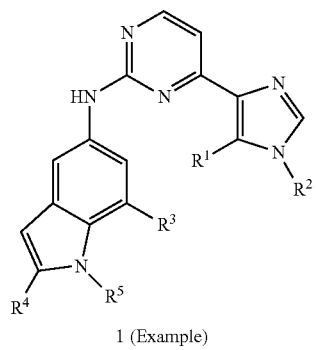

1 (Example)

wherein $R^1$, $R^2$, $R^3$, $R^4$ and $R^5$ are herein defined as aforementioned.

4.1 Intermediate Products 4.1.1 Compounds with Formula 3 According to Scheme 1a

Synthesis of 1-(1-Isopropyl-1H-imidazol-4-yl)-ethanone (3.1) for Example 17, 23, 29

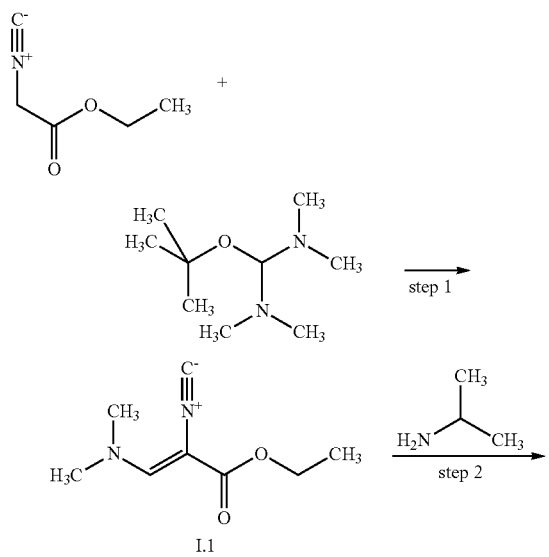

-continued

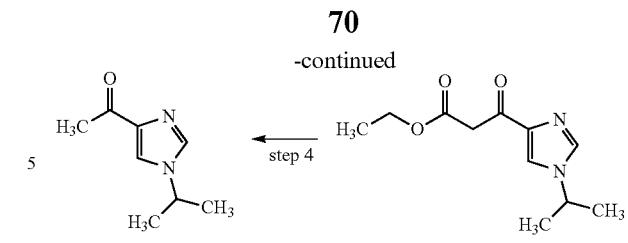

Step 1

A mixture of 5.0 ml ethyl isocyanoacetate and 12.5 ml tert-butoxy-bis(dimethylamino)methane was stirred at ambient temperature overnight. The mixture was evaporated under reduced pressure and the resulting residue was purified by column chromatography with cyclohexane/ethyl acetate (80:20→65:35) to give the intermediate I.1.

Yield: 7.1 g of 1.1 (92% of theory) Analysis: $[M+H]^+=169$

Step 2

A mixture of 7.0 g I.1 and 11.0 ml isopropylamine was stirred at 70° C. for 3 h and at ambient temperature overnight. The mixture was worked up by adding water, followed by extraction with diethylether and tetrahydrofuran. The combined organic extracts were washed with saturated brine, dried over sodium sulfate, filtered and concentrated in vacuo. The crude material was purified by flash chromatography (dichloromethane/methanol=100/0→95/5) to give the intermediate I.2.

Yield: 6.4 g I.2 (84% of theory) Analysis: $[M+H]^+=183$

Step 3

To a mixture of 6.4 g I.2 in 100 ml toluene were added 3.0 g sodium hydride in mineral oil (60%) at 50° C. followed by 30 ml ethyl acetate. The reaction mixture was stirred at 70° C. for 4 h and evaporated to give compound I.3, which was used in the next step without further purification.

Yield: 7.9 g I.3 (crude, 99% of theory) Analysis: HPLC-MS (method B): $R_t=0.92$ min Step 4

A mixture of 7.6 g I.3 and 4.5 g potassium hydroxide in 10 ml water and 80 ml ethanol was stirred under reflux for 3.5 h. The solvent was evaporated. The residue was extracted with dichloromethane and water. The combined organic extracts were washed with saturated brine, dried over sodium sulfate, filtered and concentrated in vacuo.

Yield: 3.6 g 3.1 (70% of theory) Analysis: $[M+H]^+=153$; HPLC-MS (method A): $R_t=0.28$ min 4.1.2 Synthesis of Compounds with Formula 3 According to Scheme 1a Synthesis of 1-(1,5-Dimethyl-1H-imidazol-4-yl)-ethanone (3.2) for Example 1

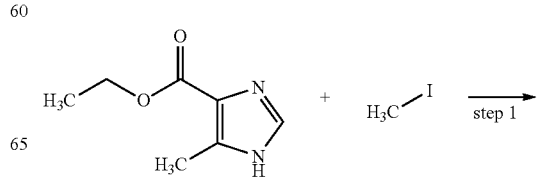

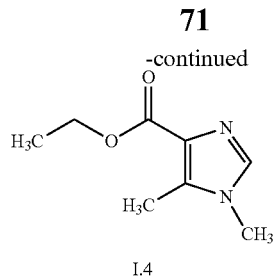

I.4

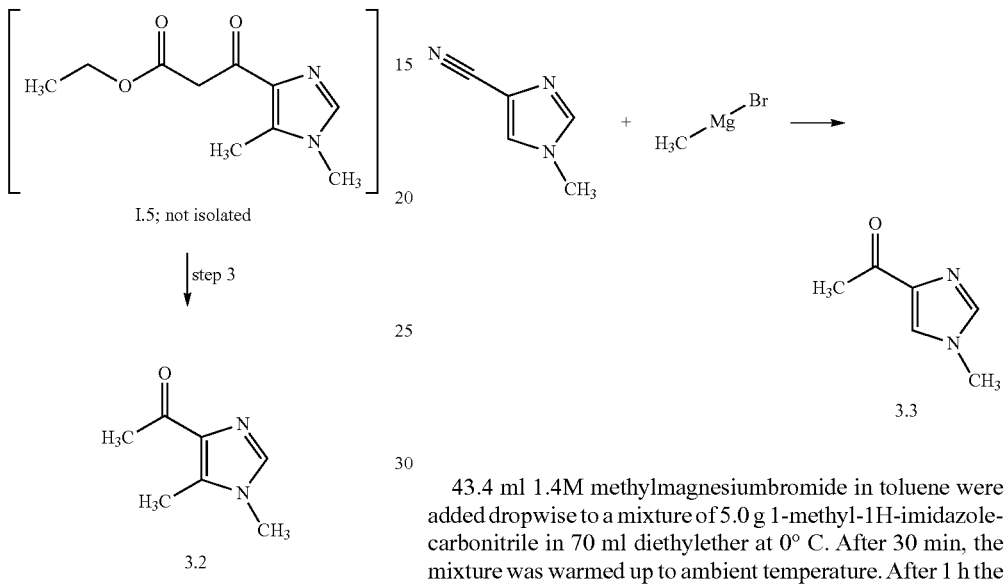

Step 1

To a stirred suspension of 5.4 g ethyl 4-methyl-5-imidazolecarboxylate in 30 ml tetrahydrofuran were added 1.4 g sodium hydride in mineral oil (60%) in portions at ambient temperature under argon atmosphere. After gas formation ceased, 2.24 ml methyl iodide were added dropwise at 0° C., then the mixture was stirred at ambient temperature overnight. The precipitate was filtered off and the filtrate was concentrated. The resulting residue was purified by column chromatography eluted with dichloromethane:methanol (100:0→87:13) to give pure intermediate I.4.

Yield: 1.0 g of I.4 (17% of theory) Analysis: [M+H]$^+$=169; HPLC-MS (method G): R$_t$=0.76 min Step 2

1.0 g I.4 and 15 ml toluene were heated to 50° C. 0.72 g sodium hydride in mineral oil (60%) were added in portions, followed by 8 ml ethyl acetate, then the mixture was stirred at 80° C. for 2 h. The solvent was removed by destillation to give compound I.5, which was used in the next step without further purification.

Analysis: [M+H]$^+$=211; HPLC-MS (method D): R$_t$=0.66 min

Step 3

Crude I.5 was taken up in 50 ml methanol and 5 ml water and treated with 0.79 g potassium hydroxide under reflux for 2 h. The solvent was evaporated and the residue extracted with dichloromethane and water. The combined organic phases were dried over magnesium sulfate, filtered and concentrated in vacuo to give the intermediate 3.2.

Yield: 0.8 g 3.2 (97% of theory over 2 steps) Analysis: [M+H]$^+$=139; HPLC-MS (method G): R$_t$=0.54 min 4.1.3 Compounds with Formula 3 According to Scheme 1a Synthesis of 1-(1-Methyl-1H-imidazol-4-yl)-ethanone (3.3) for Example 2-16, 18, 19, 22, 26-28, 32-101, 103-175

43.4 ml 1.4M methylmagnesiumbromide in toluene were added dropwise to a mixture of 5.0 g 1-methyl-1H-imidazolecarbonitrile in 70 ml diethylether at 0° C. After 30 min, the mixture was warmed up to ambient temperature. After 1 h the reaction was quenched with 1M aqueous HCl solution and neutralised with saturated sodium bicarbonate solution. The reaction mixture was extracted with dichloromethane. The combined organic extracts were dried with magnesium sulfate and concentrated under reduced pressure. The crude material was purified by flash chromatography (dichloromethane/methanol=98/2) to give the intermediate 3.3.

Yield: 4.8 g of 3.3 (75% content; 62% of theory); Analysis: [M+H]$^+$=125

4.1.4 Synthesis of Compounds with Formula 4: Reaction 2 from Scheme 1a

Synthesis of 3-Dimethylamino-1-(1-isopropyl-1H-imidazol-4-yl)-propenone (4.1) for Example 17, 23, 29

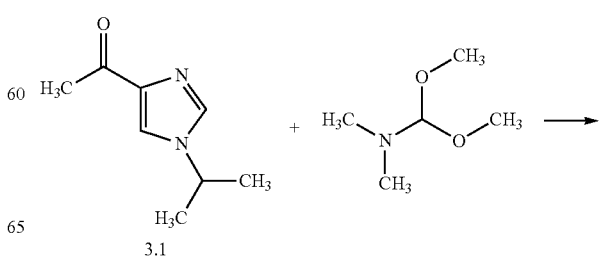

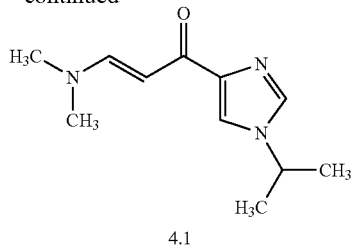

4.1

3.6 g 3.1 and 40 ml dimethoxymethyl-dimethyl-amine were refluxed for 2 days. The solvent was removed by destillation and the residue triturated with diethyl ether. The precipitate was filtered off to give 2.8 g of the intermediate 4.1. The filtrate was concentrated and purified by flash chromatography (dichloromethane/methanol=95/5) to give 0.1 g of the intermediate 4.1.

Yield: 2.9 g of 4.1 (59% of theory); Analysis: $[M+H]^+=208$

The Following Enaminones were Prepared by Using a Procedure Analogous to 3.1 and 4.1 with the corresponding amines:

3-Dimethylamino-1-(1-isobutyl-1H-imidazol-4-yl)-propenone (4.2) for Example 21, 25, 31

Yield: 1.14 g of 4.2 (86% of theory) Analysis: $[M+H]+=$ 222; HPLC-MS (method B): $R_t=1.03$ min 1-(1-cyclopropyl-1H-imidazol-4-yl)-3-dimethylaminopropenone (4.3) for Example 20, 24, 30

Yield: 3.47 g of 4.3 (81% of theory) Analysis: $[M+H]+=$ 206; HPLC-MS (method B): $R_t=0.87$ min 3-Dimethylamino-1-[1-(2-methoxy-ethyl)-1H-imidazol-4-yl)-propenone (4.4) for Example 102

Yield: 1.59 g of 4.4 (79% of theory) Analysis: $[M+H]+=$ 224; HPLC-Ms (method B): $R_t=0.78$ min The Following Enaminone was Prepared by Using a Procedure Analogous to 4.1 with Ketone 3.2:

3-Dimethylamino-1-(1,5-dimethyl-1H-imidazol-4-yl)-propenone (4.5) for Example 1

Yield: 0.23 g of 4.5 (53% of theory) Analysis $[M+H]+=$ 194; HPLC-MS (method G): $R_t=0.70$ min The Following Enaminone was Prepared by Using a Procedure Analogous to 4.1 with Ketone 3.3:

3-Dimethylamino-1-(1-methyl-1H-imidazol-4-yl)-propenone (4.6) for Example 2-16, 18, 19, 22, 26-28, 32-101, 103-175

Yield: 4.08 g of 4.6 (49% of theory) Analysis: $[M+H]+=$ 180; HPLC-MS (method J): $R_t=1.50$ min

4.1.5 Synthesis of Compounds with Formula 5

Synthesis of 7-Methyl-5-nitro-1H-indole-2-carboxylic acid ethyl ester (5.1) for Example 1, 4, 5, 8, 13, 23-25, 32-40, 97, 100, 103-145, 154-175

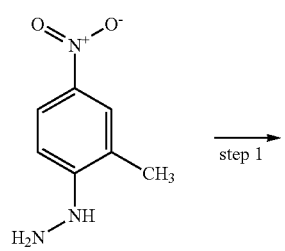

step 1

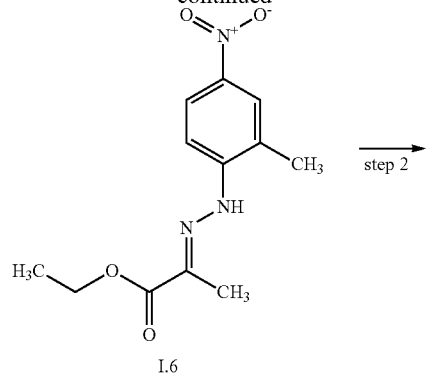

I.6 step 2

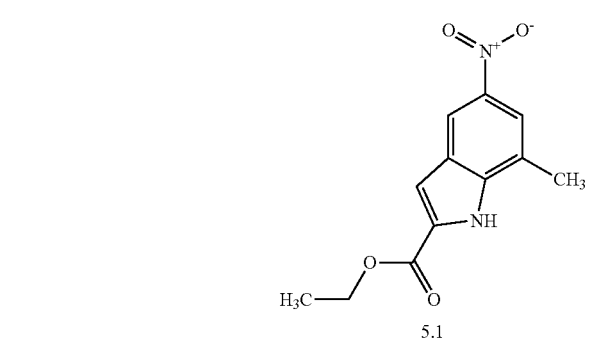

5.1

Step 1

To a stirred suspension of 7.6 g (2-methyl-4-nitro-phenyl)-hydrazine in 7 ml dioxane was added a solution of 5.1 ml 2-oxo-propionic acid ethyl ester in 7 ml dioxane. The mixture was stirred at ambient temperature for 1 h. The organic solvent was removed by destillation to give compound I.6, which was used in the next step without further purification.

Yield: 12.1 g of I.6 (99% of theory) Analysis: $[M+H]^+=$ 266; HPLC-MS (method G): $R_t=1.18$ min Step 2

A mixture of 1.0 g I.6 in 8.0 g polyphosphoric acid was stirred at 95° C. for 20 min. The mixture was quenched with ice-water. The precipitate was filtered off, washed with water and ethanol and dried to give intermediate 5.1.

Yield: 340 mg of 5.1 (36% of theory) Analysis: $[M+H]^+=$ 249; HPLC-MS (method H): $R_t=1.95$ min The Following Intermediate was Prepared by Using a Procedure Analogous to 5.1 with the Corresponding Hydrazine:

7-Chloro-5-nitro-1H-indole-2-carboxylic acid ethyl ester (5.2) for Example 3, 6, 7, 11, 12, 14, 17, 20, 21, 26-31, 41-94, 99, 102, 146-148, 151-153

Yield: 36.0 g of 5.2 (16% of theory)

$^1$H NMR: DMSO 400 MHz δ=12.900 (s, 1H), 8.664-8.659 (d, J=2 Hz, 1H), 8.119-8.113 (d, J=2.4 Hz, 1H), 7.488-7.483 (d, J=2.0 Hz, 1H), 4.370-4.310 (m, 2H), 1.345-1.309 (t, J=7.2 Hz, 3H)

The Following Compounds are Commercially Available:

5-Nitro-1H-indole-2-carboxylic acid ethyl ester (5.3) for Examples 96, 149, 150

7-Methoxy-5-nitro-1H-indole-2-carboxylic acid ethyl ester (5.4) for Examples 9, 101

4.1.6 Synthesis of Compounds with Formula 5

Synthesis of
7-Chloro-5-nitro-1H-indole-2-carboxylic acid
dimethylamide (5.5) for Example 6, 17, 20, 21,
26-28, 102

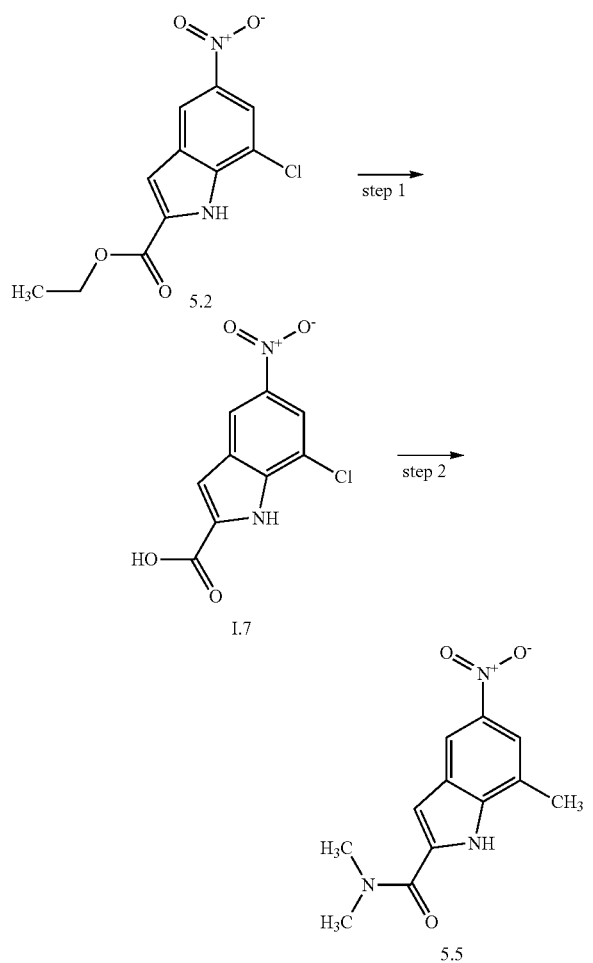

Step 1

A mixture of 18.0 g intermediate 5.2, 45 ml 1M aqueous NaOH solution and 22 ml 4M aqueous NaOH solution in 280 ml ethanol was stirred at 65° C. for 3 h and ambient temperature overnight. Ethanol was removed by destillation. The residue was acidified with 1 M aqueous HCl solution, the precipitate was filtered off and dried.

Yield: 15.5 g of I.7 (85% content; 96% of theory) Analysis: $[M+H]^-=239$; HPLC-MS (method A): $R_t=0.75$ min Step 2

15.5 g (85% content) I.7 were stirred with 24.0 g [(benzotriazol-1-yloxy)-dimethylamino-methylene]-dimethyl-ammonium tetrafluoroborate (TBTU) and 17 ml N,N-diisopropylethylamine in 150 ml N,N-dimethylformamide at ambient temperature. After 5 min, 50 ml 2M dimethylamine solution in tetrahydrofuran were added and the reaction mixture was stirred at ambient temperature overnight. 1M aqueous NaOH solution and water was added and extracted with dichloromethane. The organic layers were washed with brine, dried over sodium sulfate and concentrated in vacuo. The resulting residue was filtered through Aluminumoxide (Alox), washed with methanol and concentrated in vacuo. The residue was triturated with water, filtered off and dried.

Yield: 14.0 g of 5.5 (90% content; 85% of theory) Analysis: $[M+H]^+=268$; HPLC-MS (method B): $R_t=1.27$ min The Following Intermediate was Prepared by Using a Procedure Analogous to 5.5 with the Corresponding Ester:

7-Methyl-5-nitro-1H-indole-2-carboxylic acid dimethylamide (5.6) for Example 1, 5, 23-25

Yield: 3.80 g of 5.6 (81% of theory) Analysis: $[M+H]+=248$; $[M-H]-=246$

The Following Intermediate was Prepared by Using a Procedure Analogous to 5.5 with the Corresponding Acid (Commercially Available):

5-Nitro-1H-indole-2-carboxylic acid dimethylamide (5.7) for Example 2

Yield: 13.73 g of 5.7 (81% of theory) Analysis: $[M+H]+=234$; HPLC-MS (method B): $R_t=1.15$ min The Following Intermediate was Prepared by Using a Procedure Analogous to 5.5 with the Corresponding Amine:

(7-Chloro-5-nitro-1H-indol-2-yl)-(4-methyl-piperazin-1-yl)-methanone (5.8) for Example 29-31

Yield: 0.67 g of 5.8 (31% of theory) Analysis: $[M+H]+=323$; HPLC-MS (method C): $R_t=0.93$ min 4.1.7 Synthesis of Compounds with Formula 5

Synthesis of 7-Chloro-1-methyl-5-nitro-1H-indole-2-carboxylic acid dimethylamide (5.9) for Example 27

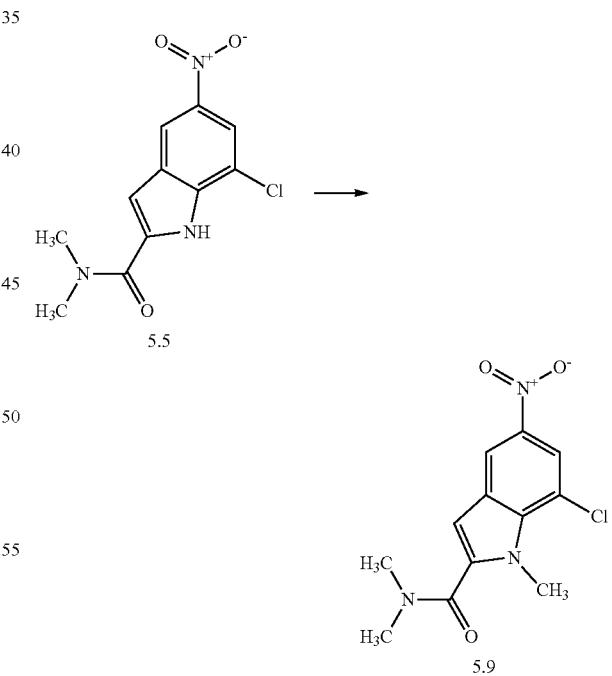

503 mg potassium tert-butoxide were added to a mixture of 1.0 g intermediate 5.5 in 14.5 ml N,N-dimethylformamide. After 25 min, 325 μl methyl iodide were added, then the mixture was stirred at ambient temperature for 2.5 h and at 70° C. for 2 h. The reaction mixture was diluted with water. The precipitate was filtered off, washed with water and dried.

Yield: 845 mg of 5.9 (80% of theory) Analysis: [M+H]⁺= 282; HPLC-MS (method B): $R_t$=1.29 min The Following Intermediates were Prepared by Using a Procedure Analogous to 5.9 with the Corresponding Alkyl Halogenids:

7-Chloro-1-isobutyl-5-nitro-1H-indole-2-carboxylic acid dimethylamide (5.10) for Example 26

Yield: 0.57 g of 5.10 (47% of theory) Analysis: [M+H]+= 324; HPLC-MS (method B): $R_t$=1.50 min 7-Chloro-1-(2-methoxy-ethyl)-5-nitro-1H-indole-2-carboxylic acid dimethylamide (5.11) for Example 28

Yield: 0.17 g of 5.11 (14% of theory) Analysis: [M+H]+= 326; HPLC-MS (method B): $R_t$=1.36 min

4.1.8 Synthesis of Compounds with Formula 6: Reaction 3 from Scheme 1a

Synthesis of 5-Amino-7-chloro-1H-indole-2-carboxylic acid dimethylamide (6.1) for Example 6, 17, 20, 21, 102

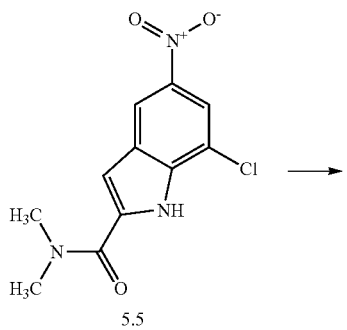

5.5

A mixture of 4.96 g 5.5 and 1.0 g platinum on carbon in 10 ml methanol and 90 ml tetrahydrofuran was hydrogenated at ambient temperature for 3 h. The catalyst was removed by filtration and the solvent was evaporated in vacuo.

Yield: 4.0 g of 6.1 (91% of theory) Analysis: [M+H]⁺=238; HPLC-MS (method L): $R_t$=1.87 min The Following Intermediates were Prepared by Using a Procedure Analogous to 6.1 with the corresponding intermediates 5:

(5-Amino-7-chloro-1H-indole-2-yl)-4(-methyl-piperazin-1-yl)-methanone (6.2) for Example 29-31

Yield: 0.65 g of 6.2 Analysis: [M+H]+=293; HPLC-MS (method B): $R_t$=0.98 min

5-Amino-7-chloro-1H-indole-2-carboxylic acid ethyl ester (6.3) for Example 3, 7, 11, 12, 14, 41-94, 99, 146-148, 151-153

Yield: 1.50 g of 6.3 (84% of theory)

5-Amino-7-chloro-1-methyl-1H-indole-2-carboxylic acid dimethylamide (6.4) for Example 27

Yield: 0.76 g of 6.4 (100% of theory) Analysis: [M+H]+= 252; HPLC-MS (method C): $R_t$=0.68

5-Amino-7-chloro-1-isobutyl-1H-indole-2-carboxylic acid dimethylamide (6.5) for Example 26

Yield: 0.52 g of 6.5 (100% of theory) Analysis: [M+H]+= 294; HPLC-MS (method B): $R_t$=1.28 min 5-Amino-7-chloro-1-(2-methoxy-ethyl)-1H-indole-2-carboxylic acid dim ethylamide (6.6) for Example 28

Yield: 0.16 g of 6.6 (99% of theory) Analysis: [M+H]+= 296; HPLC-MS (method B): $R_t$=1.36 min The Following Intermediates were Prepared by Using a Procedure Analogous to 6.1 with the Corresponding Intermediates 5 (Using Pd/C Instead of Pt/C):

5-Amino-7-methyl-1H-indole-2-carboxylic acid dimethylamide (6.7) for Example 1, 5, 23-25

Yield: 3.20 g of 6.7 (96% of theory) Analysis: [M+H]+= 218

5-Amino-7-methyl-1H-indole-2-carboxylic acid ethyl ester (6.8) for Example 4, 8, 13, 32-40, 97, 100, 103-145, 154-175

Yield: 3.94 g of 6.8 (90% of theory) Analysis: [M+H]+= 219; HPLC-MS (method B): R=1.10 min 5-Amino-1H-indole-2-carboxylic acid ethyl ester (6.9) for Example 96, 149, 150

Yield: 8.46 g of 6.9 (97% of theory) Analysis: [M+H]+= 205

5-Amino-1H-indole-2-carboxylic acid dimethylamide (6.10) for Example 2

Yield: 3.70 g of 6.10 (90% of theory) Analysis: [M+H]+= 204

5-Amino-7-methoxy-1H-indole-2-carboxylic acid ethyl ester (6.11) for Example 9, 101

Yield: 1.8 g of 6.11 Analysis: [M+H]+=235

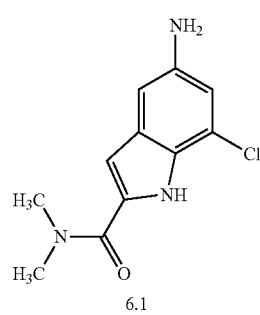

6.1

4.1.9 Synthesis of Compounds with Formula 6
Synthesis of 5-Amino-7-bromo-1H-indole-2-carboxylic acid dimethylamide (6.12) for Example 10, 15, 16, 18, 19, 22
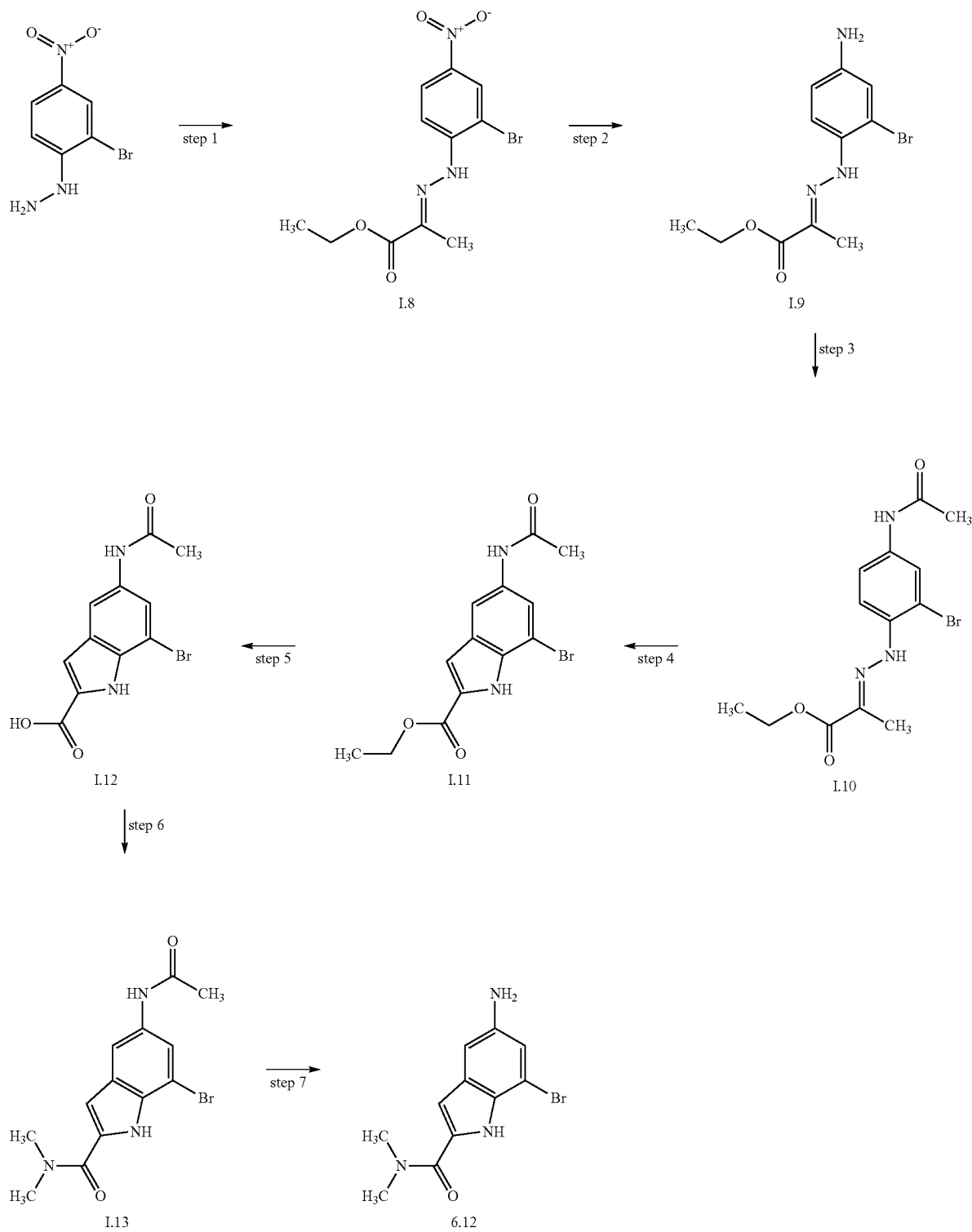

Step 1

A mixture of 45.0 g (2-bromo-4-nitro-phenyl)-hydrazine and 22.0 ml 2-oxo-propionic acid ethyl ester in 220 ml dioxane was stirred at ambient temperature for 2 h. The organic solvent was removed by destillation. The resulting residue was triturated with diethyl ether. The precipitate was filtered off and dried to give 54.0 g of compound I.8. The filtrate was concentrated in vacuo to give 10.0 g of compound I.8.

Yield: 64.0 g of I.8 (99% of theory) Analysis: $[M+H]^+=$ 330; HPLC-MS (method A): $R_t=0.97$ min Step 2

A mixture of 3.0 g I.8 and 0.3 g Raney nickel in 90 ml ethyl acetate was hydrogenated at 60° C. for 7 h. The catalyst was removed by filtration and the solvent was evaporated in vacuo to give compound I.9.

Yield: 3.0 g of I.9 (87% content; 97% of theory) Analysis: $[M+H]^+=300$; HPLC-MS (method S): $R_t=0.60$ min Step 3

A mixture of 6.7 g I.9 and 2.2 ml acetic anhydride in 100 ml N,N-dimethylformamide was stirred at ambient temperature overnight. The solvent was removed by destillation, the residue taken up in ethyl acetate and washed with brine. The combined organic phases were dried over magnesium sulfate, filtered and concentrated in vacuo.

Yield: 6.65 g of I.10 (87% of theory) Analysis: $[M+H]^+=$ 342; HPLC-MS (method B): $R_t=1.32$ min Step 4

A mixture of 11.3 g compound I.10 in 110 g polyphosphoric acid was stirred at 90° C. for 6 h. The mixture was quenched with water. The precipitate was filtered off and dried.

Yield: 7.44 g of I.11 (69% of theory) Analysis: $[M+H]^+=$ 325; HPLC-MS (method B): $R_t=1.24$ min Step 5

A mixture of 4.0 g compound I.11 and 15.4 ml 4M aqueous NaOH solution in 50 ml ethanol was stirred at ambient temperature for 1 h. Ethanol was removed by destillation. The residue was acidified with 1 M aqueous HCl solution, the precipitate was filtered off and dried.

Yield: 3.1 g of I.12 (85% of theory) Analysis: $[M+H]^+=$ 297; HPLC-MS (method C): $R_t=0.91$ min Step 6

1.95 g I.12 were stirred with 2.11 g [(benzotriazol-1-yloxy)-dimethylamino-methylene]-dimethyl-ammonium tetrafluoroborate (TBTU) and 1.12 ml N,N-diisopropylethylamine in 75 ml N,N-dimethylformamide at ambient temperature. After 5 min, 50 ml 2M dimethylamine solution in tetrahydrofuran were added and the reaction mixture was stirred at ambient temperature for 1 h. The solvent was removed by destillation and the residue was purified by flash chromatography (cyclohexane:ethyl acetate=50:50→0:100→ethyl acetate:methanol 100:0→95:5).

Yield: 1.3 g of I.13 (61% of theory) Analysis: $[M+H]^+=$ 324; HPLC-MS (method B): $R_t=1.03$ min Step 7

A mixture of 3.34 g I.13 and 6 ml hydrochlorid acid (32%) in 32 ml ethanol was refluxed for 5 h. The solvent was removed by destillation. The residue was taken up in water, neutralized with saturated $NaHCO_3$ solution and extracted with dichloromethane. The combined organic phases were dried and concentrated in vacuo.

Yield: 1.65 g of 6.12 (57% of theory) Analysis: $[M+H]^+=$ 282; HPLC-MS (method B): $R_t=0.96$ min 4.1.10 Synthesis of Compounds with Formula 7: Reaction 4 from Scheme 1a Synthesis of 7-Chloro-5-guanidino-1H-indole-2-carboxylic acid dimethylamide tosylate (7.1) for Example 6, 17, 20, 21, 102

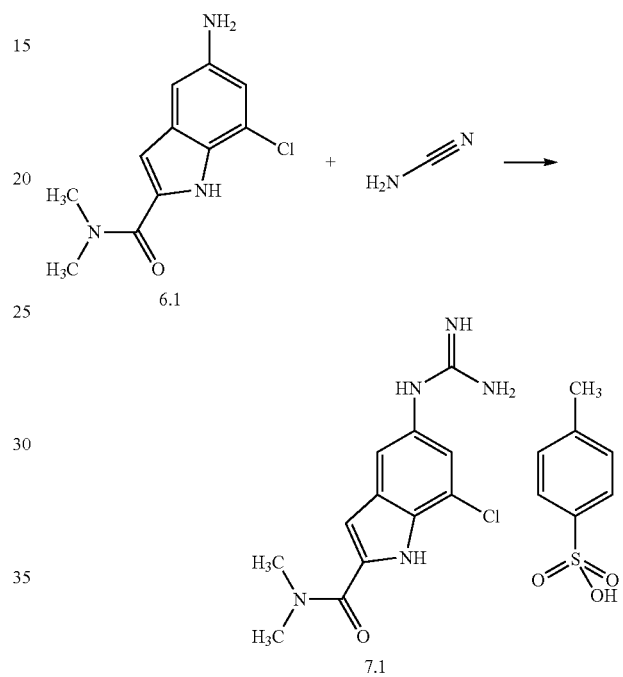

To a stirred mixture of 1.9 g 6.1 in 50 ml dioxane were added 1.5 g p-toluenesulfonic acid and 0.5 g cyanamide. The reaction mixture was stirred at 110° C. for 2 h, then at ambient temperature for 3 days. The precipitate was filtered, washed with dioxane and dried to give the intermediate 7.1.

Yield: 3.2 g 7.1 (89% of theory) Analysis: $[M+H]^+=280$; HPLC-MS (method E): $R_t=1.11$ min The Following Intermediates were Prepared by Using a Procedure Analogous to 7.1 with the Corresponding Anilines 6:

N-[7-Chloro-2-(4-methyl-piperazine-1-carbonyl)-1H-indol-5yl]-guanidine tosylate (7.2) for Example 29-31

Yield: 0.73 g of 7.2 (65% of theory) Analysis: [M+H]+= 335; HPLC-MS (method B): R=1.10 min 7-Chloro-5-guanidino-1H-indole-2-carboxylic acid ethyl ester tosylate (7.3) for Example 3, 7, 11, 12, 14, 41-94, 99, 146-148, 151-153

Yield: 3.0 g of 7.3 (82% of theory) Analysis: [M+H]+=281/ 283 (Cl); HPLC-MS (method D): $R_t=0.92$ min 7-Chloro-5-guanidino-1-methyl-1H-indole-2-carboxylic acid dimethylamide tosylate (7.4) for Example 27

Yield: 0.72 g of 7.4 (52% of theory) Analysis: [M+H]+= 294; HPLC-MS (method B) R=1.22 min 7-Chloro-5-guanidino-1-isobutyl-1H-indole-2-carboxylic acid dimethylamide tosylate (7.5) for Example 26

Yield: 0.62 g of 7.5 (68% of theory) Analysis: [M+H]+= 336; HPLC-MS (method B) $R_t=1.28$ min 7-Chloro-5-guanidino-1-(2-methoxy-ethyl)-1H-indole-2-carboxylic acid dimethylamide tosylate (7.6) for Example 28

Yield: 0.39 g of 7.6 Analysis: [M+H]+=338; HPLC-MS (method B) $R_t$=1.29 min

5-Guanidino-7-methyl-1H-indole-2-carboxylic acid dimethylamide tosylate (7.7) for Example 1, 5, 23-25

Yield: 0.56 g of 7.7 (95% of theory) Analysis: [M+H]+=26

5-Guanidino-7-methyl-1H-indole-2-carboxylic acid ethyl ester tosylate (7.8) for Example 4, 8, 13, 32-40, 97, 100, 103-145, 154-175

Yield: 7.70 g of 7.8 (95% of theory)

5-Guanidino-1H-indole-2-carboxylic acid ethyl ester tosylate (7.9) for Example 96, 149, 150

Yield: 7.10 g of 7.9 (99% of theory) Analysis: [M+

5-Guanidino-1H-indole-2-carboxylic acid dimethylamide tosylate (7.10) for Example 2

Yield: 3.80 g of 7.10 (71% of theory)

5-Guanidino-7-methoxy-1H-indole-2-carboxylic acid ethyl ester tosylate (7.11) for Example 9, 101

Yield: 3.42 g of 7.11 (85% of content, 109% of theory) Analysis: [M+H]+=277

7-Bromo-5-guanidino-1H-indole-2-carboxylic acid dimethylamide tosylate (7.12) for Example 10, 15, 16, 18, 19, 22

Yield: 2.22 g of 7.12 (76% of theory) Analysis: [M+H]+=324; HPLC-MS (method B) R=1.04 min 4.1.11 Synthesis of Compounds with Formula 8 According to Scheme 1b (or with Formula 1 According to Scheme 1a): Reaction 5 from Scheme 1a Synthesis of 7-Chloro-5-[4-(1-methyl-1H-imidazol-4-yl)-pyrimidin-2-ylamino]-1H-indole-2-carboxylic acid methyl ester (Example 99) and 7-Chloro-5-[4-(1-methyl-1H-imidazol-4-yl)-pyrimidin-2-ylamino]-1H-indole-2-carboxylic acid (8.1/Example 98) for Example 3, 7, 11, 12, 14, 41-94, 146-148, 151-153

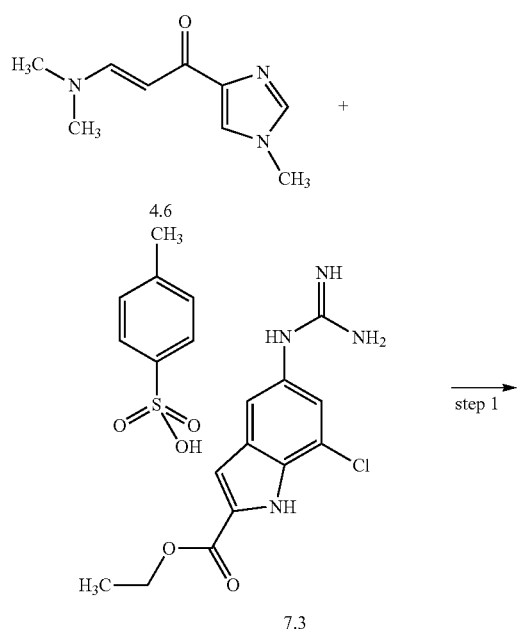

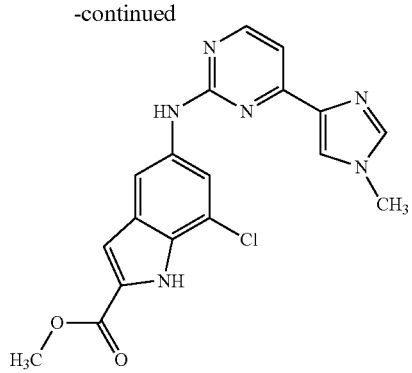

Example 99

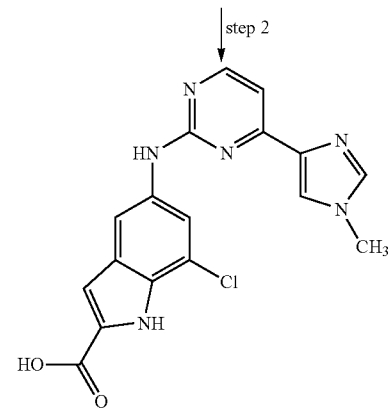

8.1/Example 98

Step 1

A mixture of 0.48 g 4.6, 1.20 g 7.3 and 5.0 ml 0.5 M sodium methylate in methanol was stirred at 140° C. for 30 min under microwave irradiation. The reaction mixture was diluted with dichloromethane and methanol, filtered through Alox. The filtrate was concentrated in vacuo and purified by flash chromatography (dichloromethane/methanol 100:0→90:10). A small part was triturated with diethyl ether. The precipitate was filtered off, washed with diethyl ether and dried to give example 99.

Yield: 20 mg of Example 99 (2% of theory) Analysis: [M+H]⁺=383; HPLC-MS (method D): $R_t$=1.05 min Step 2

The rest of the residue was taken up in 20 ml methanol and 20 ml tetrahydrofuran and treated with 5 mL 1M aqueous NaOH solution at 60° C. for 2 hours. The organic solvent was removed by destillation and the residue was acidified with 1 M aqueous HCl solution. The precipitate was filtered off, washed with water and dried to give intermediate 8.1/Example 98.

Yield: 180 mg of 8.1/Example 98 (18% of theory) Analysis: [M+H]⁺=369; HPLC-MS (method D): $R_t$=0.95 min The Following Acids were Prepared by Using a Procedure Analogous to 8.1 with the Corresponding Guanidines 7:

7-Methoxy-5-[4-(1-methyl-1H-imidazol-4-yl)-pyrimidin-2-ylamino]-1H-indole-2-carboxylic acid (8.2) for Example 9, 101

7-Methyl-5-[4-(1-methyl-1H-imidazol-4-yl)-pyrimidin-2-ylamino]-1H-indole-2-carboxylic acid (8.3/Example 97) for Example 4, 8, 13, 32-40, 100, 103-145, 154-175

5-[4-(1-Methyl-1H-imidazol-4-yl)-pyrimidin-2-ylamino]-1H-indole-2-carboxylic acid (8.4/Example 96) for Example 149, 150

4.1.12 Synthesis of Compounds with Formula 10 According to Scheme 1c (or with Formula 1 According to Scheme 1a): Reaction 5 from Scheme 1a Synthesis of 7-Bromo-5-[4-(1-methyl-1H-imidazol-4-yl)-pyrimidin-2-ylamino]-1H-indole-2-carboxylic acid dimethylamide (10.1/Example 15) for Example 10, 16, 18, 19, 22

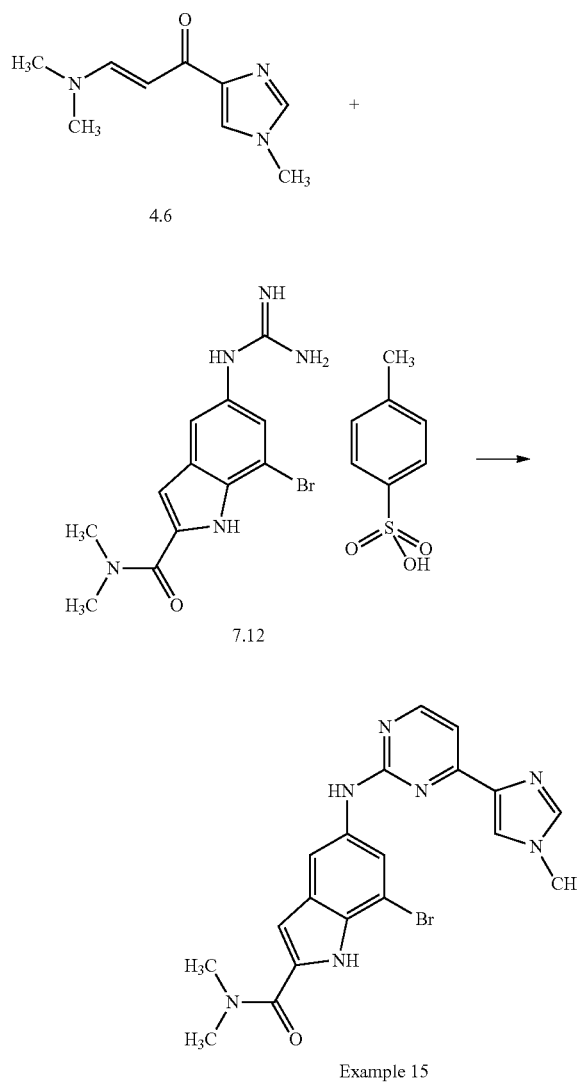

Example 15

A mixture of 1.6 g 4.6, 2.2 g 7.12 and 2.5 g potassium tert-butoxide in 30 ml N,N-dimethylformamide was stirred at 150° C. for 1.5 h under microwave irradiation. The reaction mixture was concentrated in vacuo and the resulting residue was purified by flash chromatography (dichloromethane/methanol 100:0→90:10) to give intermediate 10.1/Example 15.

Yield: 670 mg of 10.1/Example 15 (34% of theory) Analysis: [M+H]$^+$=440; HPLC-MS (method C): R$_f$=0.97 min

4.1.13 Synthesis of Amines with Formula 9 According to Scheme 1b

Synthesis of cis-4-(2-Dimethylamino-ethyl)-cyclohexylamine (9.1) for Example 87

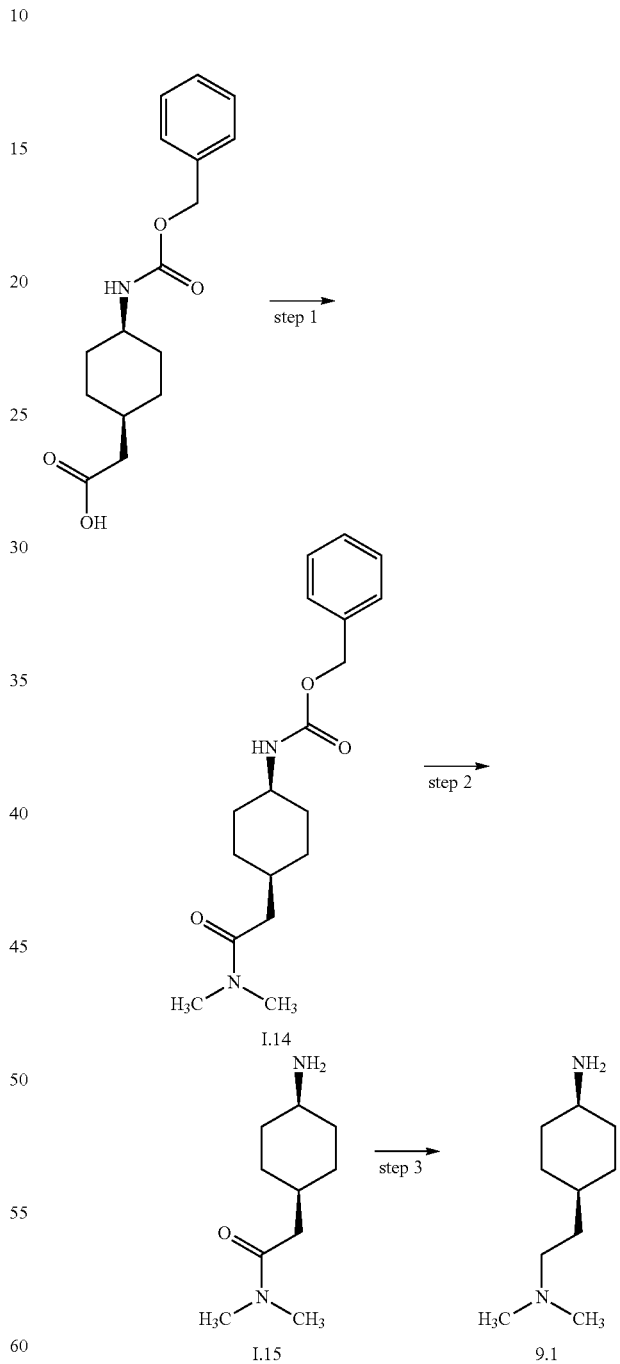

Step 1

3.0 g cis-(4-Benzyloxycarbonylamino-cyclohexyl)-acetic acid were stirred with 4.0 g [(benzotriazol-1-yloxy)-dimethylamino-methylene]-dimethyl-ammonium tetrafluoroborate (TBTU) and 1.45 ml triethylamine in 40 ml tetrahydrofuran at ambient temperature. After 1 h, 15.5 ml 2M dimethylamine solution in tetrahydrofuran were added and the reaction mixture was stirred at ambient temperature overnight. The reaction mixture was diluted with ethyl acetate and washed with saturated aqueous potassium carbonate solution, 1 M aqueous HCl solution and brine. The combined organic phases were dried over sodium sulfate, filtered and concentrated in vacuo.

Yield: 3.2 g of I.14 (98% of theory) Analysis: [M+H]$^+$=318

Step 2

A mixture of 3.2 g I.14 and 0.4 g palladium on carbon in 70 ml methanol was hydrogenated at ambient temperature. The catalyst was removed by filtration and the solvent was evaporated in vacuo.

Yield: 2.0 g of 1.15 (crude, 99% of theory) Analysis: [M+H]$^+$=185

Step 3

15 ml tetrahydrofuran were heated to 60° C. 1.24 g lithium aluminium hydride were added and stirred at 60° C. for 10 min, then 2.0 g I.15 (crude) in 15 ml tetrahydrofuran were added dropwise and the reaction mixture was stirred at 60° C. for 4 h and at ambient temperature overnight. The mixture was quenched with water and 1 M aqueous NaOH solution, filtered through Celite and washed with tetrahydrofuran. The filtrate was concentrated in vacuo.

Yield: 1.6 g of 9.1 (87% of theory) Analysis: [M+H]$^+$=171

4.1.14 Synthesis of Amines with Formula 9 According to Scheme 1b

Synthesis of 1-Methyl-4-oxa-1,9-diaza-spiro[5.5]undecan-2-one hydrochloride (9.2) for Example 34, 49, 150

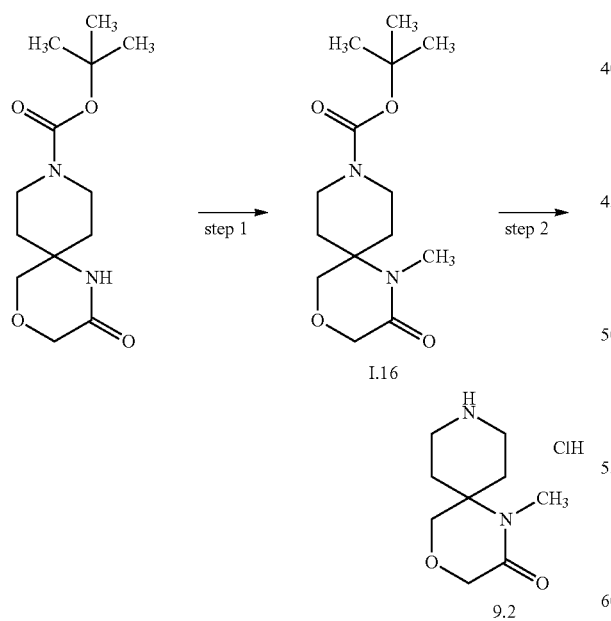

Step 1

To a solution of 6.7 g 2-Oxo-4-oxa-1,9-diaza-spiro[5.5]undecane-9-carboxylic acid tert-butyl ester in 70 ml tert-amyl alcohol were added 4.17 g potassium tert-butoxide, then 2.3 ml iodomethane. The reaction mixture was stirred at ambient temperature overnight. To the mixture were added 1.5 ml iodomethane and it was stirred at ambient temperature for 1.5 h. The solvent was evaporated. The residue was triturated with hot ethyl acetate, the precipitate was filtered off, triturated with dichloromethane and filtered off. The combined filtrates were evaporated. The residue was recrystallized with ethyl acetate. The precipitate was filtered off and purified by flash chromatography (dichloromethane/methanol=100:0→96:4) to give pure compound I.16.

Yield: 5.7 g of I.16 (81% of theory) Analysis: [M+H]$^+$=285

Step 2

To a solution of 5.7 g I.16 in 15 ml dioxane were added 22.5 ml 4 M hydrochloric acid in dioxane. The reaction mixture was stirred at ambient temperature for 2 days, then diluted with diisopropyl ether. The precipitate was filtered off, washed with diisopropyl ether and dried.

Yield: 4.4 g of 9.2 (99% of theory) Analysis: [M+H]$^+$=185

4.1.15 Synthesis of Amines with Formula 9 According to Scheme 1b

Synthesis of 4-(3-Methoxy-azetidin-1-yl)-piperidine (9.3) for Example 70

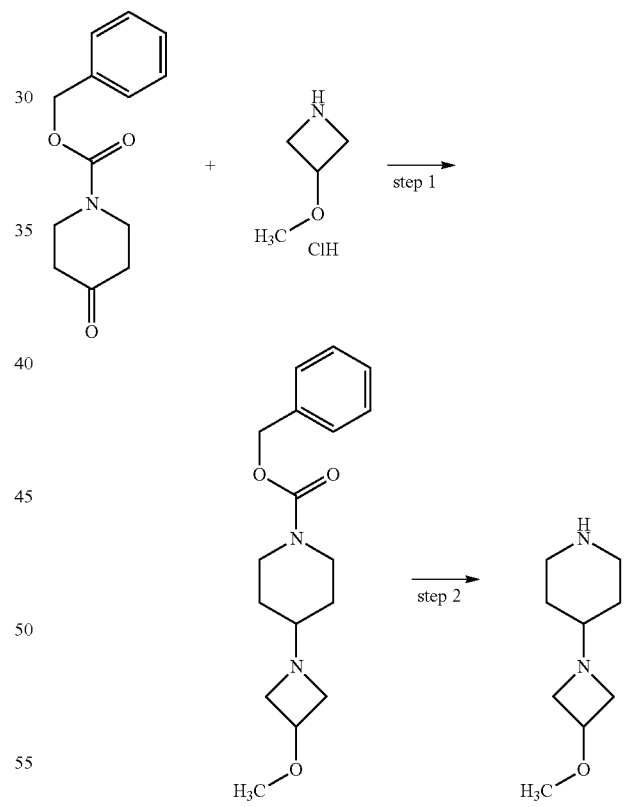

Step 1

A mixture of 5.0 g 1-(Benzyloxycarbonyl)-4-piperidinone and 2.9 g 3-Methoxy-azetidine hydrochloride in 20 ml tetrahydrofuran was acidified with glacial acetic acid (pH 5-6) and stirred at ambient temperature for 40 min. The mixture was cooled with ice, 7.8 g sodium triacetoxyborohydride were added and the mixture was stirred at ambient temperature overnight. The mixture was quenched with aqueous potassium carbonate solution and extracted with ethyl acetate. The combined organic phases were washed with saturated brine, dried over sodium sulfate, filtered and concentrated in vacuo.

Yield: 6.5 g of I.17 (99% of theory) Analysis: $[M+H]^+$= 305; HPLC-MS (method P) $R_f$=0.90 min Step 2

A mixture of 6.5 g I.17 and 0.8 g palladium on carbon in 20 ml methanol was hydrogenated at ambient temperature for 15 h. The catalyst was removed by filtration and the solvent was evaporated in vacuo.

Yield: 3.55 g of 9.3 (98% of theory) Analysis: $[M+H]^+$= 171; HPLC-MS (method Q) $R_f$=0.90 min

4.1.16 Synthesis of Amines with Formula 9 According to Scheme 1b

Synthesis of 1-Isopropyl-4,5,6,7-tetrahydro-1H-pyrazolo[4,3-c]pyridine hydrochloride (9.4) for Example 113

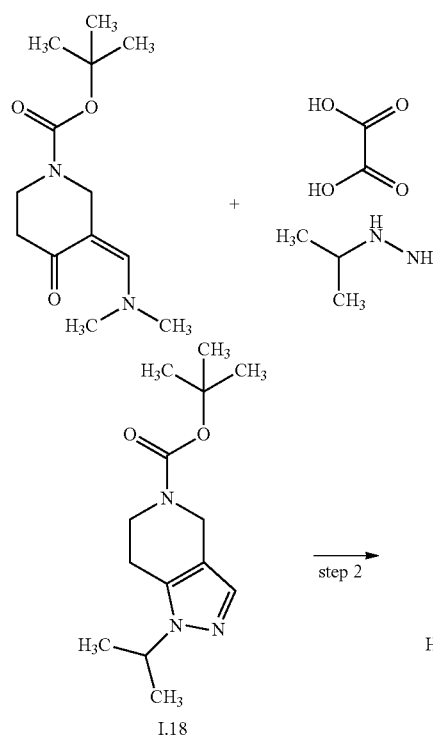

Step 1

A mixture of 1.0 g 3-Dimethylaminomethylene-4-oxo-piperidine-1-carboxylic acid tert-butyl ester and 0.8 g isopropylhydrazine oxalate in 10 ml ethanol was stirred at 140° C. for 5 min under microwave irradiation. The solvent was removed by destillation. The residue was taken up in ethyl acetate and extracted with water. The combined organic phases were washed with saturated brine, dried over sodium sulfate, filtered and concentrated in vacuo.

Yield: 940 mg of I.18 (90% of theory) Analysis: $[M+H]^+$= 266; HPLC-MS (method R) $R_f$=1.29 min Step 2

To a solution of 2.2 g I.18 in 100 ml dichloromethane were added 16 ml 2 M HCl solution in diethylether at 0° C. The resulting mixture was stirred at ambient temperature for 4 days. The solvent was removed by destillation to give crude intermediate 9.4.

Yield: 2.1 g of 9.4 (crude, 100% of theory) Analysis: $[M+H]^+$=166

The Synthesis of the Following Compound is Described in the Literature:

3-Methyl-2,3,4,5-tetrahydro-1H-benzo[d]azepin-7-ylamine (9.5) for Example 58: Journal of Heterocyclic Chemistry, 1971, vol. 8, page 779 and WO2008/80891

(R)-3-(3-fluoropyrrolidin-1-yl)propan-1-amine (9.6) for Example 89: WO 2009053737 A2

All the others used amines (9) are commercially available.

4.2 Synthesis of the Examples of Formula 1

4.2.1 Reaction 5 from Scheme 1a

Example 1

5-[4-(1,5-Dimethyl-1H-imidazol-4-yl)-pyrimidin-2-ylamino]-7-methyl-1H-indole-2-carboxylic acid dimethylamide

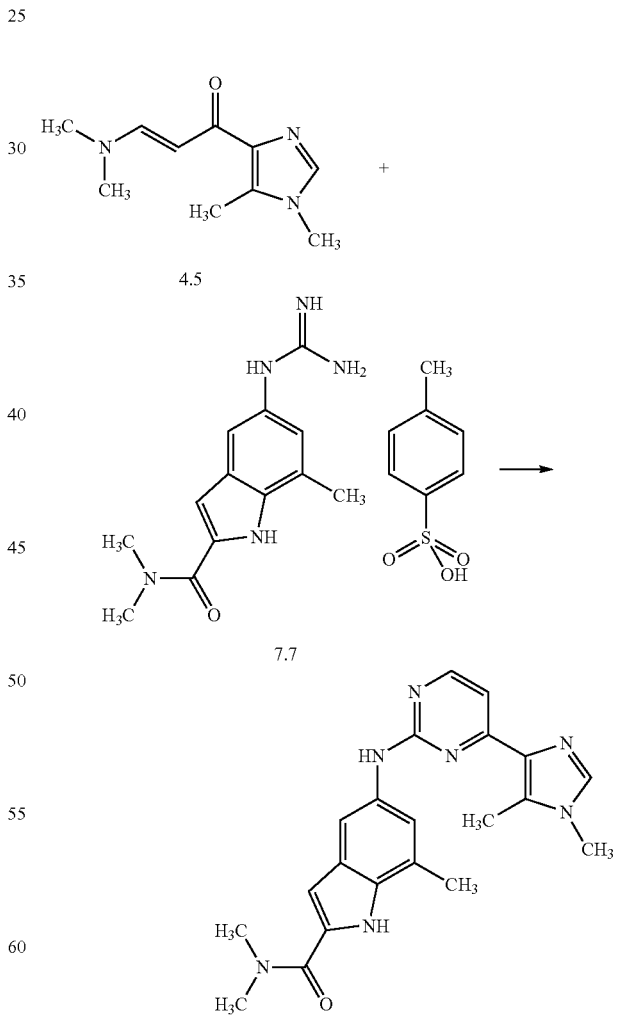

Example 1

A mixture of 42.5 mg 4.5, 80.0 mg 7.7 and 10.8 mg sodium methylate in 2 ml methanol was stirred at 140° C. for 60 min under microwave irradiation. The resulting mixture was purified by preparative HPLC. The combined product fractions were evaporated. The residue was dissolved in acetonitrile/water 1/1 and lyophilized to obtain the Example 1.

Yield: 12 mg Example 1 (14% of theory); Analysis [M+H]$^+$= 390; HPLC-MS (method D) R$_f$=0.96 min 4.2.2 Reaction 6 from Scheme 1b Example 7

7-Chloro-5-[4-(1-methyl-1H-imidazol-4-yl)-pyrimidin-2-ylamino]-1H-indole-2-carboxylic acid methylamide Yield: 30 mg Example 7 (39% of theory) Analysis: [M+H]$^+$= 382; HPLC-MS (method E): R$_f$=1.43 min 4.2.3 Reaction 7 from Scheme 1c Example 19

5-[4-(1-methyl-1H-imidazol-4-yl)-pyrimidin-2-ylamino]-7-(1-methyl-1H-pyrazol-4-yl)-1H-indole-2-carboxylic acid dimethylamide

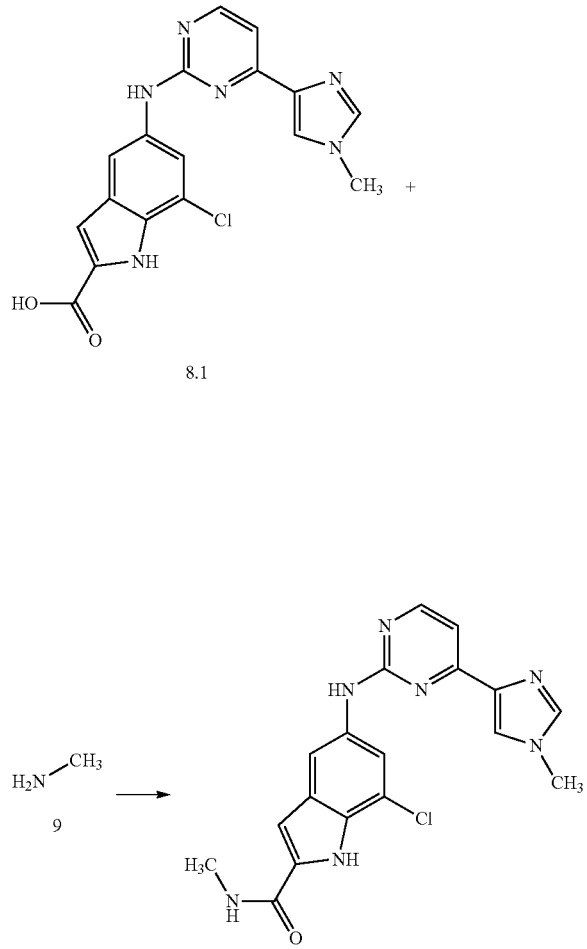

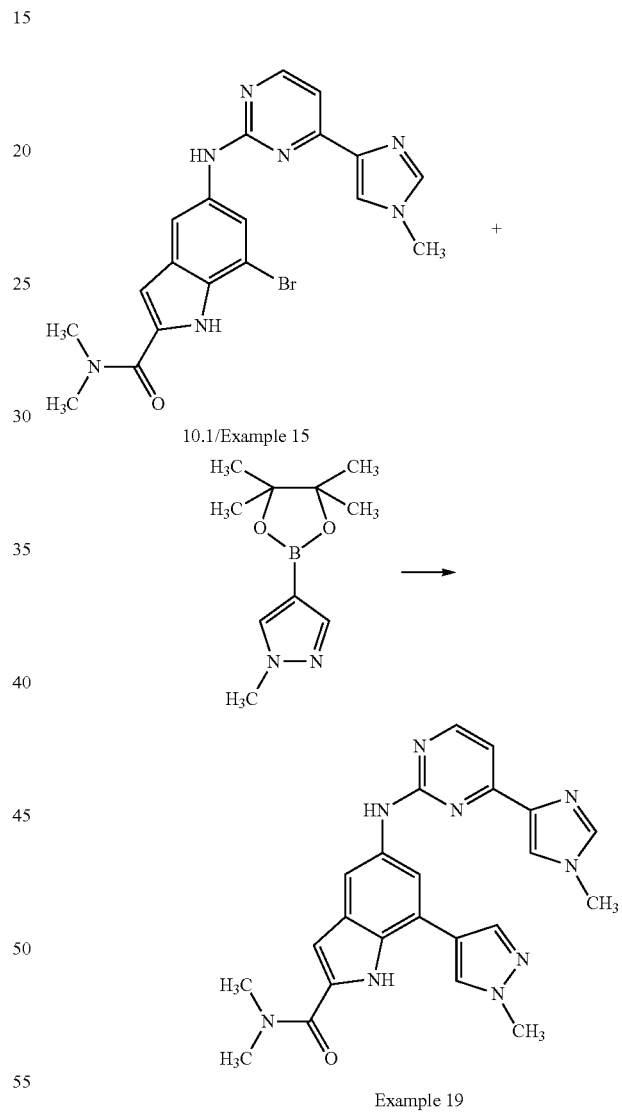

74 mg 8.1 were stirred with 64 mg [(benzotriazol-1-yloxy)-dimethylamino-methylene]-dimethyl-ammonium tetrafluoroborate (TBTU) and 69 μl N,N-diisopropylethylamine in 2 ml N,N-dimethylformamide at ambient temperature. After 10 min, 0.5 ml 2M methylamine solution in tetrahydrofuran were added and the reaction mixture was stirred at ambient temperature overnight. The resulting mixture was purified by preparative HPLC. The combined product fractions were evaporated. The residue was dissolved in acetonitrile/water 1/1 and lyophilized to obtain the example 7.

A mixture of 50.0 mg 10.1, 23.6 mg 1-methyl-4-(4,4,5,5-tetramethyl-1,3,2-dioxaborolan-2-yl)-1H pyrazole, 8.3 mg 1,1'bis(diphenylphosphino)ferrocenedichloropalladium(II) and 23.5 mg potassium carbonate in 400 μl dioxane and 200 μl water was stirred at 100° C. for 15 min under microwave irradiation under argon atmosphere. The solvent was removed by destillation and the residue was purified by preparative HPLC. The combined product fractions were concentrated and lyophilized to obtain the example 19.

Yield: 43 mg Example 19 (86% of theory); Analysis [M+H]⁺=442; HPLC-MS (method F) $R_f$=0.52 min

4.2.4 Reaction 8 from Scheme 1d

Example 22

7-(Furan-2-ylmethylsulfanyl)-5-[4-(1-methyl-1H-imidazol-4-yl)-pyrimidin-2-ylamino]-1H-indole-2-carboxylic acid dimethylamide

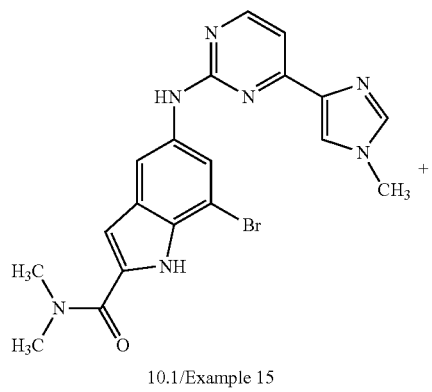

10.1/Example 15

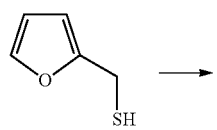

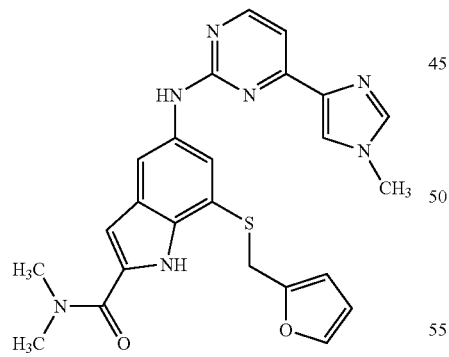

Example 22

A mixture of 50.0 mg 10.1, 12.7 μl furan-2-yl-methanethiol, 10.4 mg tris(dibenzylideneacetone)dipalladium(0), 6.6 mg Xantphos and 40 μl N,N-diisopropylethylamine in 0.5 ml dioxane was stirred at 110° C. for 1.5 h under argon atmosphere. The solvent was removed by destillation and the residue was purified by preparative HPLC. The combined product fractions were concentrated and lyophilized to obtain the example 22.

Yield: 38 mg Example 22 (71% of theory); Analysis [M+H]⁺=474; HPLC-MS (method F) $R_f$=0.60 min

4.2.5 Reaction 9 from Scheme 1e

Example 171

[4-(1-Methyl-1H-imidazol-4-yl)-pyrimidin-2-yl]-[7-methyl-2-(3-methyl-[1,2,4]oxadiazol-5-yl)-1H-indol-5-yl]-amine

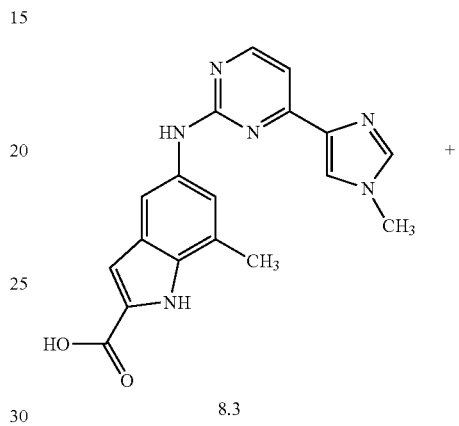

8.3

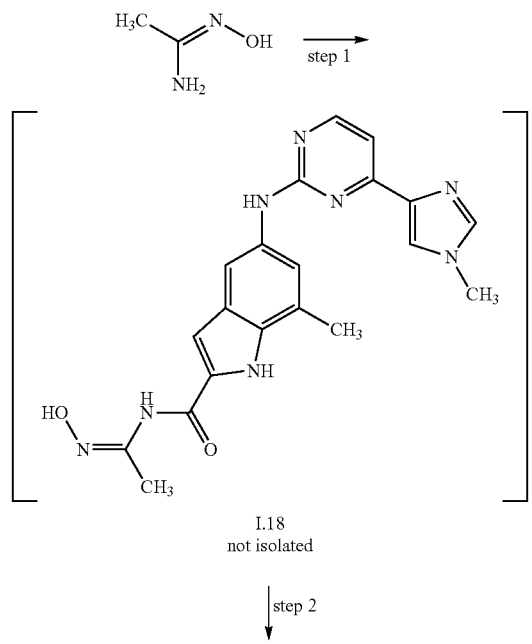

I.18
not isolated

↓ step 2

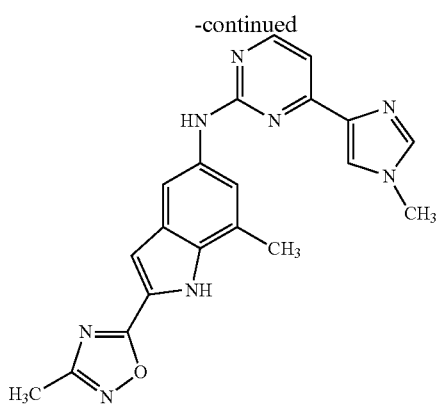

Example 171

Step 1

70 mg 8.3 were stirred with 64 mg [(benzotriazol-1-yloxy)-dimethylamino-methylene]-dimethyl-ammonium tetrafluoroborate (TBTU) and 69 μl N,N-diisopropylethylamine in 1 ml N,N-dimethylformamide at ambient temperature. After 10 min, 15 mg N-hydroxyacetamidine were added and the reaction mixture was stirred at ambient temperature for 2 h to give compound I.18, which was used in the next step without further purification.

Step 2

The reaction mixture (contains I.18) was stirred at 115° C. for 2 h. The resulting mixture was purified by preparative HPLC. The combined product fractions were evaporated. The residue was dissolved in acetonitrile/water 1/1 and lyophilized to obtain the example 171.

Yield: 25 mg Example 171 (32% of theory) Analysis: [M+H]$^+$=387; HPLC-MS (method D): R$_t$=1.07 min 4.2.6 Reaction 10 from Scheme 1f Examples 174 and 175

7-Methyl-5-[4-(1-methyl-1H-imidazol-4-yl)-pyrimidin-2-ylamino]-1H-indole-2-carboxylic acid N'-hydroxymethyl-hydrazide and [4-(1-Methyl-1H-imidazol-4-yl)-pyrimidin-2-yl]-[7-methyl-2-[1,3,4]oxadiazol-2-yl)-1H-indol-5-yl]-amine

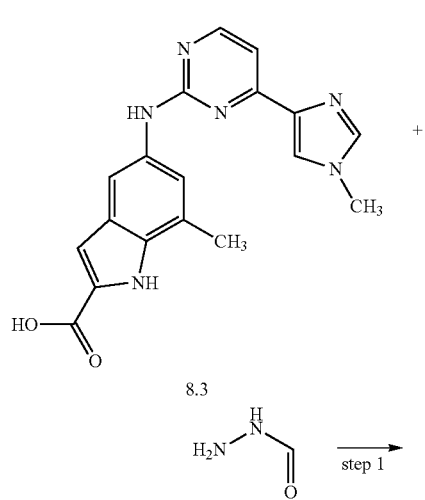

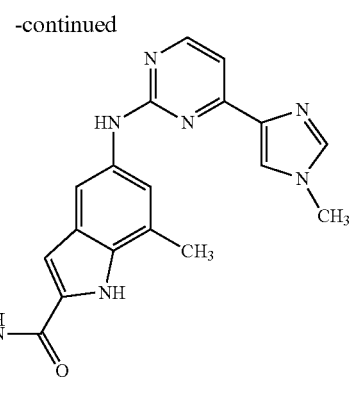

Example 174

| step 2

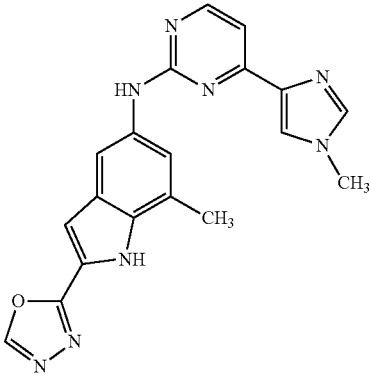

Example 175

Step 1

279 mg 8.3 were stirred with 257 mg [(benzotriazol-1-yloxy)-dimethylamino-methylene]-dimethyl-ammonium tetrafluoroborate (TBTU) and 275 μl N,N-diisopropylethylamine in 4 ml N,N-dimethylformamide at ambient temperature. After 10 min, 48 mg formic acid hydrazide were added and the reaction mixture was stirred at ambient temperature for 1 h. The resulting mixture was purified by preparative HPLC. The combined product fractions were evaporated and the precipitating product collected by filtration, washed with water and dried to give example 174.

Yield: 150 mg Example 174 (48% of theory) Analysis: [M+H]$^+$=391; HPLC-MS (method G): R$_t$=0.72 min Step 2

A mixture of 40 mg example 174 and 500 μl phosphorus oxychloride was stirred at 80° C. for 2 h. The resulting mixture was concentrated in vacuo and the resulting residue purified by preparative HPLC. The combined product fractions were evaporated. The residue was dissolved in acetonitrile/water 1/1 and lyophilized to obtain the example 175.

Yield: 15 mg Example 175 (39% of theory) Analysis: [M+H]⁺=373; HPLC-MS (method D): $R_t$=0.94 min 4.2.7 Reaction 11 from Scheme 1g Example 4

7-Methyl-5-[4-(1-methyl-1H-imidazol-4-yl)-pyrimidin-2-ylamino]-1H-indole-2-carboxylic acid amide

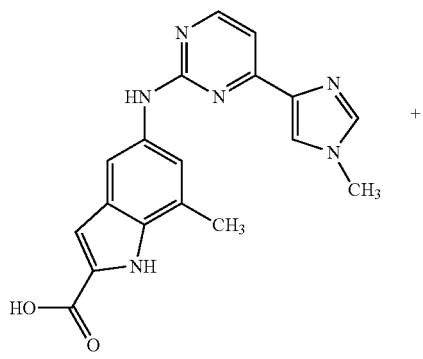

8.3

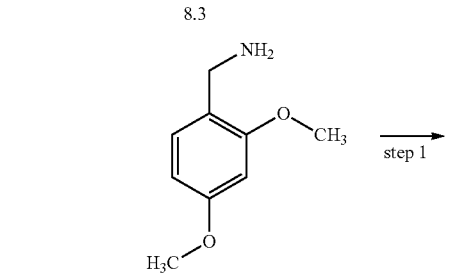

step 1

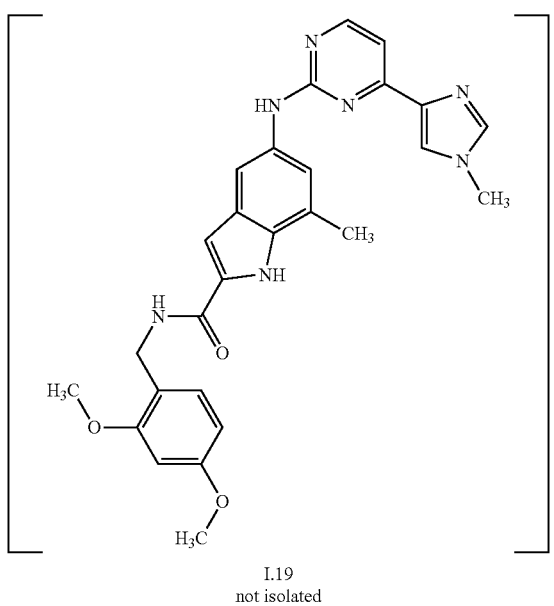

I.19
not isolated step 2

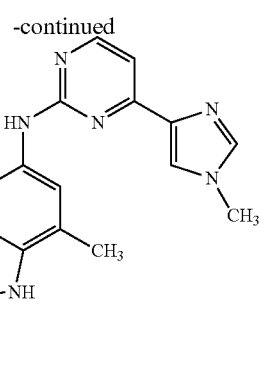

Example 4

Step 1

261 mg 8.3 were stirred with 241 mg [(benzotriazol-1-yloxy)-dimethylamino-methylene]-dimethyl-ammonium tetrafluoroborate (TBTU) and 258 μl N,N-diisopropylethylamine in 20 ml N,N-dimethylformamide at ambient temperature. After 10 min, 125 mg 2,4-dimethoxybenzylamine were added and the reaction mixture was stirred at ambient temperature for 1 h. The reaction mixture was diluted with water and the precipitate was filtered off to give compound I.19, which was used in the next step without further purification.

Analysis: [M+H]⁺=498; HPLC-MS (method D): $R_t$=1.16 min

Step 2

Crude compound I.19 was taken up in 10 mL dichloromethane and treated with 10 mL trifluoroacetic acid at ambient temperature for 2 h. The solvent was removed by destillation and the residue triturated with water. The precipitate was filtered off and the filtrate was purified by preparative HPLC. The combined product fractions were evaporated to obtain the example 4.

Yield: 160 mg Example 4 (61% of theory) Analysis: [M+H]⁺=348; HPLC-MS (method D): $R_t$=0.82 min 4.3 Chromatographic Methods HPLC-MS Methods The example compounds prepared according to the foregoing synthesis schemes were characterised by the following chromatographic methods, which—if they were carried out are specified individually in Table 1.

Method A:
Waters Acquity mit DA-und MS-Detektor
Eluent A: Water (+0.13% TFA)
Eluent B: Methanol (+0.05% TFA)

| Time [min] | % A | % B | Flow rate [mL/min] |
| --- | --- | --- | --- |
| 0.00 | 99 | 1 | 1.3 |
| 0.05 | 99 | 1 | 1.3 |
| 1.05 | 0 | 100 | 1.3 |
| 1.20 | 0 | 100 | 1.3 |

The stationary phase used was a Waters XBridge BEH C18, 2.1×30 mm, 1.7 μm, column temperature: 60° C.

Method B:
Waters Alliance mit DA-und MS-Detektor
Eluent A: Water (+0.1% NH₄OH)
Eluent B: Methanol

| Time [min] | % A | % B | Flow rate [mL/min] |
|---|---|---|---|
| 0.00 | 95 | 5 | 4 |
| 0.20 | 95 | 5 | 4 |
| 1.50 | 0 | 100 | 4 |
| 1.75 | 0 | 100 | 4 |

The stationary phase used was a Waters XBridge C18, 4.6×30 mm, 3.5 µm, column temperature: 60° C.
Method C:
Waters Alliance mit DA-und MS-Detektor
Eluent A: Water (+0.1% TFA)
Eluent B: Methanol

| Time [min] | % A | % B | Flow rate [mL/min] |
|---|---|---|---|
| 0.00 | 95 | 5 | 4 |
| 1.60 | 0 | 100 | 4 |
| 1.85 | 0 | 100 | 4 |
| 1.90 | 95 | 5 | 4 |

The stationary phase used was a Waters XBridge C18, 4.6×30 mm, 3.5 µm, column temperature: 60° C.
Method D:
Agilent 1200 mit DA-und MS-Detektor
Eluent A: Water (+0.1% TFA)
Eluent B: Methanol

| Time [min] | % A | % B | Flow rate [mL/min] |
|---|---|---|---|
| 0.00 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

The stationary phase used was a Waters Sunfire C18, 3×30 mm, 2.5 µm, column temperature: 60° C.
Method E:
Waters ZQ2000 MS; Alliance 2695 HPLC pump, PDA2996 210-500 nm detector, Waters 2700 AS
Eluent A: Water (+0.1% TFA)
Eluent B: Methanol

| Time [min] | % A | % B | Flow rate [mL/min] |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |

The stationary phase used was a Waters Sunfire C18, 4.6×50 mm, 3.5 µm, column temperature: 60° C.
Method F:
Waters Acquity mit DA- and MS-Detektor
Eluent A: Water (+0.1% TFA)
Eluent B: Methanol

| Time [min] | % A | % B | Flow rate [mL/min] |
|---|---|---|---|
| 0.00 | 95 | 5 | 1.4 |
| 0.05 | 95 | 5 | 1.4 |
| 1.00 | 0 | 100 | 1.4 |
| 1.10 | 0 | 100 | 1.4 |

The stationary phase used was a Waters XBridge C18, 2.1×20 mm, 2.5 µm, column temperature: 60° C.
Method G:
Agilent 1200 mit DA-und MS-Detektor
Eluent A: Water (+0.1% NH$_4$OH)
Eluent B: Methanol

| Time [min] | % A | % B | Flow rate [mL/min] |
|---|---|---|---|
| 0.00 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

The stationary phase used was a Waters XBridge C18, 3×30 mm, 2.5 µm, column temperature: 60° C.
Method H:
Waters 1525 mit DA-und MS-Detektor
Eluent A: Water (+0.1% TFA)
Eluent B: Methanol

| Time [min] | % A | % B | Flow rate [mL/min] |
|---|---|---|---|
| 0.00 | 95 | 5 | 4 |
| 0.05 | 95 | 5 | 3 |
| 2.05 | 0 | 100 | 3 |
| 2.10 | 0 | 100 | 4.5 |
| 2.40 | 0 | 100 | 4.5 |

The stationary phase used was a Waters Sunfire C18, 4.6×30 mm, 2.5 µm, column temperature: 60° C.
Method I:
Waters ZQ2000 MS; Alliance 2790 HPLC pump, PDA2996 210-500 nm detector, Waters 2700 AS
Eluent A: Water (+0.1% TFA)
Eluent B: Methanol

| Time [min] | % A | % B | Flow rate [mL/min] |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |

The stationary phase used was a Waters Sunfire C18, 4.6×50 mm, 3.5 µm, column temperature: 60° C.
Method J:
Waters ZQ2000 MS; Agilent HP100, binary pump, DAD 210-500 nm detector, Waters 2700AS
Eluent A: Water (+0.1% NH$_4$OH)
Eluent B: Methanol

| Time [min] | % A | % B | Flow rate [mL/min] |
|---|---|---|---|
| 0.00 | 95 | 5 | 1.5 |
| 2.00 | 0 | 100 | 1.5 |

The stationary phase used was a Waters XBridge C18, 4.6×50 mm, 3.5 µm, column temperature: 40° C.
Method K:
Waters ZQ2000 MS; Agilent HP100, binary pump, DAD 210-500 nm detector, Gilson 215AS
Eluent A: Water (+0.1% TFA)
Eluent B: Acetonitrile (+0.08% TFA)

| Time [min] | % A | % B | Flow rate [mL/min] |
|---|---|---|---|
| 0.00 | 95 | 5 | 1.5 |
| 2.00 | 0 | 100 | 1.5 |
| 2.50 | 0 | 100 | 1.5 |
| 2.60 | 95 | 5 | 1.5 |

The stationary phase used was a Waters Sunfire C18, 4.6×50 mm, 3.5 μm, column temperature: 60° C.

Method L:

Waters ZQ2000 MS; Agilent HP100, binary pump, DAD 210-500 nm detector, Waters 2700AS Eluent A: Water (+0.032% $NH_4OH$)

Eluent B: Methanol

| Time [min] | % A | % B | Flow rate [mL/min] |
|---|---|---|---|
| 0.00 | 95 | 5 | 1.5 |
| 2.00 | 0 | 100 | 1.5 |

The stationary phase used was a Waters XBridge C18, 4.6×50 mm, 3.5 μm, column temperature: 40° C.

Method M:

Waters ZQ2000 MS; Agilent HP100, binary pump, DAD 210-500 nm detector, Gilson 215AS Eluent A: Water (+0.1% $NH_4OH$)

Eluent B: Methanol

| Time [min] | % A | % B | Flow rate [mL/min] |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |

The stationary phase used was a Waters XBridge C18, 4.6×50 mm, 3.5 μm, column temperature: 60° C.

Method N:

Waters SQD MS; Acquity UPLC pump, DAD 210-500 nm detector

Eluent A: Water (+0.1% $NH_4OH$)

Eluent B: Acetonitrile

| Time [min] | % A | % B | Flow rate [mL/min] |
|---|---|---|---|
| 0.00 | 95 | 5 | 1.5 |
| 0.70 | 0 | 100 | 1.5 |
| 0.80 | 0 | 100 | 1.5 |
| 0.81 | 95 | 5 | 1.5 |
| 1.90 | 95 | 5 | 0.2 |
| 2.00 | 0 | 100 | 0.2 |
| 3.00 | 0 | 100 | 0.2 |

The stationary phase used was a Waters XBridge C18, 2.1×50 mm, 1.7 μm, column temperature: 60° C.

Method O:

Waters ZQ2000 MS; Agilent HP100, binary pump, DAD 210-500 nm detector, Gilson 215AS Eluent A: Water (+0.1% TFA)

Eluent B: Methanol

| Time [min] | % A | % B | Flow rate [mL/min] |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |

The stationary phase used was a Waters Sunfire C18, 4.6×50 mm, 3.5 μm, column temperature: 60° C.

Method P:

Agilent 1100 MS; Agilent HP1100, binary pump, 254 nm+230 nm

Eluent A: Water (+0.1% formic acid)

Eluent B: Acetonitrile (+0.1% formic acid)

| Time [min] | % A | % B | Flow rate [mL/min] |
|---|---|---|---|
| 0.00 | 95 | 5 | 1.6 |
| 0.10 | 95 | 5 | 1.6 |
| 1.75 | 5 | 95 | 1.6 |
| 1.90 | 5 | 95 | 1.6 |
| 1.95 | 95 | 5 | 1.6 |
| 2.00 | 95 | 5 | 1.6 |

The stationary phase used was an Agilent Stable Bond C18, 3.0×30 mm, 1.8 μm, column temperature: 25° C.

Method Q:

Agilent 1200 MS; Agilent HP1200, binary pump, 254 nm+230 nm

Eluent A: Water (+0.1% $NH_4OH$)

Eluent B: Acetonitrile (+0.1% $NH_4OH$)

| Time [min] | % A | % B | Flow rate [mL/min] |
|---|---|---|---|
| 0.00 | 95 | 5 | 1.4 |
| 1.80 | 10 | 90 | 1.4 |
| 2.00 | 10 | 90 | 1.4 |
| 2.20 | 95 | 5 | 1.4 |

The stationary phase used was a Waters XBridge C18, 3.0×30 mm, 2.5 μm, column temperature: 25° C.

Method R:

Waters ZQ MS; Waters 2690/2695, DAD 210-500 nm detector, Waters 2700AS

Eluent A: Water (+0.1% TFA)

Eluent B: Acetonitrile (+0.1% TFA)

| Time [min] | % A | % B | Flow rate [mL/min] |
|---|---|---|---|
| 0.00 | 95 | 5 | 2.5 |
| 0.20 | 95 | 5 | 2.5 |
| 1.50 | 2 | 98 | 2.5 |
| 1.70 | 2 | 98 | 2.5 |
| 1.90 | 95 | 5 | 2.5 |
| 2.20 | 95 | 5 | 2.5 |

The stationary phase used was a Merck Chromolith TM Flash RP-18e, 4.6×25 mm, column temperature: 25° C.

Method S:
Waters Acquity mit DA- and MS-Detektor
Eluent A: Water (+0.1% TFA)
Eluent B: Methanol

| Time [min] | % A | % B | Flow rate [mL/min] |
|---|---|---|---|
| 0.00 | 99 | 1 | 1.5 |
| 0.05 | 99 | 1 | 1.5 |
| 1.05 | 0 | 100 | 1.5 |
| 1.20 | 0 | 100 | 1.5 |

The stationary phase used was a Waters XBridge BEH C18, 2.1×30 mm, 1.7 µm, column temperature: 60° C.

5. EXAMPLES

The following Examples were prepared analogously to the methods of synthesis described above. These compounds are suitable as Syk inhibitors and have $IC_{50}$-values measured in the in vitro assay of less than or equal to 1 µM. The $IC_{50}$-values are shown in the following Table 1 and were experimentally determined as follows:

In Vitro Syk Kinase Test

Recombinant human Syk (amino acids 342-635) was expressed as a fusion protein with an N-terminal GST tag, affinity-purified and deep-frozen at a concentration of approx. 50-100 µM in test buffer (25 mM HEPES pH7.5; 25 mM $MgCl_2$; 5 mM $MnCl_2$; 50 mM KCl; either 0.2% BSA or 0.2% HSA or 1% HSA (varies from example to example depending on the used assay, for details see Table 1); 0.01% CHAPS; 100 µM $Na_3VO_4$; 0.5 mM DTT) and 10% glycerol at −80° C. until use.

The catalytic activity of the GST-Syk kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the protein kinase.

Method

The test compounds were dissolved in 100% DMSO at a concentration of 10 mM and diluted in DMSO to a concentration of 1 mM. All further dilutions of the substances were carried out with 7.5% DMSO in test buffer until a concentration was reached which was 7.5 times above the final test concentration (final concentration of the compounds: 30 µM to 1 nM). 2 µl aliquots of these dilutions were transferred into a 384-well Optiplate (Perkin Elmer, #6007290). GST-Syk was diluted to 6.0 nM in the test buffer and 10 µl of this dilution were used in the kinase test (final concentration of Syk=4 nM in a total volume of 15 µl). After 15 minutes incubation at room temperature 3 µl of a mixture of 750 nM ATP and 100 µg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl Kinase-Glo® solution (Promega, Cat. # V6712) (heated to room temperature) were added to each well and incubation was continued for a further 15 minutes. The plates were read in a Microplate Scintillation and Luminescence Counter (Canberra Packard GmbH).

Data Evaluation and Calculation:

The output file of the "Counter" is a text file that contains the well number and measured counts in two columns. For data evaluation and calculation, the measurement of the negative control was set as 100% inhibition and the measurement of the positive control was set as 0% inhibition. Based on this values the % inherent value for the measurement of each substance concentration was calculated using an "MS-Excel-VB macro". Normally, the inhibition values calculated are between 100% and 0% inhibition values but may also occur outside these limits in individual cases. The $IC_{50}$ values were calculated from the % inhibition values using "GraphPad-Prism" software (Version 5) (GraphPad Software Inc.).

The following Examples of formula 1

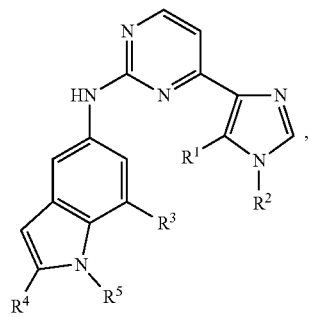

having the following properties were prepared according to the methods of synthesis described above:

TABLE 1

Example compounds, their experimentally determined IC₅₀-values and details on the methods of preparing them

| Example No. | Structure | Syk Enzyme IC₅₀ [μM] (0.2% BSA) | Syk Enzyme IC50 [μM] (0.2% HSA) | Syk Enzyme IC₅₀ [μM] (1% HSA) | Method of preparation | Analytic data |
|---|---|---|---|---|---|---|
| 1 | 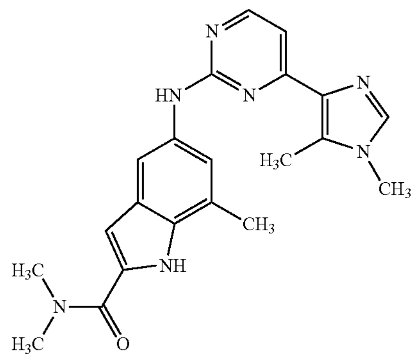 [SMILES: Cc1cc(Nc2nccc(-c3ncn(C)c3C)n2)cc2cc(C(=O)N(C)C)[nH]c12] | | 0.0074 | 0.0130 | Starting from 7.7 see description 4.2.1 | HPLC: method D Rt = 0.96 min |
| 2 | 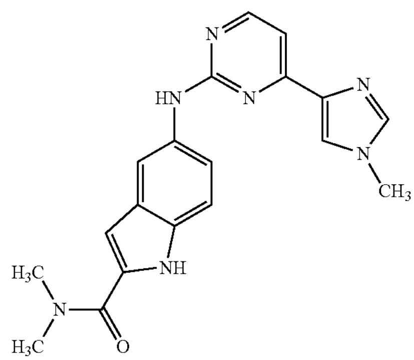 [SMILES: CN(C)C(=O)c1cc2cc(Nc3nccc(-c4cn(C)cn4)n3)ccc2[nH]1] | 0.1330 | | | Starting from 7.10 and 4.6 analogous to Example 1 | HPLC: method B Rt = 1.09 min |
| 3 | 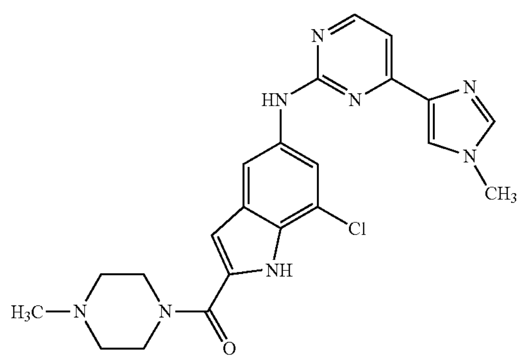 [SMILES: CN1CCN(C(=O)c2cc3cc(Nc4nccc(-c5cn(C)cn5)n4)cc(Cl)c3[nH]2)CC1] | 0.0114 | 0.0019 | 0.0016 | Starting from 8.1 analogous to Example 7 | HPLC: method G Rt = 1.06 min |
| 4 | 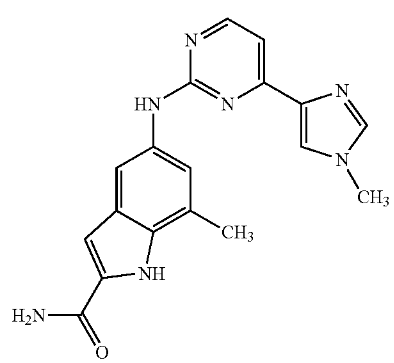 [SMILES: Cc1cc(Nc2nccc(-c3cn(C)cn3)n2)cc2cc(C(N)=O)[nH]c12] | | 0.0005 | 0.0009 | Starting from 8.3 see description 4.27 | HPLC: method D Rt = 0.82 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 5 | 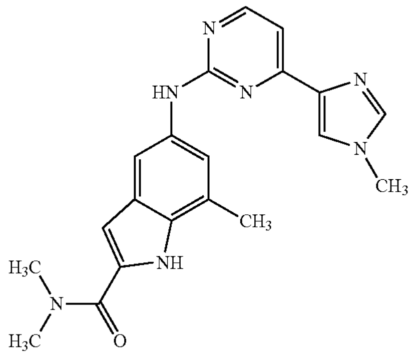 [SMILES: Cc1cc(Nc2nccc(-c3cn(C)cn3)n2)cc2cc(C(=O)N(C)C)[nH]c12] | 0.0123 | 0.0201 | 0.0367 | Starting from 7.7 and 4.6 analogous to Example 1 | HPLC: method E Rt = 1.35 min |
| 6 | 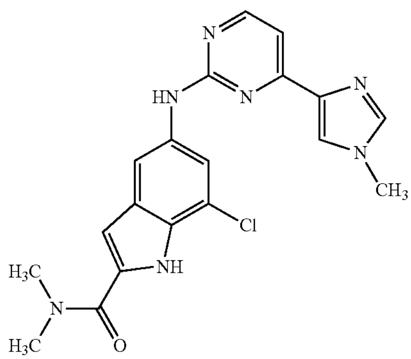 [SMILES: CN(C)C(=O)c1cc2cc(Nc3nccc(-c4cn(C)cn4)n3)cc(Cl)c2[nH]1] | 0.0015 | 0.0018 | 0.0028 | Starting from 7.1 and 4.6 analogous to Example 1 | HPLC: method E Rt = 1.46 min |
| 7 | 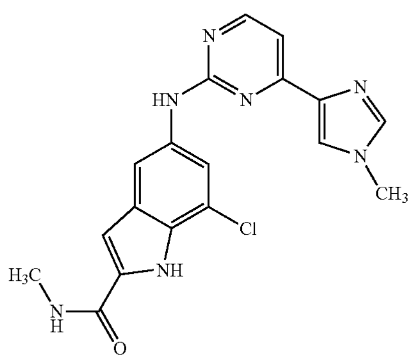 [SMILES: CNC(=O)c1cc2cc(Nc3nccc(-c4cn(C)cn4)n3)cc(Cl)c2[nH]1] | 0.0014 | | | Starting from 8.1 see description 4.2.2 | HPLC: method E Rt = 1.43 min |
| 8 | 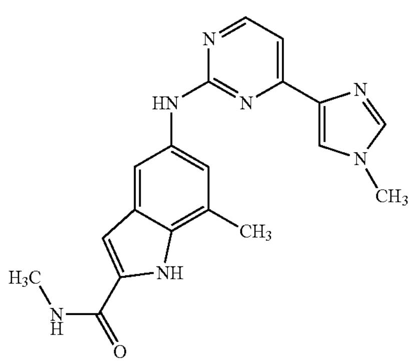 [SMILES: CNC(=O)c1cc2cc(Nc3nccc(-c4cn(C)cn4)n3)cc(C)c2[nH]1] | 0.0051 | 0.0009 | 0.0010 | Starting from 8.3 analogous to Example 7 | HPLC: method A Rt = 0.58 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 9 | 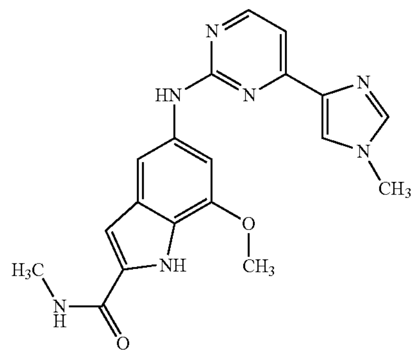 [SMILES: CNC(=O)c1cc2cc(Nc3nccc(-c4cn(C)cn4)n3)cc(OC)c2[nH]1] | 0.0071 | | | Starting from 8.2 analogous to Example 7 | HPLC: method B Rt = 1.09 min |
| 10 | 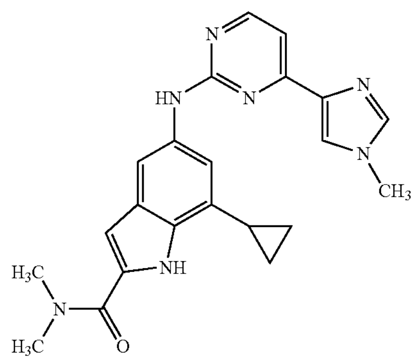 [SMILES: CN(C)C(=O)c1cc2cc(Nc3nccc(-c4cn(C)cn4)n3)cc(C3CC3)c2[nH]1] | | 0.0018 | 0.0028 | Starting from 10.1 analogous to Example 19 | HPLC: method B Rt = 1.23 min |
| 11 | 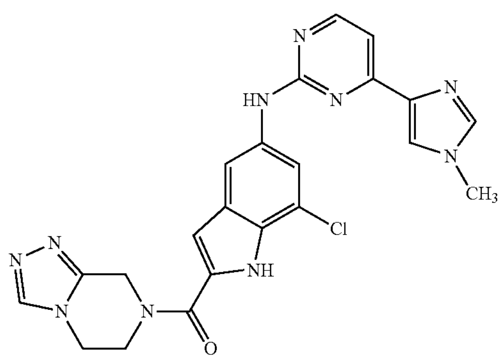 [SMILES: Cn1cnc(-c2ccnc(Nc3cc(Cl)c4[nH]c(C(=O)N5CCn6cnnc6C5)cc4c3)n2)c1] | 0.0076 | | | Starting from 8.1 analogous to Example 7 | HPLC: method M Rt = 1.32 min |
| 12 | 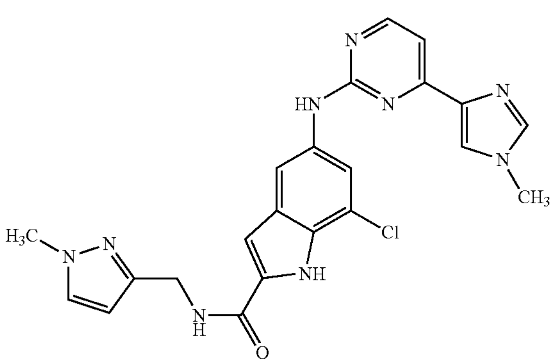 [SMILES: Cn1cnc(-c2ccnc(Nc3cc(Cl)c4[nH]c(C(=O)NCc5ccn(C)n5)cc4c3)n2)c1] | 0.0017 | | | Starting from 8.1 analogous to Example 7 | HPLC: method G Rt = 1.03 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 13 | 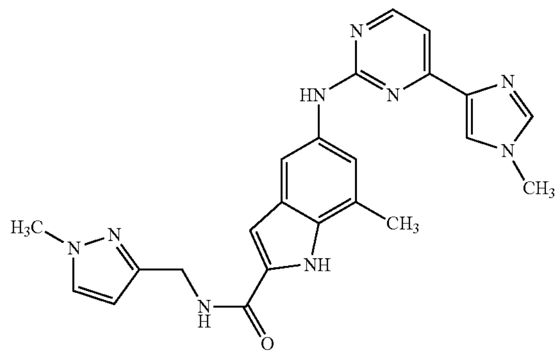 [SMILES: Cc1cc(Nc2nccc(-c3cn(C)cn3)n2)cc2cc(C(=O)NCc3ccn(C)n3)[nH]c12] | 0.0018 | | | Starting from 8.3 analogous to Example 7 | HPLC: method J Rt = 2.08 min |
| 14 | 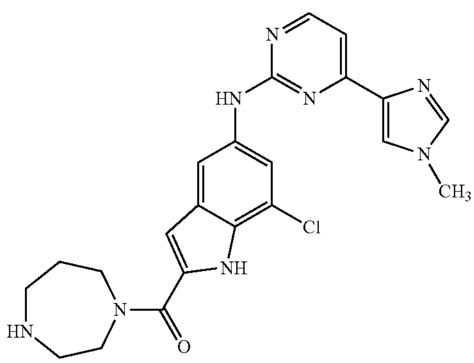 [SMILES: Cn1cnc(-c2ccnc(Nc3cc(Cl)c4[nH]c(C(=O)N5CCCNCC5)cc4c3)n2)c1] | 0.0086 | | | Starting from 8.1 analogous to Example 7 | HPLC: method J Rt = 2.18 min |
| 15 | 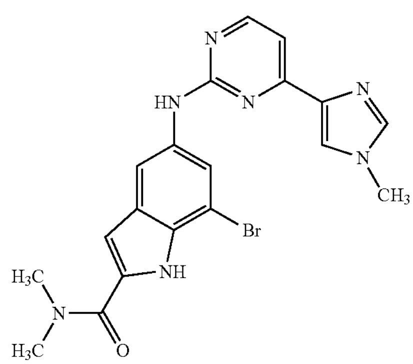 | 0.0011 | 0.0068 | | Starting from 7.12 see description 4.1.12 | HPLC: method B Rt = 1.20 min |
| 16 | 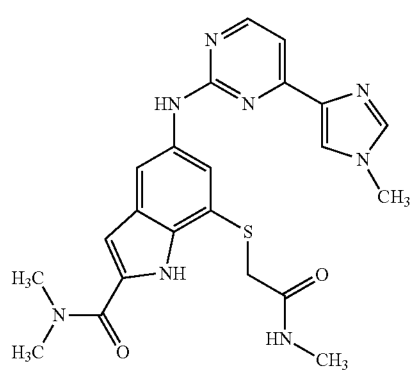 [SMILES: CNC(=O)CSc1cc(Nc2nccc(-c3cn(C)cn3)n2)cc2cc(C(=O)N(C)C)[nH]c12] | 0.5036 | 1.0400 | | Starting from 10.1 analogous to Example 22 | HPLC: method B Rt = 1.12 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 17 | 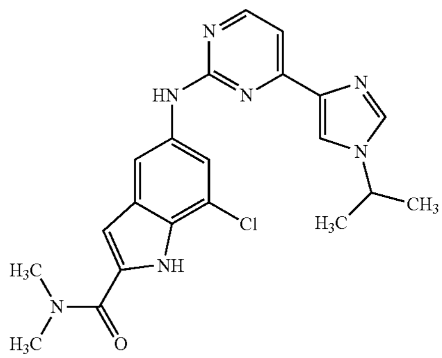 [SMILES: CC(C)n1cnc(-c2ccnc(Nc3cc(Cl)c4[nH]c(C(=O)N(C)C)cc4c3)n2)c1] | | 0.0009 | 0.0212 | Starting from 7.1 and 4.1 analogous to Example 1 | HPLC: method B Rt = 1.30 min |
| 18 | 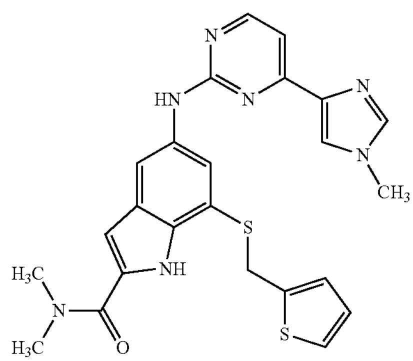 [SMILES: CN(C)C(=O)c1cc2cc(Nc3nccc(-c4cn(C)cn4)n3)cc(SCc3cccs3)c2[nH]1] | | 0.0150 | 0.0796 | Starting from 10.1 analogous to Example 22 | HPLC: method F Rt = 0.63 min |
| 19 | 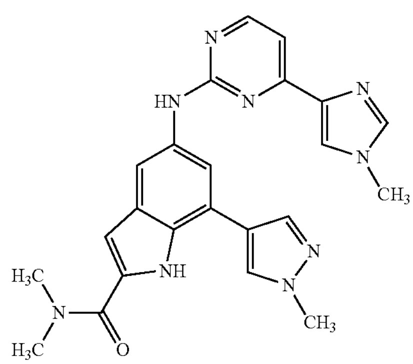 [SMILES: CN(C)C(=O)c1cc2cc(Nc3nccc(-c4cn(C)cn4)n3)cc(-c3cnn(C)c3)c2[nH]1] | | 0.0081 | 0.0102 | Starting from 10.1 see description 4.2.3 | HPLC: method F Rt = 0.52 min |
| 20 | 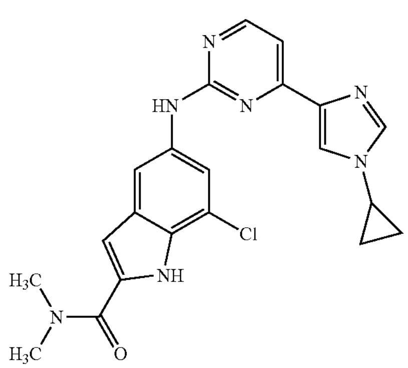 [SMILES: CN(C)C(=O)c1cc2cc(Nc3nccc(-c4cn(C5CC5)cn4)n3)cc(Cl)c2[nH]1] | | 0.0132 | 0.0796 | Starting from 7.1 and 4.3 analogous to Example 1 | HPLC: method F Rt = 0.58 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 21 | 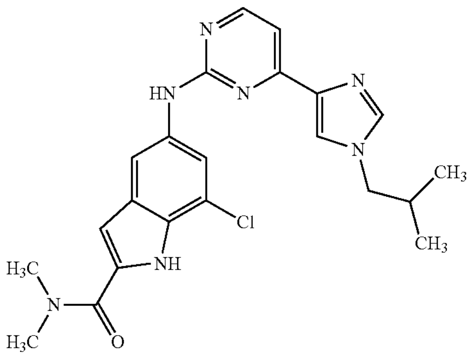 [SMILES: CC(C)Cn1cnc(-c2ccnc(Nc3cc(Cl)c4[nH]c(C(=O)N(C)C)cc4c3)n2)c1] | | 0.1209 | 0.4373 | Starting from 7.1 and 4.2 analogous to Example 1 | HPLC: method F Rt = 0.63 min |
| 22 | 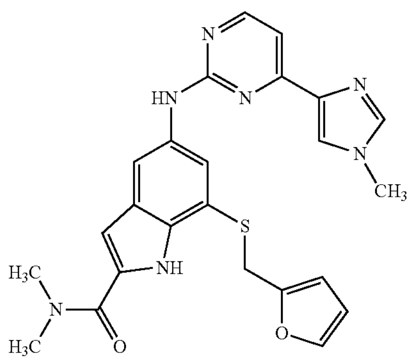 [SMILES: CN(C)C(=O)c1cc2cc(Nc3nccc(-c4cn(C)cn4)n3)cc(SCc3ccco3)c2[nH]1] | | 0.0804 | 0.1597 | Starting from 10.1 see description 4.2.4 | HPLC: method F Rt = 0.60 min |
| 23 | 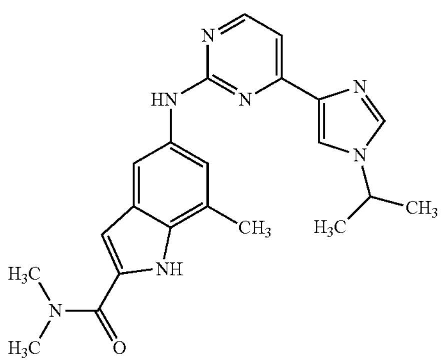 [SMILES: Cc1cc(Nc2nccc(-c3cn(C(C)C)cn3)n2)cc2cc(C(=O)N(C)C)[nH]c12] | | 0.0677 | 0.0608 | Starting from 7.7 and 4.1 analogous to Example 1 | HPLC: method C Rt = 0.97 min |
| 24 | 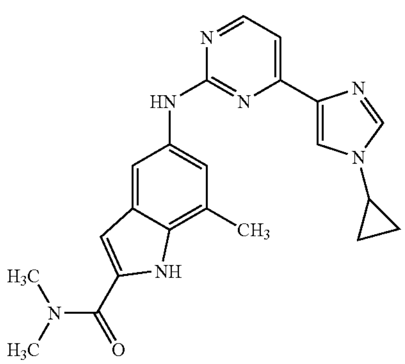 [SMILES: Cc1cc(Nc2nccc(-c3cn(C4CC4)cn3)n2)cc2cc(C(=O)N(C)C)[nH]c12] | | 0.0888 | 0.2054 | Starting from 7.7 and 4.3 analogous to Example 1 | HPLC: method C Rt = 0.97 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 25 | 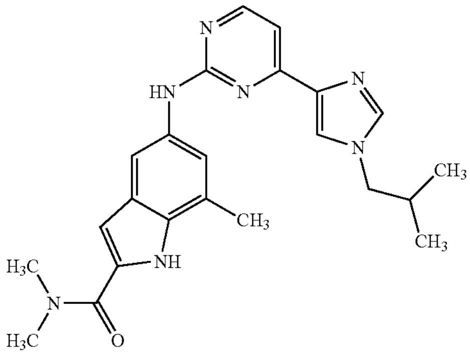 [SMILES: Cc1cc(Nc2nccc(-c3cn(CC(C)C)cn3)n2)cc2cc(C(=O)N(C)C)[nH]c12] | | 0.0891 | 0.1199 | Starting from 7.7 and 4.2 analogous to Example 1 | HPLC: method C Rt = 1.08 min |
| 26 | 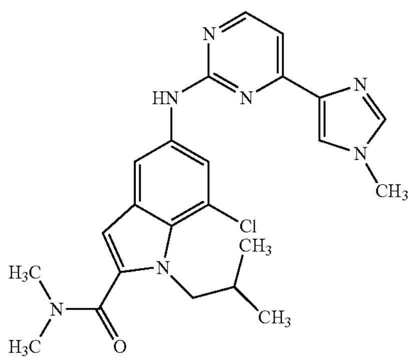 [SMILES: CC(C)Cn1c(C(=O)N(C)C)cc2cc(Nc3nccc(-c4cn(C)cn4)n3)cc(Cl)c21] | | 0.1087 | 0.3474 | Starting from 7.5 and 4.6 analogous to Example 1 | HPLC: method C Rt = 1.22 min |
| 27 | 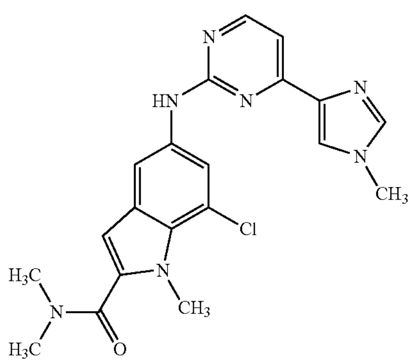 [SMILES: CN(C)C(=O)c1cc2cc(Nc3nccc(-c4cn(C)cn4)n3)cc(Cl)c2n1C] | | 0.0234 | 0.0227 | Starting from 7.4 and 4.6 analogous to Example 1 | HPLC: method C Rt = 0.99 min |
| 28 | 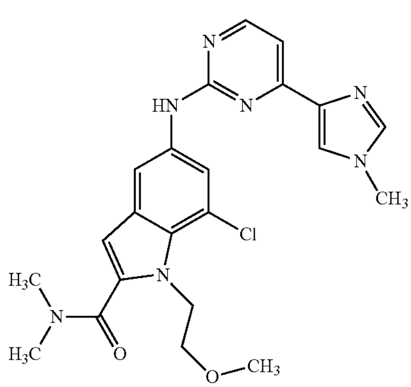 [SMILES: COCCn1c(C(=O)N(C)C)cc2cc(Nc3nccc(-c4cn(C)cn4)n3)cc(Cl)c21] | | 0.0850 | 0.2451 | Starting from 7.6 and 4.6 analogous to Example 1 | HPLC: method C Rt = 1.02 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 29 | 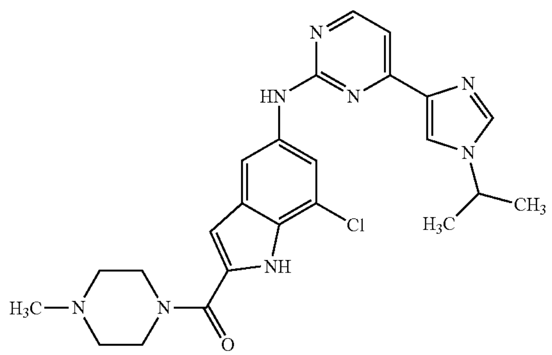 [SMILES: CC(C)n1cnc(-c2ccnc(Nc3cc(Cl)c4[nH]c(C(=O)N5CCN(C)CC5)cc4c3)n2)c1] | | 0.0009 | 0.0033 | Starting from 7.2 and 4.1 analogous to Example 1 | HPLC: method B Rt = 1.28 min |
| 30 | 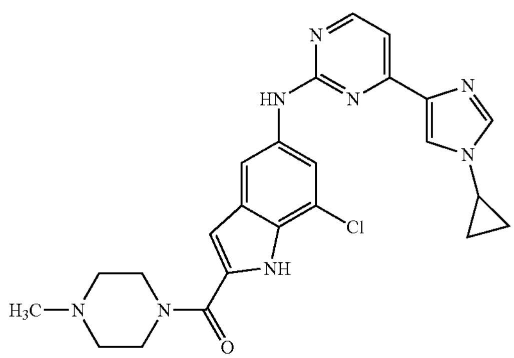 [SMILES: CN1CCN(C(=O)c2cc3cc(Nc4nccc(-c5cn(C6CC6)cn5)n4)cc(Cl)c3[nH]2)CC1] | | 0.0016 | 0.0323 | Starting from 7.2 and 4.3 analogous to Example 1 | HPLC: method B Rt = 1.27 min |
| 31 | 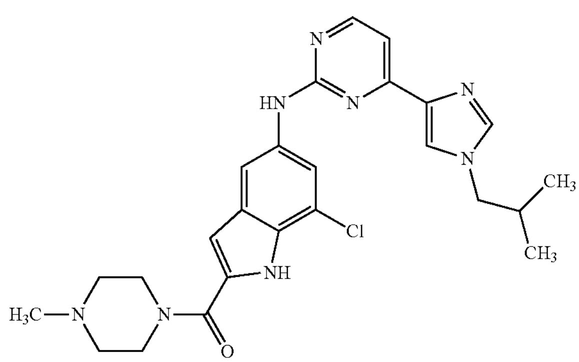 [SMILES: CC(C)Cn1cnc(-c2ccnc(Nc3cc(Cl)c4[nH]c(C(=O)N5CCN(C)CC5)cc4c3)n2)c1] | | 0.0024 | 0.0083 | Starting from 7.2 and 4.2 analogous to Example 1 | HPLC: method B Rt = 1.34 min |
| 32 | 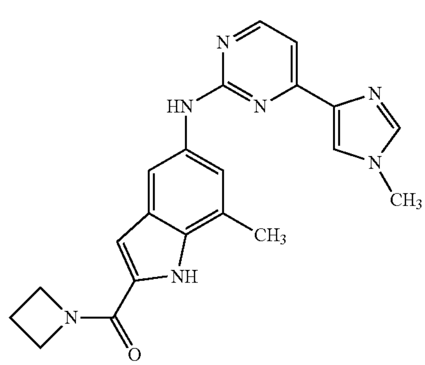 [SMILES: Cc1cc(Nc2nccc(-c3cn(C)cn3)n2)cc2cc(C(=O)N3CCC3)[nH]c12] | 0.0055 | | | Starting from 8.3 analogous to Example 7 | HPLC: method K Rt = 1.13 min |

TABLE 1-continued

Example compounds, their experimentally determined IC50-values and details on the methods of preparing them

| Example No. | Structure | Syk Enzyme IC50 [µM] (0.2% BSA) | Syk Enzyme IC50 [µM] (0.2% HSA) | Syk Enzyme IC50 [µM] (1% HSA) | Method of preparation | Analytic data |
|---|---|---|---|---|---|---|
| 33 | 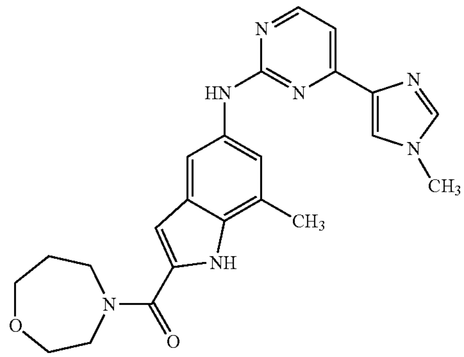 [SMILES: Cc1cc(Nc2nccc(-c3cn(C)cn3)n2)cc2cc(C(=O)N3CCCOCC3)[nH]c12] | 0.0089 | | | Starting from 8.3 analogous to Example 7 | HPLC: method K Rt = 1.12 min |
| 34 | 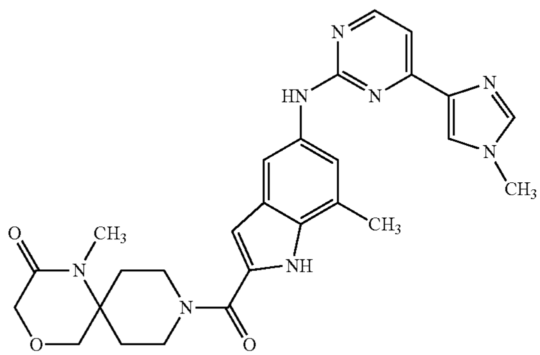 [SMILES: Cc1cc(Nc2nccc(-c3cn(C)cn3)n2)cc2cc(C(=O)N3CCC4(CC3)COCC(=O)N4C)[nH]c12] | 0.0006 | | | Starting from 8.3 analogous to Example 7 | HPLC: method K Rt = 1.09 min |
| 35 | 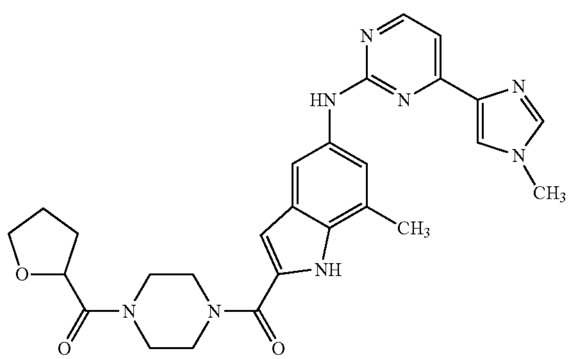 [SMILES: Cc1cc(Nc2nccc(-c3cn(C)cn3)n2)cc2cc(C(=O)N3CCN(C(=O)C4CCCO4)CC3)[nH]c12] | 0.0208 | | | Starting from 8.3 analogous to Example 7 | HPLC: method K Rt = 1.07 min |
| 36 | 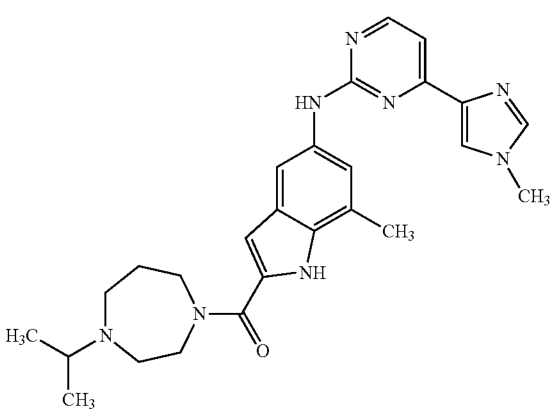 [SMILES: Cc1cc(Nc2nccc(-c3cn(C)cn3)n2)cc2cc(C(=O)N3CCCN(C(C)C)CC3)[nH]c12] | 0.0142 | | | Starting from 8.3 analogous to Example 7 | HPLC: method K Rt = 0.99 min |

TABLE 1-continued

Example compounds, their experimentally determined IC₅₀-values and details on the methods of preparing them

| Example No. | Structure | Syk Enzyme IC₅₀ [μM] (0.2% BSA) | Syk Enzyme IC50 [μM] (0.2% HSA) | Syk Enzyme IC₅₀ [μM] (1% HSA) | Method of preparation | Analytic data |
|---|---|---|---|---|---|---|
| 37 | 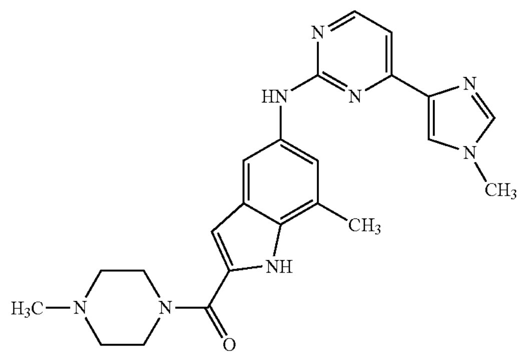 [SMILES: Cc1cc(Nc2nccc(-c3cn(C)cn3)n2)cc2cc(C(=O)N3CCN(C)CC3)[nH]c12] | 0.0219 | | | Starting from 8.3 analogous to Example 7 | HPLC: method K Rt = 0.94 min |
| 38 | 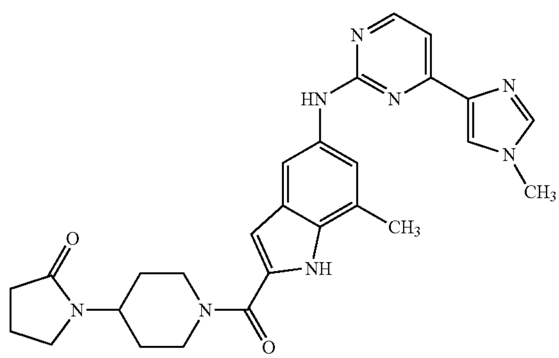 [SMILES: Cc1cc(Nc2nccc(-c3cn(C)cn3)n2)cc2cc(C(=O)N3CCC(N4CCCC4=O)CC3)[nH]c12] | 0.0111 | | | Starting from 8.3 analogous to Example 7 | HPLC: method K Rt = 1.12 min |
| 39 | 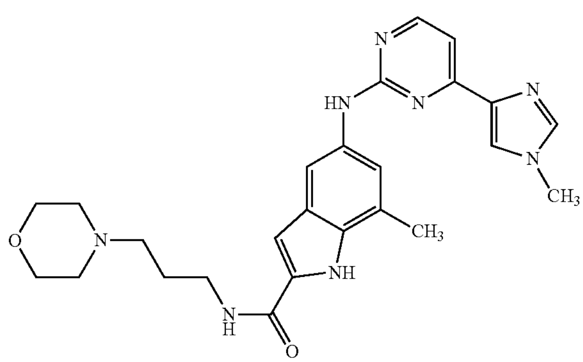 [SMILES: Cc1cc(Nc2nccc(-c3cn(C)cn3)n2)cc2cc(C(=O)NCCCN3CCOCC3)[nH]c12] | 0.0141 | | | Starting from 8.3 analogous to Example 7 | HPLC: method K Rt = 0.98 min |
| 40 | 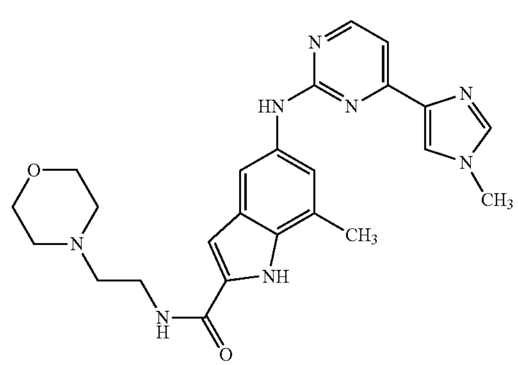 [SMILES: Cc1cc(Nc2nccc(-c3cn(C)cn3)n2)cc2cc(C(=O)NCCN3CCOCC3)[nH]c12] | 0.0113 | | | Starting from 8.3 analogous to Example 7 | HPLC: method K Rt = 0.97 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 41 | 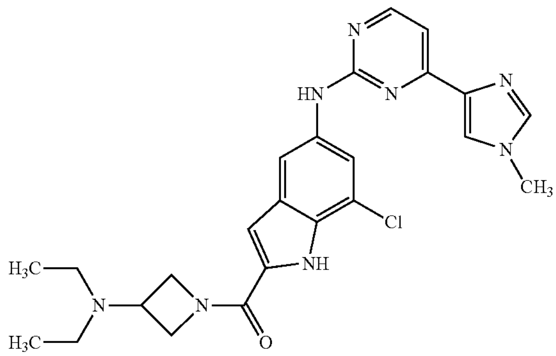 [SMILES: CCN(CC)C1CN(C(=O)c2cc3cc(Nc4nccc(-c5cn(C)cn5)n4)cc(Cl)c3[nH]2)C1] | 0.0006 | | | Starting from 8.1 analogous to Example 7 | HPLC: method K Rt = 0.99 min |
| 42 | 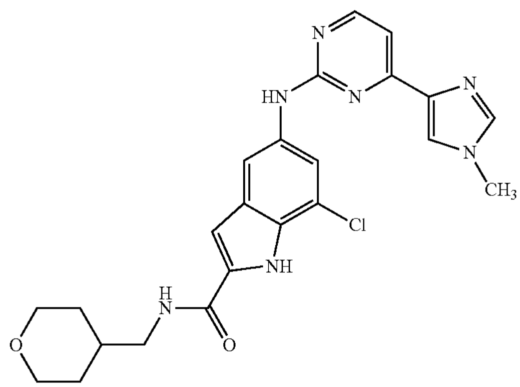 [SMILES: Cn1cnc(-c2ccnc(Nc3cc(Cl)c4[nH]c(C(=O)NCC5CCOCC5)cc4c3)n2)c1] | 0.0014 | | | Starting from 8.1 analogous to Example 7 | HPLC: method K Rt = 1.23 min |
| 43 | 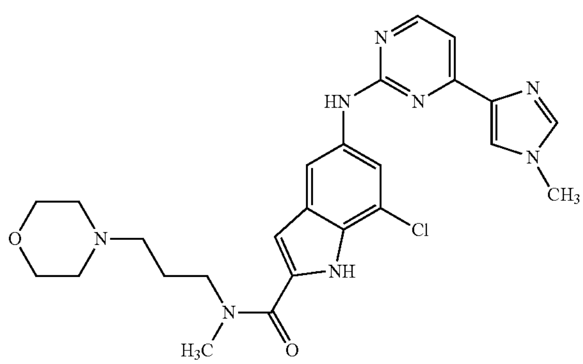 [SMILES: CN(CCCN1CCOCC1)C(=O)c1cc2cc(Nc3nccc(-c4cn(C)cn4)n3)cc(Cl)c2[nH]1] | 0.0051 | | | Starting from 8.1 analogous to Example 7 | HPLC: method K Rt = 1.05 min |
| 44 | 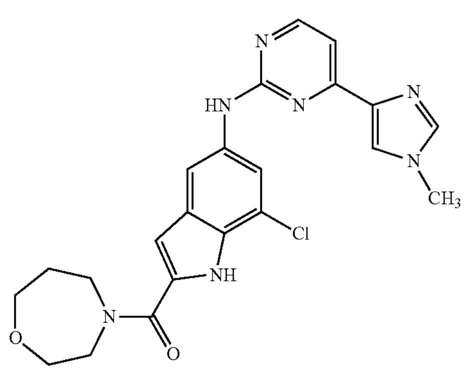 [SMILES: Cn1cnc(-c2ccnc(Nc3cc(Cl)c4[nH]c(C(=O)N5CCCOCC5)cc4c3)n2)c1] | 0.0041 | | | Starting from 8.1 analogous to Example 7 | HPLC: method K Rt = 1.19 min |

TABLE 1-continued

Example compounds, their experimentally determined IC₅₀-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 45 | 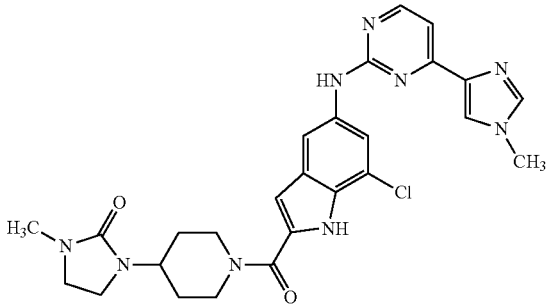 [SMILES: CN1CCN(C2CCN(C(=O)c3cc4cc(Nc5nccc(-c6cn(C)cn6)n5)cc(Cl)c4[nH]3)CC2)C1=O] | 0.0008 | | | Starting from 8.1 analogous to Example 7 | HPLC: method K Rt = 1.20 min |
| 46 | 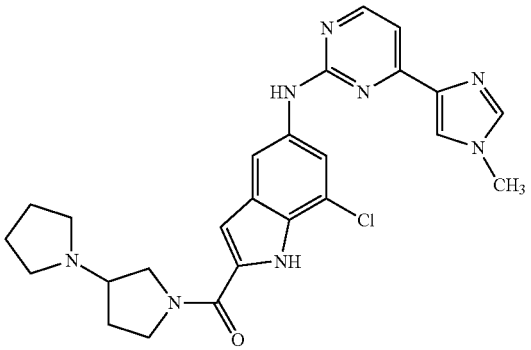 [SMILES: Cn1cnc(-c2ccnc(Nc3cc(Cl)c4[nH]c(C(=O)N5CCC(N6CCCC6)C5)cc4c3)n2)c1] | 0.0022 | | | Starting from 8.1 analogous to Example 7 | HPLC: method K Rt = 1.03 min |
| 47 | 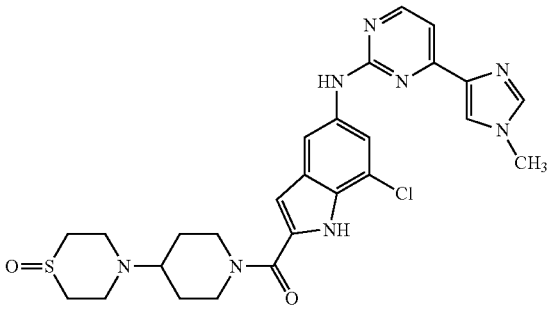 [SMILES: Cn1cnc(-c2ccnc(Nc3cc(Cl)c4[nH]c(C(=O)N5CCC(N6CCS(=O)CC6)CC5)cc4c3)n2)c1] | 0.0016 | | | Starting from 8.1 analogous to Example 7 | HPLC: method K Rt = 1.01 min |
| 48 | 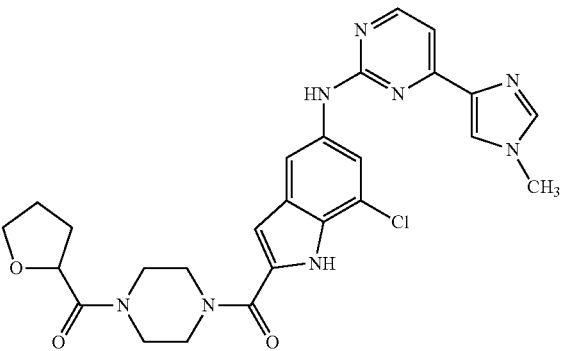 [SMILES: Cn1cnc(-c2ccnc(Nc3cc(Cl)c4[nH]c(C(=O)N5CCN(C(=O)C6CCCO6)CC5)cc4c3)n2)c1] | 0.0020 | | | Starting from 8.1 analogous to Example 7 | HPLC: method K Rt = 1.17 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 49 | 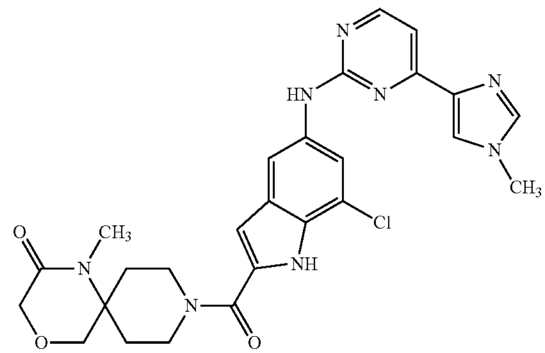 [SMILES: CN1C(=O)COCC12CCN(C(=O)c1cc3cc(Nc4nccc(-c5cn(C)cn5)n4)cc(Cl)c3[nH]1)CC2] | 0.0007 | | | Starting from 8.1 analogous to Example 7 | HPLC: method K Rt = 1.15 min |
| 50 | 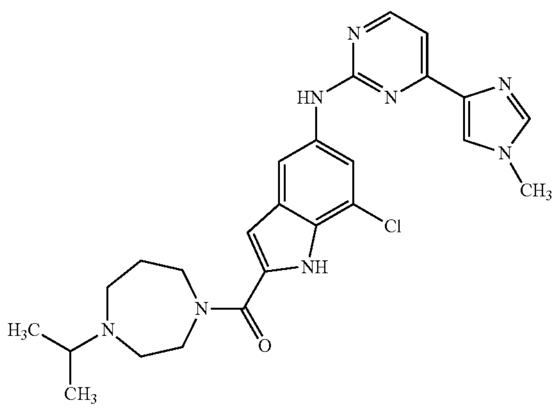 [SMILES: CC(C)N1CCCN(C(=O)c2cc3cc(Nc4nccc(-c5cn(C)cn5)n4)cc(Cl)c3[nH]2)CC1] | 0.0019 | | | Starting from 8.1 analogous to Example 7 | HPLC: method K Rt = 1.04 min |
| 51 | 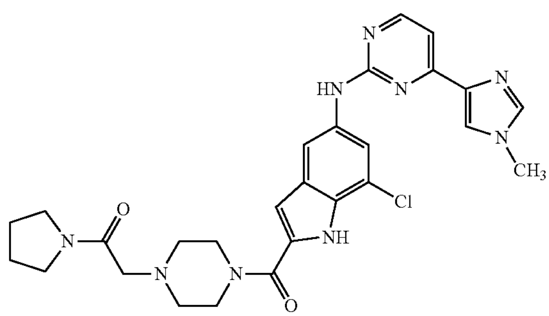 [SMILES: Cn1cnc(-c2ccnc(Nc3cc(Cl)c4[nH]c(C(=O)N5CCN(CC(=O)N6CCCC6)CC5)cc4c3)n2)c1] | 0.0036 | | | Starting from 8.1 analogous to Example 7 | HPLC: method K Rt = 1.04 min |
| 52 | 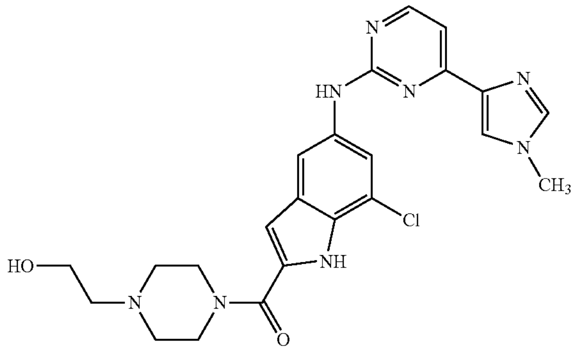 [SMILES: Cn1cnc(-c2ccnc(Nc3cc(Cl)c4[nH]c(C(=O)N5CCN(CCO)CC5)cc4c3)n2)c1] | 0.0038 | | | Starting from 8.1 analogous to Example 7 | HPLC: method K Rt = 0.99 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 53 | 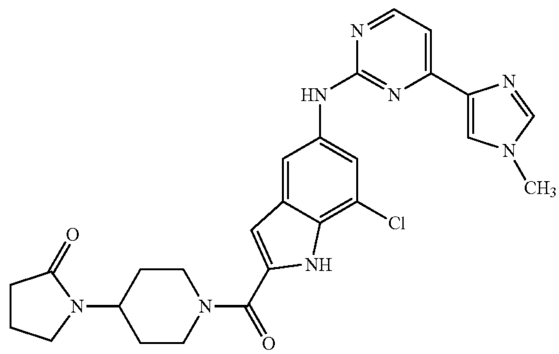 [SMILES: Cn1cnc(-c2ccnc(Nc3cc(Cl)c4[nH]c(C(=O)N5CCC(N6CCCC6=O)CC5)cc4c3)n2)c1] | 0.0010 | | | Starting from 8.1 analogous to Example 7 | HPLC: method K Rt = 1.18 min |
| 54 | 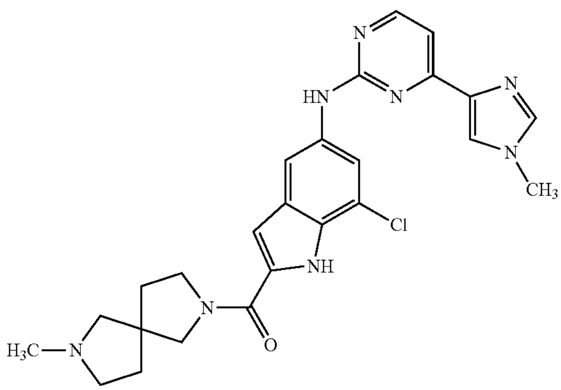 [SMILES: CN1CCC2(CCN(C(=O)c3cc4cc(Nc5nccc(-c6cn(C)cn6)n5)cc(Cl)c4[nH]3)C2)C1] | 0.0013 | | | Starting from 8.1 analogous to Example 7 | HPLC: method K Rt = 1.04 min |
| 55 | 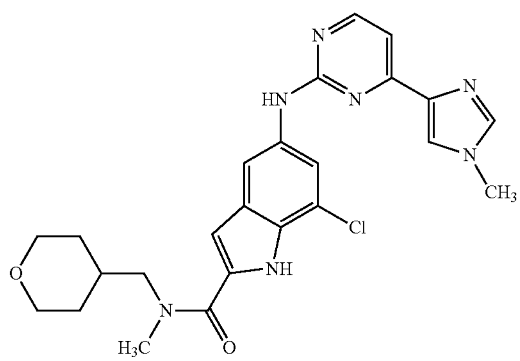 [SMILES: CN(CC1CCOCC1)C(=O)c1cc2cc(Nc3nccc(-c4cn(C)cn4)n3)cc(Cl)c2[nH]1] | 0.0014 | | | Starting from 8.1 analogous to Example 7 | HPLC: method K Rt = 1.25 min |
| 56 | 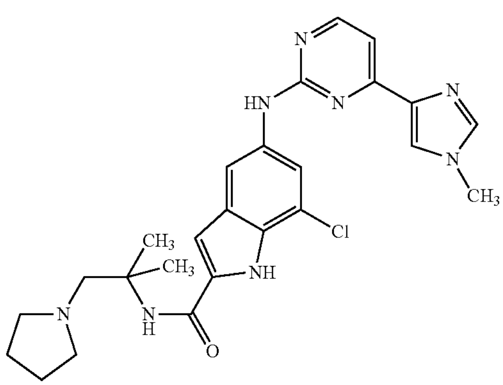 [SMILES: Cn1cnc(-c2ccnc(Nc3cc(Cl)c4[nH]c(C(=O)NC(C)(C)CN5CCCC5)cc4c3)n2)c1] | 0.0078 | | | Starting from 8.1 analogous to Example 7 | HPLC: method M Rt = 1.83 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 57 | 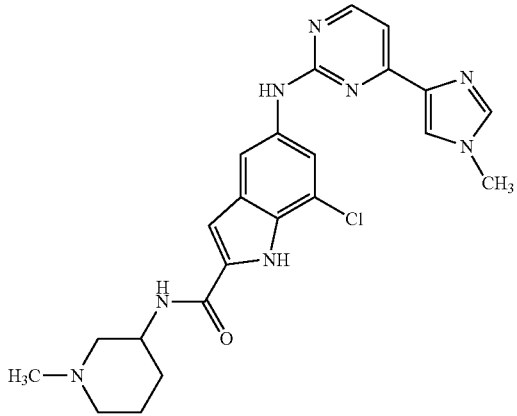 [SMILES: CN1CCCC(NC(=O)c2cc3cc(Nc4nccc(-c5cn(C)cn5)n4)cc(Cl)c3[nH]2)C1] | | 0.0065 | | Starting from 8.1 analogous to Example 7 | HPLC: method M Rt = 1.63 min |
| 58 | 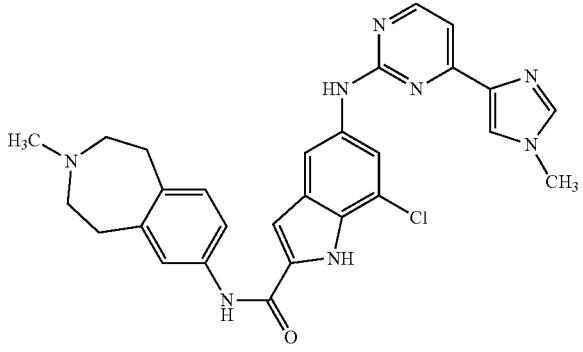 [SMILES: CN1CCc2ccc(NC(=O)c3cc4cc(Nc5nccc(-c6cn(C)cn6)n5)cc(Cl)c4[nH]3)cc2CC1] | | 0.0085 | | Starting from 8.1 analogous to Example 7 | HPLC: method M Rt = 1.82 min |
| 59 | 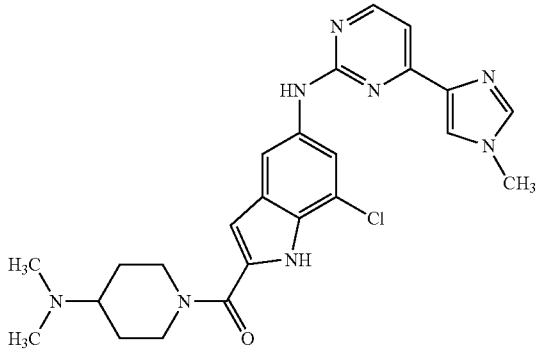 | | 0.0119 | | Starting from 8.1 analogous to Example 7 | HPLC: method M Rt = 1.63 min |

TABLE 1-continued

Example compounds, their experimentally determined IC50-values and details on the methods of preparing them

| Example No. | Structure | Syk Enzyme IC50 [μM] (0.2% BSA) | Syk Enzyme IC50 [μM] (0.2% HSA) | Syk Enzyme IC50 [μM] (1% HSA) | Method of preparation | Analytic data |
|---|---|---|---|---|---|---|
| 60 | 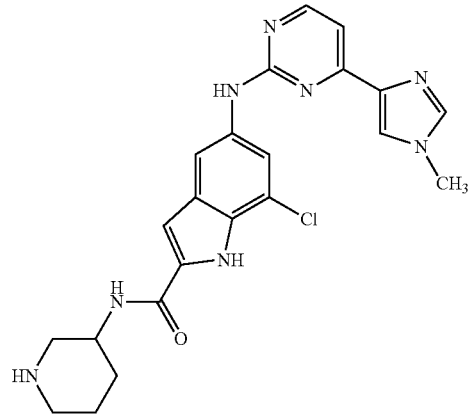 [SMILES: Cn1cnc(-c2ccnc(Nc3cc(Cl)c4[nH]c(C(=O)NC5CCCNC5)cc4c3)n2)c1] | 0.0055 | 0.0111 | | Starting from 8.1 analogous to Example 7 | HPLC: method M Rt = 1.55 min |
| 61 | 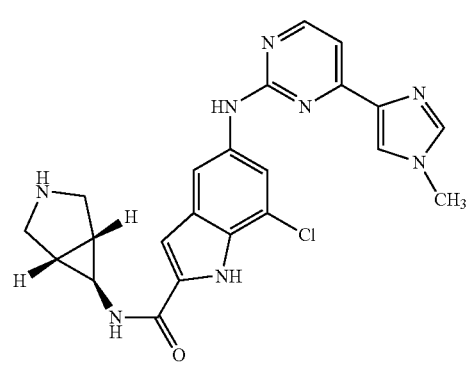 [SMILES: Cn1cnc(-c2ccnc(Nc3cc(Cl)c4[nH]c(C(=O)N[C@H]5[C@@H]6CNC[C@@H]65)cc4c3)n2)c1] | 0.0110 | 0.0082 | | Starting from 8.1 analogous to Example 7 | HPLC: method D Rt = 0.74 min |
| 62 | 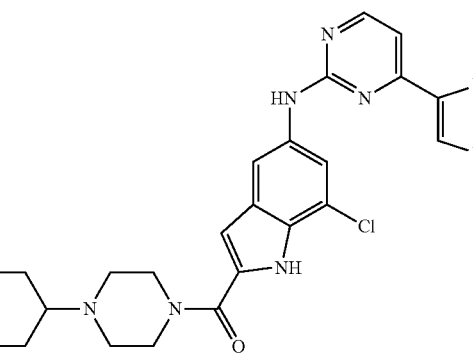 | 0.0023 | | | Starting from 8.1 analogous to Example 7 | HPLC: method M Rt = 1.54 min |
| 63 | 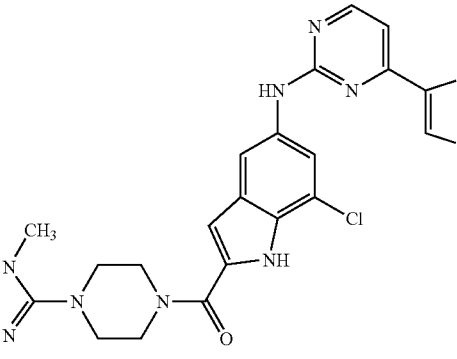 | 0.0099 | | | Starting from 8.1 analogous to Example 7 | HPLC: method M Rt = 1.55 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 64 | 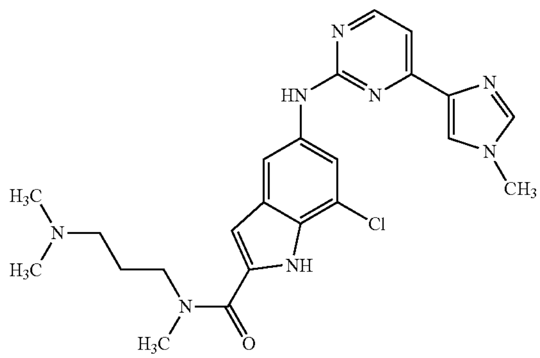 [SMILES: CN(C)CCCN(C)C(=O)c1cc2cc(Nc3nccc(-c4cn(C)cn4)n3)cc(Cl)c2[nH]1] | 0.0037 | | | Starting from 8.1 analogous to Example 7 | HPLC: method M Rt = 1.63 min |
| 65 | 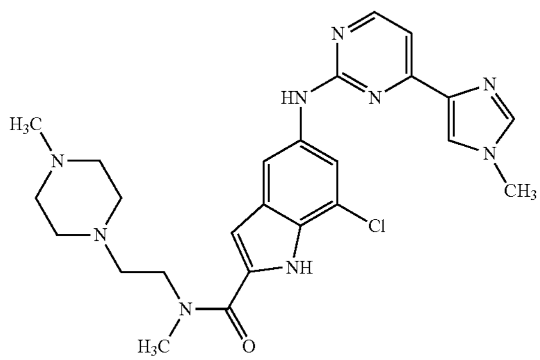 [SMILES: CN1CCN(CCN(C)C(=O)c2cc3cc(Nc4nccc(-c5cn(C)cn5)n4)cc(Cl)c3[nH]2)CC1] | 0.0075 | | | Starting from 8.1 analogous to Example 7 | HPLC: method M Rt = 1.51 min |
| 66 | 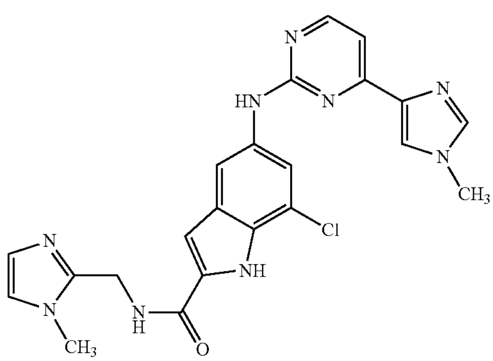 [SMILES: Cn1cnc(-c2ccnc(Nc3cc(Cl)c4[nH]c(C(=O)NCc5nccn5C)cc4c3)n2)c1] | 0.0016 | | | Starting from 8.1 analogous to Example 7 | HPLC: method M Rt = 1.52 min |
| 67 | 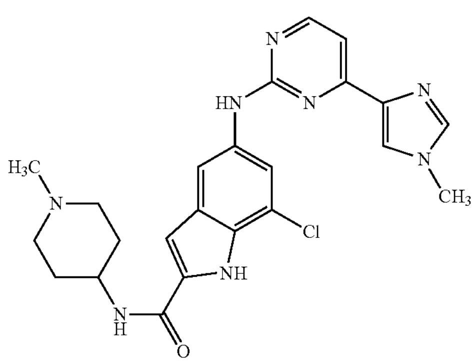 [SMILES: CN1CCC(NC(=O)c2cc3cc(Nc4nccc(-c5cn(C)cn5)n4)cc(Cl)c3[nH]2)CC1] | 0.0057 | 0.0079 | | Starting from 8.1 analogous to Example 7 | HPLC: method M Rt = 1.64 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 68 | 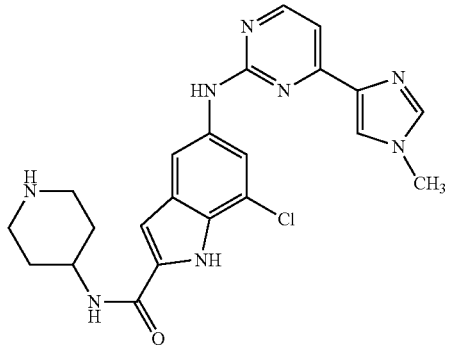 [SMILES: Cn1cnc(-c2ccnc(Nc3cc(Cl)c4[nH]c(C(=O)NC5CCNCC5)cc4c3)n2)c1] | 0.0102 | 0.0049 | | Starting from 8.1 analogous to Example 7 | HPLC: method M Rt = 1.56 min |
| 69 | 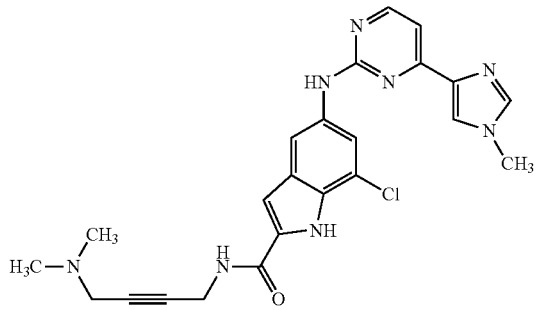 [SMILES: CN(C)CC#CCNC(=O)c1cc2cc(Nc3nccc(-c4cn(C)cn4)n3)cc(Cl)c2[nH]1] | 0.0073 | | | Starting from 8.1 analogous to Example 7 | HPLC: method M Rt = 1.64 min |
| 70 | 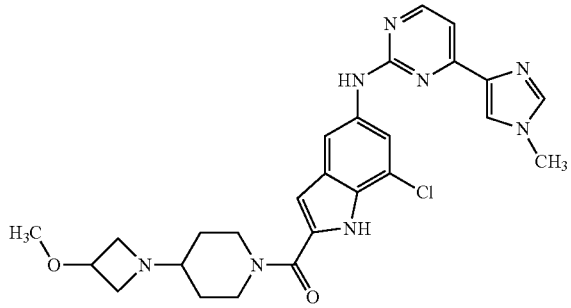 [SMILES: COC1CN(C2CCN(C(=O)c3cc4cc(Nc5nccc(-c6cn(C)cn6)n5)cc(Cl)c4[nH]3)CC2)C1] | 0.0062 | | | Starting from 8.1 analogous to Example 7 | HPLC: method M Rt = 1.43 min |
| 71 | 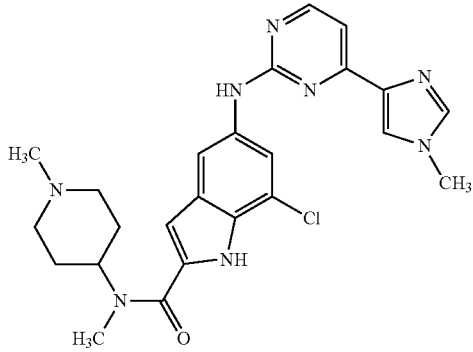 [SMILES: CN1CCC(N(C)C(=O)c2cc3cc(Nc4nccc(-c5cn(C)cn5)n4)cc(Cl)c3[nH]2)CC1] | 0.0040 | 0.0128 | | Starting from 8.1 analogous to Example 7 | HPLC: method D Rt = 0.82 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 72 | 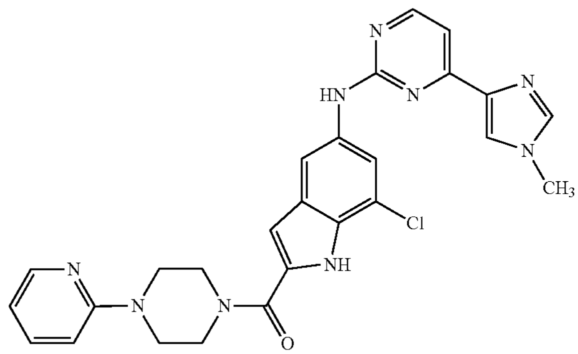 [SMILES: Cn1cnc(-c2ccnc(Nc3cc(Cl)c4[nH]c(C(=O)N5CCN(c6ccccn6)CC5)cc4c3)n2)c1] | 0.0091 | | | Starting from 8.1 analogous to Example 7 | HPLC: method M Rt = 1.66 min |
| 73 | 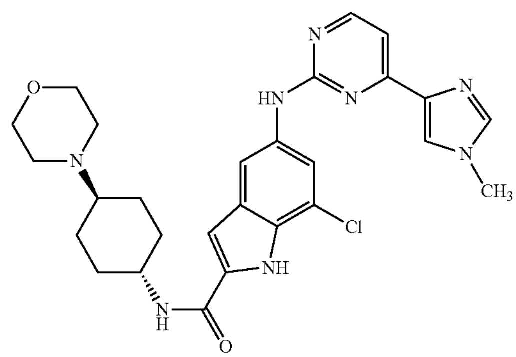 [SMILES: Cn1cnc(-c2ccnc(Nc3cc(Cl)c4[nH]c(C(=O)N[C@H]5CC[C@H](N6CCOCC6)CC5)cc4c3)n2)c1] | 0.0112 | | | Starting from 8.1 analogous to Example 7 | HPLC: method D Rt = 0.88 min |
| 74 | 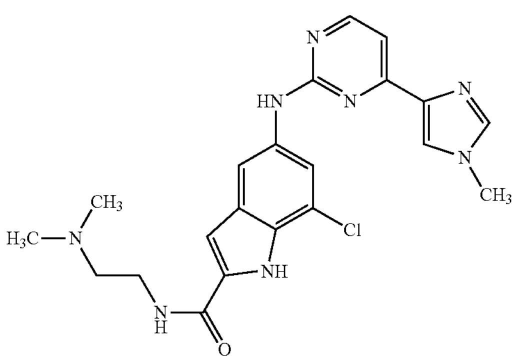 [SMILES: CN(C)CCNC(=O)c1cc2cc(Nc3nccc(-c4cn(C)cn4)n3)cc(Cl)c2[nH]1] | 0.0050 | | | Starting from 8.1 analogous to Example 7 | HPLC: method M Rt = 1.55 min |
| 75 | 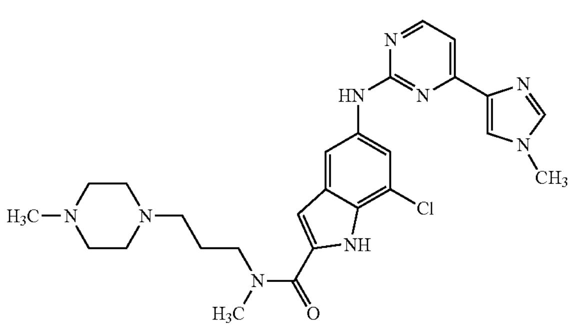 [SMILES: CN1CCN(CCCN(C)C(=O)c2cc3cc(Nc4nccc(-c5cn(C)cn5)n4)cc(Cl)c3[nH]2)CC1] | 0.0135 | | | Starting from 8.1 analogous to Example 7 | HPLC: method M Rt = 1.51 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 76 | 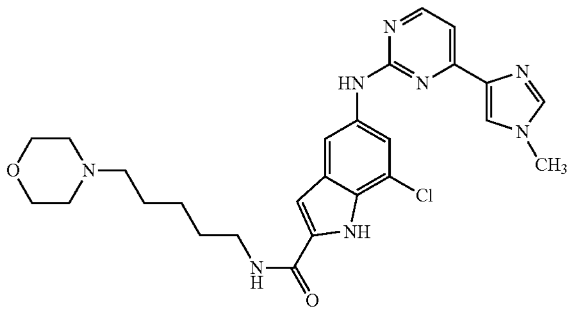 [SMILES: Cn1cnc(-c2ccnc(Nc3cc(Cl)c4[nH]c(C(=O)NCCCCCN5CCOCC5)cc4c3)n2)c1] | 0.0072 | | | Starting from 8.1 analogous to Example 7 | HPLC: method M Rt = 1.66 min |
| 77 | 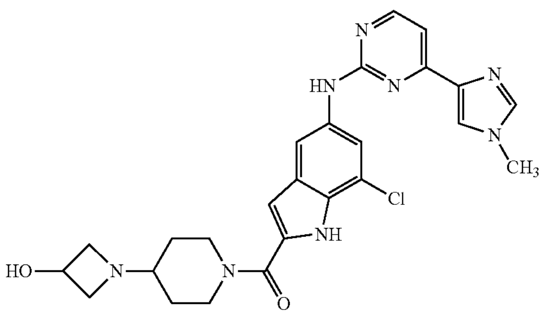 [SMILES: Cn1cnc(-c2ccnc(Nc3cc(Cl)c4[nH]c(C(=O)N5CCC(N6CC(O)C6)CC5)cc4c3)n2)c1] | 0.0107 | | | Starting from 8.1 analogous to Example 7 | HPLC: method M Rt = 1.41 min |
| 78 | 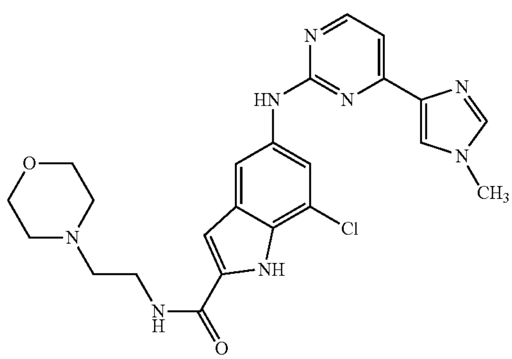 [SMILES: Cn1cnc(-c2ccnc(Nc3cc(Cl)c4[nH]c(C(=O)NCCN5CCOCC5)cc4c3)n2)c1] | 0.0024 | 0.0039 | | Starting from 8.1 analogous to Example 7 | HPLC: method M Rt = 1.52 min |
| 79 | 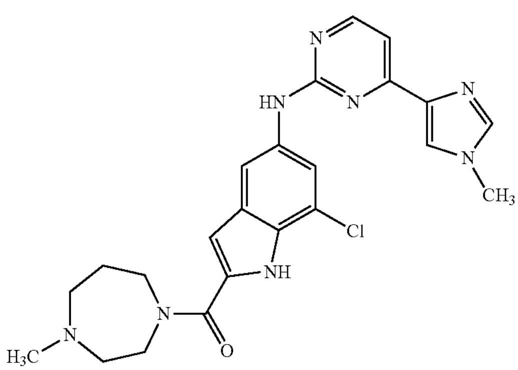 [SMILES: CN1CCCN(C(=O)c2cc3cc(Nc4nccc(-c5cn(C)cn5)n4)cc(Cl)c3[nH]2)CC1] | 0.0079 | | | Starting from 8.1 analogous to Example 7 | HPLC: method M Rt = 1.54 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 80 | 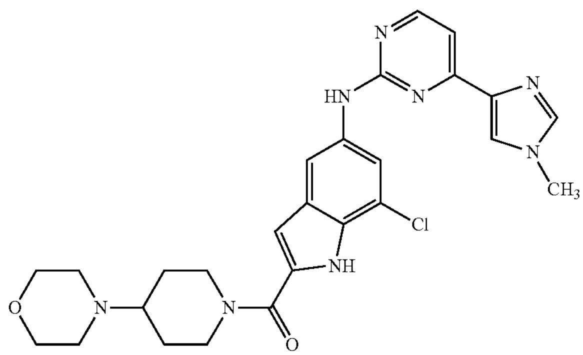 [SMILES: Cn1cnc(-c2ccnc(Nc3cc(Cl)c4[nH]c(C(=O)N5CCC(N6CCOCC6)CC5)cc4c3)n2)c1] | 0.0029 | | | Starting from 8.1 analogous to Example 7 | HPLC: method M Rt = 1.55 min |
| 81 | 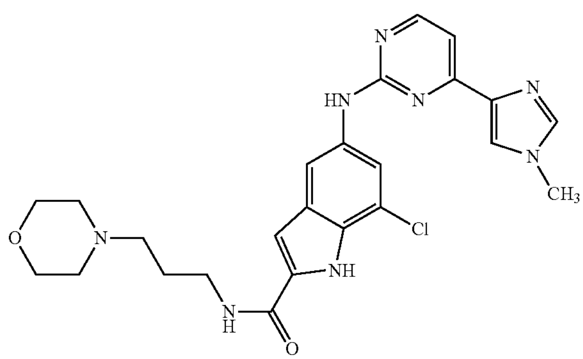 [SMILES: Cn1cnc(-c2ccnc(Nc3cc(Cl)c4[nH]c(C(=O)NCCCN5CCOCC5)cc4c3)n2)c1] | 0.0097 | | | Starting from 8.1 analogous to Example 7 | HPLC: method M Rt = 1.53 min |
| 82 | 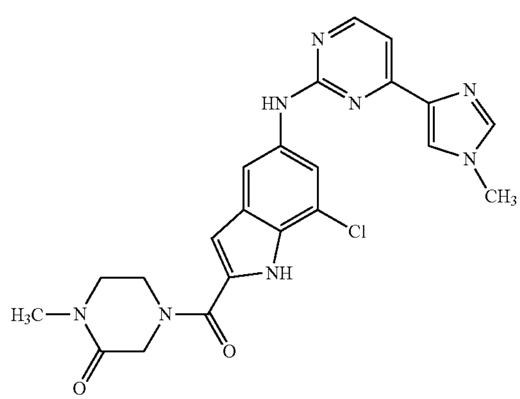 [SMILES: CN1CCN(C(=O)c2cc3cc(Nc4nccc(-c5cn(C)cn5)n4)cc(Cl)c3[nH]2)CC1=O] | 0.0027 | | | Starting from 8.1 analogous to Example 7 | HPLC: method M Rt = 1.43 min |
| 83 | 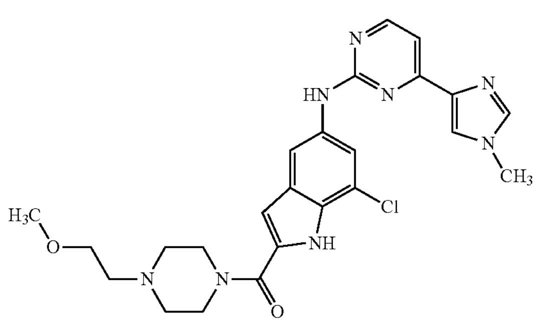 [SMILES: COCCN1CCN(C(=O)c2cc3cc(Nc4nccc(-c5cn(C)cn5)n4)cc(Cl)c3[nH]2)CC1] | 0.0024 | | | Starting from 8.1 analogous to Example 7 | HPLC: method M Rt = 1.56 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 84 | 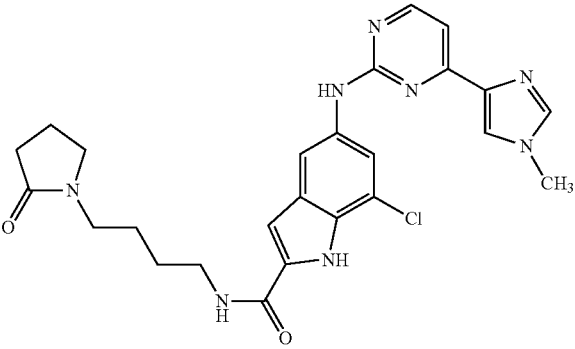 [SMILES: Cn1cnc(-c2ccnc(Nc3cc(Cl)c4[nH]c(C(=O)NCCCCN5CCCC5=O)cc4c3)n2)c1] | 0.0067 | 0.0022 | | Starting from 8.1 analogous to Example 7 | HPLC: method M Rt = 1.57 min |
| 85 | 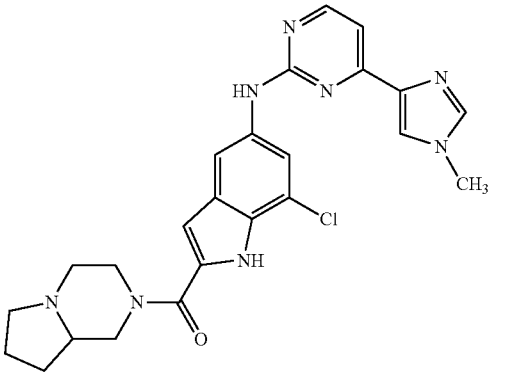 [SMILES: Cn1cnc(-c2ccnc(Nc3cc(Cl)c4[nH]c(C(=O)N5CCN6CCCC6C5)cc4c3)n2)c1] | 0.0036 | | | Starting from 8.1 analogous to Example 7 | HPLC: method M Rt = 1.64 min |
| 86 | 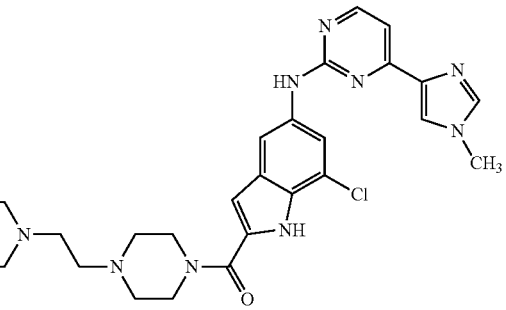 | 0.0040 | | | Starting from 8.1 analogous to Example 7 | HPLC: method D Rt = 0.80 min |
| 87 | 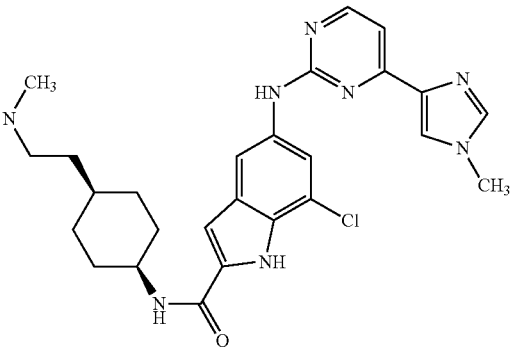 | 0.0106 | | | Starting from 8.1 analogous to Example 7 | HPLC: method D Rt = 0.95 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 88 | 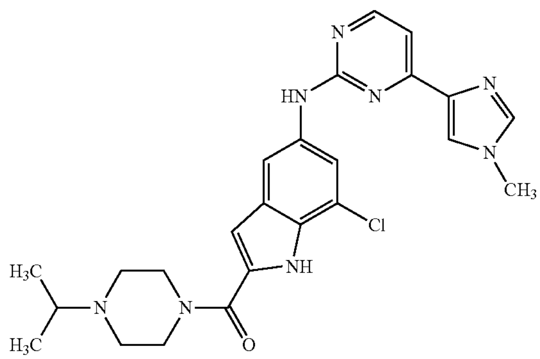 [SMILES: CC(C)N1CCN(C(=O)c2cc3cc(Nc4nccc(-c5cn(C)cn5)n4)cc(Cl)c3[nH]2)CC1] | 0.0064 | | | Starting from 8.1 analogous to Example 7 | HPLC: method M Rt = 1.65 min |
| 89 | Chiral | 0.0066 | | | Starting from 8.1 analogous to Example 7 | HPLC: method M Rt = 1.64 min |
| 90 | 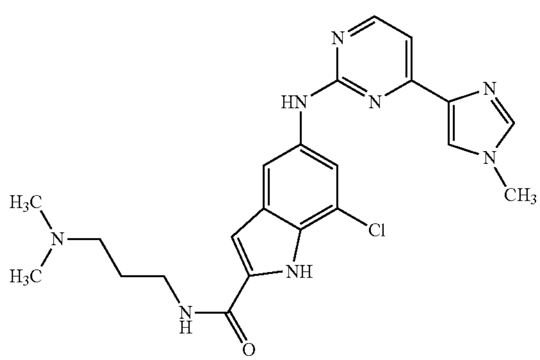 [SMILES: CN(C)CCCNC(=O)c1cc2cc(Nc3nccc(-c4cn(C)cn4)n3)cc(Cl)c2[nH]1] | 0.0038 | | | Starting from 8.1 analogous to Example 7 | HPLC: method M Rt = 1.62 min |
| 91 | 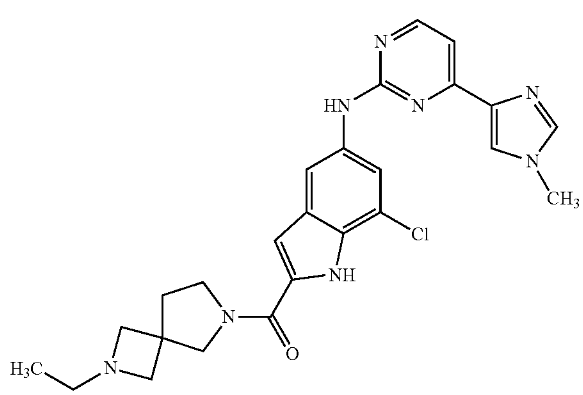 [SMILES: CCN1CC2(CCN(C(=O)c3cc4cc(Nc5nccc(-c6cn(C)cn6)n5)cc(Cl)c4[nH]3)C2)C1] | 0.0087 | | | Starting from 8.1 analogous to Example 7 | HPLC: method M Rt = 1.59 min |

TABLE 1-continued

Example compounds, their experimentally determined IC₅₀-values and details on the methods of preparing them

| Example No. | Structure | Syk Enzyme IC₅₀ [μM] (0.2% BSA) | Syk Enzyme IC50 [μM] (0.2% HSA) | Syk Enzyme IC₅₀ [μM] (1% HSA) | Method of preparation | Analytic data |
|---|---|---|---|---|---|---|
| 92 | 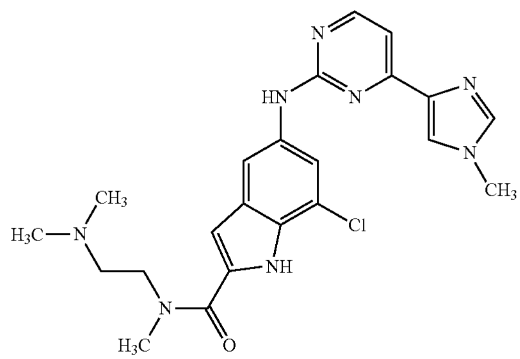 [SMILES: CN(C)CCN(C)C(=O)c1cc2cc(Nc3nccc(-c4cn(C)cn4)n3)cc(Cl)c2[nH]1] | 0.0125 | | | Starting from 8.1 analogous to Example 7 | HPLC: method M Rt = 1.61 min |
| 93 | 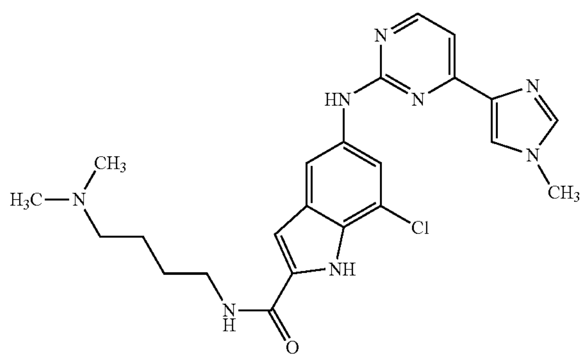 [SMILES: CN(C)CCCCNC(=O)c1cc2cc(Nc3nccc(-c4cn(C)cn4)n3)cc(Cl)c2[nH]1] | 0.0032 | | | Starting from 8.1 analogous to Example 7 | HPLC: method M Rt = 1.69 min |
| 94 | 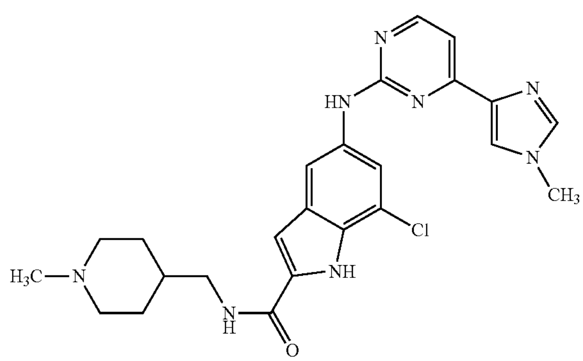 [SMILES: CN1CCC(CNC(=O)c2cc3cc(Nc4nccc(-c5cn(C)cn5)n4)cc(Cl)c3[nH]2)CC1] | 0.0069 | | | Starting from 8.1 analogous to Example 7 | HPLC: method M Rt = 1.67 min |
| 95 | 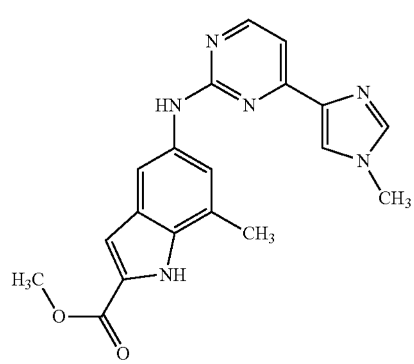 [SMILES: COC(=O)c1cc2cc(Nc3nccc(-c4cn(C)cn4)n3)cc(C)c2[nH]1] | 0.0014 | 0.0125 | | Starting from 7.8 analogous to Example 99 | HPLC: method H Rt = 1.45 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 96 | 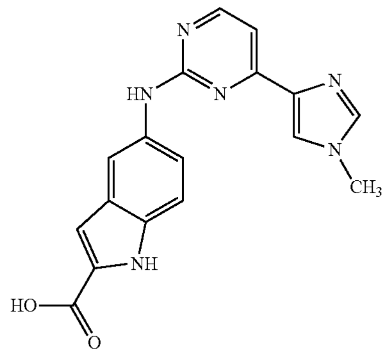 [SMILES: Cn1cnc(-c2ccnc(Nc3ccc4[nH]c(C(=O)O)cc4c3)n2)c1] | | 0.0798 | 0.1082 | Starting from 7.9 see 4.1.11 comound. 8.4 | HPLC: method D Rt = 0.82 min |
| 97 | 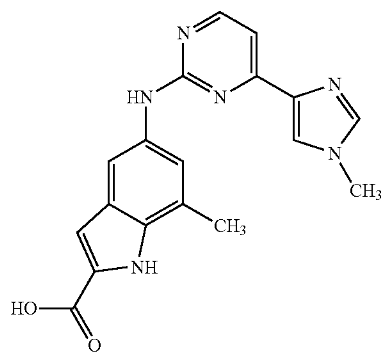 [SMILES: Cc1cc(Nc2nccc(-c3cn(C)cn3)n2)cc2cc(C(=O)O)[nH]c12] | | 0.0025 | 0.0092 | Starting from 7.8 see 4.1.11 compound 8.3 | HPLC: method D Rt = 0.88 min |
| 98 | 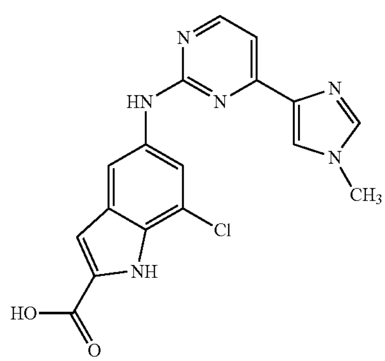 [SMILES: Cn1cnc(-c2ccnc(Nc3cc(Cl)c4[nH]c(C(=O)O)cc4c3)n2)c1] | | 0.0028 | 0.0083 | Starting from 7.3 see description 4.1.11 compound 8.1 | HPLC: method D Rt = 0.95 min |
| 99 | 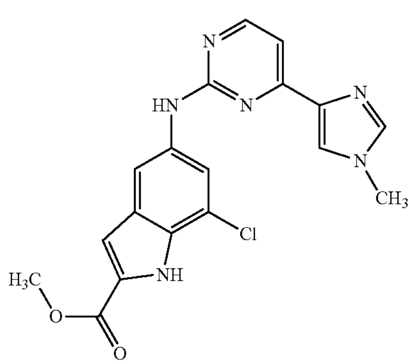 [SMILES: COC(=O)c1cc2cc(Nc3nccc(-c4cn(C)cn4)n3)cc(Cl)c2[nH]1] | | 0.0047 | 0.0157 | Starting from 7.3 see description 4.1.11 | HPLC: method D Rt = 1.05 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 100 | 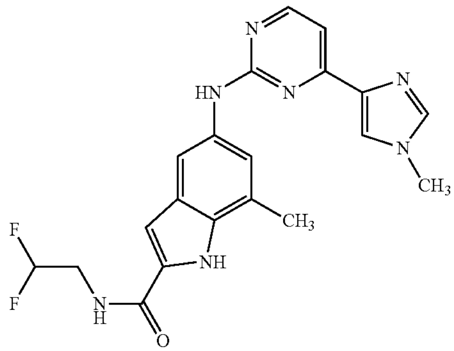 [SMILES: Cc1cc(Nc2nccc(-c3cn(C)cn3)n2)cc2cc(C(=O)NCC(F)F)[nH]c12] | | 0.0047 | 0.0216 | Starting from 8.3 analogous to Example 7 | HPLC: method D Rt = 0.94 min |
| 101 | 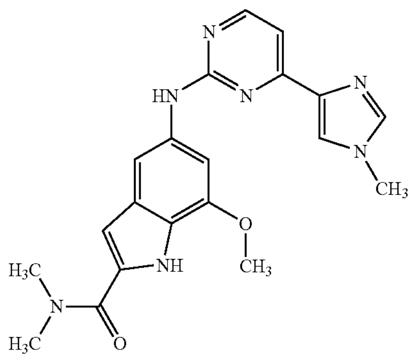 [SMILES: COc1cc(Nc2nccc(-c3cn(C)cn3)n2)cc2cc(C(=O)N(C)C)[nH]c12] | | 0.0018 | 0.0043 | Starting from 8.2 analogous to Example 7 | HPLC: method B Rt = 1.13 min |
| 102 | 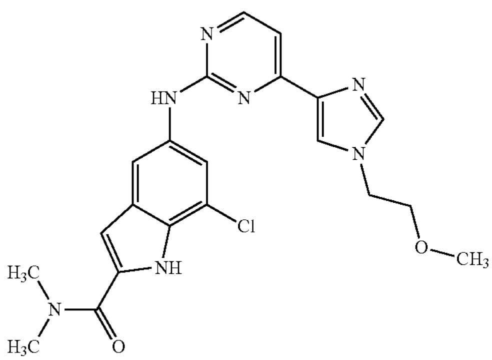 | | 0.0051 | 0.0117 | Starting from 7.1 and 4.4 analogous to Example 1 | HPLC: method B Rt = 1.22 min |
| 103 | 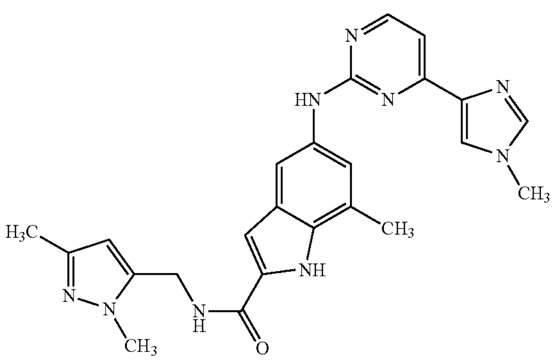 [SMILES: Cc1cc(CNC(=O)c2cc3cc(Nc4nccc(-c5cn(C)cn5)n4)cc(C)c3[nH]2)n(C)n1] | | 0.0012 | 0.0058 | Starting from 8.3 analogous to Example 7 | HPLC: method O Rt = 1.03 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 104 | 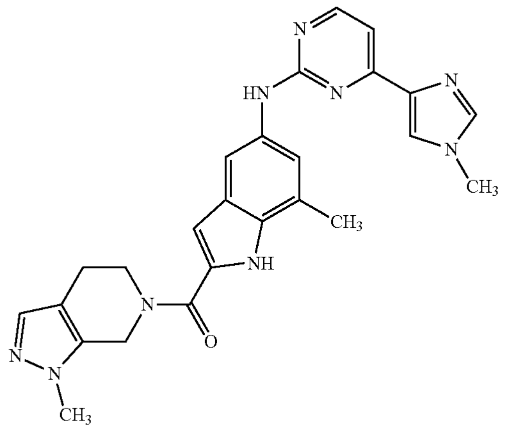 [SMILES: Cc1cc(Nc2nccc(-c3cn(C)cn3)n2)cc2cc(C(=O)N3CCc4cnn(C)c4C3)[nH]c12] | | 0.0159 | 0.0344 | Starting from 8.3 analogous to Example 7 | HPLC: method O Rt = 1.09 min |
| 105 | 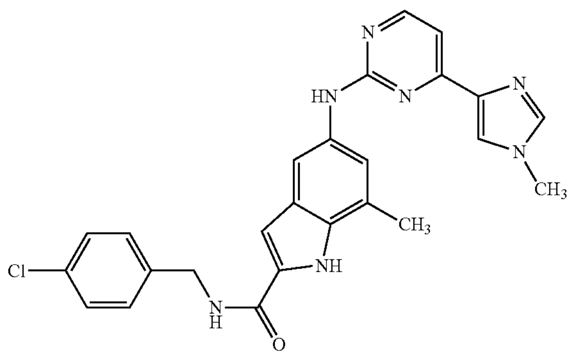 [SMILES: Cc1cc(Nc2nccc(-c3cn(C)cn3)n2)cc2cc(C(=O)NCc3ccc(Cl)cc3)[nH]c12] | | 0.0137 | | Starting from 8.3 analogous to Example 7 | HPLC: method O Rt = 1.38 min |
| 106 | Chiral | | 0.0115 | | Starting from 8.3 analogous to Example 7 | HPLC: method O Rt = 1.08 min |
| 107 | 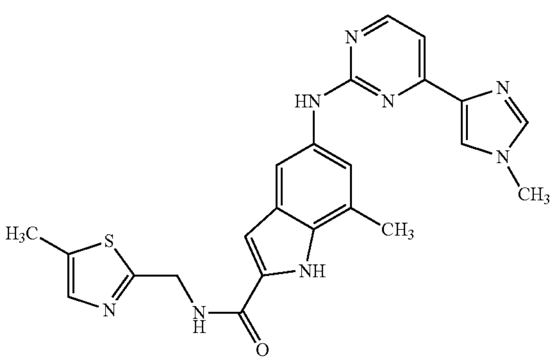 [SMILES: Cc1cnc(CNC(=O)c2cc3cc(Nc4nccc(-c5cn(C)cn5)n4)cc(C)c3[nH]2)s1] | | 0.0014 | 0.0034 | Starting from 8.3 analogous to Example 7 | HPLC: method O Rt = 1.13 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
| --- | --- | --- | --- | --- | --- | --- |
| 108 | 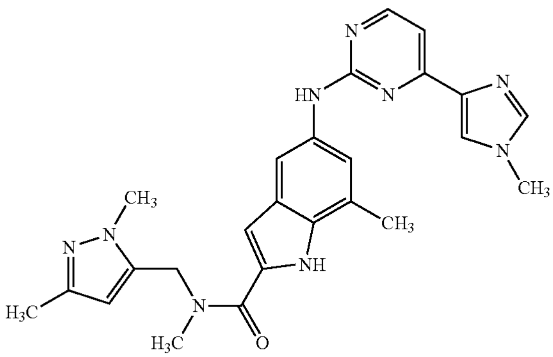 [SMILES: Cc1cc(CN(C)C(=O)c2cc3cc(Nc4nccc(-c5cn(C)cn5)n4)cc(C)c3[nH]2)n(C)n1] | | 0.0080 | 0.0149 | Starting from 8.3 analogous to Example 7 | HPLC: method O Rt = 1.09 min |
| 109 | 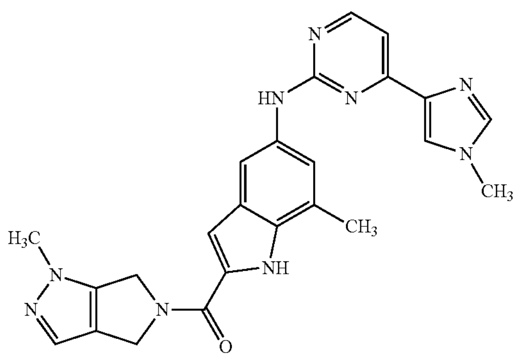 [SMILES: Cc1cc(Nc2nccc(-c3cn(C)cn3)n2)cc2cc(C(=O)N3Cc4cnn(C)c4C3)[nH]c12] | | 0.0089 | | Starting from 8.3 analogous to Example 7 | HPLC: method O Rt = 1.12 min |
| 110 | 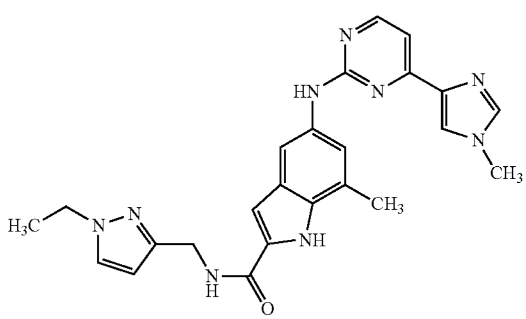 [SMILES: CCn1ccc(CNC(=O)c2cc3cc(Nc4nccc(-c5cn(C)cn5)n4)cc(C)c3[nH]2)n1] | | 0.0006 | 0.0017 | Starting from 8.3 analogous to Example 7 | HPLC: method O Rt = 1.09 min |
| 111 | 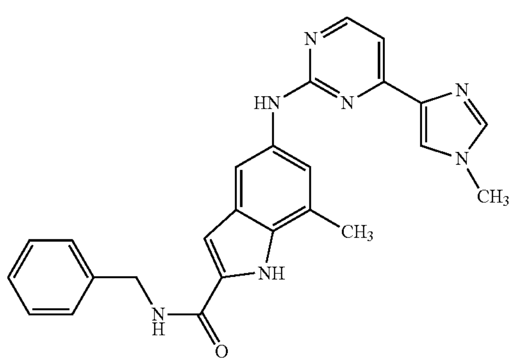 [SMILES: Cc1cc(Nc2nccc(-c3cn(C)cn3)n2)cc2cc(C(=O)NCc3ccccc3)[nH]c12] | | 0.0167 | | Starting from 8.3 analogous to Example 7 | HPLC: method D Rt = 1.10 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 112 | 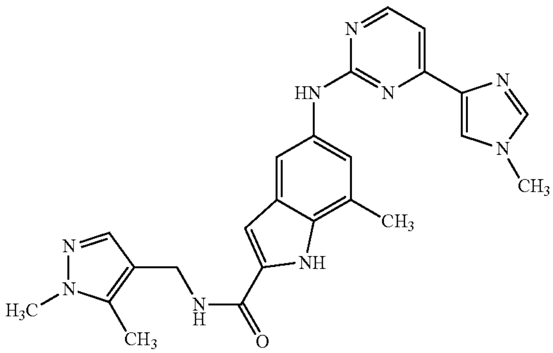 [SMILES: Cc1cc(Nc2nccc(-c3cn(C)cn3)n2)cc2cc(C(=O)NCc3cnn(C)c3C)[nH]c12] | | 0.0009 | 0.0021 | Starting from 8.3 analogous to Example 7 | HPLC: method O Rt = 1.02 min |
| 113 | 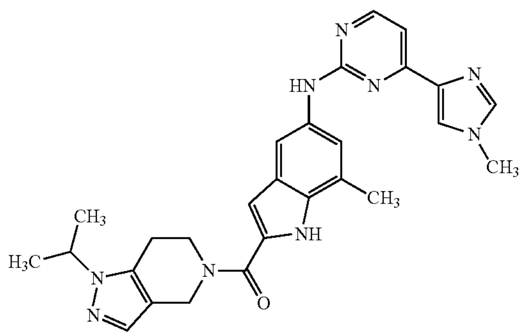 [SMILES: Cc1cc(Nc2nccc(-c3cn(C)cn3)n2)cc2cc(C(=O)N3CCc4c(cnn4C(C)C)C3)[nH]c12] | | 0.0076 | 0.0158 | Starting from 8.3 analogous to Example 7 | HPLC: method O Rt = 1.17 min |
| 114 | 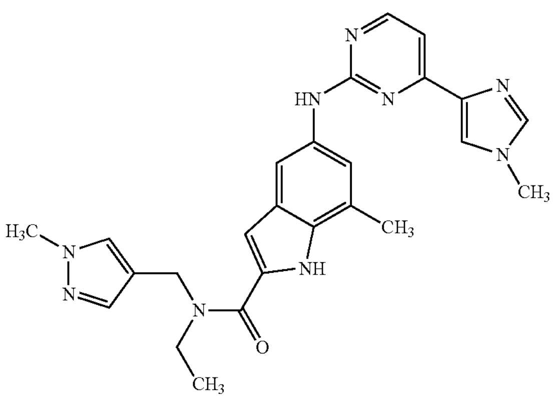 [SMILES: CCN(Cc1cnn(C)c1)C(=O)c1cc2cc(Nc3nccc(-c4cn(C)cn4)n3)cc(C)c2[nH]1] | | 0.0140 | 0.0229 | Starting from 8.3 analogous to Example 7 | HPLC: method O Rt = 1.10 min |
| 115 | 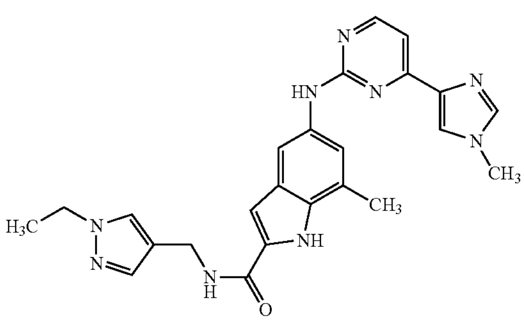 [SMILES: CCn1cc(CNC(=O)c2cc3cc(Nc4nccc(-c5cn(C)cn5)n4)cc(C)c3[nH]2)cn1] | | 0.0054 | 0.0179 | Starting from 8.3 analogous to Example 7 | HPLC: method O Rt = 1.06 min |

TABLE 1-continued

Example compounds, their experimentally determined IC₅₀-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 116 | 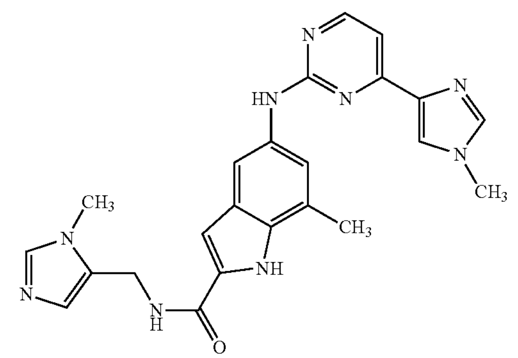 [SMILES: Cc1cc(Nc2nccc(-c3cn(C)cn3)n2)cc2cc(C(=O)NCc3cncn3C)[nH]c12] | | 0.0079 | 0.0245 | Starting from 8.3 analogous to Example 7 | HPLC: method O Rt = 0.75 min |
| 117 | 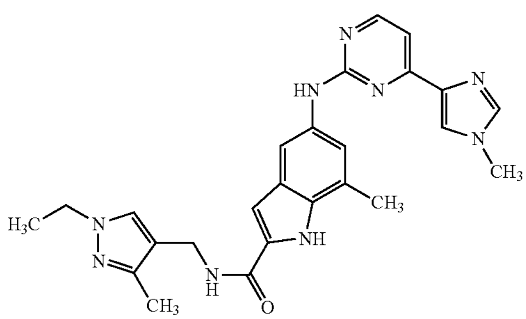 [SMILES: CCn1cc(CNC(=O)c2cc3cc(Nc4nccc(-c5cn(C)cn5)n4)cc(C)c3[nH]2)c(C)n1] | | 0.0035 | 0.0111 | Starting from 8.3 analogous to Example 7 | HPLC: method O Rt = 1.07 min |
| 118 | 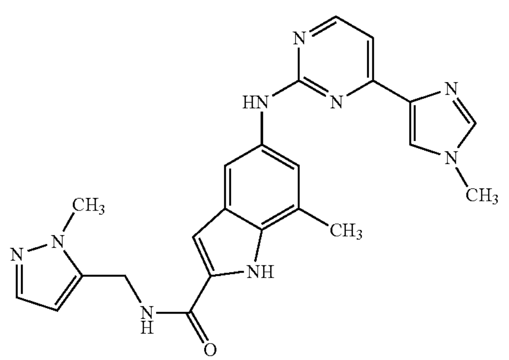 [SMILES: Cc1cc(Nc2nccc(-c3cn(C)cn3)n2)cc2cc(C(=O)NCc3ccnn3C)[nH]c12] | | 0.0019 | 0.0017 | Starting from 8.3 analogous to Example 7 | HPLC: method O Rt = 1.01 min |
| 119 | 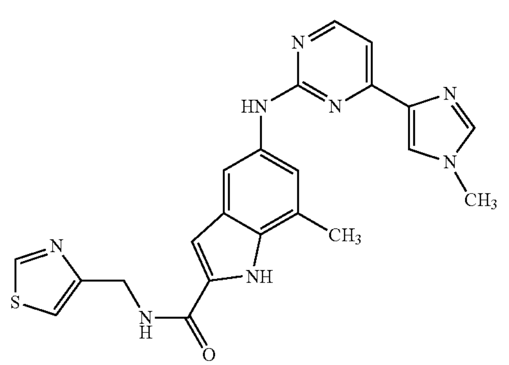 [SMILES: Cc1cc(Nc2nccc(-c3cn(C)cn3)n2)cc2cc(C(=O)NCc3cscn3)[nH]c12] | | 0.0092 | | Starting from 8.3 analogous to Example 7 | HPLC: method O Rt = 1.03 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 120 | 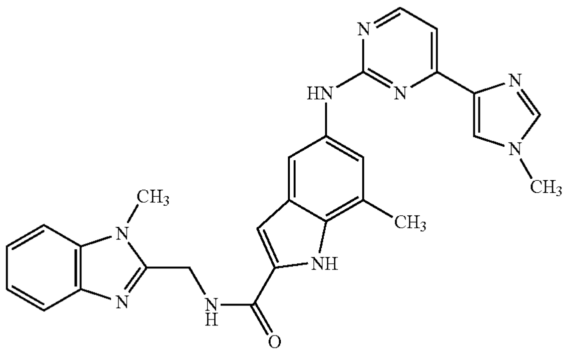 [SMILES: Cc1cc(Nc2nccc(-c3cn(C)cn3)n2)cc2cc(C(=O)NCc3nc4ccccc4n3C)[nH]c12] | | | 0.0013 | Starting from 8.3 analogous to Example 7 | HPLC: method D Rt = 0.90 min |
| 121 | 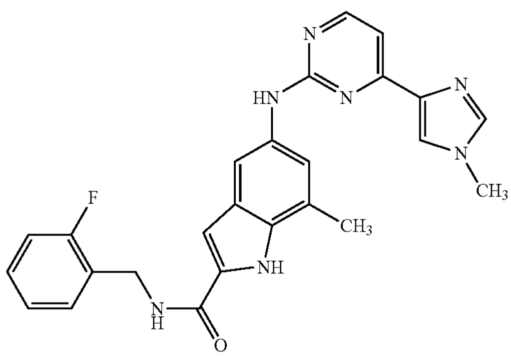 [SMILES: Cc1cc(Nc2nccc(-c3cn(C)cn3)n2)cc2cc(C(=O)NCc3ccccc3F)[nH]c12] | 0.0008 | 0.0029 | | Starting from 8.3 analogous to Example 7 | HPLC: method O Rt = 1.26 min |
| 122 | 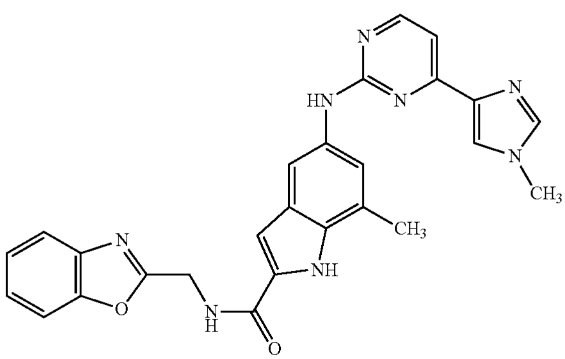 [SMILES: Cc1cc(Nc2nccc(-c3cn(C)cn3)n2)cc2cc(C(=O)NCc3nc4ccccc4o3)[nH]c12] | | | 0.0061 | Starting from 8.3 analogous to Example 7 | HPLC: method O Rt = 1.22 min |
| 123 | 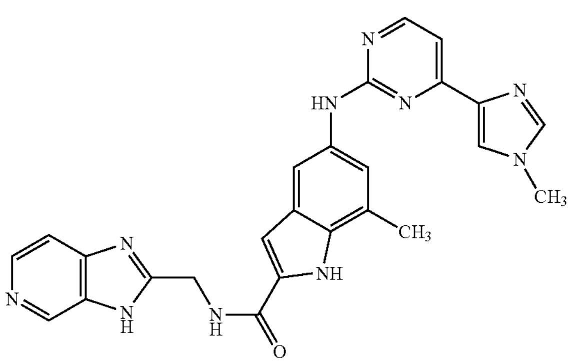 [SMILES: Cc1cc(Nc2nccc(-c3cn(C)cn3)n2)cc2cc(C(=O)NCc3nc4ccncc4[nH]3)[nH]c12] | 0.0006 | 0.0028 | | Starting from 8.3 analogous to Example 7 | HPLC: method O Rt = 0.76 min |

TABLE 1-continued

Example compounds, their experimentally determined IC₅₀-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
| --- | --- | --- | --- | --- | --- | --- |
| 124 | 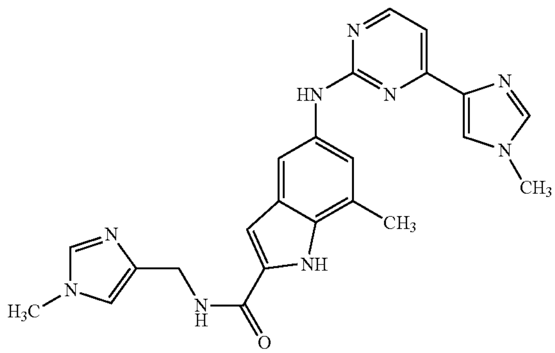 [SMILES: Cc1cc(Nc2nccc(-c3cn(C)cn3)n2)cc2cc(C(=O)NCc3cn(C)cn3)[nH]c12] | | | 0.0045 | Starting from 8.3 analogous to Example 7 | HPLC: method O Rt = 0.75 min |
| 125 | 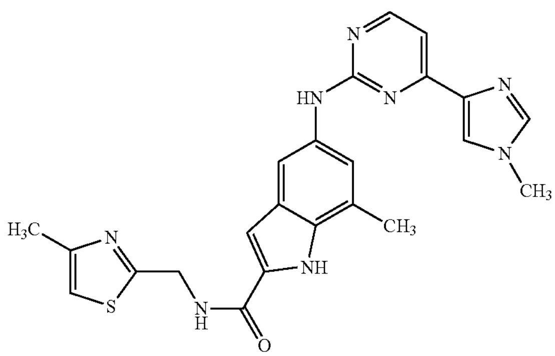 [SMILES: Cc1csc(CNC(=O)c2cc3cc(Nc4nccc(-c5cn(C)cn5)n4)cc(C)c3[nH]2)n1] | | | 0.0048 | Starting from 8.3 analogous to Example 7 | HPLC: method O Rt = 1.11 min |
| 126 | 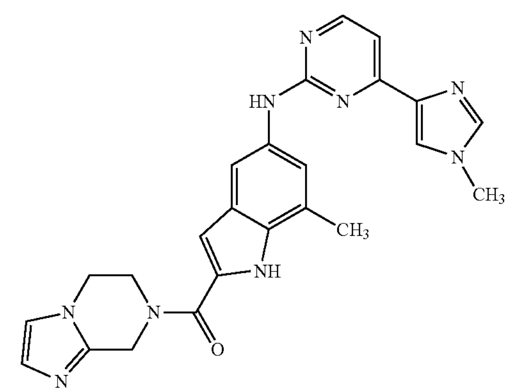 [SMILES: Cc1cc(Nc2nccc(-c3cn(C)cn3)n2)cc2cc(C(=O)N3CCn4ccnc4C3)[nH]c12] | 0.0167 | 0.0363 | | Starting from 8.3 analogous to Example 7 | HPLC: method O Rt = 0.71 min |
| 127 | 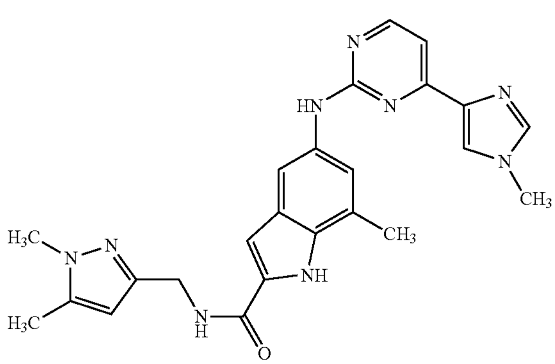 [SMILES: Cc1cc(Nc2nccc(-c3cn(C)cn3)n2)cc2cc(C(=O)NCc3cc(C)n(C)n3)[nH]c12] | 0.0018 | 0.0056 | | Starting from 8.3 analogous to Example 7 | HPLC: method O Rt = 1.06 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 128 | 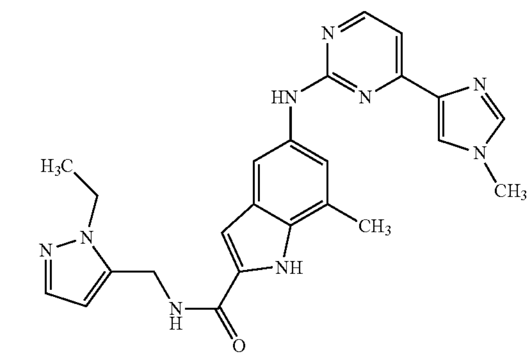 [SMILES: CCn1nccc1CNC(=O)c1cc2cc(Nc3nccc(-c4cn(C)cn4)n3)cc(C)c2[nH]1] | | | 0.0039 | Starting from 8.3 analogous to Example 7 | HPLC: method G Rt = 1.04 min |
| 129 | 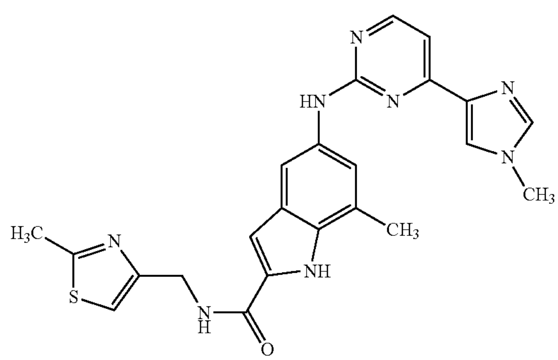 [SMILES: Cc1nc(CNC(=O)c2cc3cc(Nc4nccc(-c5cn(C)cn5)n4)cc(C)c3[nH]2)cs1] | 0.0033 | 0.0076 | | Starting from 8.3 analogous to Example 7 | HPLC: method O Rt = 1.08 min |
| 130 | 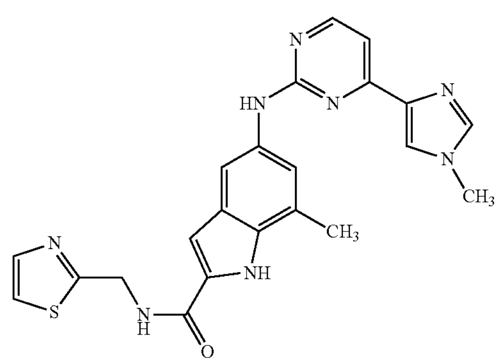 [SMILES: Cc1cc(Nc2nccc(-c3cn(C)cn3)n2)cc2cc(C(=O)NCc3nccs3)[nH]c12] | | | 0.0033 | Starting from 8.3 analogous to Example 7 | HPLC: method G Rt = 1.03 min |
| 131 | 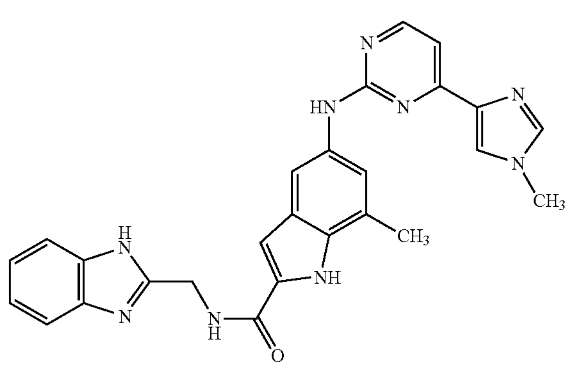 [SMILES: Cc1cc(Nc2nccc(-c3cn(C)cn3)n2)cc2cc(C(=O)NCc3nc4ccccc4[nH]3)[nH]c12] | | | 0.0045 | Starting from 8.3 analogous to Example 7 | HPLC: method D Rt = 0.90 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 132 | 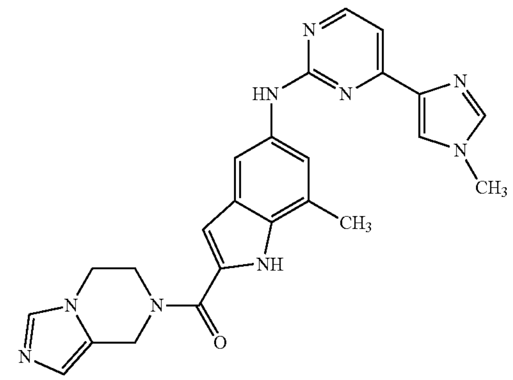 [SMILES: Cc1cc(Nc2nccc(-c3cn(C)cn3)n2)cc2cc(C(=O)N3CCn4cncc4C3)[nH]c12] | | 0.0124 | 0.0221 | Starting from 8.3 analogous to Example 7 | HPLC: method O Rt = 0.66 min |
| 133 | 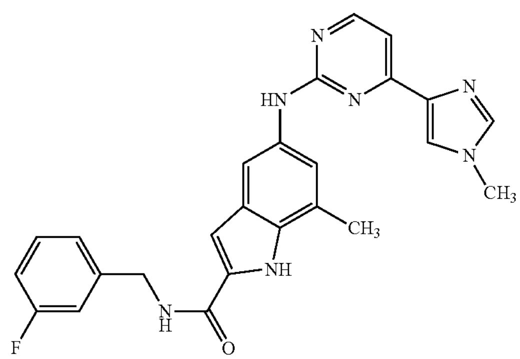 [SMILES: Cc1cc(Nc2nccc(-c3cn(C)cn3)n2)cc2cc(C(=O)NCc3cccc(F)c3)[nH]c12] | | 0.0098 | | Starting from 8.3 analogous to Example 7 | HPLC: method O Rt = 1.28 min |
| 134 | 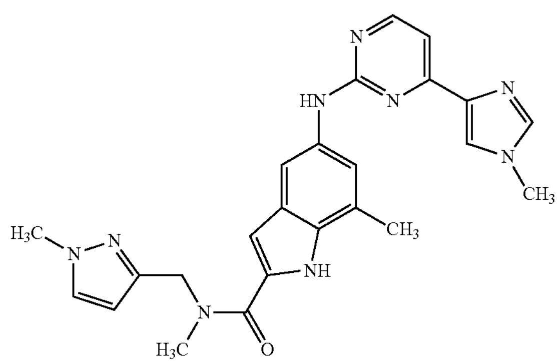 | | 0.0090 | 0.0216 | Starting from 8.3 analogous to Example 7 | HPLC: method O Rt = 1.07 min |
| 135 | 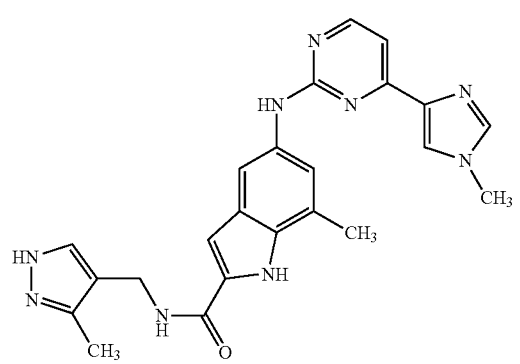 [SMILES: Cc1n[nH]cc1CNC(=O)c1cc2cc(Nc3nccc(-c4cn(C)cn4)n3)cc(C)c2[nH]1] | | 0.0083 | | Starting from 8.3 analogous to Example 7 | HPLC: method O Rt = 0.91 min |

TABLE 1-continued

Example compounds, their experimentally determined IC₅₀-values and details on the methods of preparing them

| Example No. | Structure | Syk Enzyme IC₅₀ [µM] (0.2% BSA) | Syk Enzyme IC50 [µM] (0.2% HSA) | Syk Enzyme IC₅₀ [µM] (1% HSA) | Method of preparation | Analytic data |
|---|---|---|---|---|---|---|
| 136 | 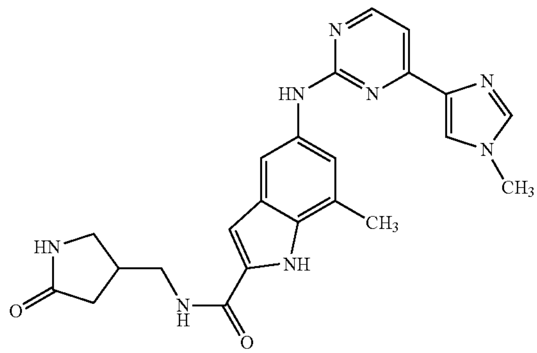 [SMILES: Cc1cc(Nc2nccc(-c3cn(C)cn3)n2)cc2cc(C(=O)NCC3CNC(=O)C3)[nH]c12] | | | 0.0092 | Starting from 8.3 analogous to Example 7 | HPLC: method O Rt = 0.89 min |
| 137 | 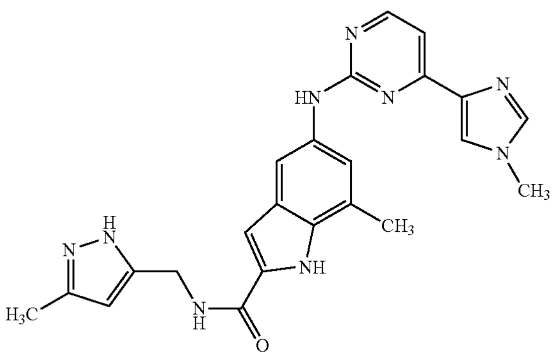 [SMILES: Cc1cc(CNC(=O)c2cc3cc(Nc4nccc(-c5cn(C)cn5)n4)cc(C)c3[nH]2)[nH]n1] | | | 0.0022 | Starting from 8.3 analogous to Example 7 | HPLC: method G Rt = 1.00 min |
| 138 | 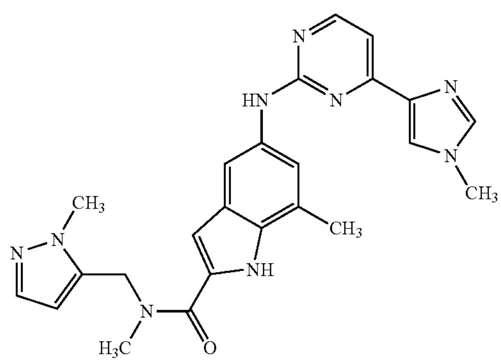 [SMILES: Cc1cc(Nc2nccc(-c3cn(C)cn3)n2)cc2cc(C(=O)N(C)Cc3ccnn3C)[nH]c12] | | 0.0034 | 0.0073 | Starting from 8.3 analogous to Example 7 | HPLC: method O Rt = 1.05 min |
| 139 | 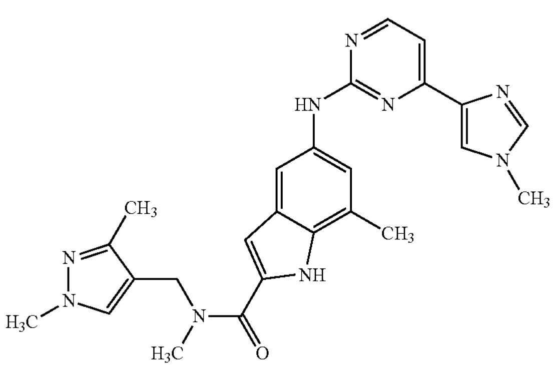 [SMILES: Cc1nn(C)cc1CN(C)C(=O)c1cc2cc(Nc3nccc(-c4cn(C)cn4)n3)cc(C)c2[nH]1] | | 0.0050 | 0.0172 | Starting from 8.3 analogous to Example 7 | HPLC: method O Rt = 1.06 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 140 | 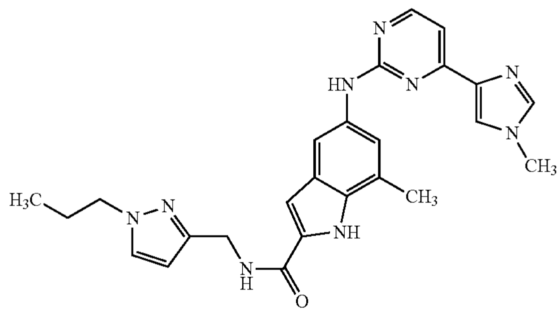 [SMILES: CCCn1ccc(CNC(=O)c2cc3cc(Nc4nccc(-c5cn(C)cn5)n4)cc(C)c3[nH]2)n1] | | | 0.0165 | Starting from 8.3 analogous to Example 7 | HPLC: method O Rt = 1.17 min |
| 141 | Chiral | | | 0.0037 | Starting from 8.3 analogous to Example 7 | HPLC: method O Rt = 1.08 min |
| 142 | 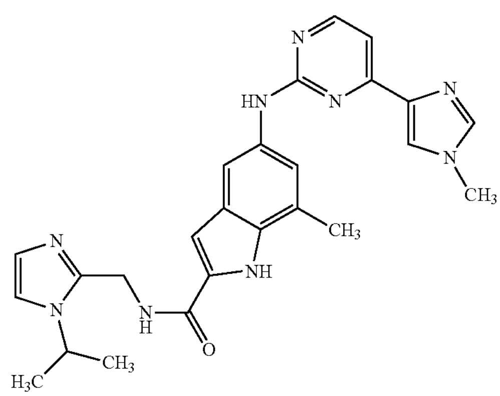 [SMILES: Cc1cc(Nc2nccc(-c3cn(C)cn3)n2)cc2cc(C(=O)NCc3nccn3C(C)C)[nH]c12] | | | 0.0134 | Starting from 8.3 analogous to Example 7 | HPLC: method O Rt = 0.83 min |
| 143 | 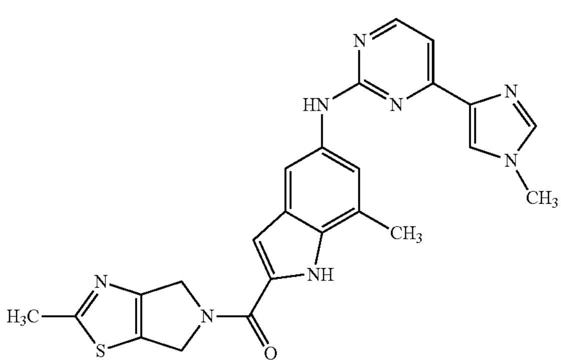 [SMILES: Cc1nc2c(s1)CN(C(=O)c1cc3cc(Nc4nccc(-c5cn(C)cn5)n4)cc(C)c3[nH]1)C2] | | 0.0035 | 0.0159 | Starting from 8.3 analogous to Example 7 | HPLC: method O Rt = 1.23 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 144 | 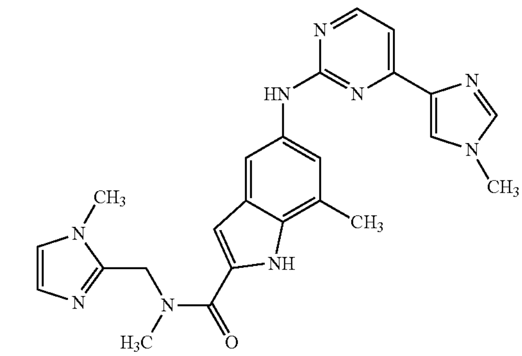 [SMILES: Cc1cc(Nc2nccc(-c3cn(C)cn3)n2)cc2cc(C(=O)N(C)Cc3nccn3C)[nH]c12] | | 0.0121 | 0.0243 | Starting from 8.3 analogous to Example 7 | HPLC: method O Rt = 0.73 min |
| 145 | 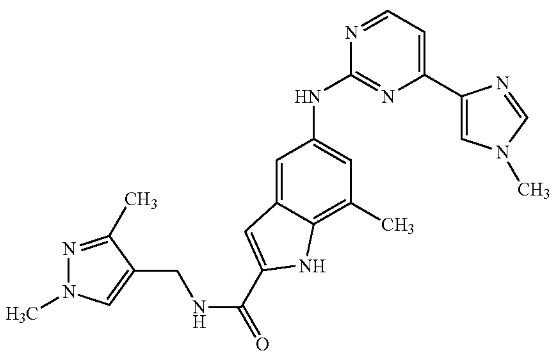 [SMILES: Cc1nn(C)cc1CNC(=O)c1cc2cc(Nc3nccc(-c4cn(C)cn4)n3)cc(C)c2[nH]1] | | 0.0012 | 0.0034 | Starting from 8.3 analogous to Example 7 | HPLC: method O Rt = 1.02 min |
| 146 | 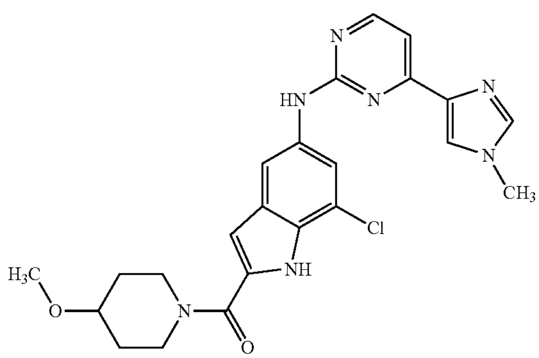 [SMILES: COC1CCN(C(=O)c2cc3cc(Nc4nccc(-c5cn(C)cn5)n4)cc(Cl)c3[nH]2)CC1] | | | 0.0121 | Starting from 8.1 analogous to Example 7 | HPLC: method N Rt = 0.38 min |
| 147 | 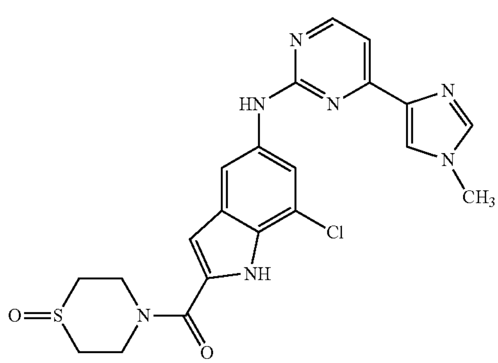 [SMILES: Cn1cnc(-c2ccnc(Nc3cc(Cl)c4[nH]c(C(=O)N5CCS(=O)CC5)cc4c3)n2)c1] | | | 0.0083 | Starting from 8.1 analogous to Example 7 | HPLC: method N Rt = 0.33 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 148 | 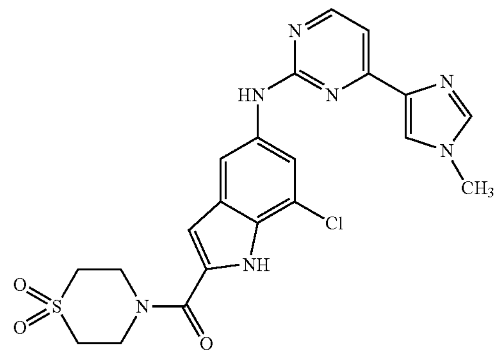 [SMILES: Cn1cnc(-c2ccnc(Nc3cc(Cl)c4[nH]c(C(=O)N5CCS(=O)(=O)CC5)cc4c3)n2)c1] | | | 0.0037 | Starting from 8.1 analogous to Example 7 | HPLC: method N Rt = 0.35 min |
| 149 | 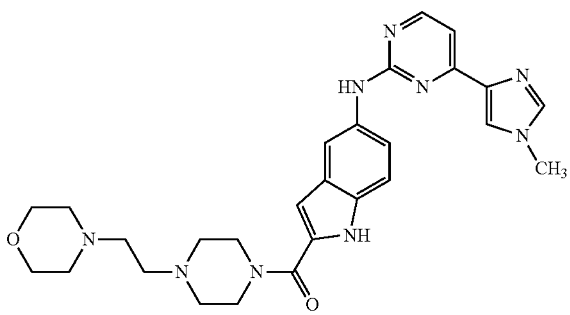 [SMILES: Cn1cnc(-c2ccnc(Nc3ccc4[nH]c(C(=O)N5CCN(CCN6CCOCC6)CC5)cc4c3)n2)c1] | | 0.0692 | 0.0839 | Starting from 8.4 analogous to Example 7 | HPLC: method N Rt = 0.34 min |
| 150 | 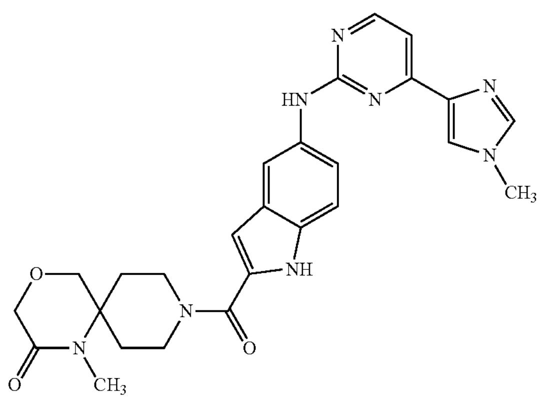 [SMILES: CN1C(=O)COCC12CCN(C(=O)c1cc3cc(Nc4nccc(-c5cn(C)cn5)n4)ccc3[nH]1)CC2] | | | 0.0112 | Starting from 8.4 analogous to Example 7 | HPLC: method D Rt = 0.87 min |
| 151 | 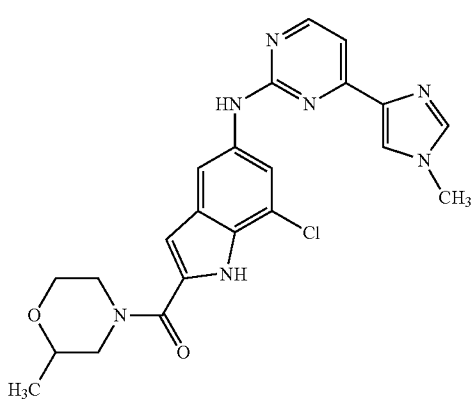 [SMILES: CC1CN(C(=O)c2cc3cc(Nc4nccc(-c5cn(C)cn5)n4)cc(Cl)c3[nH]2)CCO1] | | | 0.0109 | Starting from 8.1 analogous to Example 7 | HPLC: method N Rt = 0.38 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 152 | 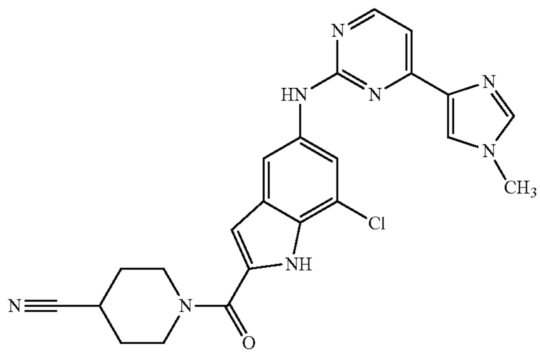 [SMILES: Cn1cnc(-c2ccnc(Nc3cc(Cl)c4[nH]c(C(=O)N5CCC(C#N)CC5)cc4c3)n2)c1] | | | 0.0051 | Starting from 8.1 analogous to Example 7 | HPLC: method D Rt = 0.99 min |
| 153 | 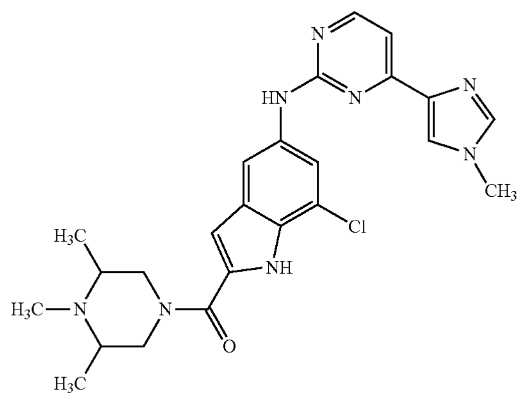 [SMILES: CC1CN(C(=O)c2cc3cc(Nc4nccc(-c5cn(C)cn5)n4)cc(Cl)c3[nH]2)CC(C)N1C] | | | 0.0131 | Starting from 8.1 analogous to Example 7 | HPLC: method N Rt = 0.39 min |
| 154 | 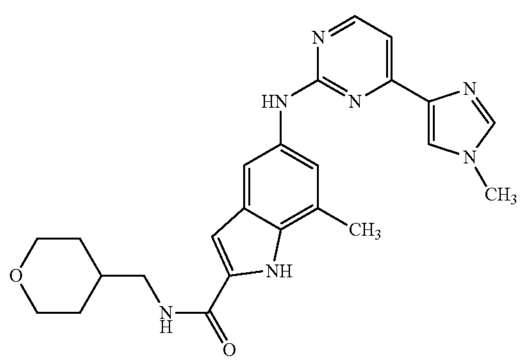 [SMILES: Cc1cc(Nc2nccc(-c3cn(C)cn3)n2)cc2cc(C(=O)NCC3CCOCC3)[nH]c12] | | | 0.0043 | Starting from 8.3 analogous to Example 7 | HPLC: method G Rt = 1.04 min |
| 155 | 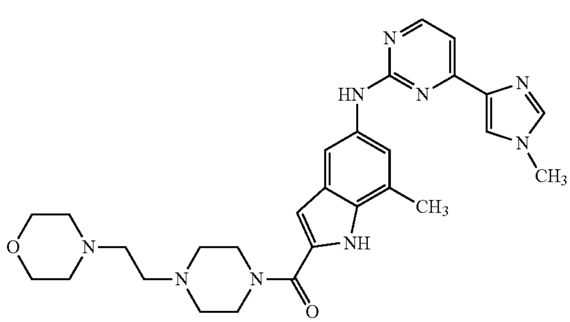 [SMILES: Cc1cc(Nc2nccc(-c3cn(C)cn3)n2)cc2cc(C(=O)N3CCN(CCN4CCOCC4)CC3)[nH]c12] | | 0.0113 | 0.0149 | Starting from 8.3 analogous to Example 7 | HPLC: method N Rt = 0.41 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 156 | 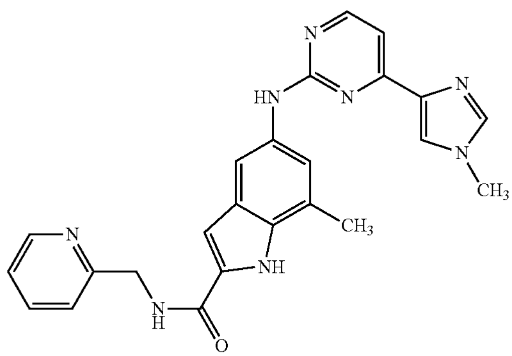 [SMILES: Cc1cc(Nc2nccc(-c3cn(C)cn3)n2)cc2cc(C(=O)NCc3ccccn3)[nH]c12] | | 0.0005 | 0.0011 | Starting from 8.3 analogous to Example 7 | HPLC: method O Rt = 0.78 min |
| 157 | 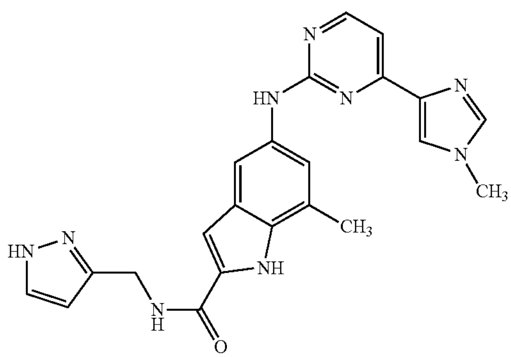 [SMILES: Cc1cc(Nc2nccc(-c3cn(C)cn3)n2)cc2cc(C(=O)NCc3cc[nH]n3)[nH]c12] | | | 0.0040 | Starting from 8.3 analogous to Example 7 | HPLC: method G Rt = 0.98 min |
| 158 | 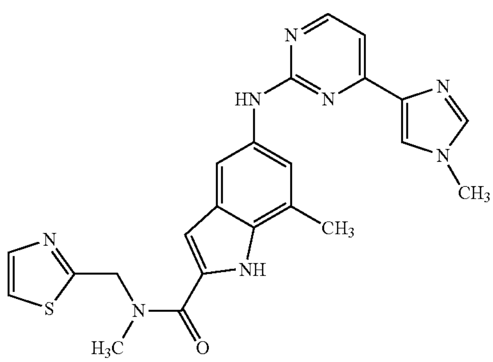 [SMILES: Cc1cc(Nc2nccc(-c3cn(C)cn3)n2)cc2cc(C(=O)N(C)Cc3nccs3)[nH]c12] | | 0.0069 | 0.0247 | Starting from 8.3 analogous to Example 7 | HPLC: method O Rt = 1.10 min |
| 159 | 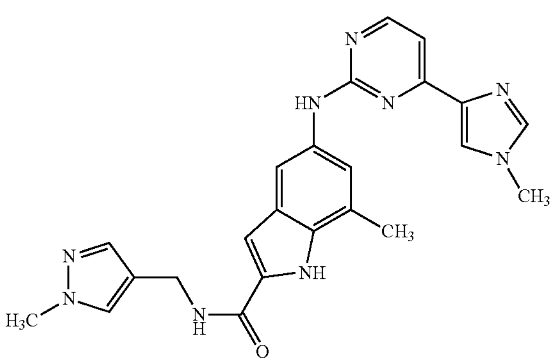 [SMILES: Cc1cc(Nc2nccc(-c3cn(C)cn3)n2)cc2cc(C(=O)NCc3cnn(C)c3)[nH]c12] | | | 0.0102 | Starting from 8.3 analogous to Example 7 | HPLC: method O Rt = 0.99 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 160 | 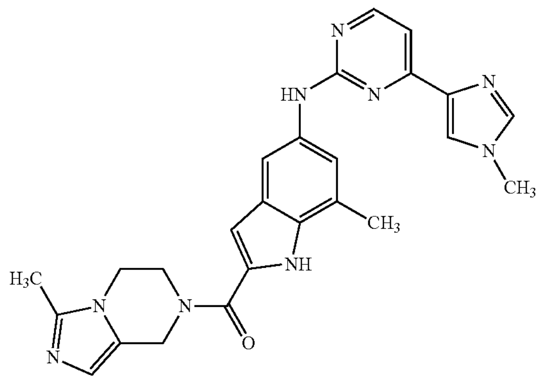 [SMILES: Cc1cc(Nc2nccc(-c3cn(C)cn3)n2)cc2cc(C(=O)N3CCn4c(cnc4C)C3)[nH]c12] | | 0.0213 | 0.0216 | Starting from 8.3 analogous to Example 7 | HPLC: method O Rt = 0.73 min |
| 161 | 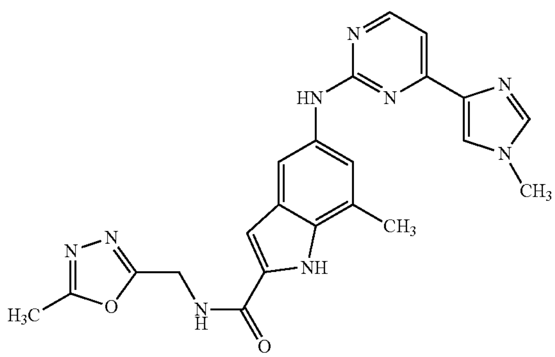 [SMILES: Cc1nnc(CNC(=O)c2cc3cc(Nc4nccc(-c5cn(C)cn5)n4)cc(C)c3[nH]2)o1] | | | 0.0096 | Starting from 8.3 analogous to Example 7 | HPLC: method O Rt = 0.92 min |
| 162 | 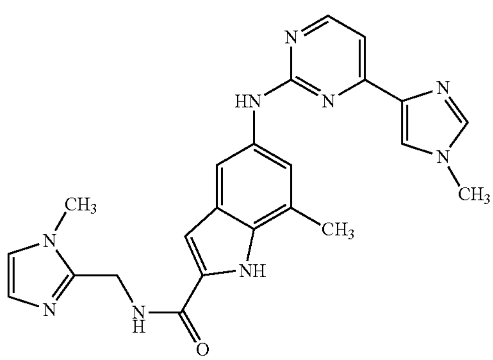 [SMILES: Cc1cc(Nc2nccc(-c3cn(C)cn3)n2)cc2cc(C(=O)NCc3nccn3C)[nH]c12] | | | 0.0035 | Starting from 8.3 analogous to Example 7 | HPLC: method G Rt = 1.00 min |
| 163 | 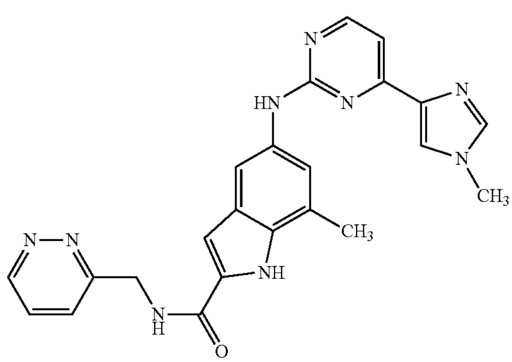 | | | 0.0038 | Starting from 8.3 analogous to Example 7 | HPLC: method G Rt = 0.96 min |

TABLE 1-continued

Example compounds, their experimentally determined IC50-values and details on the methods of preparing them

| Example No. | Structure | Syk Enzyme IC50 [μM] (0.2% BSA) | Syk Enzyme IC50 [μM] (0.2% HSA) | Syk Enzyme IC50 [μM] (1% HSA) | Method of preparation | Analytic data |
|---|---|---|---|---|---|---|
| 164 | 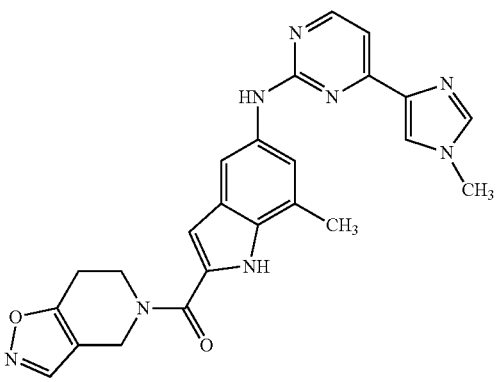 [SMILES: Cc1cc(Nc2nccc(-c3cn(C)cn3)n2)cc2cc(C(=O)N3CCc4oncc4C3)[nH]c12] | | 0.0063 | 0.0115 | Starting from 8.3 analogous to Example 7 | HPLC: method O Rt = 1.03 min |
| 165 | 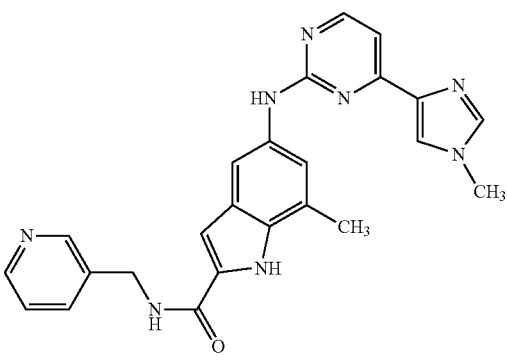 [SMILES: Cc1cc(Nc2nccc(-c3cn(C)cn3)n2)cc2cc(C(=O)NCc3cccnc3)[nH]c12] | | 0.0015 | 0.0018 | Starting from 8.3 analogous to Example 7 | HPLC: method O Rt = 0.76 min |
| 166 | 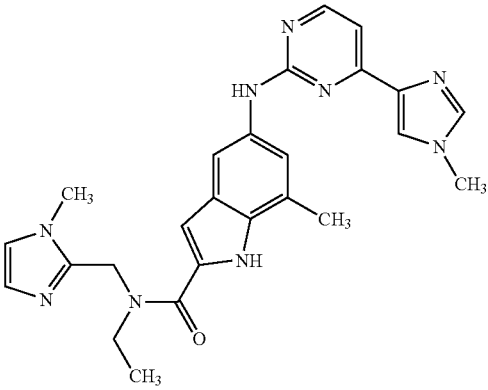 [SMILES: CCN(Cc1nccn1C)C(=O)c1cc2cc(Nc3nccc(-c4cn(C)cn4)n3)cc(C)c2[nH]1] | | 0.0133 | 0.0289 | Starting from 8.3 analogous to Example 7 | HPLC: method O Rt = 0.78 min |
| 167 | 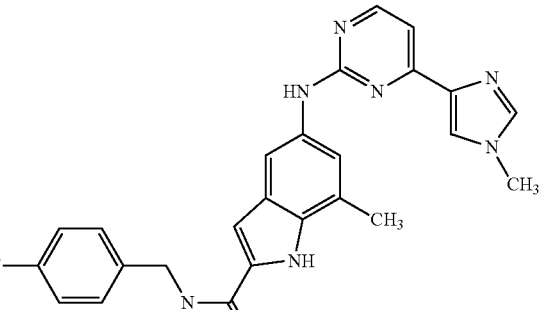 | | | 0.0120 | Starting from 8.3 analogous to Example 7 | HPLC: method O Rt = 1.28 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 168 | 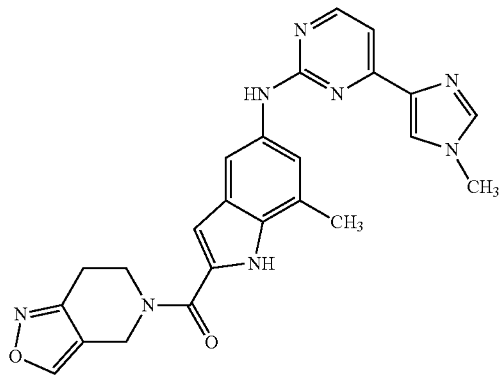 [SMILES: Cc1cc(Nc2nccc(-c3cn(C)cn3)n2)cc2cc(C(=O)N3CCc4nocc4C3)[nH]c12] | | 0.0075 | 0.0187 | Starting from 8.3 analogous to Example 7 | HPLC: method O Rt = 1.03 min |
| 169 | 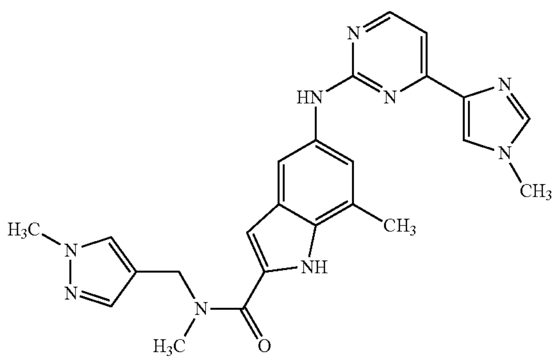 [SMILES: Cc1cc(Nc2nccc(-c3cn(C)cn3)n2)cc2cc(C(=O)N(C)Cc3cnn(C)c3)[nH]c12] | | 0.0051 | 0.0099 | Starting from 8.3 analogous to Example 7 | HPLC: method O Rt = 1.03 min |
| 170 | 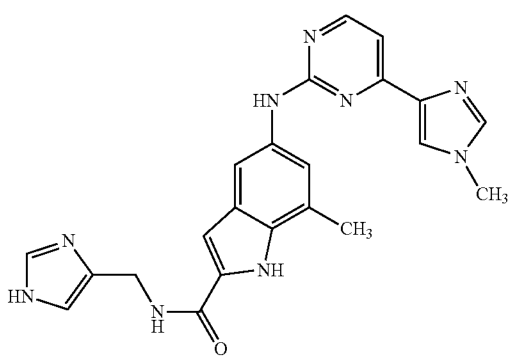 [SMILES: Cc1cc(Nc2nccc(-c3cn(C)cn3)n2)cc2cc(C(=O)NCc3c[nH]cn3)[nH]c12] | | 0.0020 | 0.0063 | Starting from 8.3 analogous to Example 7 | HPLC: method O Rt = 0.75 min |
| 171 | 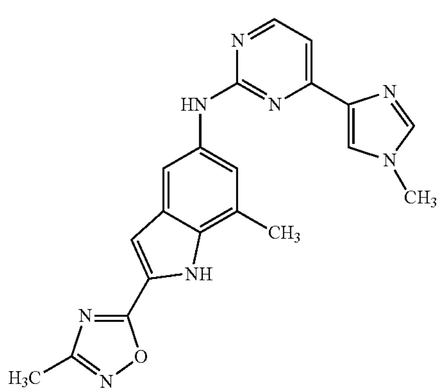 [SMILES: Cc1noc(-c2cc3cc(Nc4nccc(-c5cn(C)cn5)n4)cc(C)c3[nH]2)n1] | | 0.0014 | 0.0034 | Starting from 8.3 see description 4.2.5 | HPLC: method D Rt = 1.07 min |

TABLE 1-continued

Example compounds, their experimentally determined IC$_{50}$-values and details on the methods of preparing them

| Example No. | Structure | Syk Enzyme IC$_{50}$ [μM] (0.2% BSA) | Syk Enzyme IC50 [μM] (0.2% HSA) | Syk Enzyme IC$_{50}$ [μM] (1% HSA) | Method of preparation | Analytic data |
|---|---|---|---|---|---|---|
| 172 | 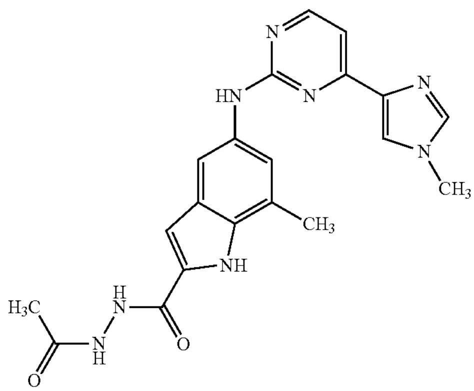 [SMILES: CC(=O)NNC(=O)c1cc2cc(Nc3nccc(-c4cn(C)cn4)n3)cc(C)c2[nH]1] | | 0.0028 | 0.0042 | analogous to Example 174 or starting from 8.3 analogous to Example 7 | HPLC: method D Rt = 0.78 min |
| 173 | 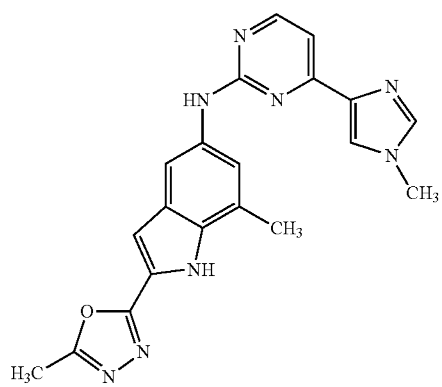 [SMILES: Cc1nnc(-c2cc3cc(Nc4nccc(-c5cn(C)cn5)n4)cc(C)c3[nH]2)o1] | | 0.0014 | 0.0022 | Starting from 8.3 analogous to Example 175 | HPLC: method D Rt = 0.99 min |
| 174 | 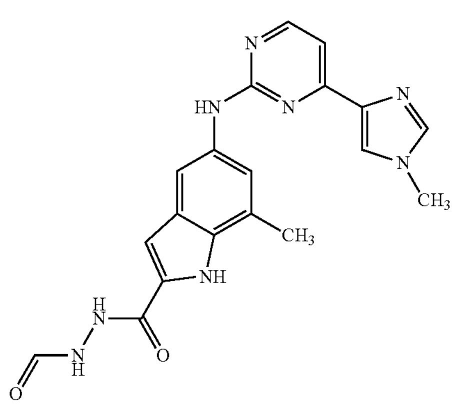 [SMILES: Cc1cc(Nc2nccc(-c3cn(C)cn3)n2)cc2cc(C(=O)NNC=O)[nH]c12] | | 0.0022 | 0.0029 | see description 4.2.6 or starting from 8.3 analogous to Example 7 | HPLC: method G Rt = 0.72 min |

TABLE 1-continued

Example compounds, their experimentally determined IC$_{50}$-values and details on the methods of preparing them

| Example No. | Structure | Syk Enzyme IC$_{50}$ [µM] (0.2% BSA) | Syk Enzyme IC50 [µM] (0.2% HSA) | Syk Enzyme IC$_{50}$ [µM] (1% HSA) | Method of preparation | Analytic data |
|---|---|---|---|---|---|---|
| 175 | 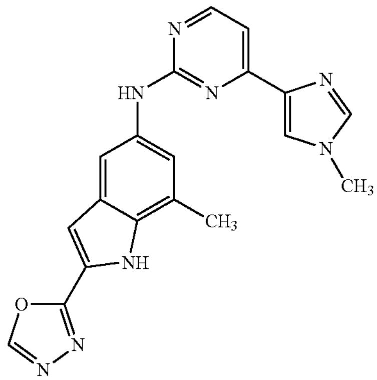 [SMILES: Cc1cc(Nc2nccc(-c3cn(C)cn3)n2)cc2cc(-c3nnco3)[nH]c12] | | 0.0005 | 0.0009 | Starting from 8.3 see description 4.2.6 | HPLC: method D Rt = 0.94 min |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as Syk-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha1-antitrypsin deficiency.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints, of the blood vessels and of the kidney or inflammatory diseases of the skin and eyes. Examples of these are rheumatoid arthritis, antibody-based glomerulonephritis, psoriasis, Kawasaki syndrome, coeliac disease (sprue), artheriosclerosis and Wegener's granulomatosis.

The compounds according to the invention are preferably also suitable for the treatment of autoimmune diseases. Examples of these are hepatitis (autoimmune-based), lupus erythematodes, anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome, sclerodermy, Bullous pemphigoid and Pemphigus vulgaris.

The compounds according to the invention are preferably also suitable for the treatment of B-cell lymphomas, like chronic lymphocytic leukaemia and non Hodgkin's lymphomas or T cell lymphomas.

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis and allergic rhinoconjunctivitis.

Most preferably, the compounds of formula 1 may be used for the treatment of a disease selected from among asthma, allergic rhinitis, rheumatoid arthritis, allergic dermatitis and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, PDE4-inhibitors, LTD4-antagonists, EGFR-inhibitors, MRP4-inhibitors, dopamine agonists, H1-antihistamines, PAF-antagonists, iNos-inhibitors, HMG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, ICE-inhibitors, LTB4-antagonists, 5-LO antagonists, FLAP-antagonists. LTB4-antagonists; cromoglycine, dissociated glucocorticoid mimetics, anti-TNF-antibodies, anti-GM-CSF antibodies, anti-CD46-antibodies, anti-IL-1-antibodies, anti-IL-2-antibodies, anti-IL-4-antibodies, anti-IL-5-antibodies, anti-IL-13-antibodies, anti-IL 18 antibodies, anti-CD30 L antibodies, anti-Ox40L-antibodies, anti-IL-4/IL-13-antibodies, or double or triple combinations thereof, such as for example combinations of one, two or three compounds selected from among the

- Syk-inhibitors of formula 1, betamimetics, corticosteroids, EGFR-inhibitors and PDE4-antagonists,
- Syk-inhibitors of formula 1, anticholinergics, betamimetics, corticosteroids, EGFR-inhibitors and PDE4-antagonists,
- Syk-inhibitors of formula 1, PDE4-inhibitors, corticosteroids and EGFR-inhibitors,
- Syk-inhibitors of formula 1, EGFR-inhibitors and PDE4-inhibitors,
- Syk-inhibitors of formula 1 and EGFR-inhibitors,
- Syk-inhibitors of formula 1, betamimetics and anticholinergics
- Syk-inhibitors of formula 1, anticholinergics, betamimetics, corticosteroids and PDE4-inhibitors,
- Syk-inhibitors of formula 1, anticholinergics, betamimetics, corticosteroids, iNOS inhibitors, HMG-CoA reductase inhibitors.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol, 6-Hydroxy-8-{1-hydroxy-2-[2-(4-methoxy-phenyl)-1,1-dimethyl-ethylamino]-ethyl}-4H-benzo[1,4]oxazine-3-one; 8-{2-[2-(2,4-Difluoro-phenyl)-1,1-dimethyl-ethylamino]-1-hydroxy-ethyl}-6-hydroxy-4H-benzo[1,4]oxazine-3-one; 8-{2-[2-(3,5-Difluoro-phenyl)-1,1-dimethyl-ethylamino]-1-hydroxy-ethyl}-6-hydroxy-4H-benzo[1,4]oxazine-3-one; 8-{2-[2-(4-Ethoxy-phenyl)-1,1-dimethyl-ethylamino]-1-hydroxy-ethyl}-6-hydroxy-4H-benzo[1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo[1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]oxazine-3-one; N-[2-Hydroxy-5-((1R)-1-hydroxy-2-{2-[4-(2-hydroxy-2-phenyl-ethylamino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)-ethylamino]-hexyloxy}-butyl)-5-methylphenyl]-urea; 4-((1R)-2-{6-[2-(2,6-Dichlorbenzyloxy)-ethoxy]-hexylamino}-1-hydroxy-ethyl)-2-hydroxymethyl-phenol; 3-(4-{6-[(2R)-2-Hydroxy-2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]hexylamino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl]ethyl}amino)propyl]phenyl}acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenylethoxy)-hexylamino]-1-hydroxy-ethyl}-8-hydroxy-1H-quinoline-2-one; (R,S)-4-(2-{[6-(2,2-Difluor-4-phenylbutoxy)hexyl]amino}-1-hydroxy-ethyl)-2-(hydroxymethyl)phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{([4,4-Difluor-6-(4-phenylbutoxy)hexyl]amino}-1-hydroxy-ethyl)-2-(hydroxymethyl)phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-4-[2-({6-[2,2-Difluor-2-(3-methylphenyl)ethoxy]hexyl}amino)-1-hydroxyethyl]-2-(hydroxymethyl)phenol; 4-(1R)-2-{[6-(2,2-Difluor-2-phenylethoxy)hexyl]amino}-1-hydroxyethyl)-2-(hydroxymethyl)phenol; (R,S)-2-(Hydroxymethyl)-4-(1-hydroxy-2-{[4,4,515-tetrafluor-6-(3-phenylpropoxy)-hexyl]amino}ethyl)phenol; (R,S)-5-(2-{[6-(2,2-Difluor-2-phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)phenol; (R,S)—N-[3-(1,1-Difluor-2-{[6-({2-hydroxy-2-[4-hydroxy-3-(hydroxymethyl)phenyl]amino)hexyl]oxy}ethyl)phenyl]-urea; 3-[3-(1,1-Difluor-2-{[6-({2-hydroxy-2-[4-hydroxy-3-(hydroxymethyl)phenyl]ethyl}amino)hexyl]

oxy}ethyl)phenyl]imidazolidine-2,4-dione; (R,S)-4-[2-({6-[2,2-Difluor-2-(3-methoxyphenyl)ethoxy]hexyl}amino)-1-hydroxyethyl]-2-(hydroxymethyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl)phenol; (R,S)-4-(2-{[6-(3,3-Difluor-3-phenylpropoxy)hexyl]amino}-1-hydroxy-ethyl)-2-(hydroxymethyl)phenol; (R,S)-(2-{([6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo[2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide; 3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyl tropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluoromethyl-xanthene-9-carboxylic acid tropenole ester-methobromide; 9-Hydroxymethyl-xanthene-9-carboxylic acid scopine ester-methobromide;

3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;

N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;

7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium;

optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among beclomethasone, betamethasone, budesonide, butixocort, ciclesonide, deflazacort, dexamethasone, etiprednole, flunisolide, fluticasone, loteprednole, mometasone, prednisolone, prednisone, rofleponide, triamcinolone, tipredane; Pregna-1,4-diene-3,20-dione, 6-fluoro-11-hydroxy-16,17-[(1-methylethylidene)bis(oxy)]-21-[[4-[(nitrooxy)methyl]benzoyl]oxy]-, (6-alpha,11-beta,16-alpha)-(9Cl); 16,17-butylidenedioxy-6,9-difluoro-11-hydroxy-17-(methylthio)androst-4-en-3-one; 6,9-Difluor-17-[(2-furanylcarbonyl)oxy]-11-hydroxy-16-methyl-3-oxo-androsta-1,4-dien-17-carbothione acid (S)-fluoromethylester; (S)-fluoromethyl 6,9-difluoro-17-[(2-furanylcarbony)oxy]-11-hydroxy-16-methyl-3-oxo-androsta-1,4-diene-17-carbothionate; 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylic acid cyanomethyl ester, each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)- fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-1(2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridiny)ethyl]-alpha,alpha-bis(trifluoromethyl)-Benzenemethanol (L-826141); N-(3,5-Dichloro-1-oxo-pyridin-4-yl)-4-difluoromethoxy-3-cyclopropylmethoxybenzamide; (−)p-[(4aR*,10bS*)-9-Ethoxy-1,2,3,4,4a,10b-hexahydro-8-methoxy-2-methylbenzo[s][1,6]naphthyridin-6-yl]N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'-[N-2-cyano-5-methyl-isothioureido]benzyl)-2-pyrrolidon; cis[4-Cyano-4-(3-cyclopentyloxy-4-methoxyphenyl)cyclohexan-1-carboxylic acid]; 2-carbomethoxy-4-cyano-4-(3-cyclopropylmethoxy-4-difluoromethoxyphenyl)cyclohexan-1-one; cis[4-Cyano-4-(3-cyclopropylmethoxy-4-difluoromethoxyphenyl)cyclohexan-1-01]; (R)-(+)-Ethyl[4-(3-cyclopentyloxy-4-methoxyphenyl)pyrrolidin-2-yliden]acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-(3-(2-(6,7-Difluor-2-quinolinyl)ethenyl)phenyl)-3-(2-(2-hydroxy-2-propyl)phenyl)thio)methylcyclopropane-acetic acid; 1-(((1(R)-3(3-(2-(2,3-Dichlorthieno[3,2-b]pyridin-5-yl)-(E)-ethenyl)phenyl)-3-(2-(1-hydroxy-1-methylethyl)phenyl)propyl)thio)methyl)cyclopropane acetic acid; [2-[[2-(4-tert-Butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethylamino)-1-oxo-2-butene-1-yl]amino}-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-cyclopropylmethoxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropylmethoxy-quinazoline, 4-[(3-chloro-4-fluoro-phenyl)amino]-6-[2-((S)-6-methyl-2-oxo-morpholine-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenylethyl-amino]-6-{[4-(N,N-bis-(2-methoxy-ethyl)-amino)-1-oxo-2-butene-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-((R)-tetrahydrofuran-3-yloxy)-quinazoline, 4-[(3-chloro-4-fluorophenyl)amino]-6-{([4-(N,N-dimethylamino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclopropyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dim ethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]amino}-7-[tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5.5-dimethyl-2-oxo-morpholine-4-yl)-1-oxo-2-butene-1-yl]amino}-quinazoline, 4-[(3-chloro-4-fluoro-phenyl)amino]-6-[2-(2.2-dimethyl-6-oxo-morpholine-4-yl)-ethoxy]-7-methoxy-quinazoline, 4-[(3-chloro-4-fluoro-phenyl)amino]-6-[2-(2.2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)amino]-7-[2-(2.2-dim ethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-piperidine-1-yl]-ethoxy}-7-methoxy-quinazoline, 4-[(3-chloro-4-fluoro-phenyl)amino]-6-[1-(tert.-butyloxycarbonyl)-piperidine-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidine-4-yloxy)-7-methoxy-quinazoline, 4-[(3-chloro-4-fluoro-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(methoxymethyl)carbonyl]-piperidine-4-yloxy}-7-methoxy-quinazoline, 4-[(3-chloro-4-fluoro-phenyl)amino]-6-(piperidine-3-yloxy)-7-methoxy-quinazoline, 4-[(3-chloro-4-fluoro-phenyl)amino]-6-[1-(2-acetylamino-ethyl)-piperidine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonylmethyl-piperidine-4-yloxy)-7-methoxy-quinazoline, 4-[(3-chloro-4-fluoro-phenyl)amino]-6-(cis-4-{N-[(tetrahydropyran-4-yl))carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1-methanesulphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert-butyloxycarbonyl)-piperidine-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[morpholine-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4-[(3-ethynylphenyl)amino]-6-(1-acetyl-piperidine-4-yloxy)-7-methoxy-quinazoline, 4-[(3-ethynyl-phenyl)amino]-6-(1-methyl-piperidine-4-yloxy)-7-methoxy-quinazoline, 4-[(3-ethynyl-phenyl)amino]-6-(1-methanesulphonyl-piperidine-4-yloxy)-7-methoxy-quinazoline, 4-[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)amino]-6-(1-isopropyloxycarbonyl-piperidine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidine-4-yloxy)-7-methoxy-quinazoline, 4-[(3-ethynyl-phenyl)amino]-6-[1-(2-methoxy-acetyl)-piperidine-4-yloxy]-7-methoxy-quinazoline, 4-[(3-ethynyl-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-piperidine-4-yloxy}-7-methoxy-quinazoline, 4-[(3-chloro-4-fluoro-phenyl)amino]-6-{1-[(2-methyl-morpholine-4-yl)carbonyl]-piperidine-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-piperidine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxyethyl)carbonyl]-piperidine-4-yloxy}-7-methoxy-quinazoline, 4-[(3-chloro-4-fluoro-phenyl)amino]-6-{1-[(3-methoxypropyl-amino)-carbonyl]-piperidine-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholine-4-yl)carbonyl]-N-methyl-amino}-cyclohexan-1-yloxy)-7-methoxy-quinazoline, 4-[(3-chloro-4-fluoro-phenyl)amino]-6-[2-(2.2-dimethyl-6-oxo-morpholine-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidine-4-yloxy)-7-methoxy-quinazoline, 4-[(3-chloro-4-fluoro-phenyl)amino]-6-(1-cyano-piperidine-4-yloxy)-7-methoxy-quinazoline, 3-Cyano-4-[(3-chlor-4-fluorphenyl)amino]-6-{[4-(N,N-dimethylamino)-1-oxo-2-butene-1-yl]amino}-7-ethoxy-quinoline, [4-[(3-chloro-4-fluoro-phenyl)amino]-6-{[4-(homomorpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX-EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines. Any reference to the above-mentioned above-mentioned PAF-antagonists includes within the scope of the present invention a reference to any pharmacologically acceptable acid addition salts thereof which may exist.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyls-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the Syk-inhibitors of formula 1 and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the Syk-inhibitors of formula 1, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA ($N^\omega$-nitro-L-arginine), L-NAME ($N^\omega$-nitro-L-argininemethylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51) (*J. Med. Chem.* 2002, 45, 1686-1689), N-[[3-(aminomethyl)phenyl] methyl]-Ethanimidamide (=1400W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1S,5S,6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylidene-amine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-yl-methyl-phenoxy)-ethoxy]-2-phenyl-pyridine (PPA250) (*J. Pharmaco Exp. Ther.* 2002, 303, 52-57), 3-{[(benzo[1,3]dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a imidazolyl-pyrimidine according to formula 1 and one or more combination partners selected from those described above.

We claim:
1. A compound of formula 1

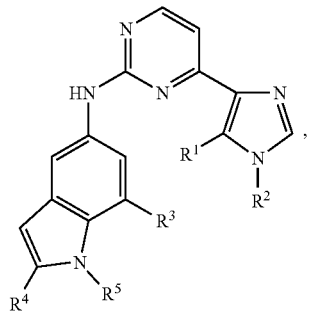

wherein
$R^1$ is selected from the group consisting of hydrogen, $C_{1-6}$-alkyl and $C_{1-6}$-haloalkyl;
$R^2$ is selected from the group consisting of hydrogen, $C_{1-6}$-alkyl, $C_{1-6}$-haloalkyl, —($C_{1-3}$-alkylene)-O—($C_{1-3}$-alkyl) and three-, four-, five- or six-membered cycloalkyl, wherein this cycloalkyl may optionally be substituted by halogen;

$R^3$ is selected from the group consisting of hydrogen, $C_{1-6}$-alkyl, halogen, —O—$C_{1-6}$-alkyl, three-, four-, five- or six-membered cycloalkyl, —S—($C_{1-3}$-alkylene)-A, —S-A and -A,
with A being a group selected from the group consisting of —CO—N($C_{1-3}$-alkyl)$_2$, —CO—NH($C_{1-3}$-alkyl), —CO—NH$_2$, five- or six-membered heteroaryl comprising 1, 2 or 3 heteroatoms each independently selected from S, O or N and five-, six- or seven-membered heterocycle comprising 1, 2 or 3 heteroatoms each independently selected from S, O or N,
wherein A may optionally be further substituted by one, two or three groups each independently selected from —$C_{1-3}$-alkyl, halogen, -oxo, —OH or $C_{1-3}$-haloalkyl;
$R^4$ is selected from the group consisting of hydrogen, -halogen, SH, —OH, —NH$_2$, —CO—Y, —CO—N(CH$_3$)—Y, —CO—N(CH$_3$)($C_{1-5}$-alkylene)-Y, —CO—N(ethyl)($C_{1-5}$-alkylene)-Y, —CO—N(ethyl)-Y, —CS—Y, —CS—N(CH$_3$)—Y, —CS—N(CH$_3$)—($C_{1-3}$-alkylene)-Y, —$C_{1-6}$-alkyl, —$C_{1-3}$-haloalkyl, —CO—NH—Y, —CO—NH—$C_{1-6}$-alkylene-Y, —CO—N(CH$_3$)—($C_{2-3}$-alkylene)-O—($C_{1-3}$-alkyl), —NH$_2$, —$C_{1-6}$-alkylene-L, —SO$_2$-phenyl, —SO$_2$—($C_{1-3}$-alkyl), —CO—N($C_{1-4}$-alkyl)$_2$ and —CO—N($C_{2-4}$-alkylene-O—$C_{1-3}$-alkyl)$_2$,
or wherein $R^4$ is a five- or six-membered heteroaromatic group comprising 1, 2 or 3 heteroatoms each independently selected from N, S or O, wherein said heteroaromatic group on any atom available for substitution may optionally be further substituted by one, two or three groups each independently selected from —$C_{1-3}$-alkyl halogen or $C_{1-3}$-haloalkyl,
with Y being a group selected from the group consisting of —NH$_2$, —NH(CH$_3$), —N(CH$_3$)$_2$, —$C_{1-6}$-alkylene-N(CH$_3$)$_2$, —O—$C_{1-3}$-alkyl, —$C_{1-3}$-haloalkyl, —OH, —N(ethyl)$_2$ and —$C_{1-5}$-alkinyl,
or with Y being a group selected from the group consisting of a four-, five-, six- or seven-membered monocyclic fully saturated or partially unsaturated heterocycle comprising 1, 2 or 3 heteroatoms each independently selected from N, S or O, a five- or six-membered monocyclic heteroaromatic group comprising 1, 2 or 3 heteroatoms each independently selected from N, S or O, —$C_{6-10}$-aryl, and $C_{3-6}$-cycloalkyl,
or with Y being a 8- to 11-membered bicyclic annellated fully saturated, partially unsaturated or aromatic heterocycle comprising 1, 2, 3 or 4 heteroatoms each independently from each other selected from N, S or O,
or with Y being an 8- to 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom,
or with Y being a six- or seven-membered fully saturated heterocycle comprising 1, 2 or 3 heteroatoms each independently selected from N, S or O, which is bridged by an additional $C_{1-3}$-alkylene-unit,
whereby each Y may optionally be substituted by one, two or three groups Z each independently from each other selected from the group consisting of halogen, -oxo, OH, —CN, —$C_{1-5}$-alkyl, —$C_{1-5}$-alkanol, —O—$C_{1-3}$-alkyl, a four-, five-, six- or seven-membered fully saturated or partially unsaturated heterocycle comprising 1, 2 or 3 heteroatoms each independently selected from N, S or O, a fully saturated or partially unsaturated $C_{3-6}$-cycloalkyl, a five- to six-membered heteroaromatic group comprising 1, 2 or 3 heteroatoms each independently selected from N, S or O, —CO—($C_{1-3}$-alkyl), —CHO, —CO-L, —$C_{1-3}$-alkylene-CO-L, —$C_{1-4}$-alkylene-O—$C_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, —$C_{1-3}$-alkyl, —O—$C_{1-3}$-alkyl, —N(methyl)$_2$, —N(ethyl)$_2$, 5- to 6-membered fully saturated, partially unsaturated or aromatic heterocycle comprising 1 or 2 heteroatoms each independently selected from N, O or S, a $C_{3-6}$-cycloalkyl and —CN, wherein each group T may also optionally be substituted by a group selected from the group consisting of $C_{1-3}$-alkyl, halogen, OH, oxo and —O—$C_{1-3}$-alkyl, whereby L denotes a 5- or 6-membered fully saturated or partially unsaturated heterocycle comprising 1 or 2 heteroatoms each independently selected from N, O or S, where the heterocycle may optionally be substituted by one, two or three groups independently selected from methyl, halogen, OH or -oxo;

$R^5$ is selected from the group consisting of hydrogen, $C_{1-6}$-alkyl, $C_{1-3}$-haloalkyl and —($C_{1-4}$-alkylene)-O—($C_{1-3}$-alkyl);

or a pharmaceutically acceptable salt thereof.

2. The compound of formula 1 according to claim 1, wherein $R^4$ is selected from the group consisting of
—CO—Y, —CO—N(CH$_3$)—Y, —CO—N(CH$_3$)($C_{1-5}$-alkylene)-Y, —CO—N(ethyl)($C_{1-5}$-alkylene)-Y, —CO—NH—Y and —CO—NH—$C_{1-6}$-alkylene-Y, or $R^4$ is a five- or six-membered heteroaromatic group comprising 1, 2 or 3 heteroatoms each independently selected from N, S or O, wherein said heteroaromatic group on any atom available for substitution may optionally be further substituted by one, two or three groups each independently selected from —$C_{1-3}$-alkyl halogen or $C_{1-3}$-haloalkyl, with Y being a group selected from the group consisting of —NH$_2$, —NH(CH$_3$), —N(CH$_3$)$_2$, —$C_{1-6}$-alkylene-N(CH$_3$)$_2$, —O—$C_{1-3}$-alkyl, —$C_{1-3}$-haloalkyl, —OH and —$C_{1-5}$-alkinyl, or with Y being a group selected from the group consisting of a four-, five-, six- or seven-membered monocyclic fully saturated or partially unsaturated heterocycle comprising 1, 2 or 3 heteroatoms each independently selected from N, S or O; a five- or six-membered monocyclic heteroaromatic group comprising 1, 2 or 3 heteroatoms each independently selected from N, S or O, —$C_{6-10}$-aryl and a $C_{3-6}$-cycloalkyl, or with Y being a 8-, 9-, 10- or 11-membered bicyclic annellated fully saturated, partially unsaturated or aromatic heterocycle comprising 1, 2, 3 or 4 heteroatoms each independently from each other selected from N, S or O, or with Y being an 8-, 9-, 10- or 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from N, S or O, which is bridged by an additional $C_{1-3}$-alkylene-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—CH$_3$, —O-ethyl, —O-(n-propyl), —O-isopropyl, a four-, five-, six- or seven-membered fully saturated or partially unsaturated heterocycle comprising 1, 2 or 3 heteroatoms each independently selected from N, S or O, a fully saturated or partially unsaturated $C_{3-6}$-cycloalkyl, a five- to six-membered heteroaromatic group comprising 1, 2 or 3 heteroatoms each independently selected from N, S or O, —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —N(methyl)$_2$, —N(ethyl)$_2$, 5- to 6-membered fully saturated, partially unsaturated or aromatic heterocycle comprising 1 or 2 heteroatoms each independently selected from N, O or S, a $C_{3-6}$-cycloalkyl and —CN, whereby L denotes a 5- or 6-membered fully saturated or partially unsaturated heterocycle comprising 1 or 2 heteroatoms each independently selected from N, O or S, which said heterocycle may optionally be substituted by one, two or three groups independently selected from methyl, halogen, OH or —oxo;

or a pharmaceutically acceptable salt thereof.

3. The compound of formula 1 according to claim 1, wherein $R^1$ is selected from the group consisting of hydrogen and methyl;

or a pharmaceutically acceptable salt thereof.

4. The compound of formula 1 according to claim 1, wherein $R^2$ is selected from the group consisting of methyl, ethyl, n-propyl, isopropyl, n-butyl, isobutyl, t-butyl, cyclopropyl, -methylene-O-methyl, and -ethylene-O-methyl;

or a pharmaceutically acceptable salt thereof.

5. The compound of formula 1 according to claim 4, wherein $R^2$ is selected from the group consisting of methyl, isopropyl, isobutyl, cyclopropyl, and -ethylene-O-methyl;

or a pharmaceutically acceptable salt thereof.

6. The compound of formula 1 according to claim 3, wherein $R^1$ is hydrogen;

and or a pharmaceutically acceptable salt thereof.

7. The compound of formula 1 according to claim 1, wherein $R^2$ is methyl, isopropyl or cyclopropyl;

or a pharmaceutically acceptable salt thereof.

8. The compound of formula 1 according to claim 7, wherein $R^2$ is methyl;

or a pharmaceutically acceptable salt thereof.

9. The compound of formula 1 according to claim 1, wherein $R^3$ is selected from the group consisting of hydrogen, methyl, ethyl, n-propyl, isopropyl, —F, —Cl, —Br, —O-methyl, —O-ethyl, —O-(n-propyl), —O-(isopropyl), cyclopropyl, —S-methylene-A, and -A, with A being a group selected from the group consisting of —CO—N(CH$_3$)$_2$, —CO—NH(CH$_3$), and five- or six-membered heteroaryl comprising 1, 2 or 3 heteroatoms each independently selected from S, O or N;

wherein A may optionally be further substituted by one, two or three groups each independently selected from methyl, ethyl, propyl or isopropyl;

or a pharmaceutically acceptable salt thereof.

10. The compound of formula 1 according to claim 1, wherein $R^3$ is selected from —Cl or methyl;

or a pharmaceutically acceptable salt thereof.

11. The compound of formula 1 according to claim 1, wherein $R^5$ is selected from the group consisting of hydrogen, methyl, ethyl, n-propyl, isopropyl, n-butyl, isobutyl, -methylene-O-methyl and -ethylene-O-methyl;

or a pharmaceutically acceptable salt thereof.

12. The compound of formula 1 according to claim 11, wherein $R^5$ is selected from the group consisting of hydrogen, methyl, isobutyl and -ethylene-O-methyl;

or a pharmaceutically acceptable salt thereof.

13. The compound of formula 1 according claim 1, wherein $R^5$ is hydrogen;

or a pharmaceutically acceptable salt thereof.

14. The compound of formula 1 according to claim 1, wherein $R^4$ is selected from the group consisting of —CO—Y, —CO—N(CH$_3$)—Y, —CO—N(CH$_3$)(C$_{1-5}$-alkylene)-Y, —CO—N(ethyl)(C$_{1-5}$-alkylene)-Y, —CO—NH—Y and —CO—NH—C$_{1-6}$-alkylene-Y, or $R^4$ is a five- or six-membered heteroaromatic group comprising 1, 2 or 3 heteroatoms each independently selected from N, S or O, wherein said heteroaromatic group on any atom available for substitution may optionally be further substituted by one, two or three groups each independently selected from methyl, ethyl, n-propyl, isopropyl, F, Cl, Br or —CF$_3$, with Y being a group selected from the group consisting of —NH$_2$, —NH(CH$_3$), —N(CH$_3$)$_2$, —C$_{1-6}$ alkylene-N(CH$_3$)$_2$, —O-methyl, —O-ethyl, —O-n-propyl, —O-isopropyl, methyl, ethyl, n-propyl, isopropyl, n-butyl, isobutyl, t-butyl, —C$_{1-3}$-haloalkyl, —OH and —CH$_2$≡CH$_3$, or with Y being a group selected from the group consisting of a four-, five-, six- or seven-membered monocyclic fully saturated or partially unsaturated heterocycle comprising 1, 2 or 3 heteroatoms each independently selected from N, S or O; a five- or six-membered monocyclic heteroaromatic group comprising 1, 2 or 3 heteroatoms each independently selected from N, S and O, —C$_{6-10}$-aryl or a C$_{3-6}$-cycloalkyl, or with Y being a 8-, 9-, 10- or 11-membered bicyclic annellated fully saturated, partially unsaturated or aromatic heterocycle comprising 1, 2, 3 or 4 heteroatoms each independently from each other selected from N, S or O, or with Y being an 8-, 9-, 10- or 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from N, S or O, which is bridged by an additional C$_{1-3}$-alkylene-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —C$_{1-5}$-alkanol, —O—CH$_3$, —O-ethyl, —O-(n-propyl), —O-isopropyl, a four-, five-, six- or seven-membered fully saturated or partially unsaturated heterocycle comprising 1, 2 or 3 heteroatoms each independently selected from N, S or O, a fully saturated or partially unsaturated C$_{3-6}$-cycloalkyl, a five- to six-membered heteroaromatic group comprising 1, 2 or 3 heteroatoms each independently selected from N, S or O, —CO-methyl, —CO-ethyl, —CO-propyl, —CHO, —CO-L, —C$_{1-3}$-alkylene-CO-L, —C$_{1-4}$-alkylene-O—C$_{1-3}$-alkyl, —N(CH$_3$)$_2$ and —N(ethyl)$_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —N(methyl)$_2$, —N(ethyl)$_2$, C$_{3-6}$-cycloalkyl, —CN, 5- to 6-membered fully saturated, partially unsaturated or aromatic heterocycle comprising 1 or 2 heteroatoms each independently selected from N, O or S, whereby L denotes a 5- or 6-membered fully saturated or partially unsaturated heterocycle comprising 1 or 2 heteroatoms each independently selected from N, O or S, wherein the heterocycle may optionally be substituted by one, two or three groups independently selected from methyl, —Cl, —Br, —F, —OH or -oxo;

or a pharmaceutically acceptable salt thereof.

15. The compound of formula 1 according to claim 14, wherein $R^4$ is selected from the group consisting of —CO—N(CH$_3$)—Y and —CO—N(CH$_3$)(C$_{1-5}$-alkylene)-Y, with Y being a group selected from the group consisting of —NH(CH$_3$), —N(CH$_3$)$_2$, —O-methyl, —CF$_3$, methyl, ethyl, and OH, or with Y being a group selected from the group consisting of a four-, five-, six- or seven-membered monocyclic fully saturated or partially unsaturated heterocycle comprising 1, 2 or 3 heteroatoms each independently selected from N, S or O, a five- or six-membered monocyclic heteroaromatic group comprising 1, 2 or 3 heteroatoms each independently selected from N, S or O, —C$_{6-10}$-aryl, cyclopropyl, cyclobutyl, cyclopentyl and cyclohexyl, or with Y being a 8-, 9-, 10- or 11-membered bicyclic annellated fully saturated, partially unsaturated or aromatic heterocycle comprising 1, 2, 3 or 4 heteroatoms each independently from each other selected from N, S or O, or with Y being an 8-, 9-, 10- or 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from N, S or O, which is bridged by an additional —CH$_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from N, S or O, a fully saturated or partially unsaturated $C_{3-6}$-cycloalkyl, a five- to six-membered heteroaromatic group comprising 1, 2 or 3 heteroatoms each independently selected from N, S or O, —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, $C_{3-6}$-cycloalkyl, —CN, 5- to 6-membered fully saturated, partially unsaturated or aromatic heterocycle comprising 1 or 2 heteroatoms each independently selected from N, O or S, whereby L denotes a 5- or 6-membered fully saturated or partially unsaturated heterocycle comprising 1 or 2 heteroatoms each independently selected from N, O or S, wherein the heterocycle may optionally be substituted by one, two or three groups independently selected from methyl, —Cl, —Br, —F, —OH or -oxo, or a pharmaceutically acceptable salt thereof.

16. The compound of formula 1 according claim 14, wherein $R^4$ is selected from the group consisting of —CO—NH—Y and —CO—NH—$C_{1-6}$-alkylene-Y, with Y being a group selected from the group consisting of —$NH(CH_3)$, —$N(CH_3)_2$, —O-methyl, —$CF_3$, methyl, ethyl and —OH, or with Y being a group selected from the group consisting of a four-, five-, six- or seven-membered monocyclic fully saturated or partially unsaturated heterocycle comprising 1, 2 or 3 heteroatoms each independently selected from N, S or O, a five- or six-membered monocyclic heteroaromatic group comprising 1, 2 or 3 heteroatoms each independently selected from N, S or O, —$C_{6-10}$-aryl, cyclopropyl, cyclobutyl, cyclopentyl and cyclohexyl, or with Y being a 8-, 9-, 10- or 11-membered bicyclic annellated fully saturated, partially unsaturated or aromatic heterocycle comprising 1, 2, 3 or 4 heteroatoms each independently from each other selected from N, S or O, or with Y being an 8-, 9-, 10- or 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from N, S or O, which is bridged by an additional —$CH_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from N, S or O, a fully saturated or partially unsaturated $C_{3-6}$-cycloalkyl, a five- to six-membered heteroaromatic group comprising 1, 2 or 3 heteroatoms each independently selected from N, S or O, —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, $C_{3-6}$-cycloalkyl, —CN, 5- to 6-membered fully saturated, partially unsaturated or aromatic heterocycle comprising 1 or 2 heteroatoms each independently selected from N, O or S, whereby L denotes a 5- or 6-membered fully saturated or partially unsaturated heterocycle comprising 1 or 2 heteroatoms each independently selected from N, O or S, wherein the heterocycle may optionally be substituted by one, two or three groups independently selected from methyl, —Cl, —Br, —F, —OH or -oxo, or a pharmaceutically acceptable salt thereof.

17. The compound of formula 1 according to claim 1, wherein $R^4$ is —CO—Y, with Y being a group selected from the group consisting of —$NH(CH_3)$, —$N(CH_3)_2$, —O-methyl, —$CF_3$, methyl, ethyl and —OH, or with Y being a group selected from the group consisting of a four-, five-, six- or seven-membered monocyclic fully saturated or partially unsaturated heterocycle comprising 1, 2 or 3 heteroatoms each independently selected from N, S or O, a five- or six-membered monocyclic heteroaromatic group comprising 1, 2 or 3 heteroatoms each independently selected from N, S or O, —$C_{6-10}$-aryl, cyclopropyl, cyclobutyl, cyclopentyl and cyclohexyl, or with Y being a 8-, 9-, 10- or 11-membered bicyclic annellated fully saturated, partially unsaturated or aromatic heterocycle comprising 1, 2, 3 or 4 heteroatoms each independently from each other selected from N, S or O, or with Y being an 8-, 9-, 10- or 11-membered bicyclic fully saturated spiro-heterocycle comprising 1, 2 or 3 heteroatoms each independently selected from N, S or O, with the proviso that this spiro-heterocycle comprises at least one N-atom and that this heterocycle is directly attached to the molecule via this N-atom, or with Y being a six- or seven-membered fully saturated heterocycle comprising 1, 2 or 3 heteroatoms each independently selected from N, S or O, which is bridged by an additional —$CH_2$-unit, whereby each Y may optionally be substituted by one, two or three groups Z each independently from each other selected from the group consisting of —F, —Cl, —Br, —I, -oxo, OH, —CN, methyl, ethyl, n-propyl, isopropyl, n-butyl, isobutyl, t-butyl, pentyl, —$C_{1-5}$-alkanol, —O—$CH_3$, —O-ethyl, —O-(n-propyl), —O-isopropyl, a four-, five-, six- or seven-membered fully saturated or partially unsaturated heterocycle comprising 1, 2 or 3 heteroatoms each independently selected from N, S or O, a fully saturated or partially unsaturated $C_{3-6}$-cycloalkyl, a five- to six-membered heteroaromatic group comprising 1, 2 or 3 heteroatoms each independently selected from N, S or O, —CO-methyl, —CO-ethyl, —CO-propyl, —CHO, —CO-L, —$C_{1-3}$-alkylene-CO-L, —$C_{1-4}$-alkylene-O—$C_{1-3}$-alkyl, —$N(CH_3)_2$ and —$N(ethyl)_2$, whereby each group Z may optionally be further substituted by one, two or three groups T each independently selected from the group consisting of -oxo, OH, halogen, methyl, ethyl, n-propyl, isopropyl, —O-methyl, —O-ethyl, —O-(n-propyl), —O-(isopropyl), —$N(methyl)_2$, —$N(ethyl)_2$, $C_{3-6}$-cycloalkyl, —CN, 5- to 6-membered fully saturated, partially unsaturated or aromatic heterocycle comprising 1 or 2 heteroatoms each independently selected from N, O or S, whereby L denotes a 5- or 6-membered fully saturated or partially unsaturated heterocycle comprising 1 or 2 heteroatoms each independently selected from N, O or S, which said heterocycle may optionally be substituted by one, two or three groups independently selected from methyl, —Cl, —Br, —F, —OH or -oxo, or a pharmaceutically acceptable salt thereof.

18. The compound of formula 1 according to claim 1, wherein
$R^4$ is a five- or six-membered heteroaromatic group comprising 1, 2 or 3 heteroatoms each independently selected from N, S or O, wherein said heteroaromatic group on any atom available for substitution may optionally be further substituted by one, two or three groups each independently selected from methyl, ethyl, F, Cl, Br, or —$CF_3$;
or a pharmaceutically acceptable salt thereof.

19. The compound of formula 1 according to claim 1, wherein
$R^4$ is an oxadiazole group that may optionally be substituted by one, two or three groups each independently selected from methyl, ethyl, F, Cl, or —$CF_3$;
or a pharmaceutically acceptable salt thereof.

20. The compound of formula 1 according to claim 1, selected from the group consisting of

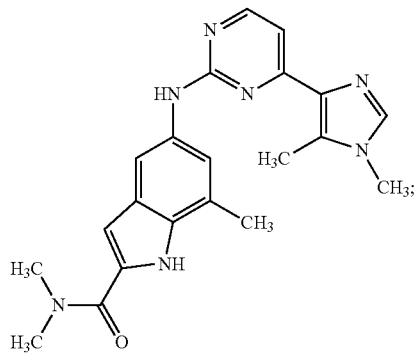

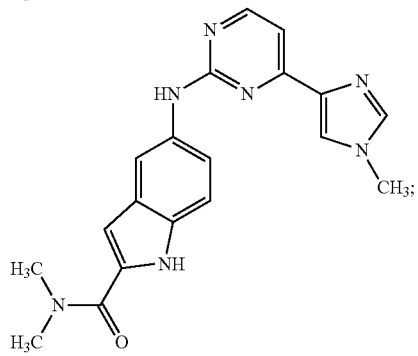

-continued

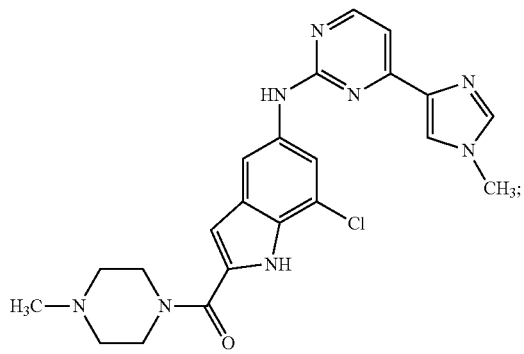

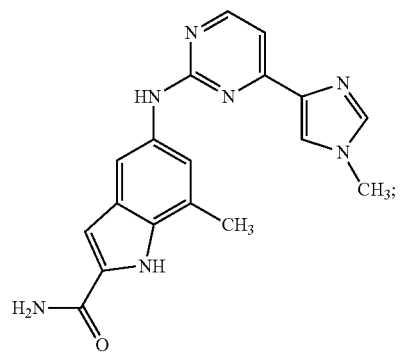

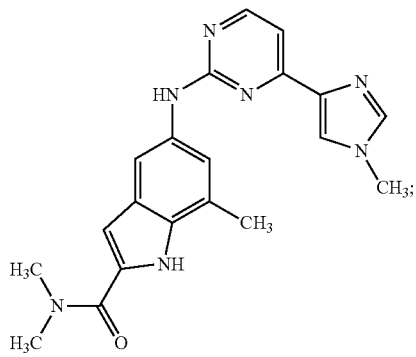

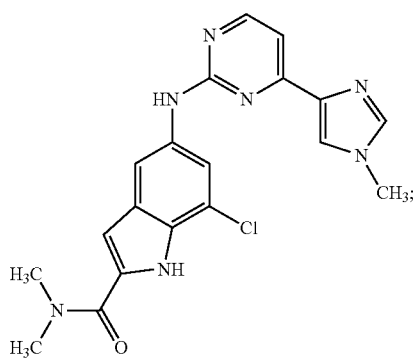

219
-continued
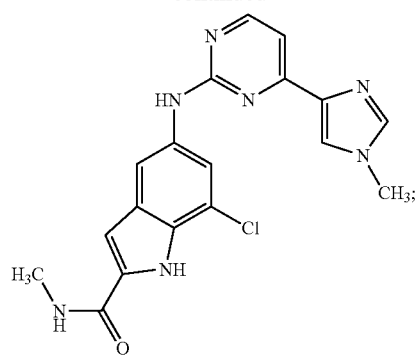
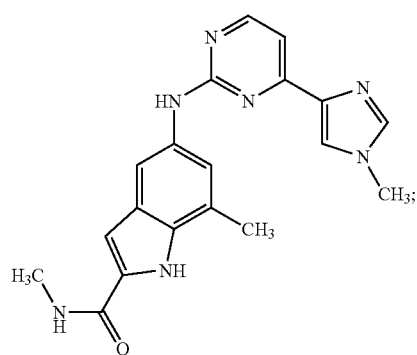
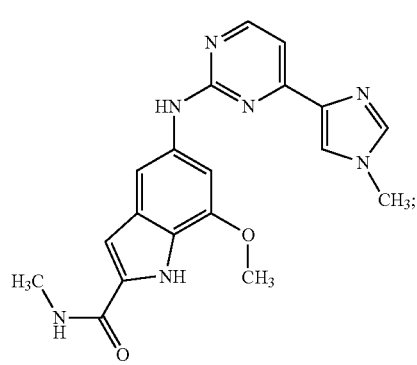
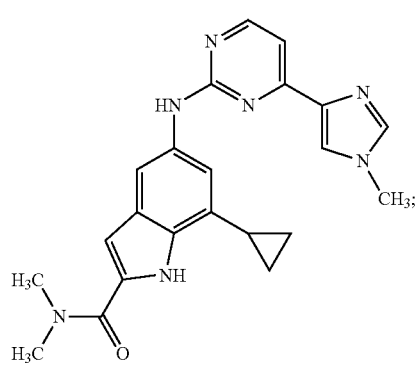
220
-continued
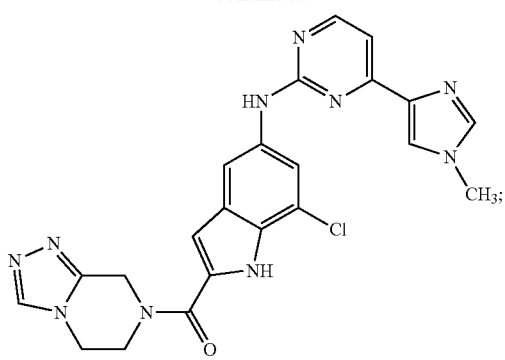
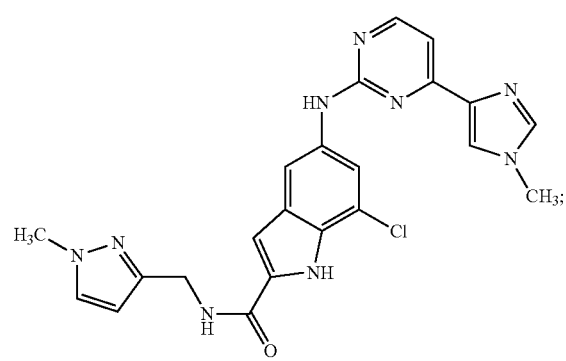
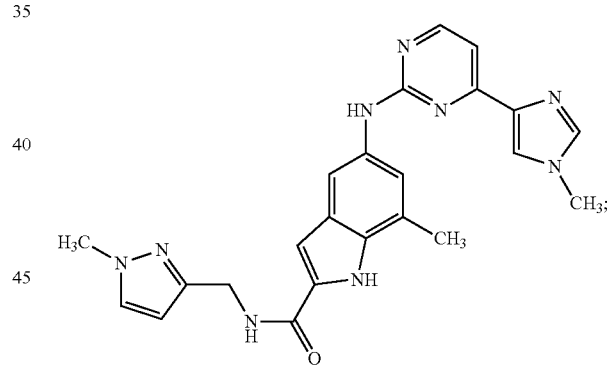
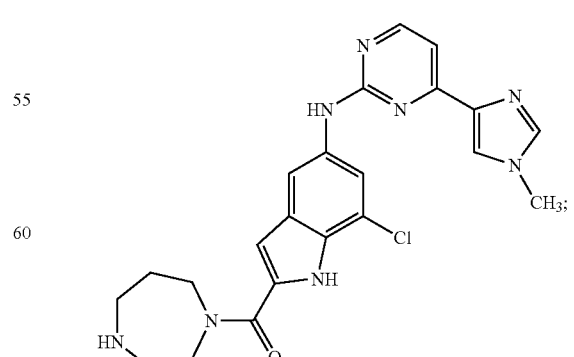

221
-continued
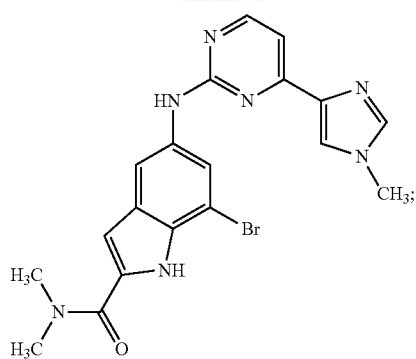
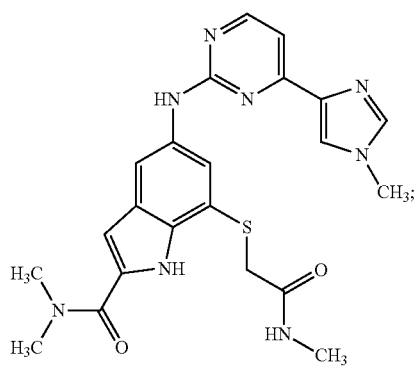
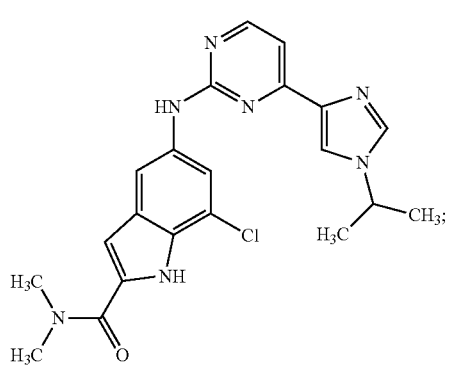
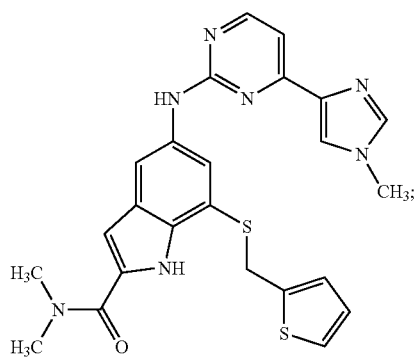
222
-continued
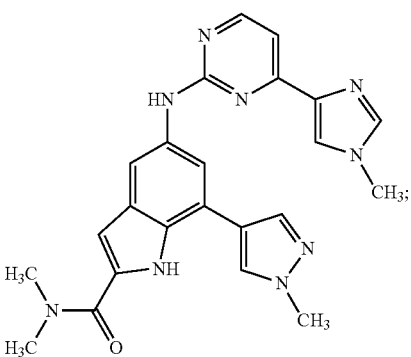
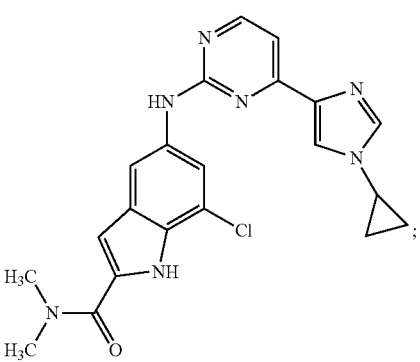
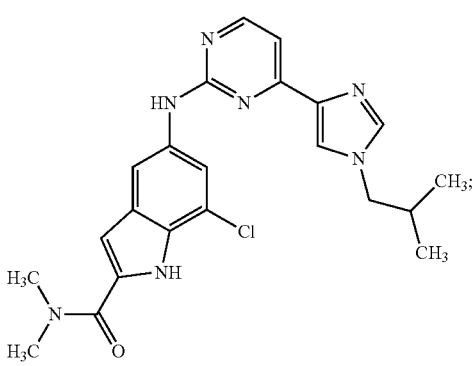
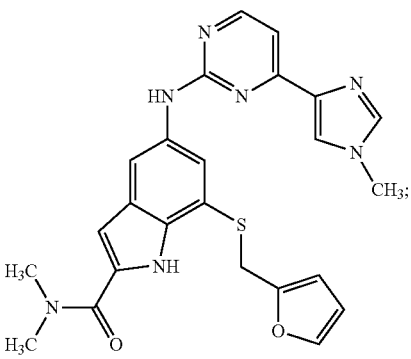

223
-continued
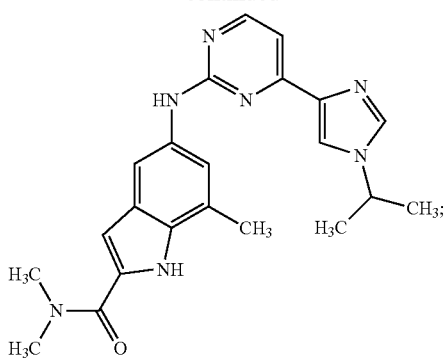
224
-continued
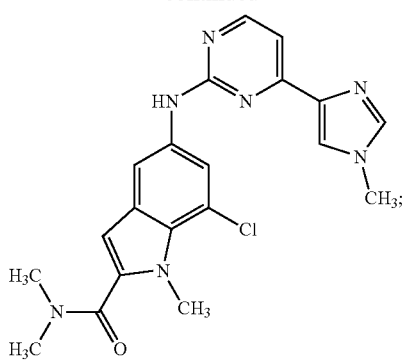
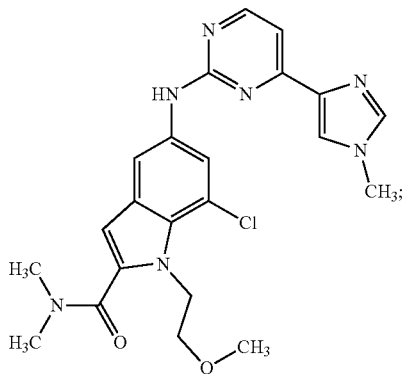
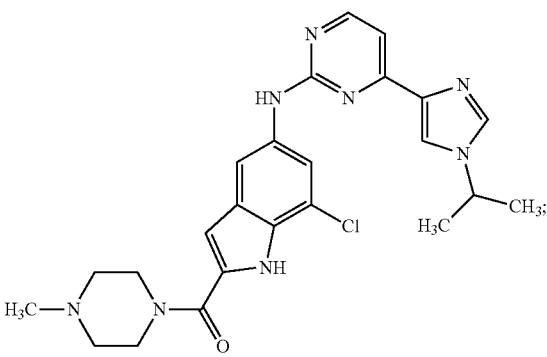
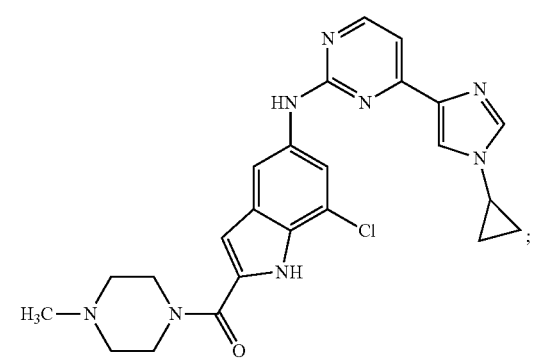

225
-continued
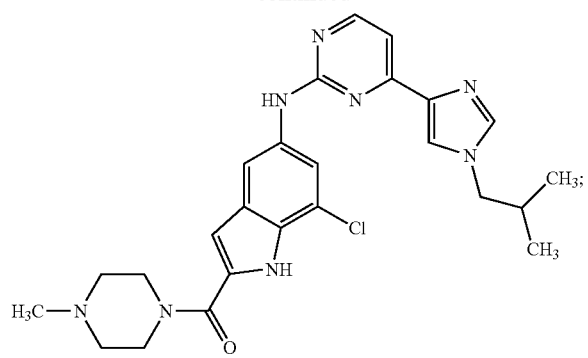
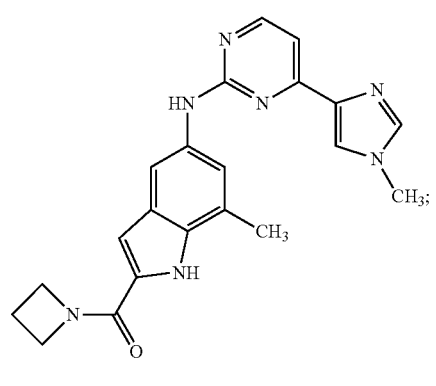
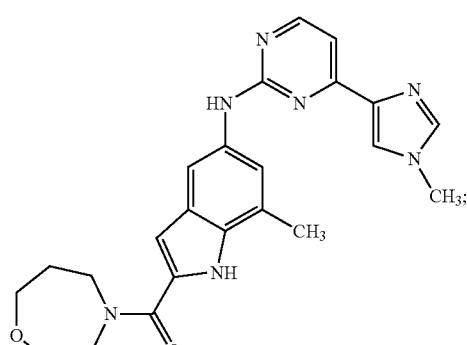
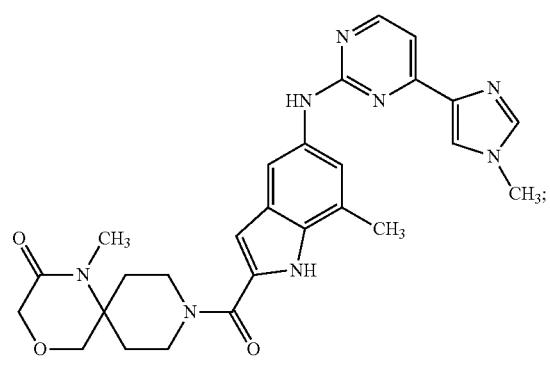
226
-continued
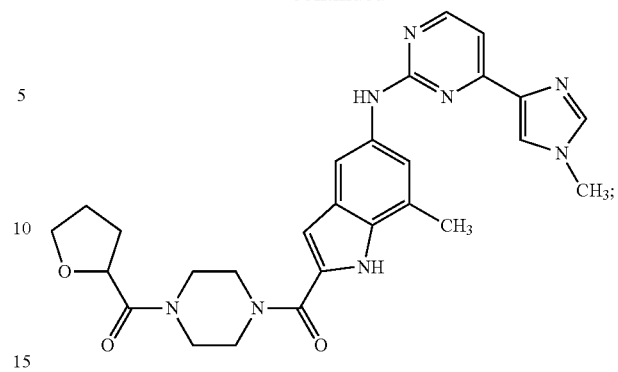
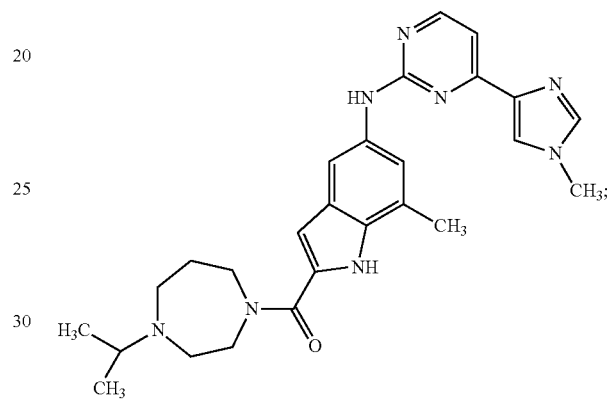
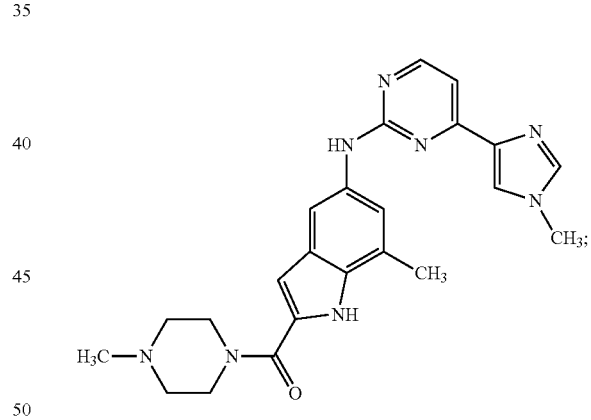
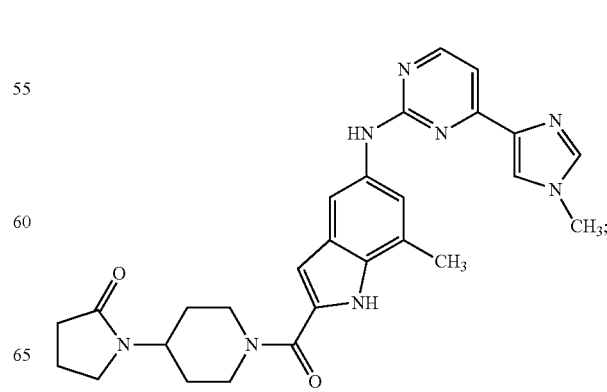

227
-continued
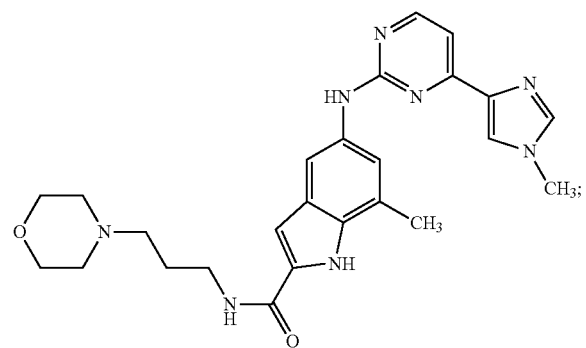
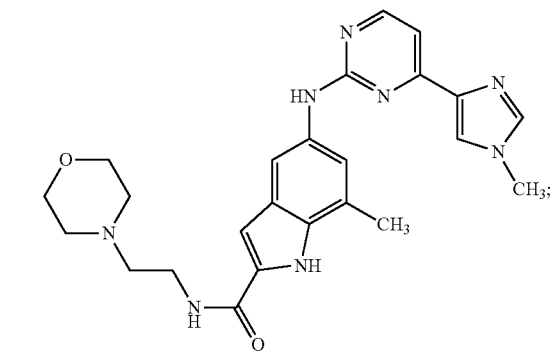
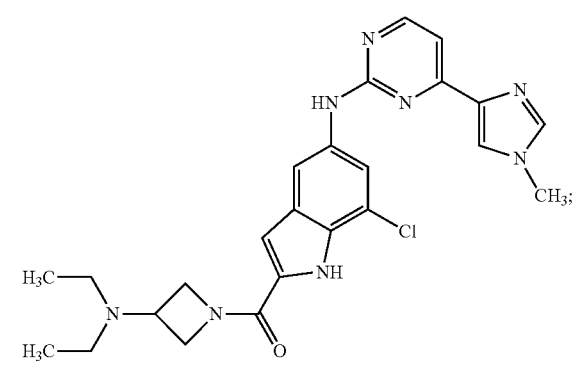
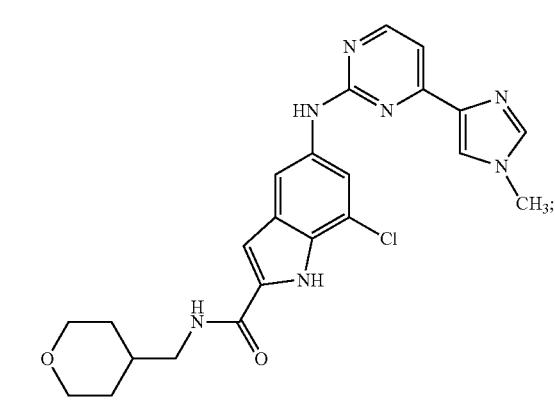
228
-continued
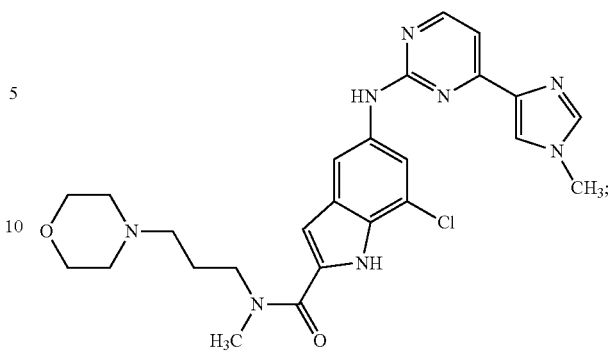
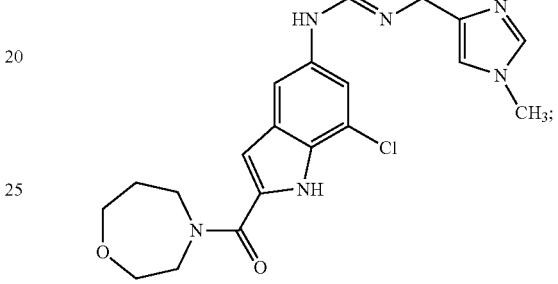
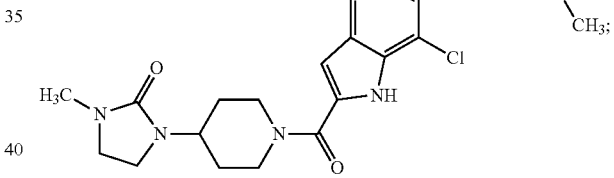
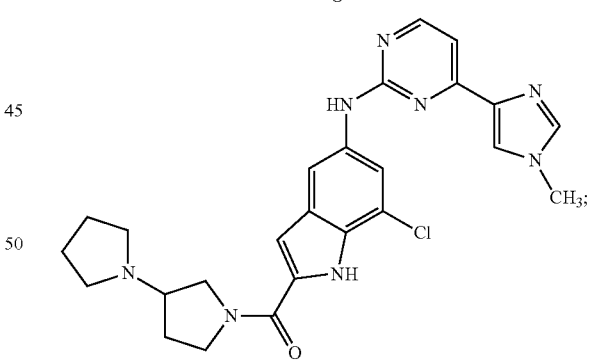
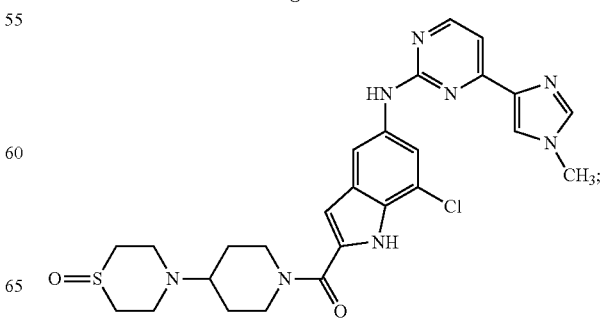

229
-continued
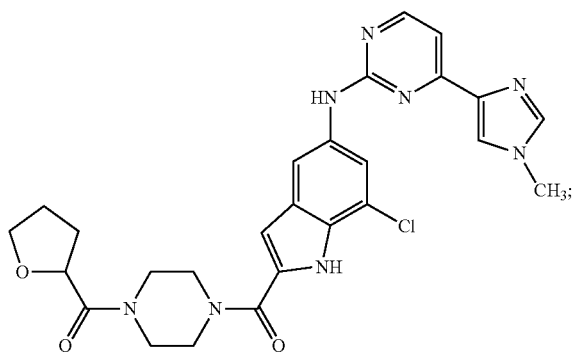
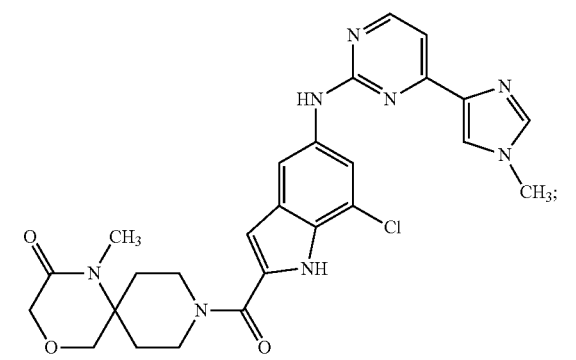
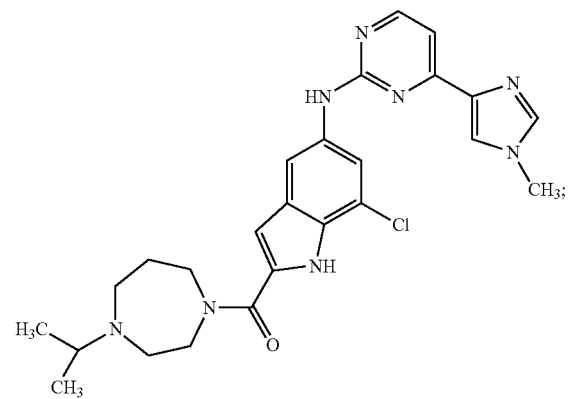
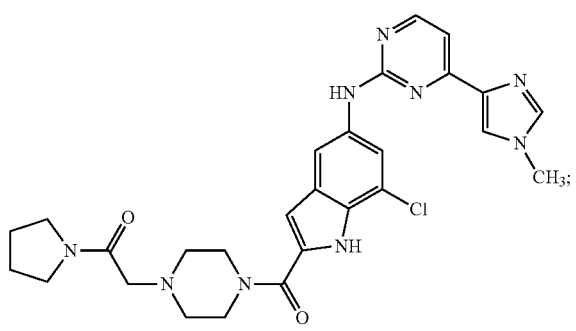
230
-continued
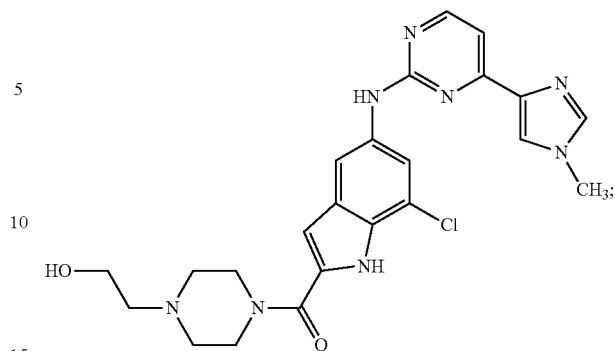
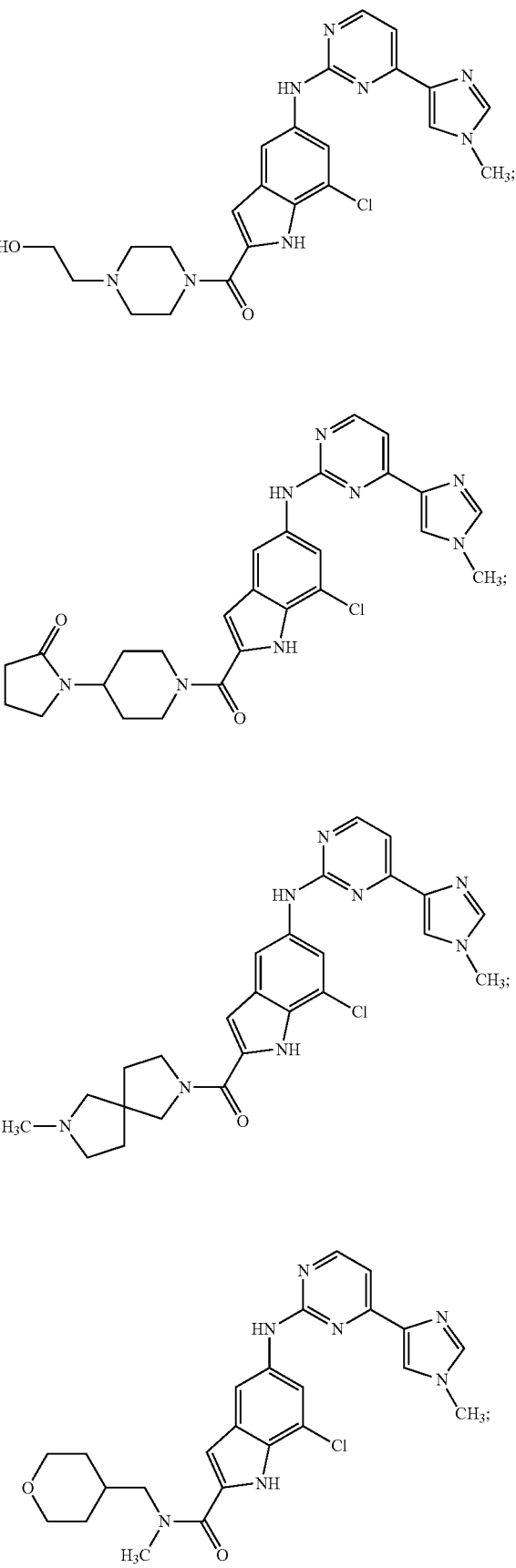

231
-continued
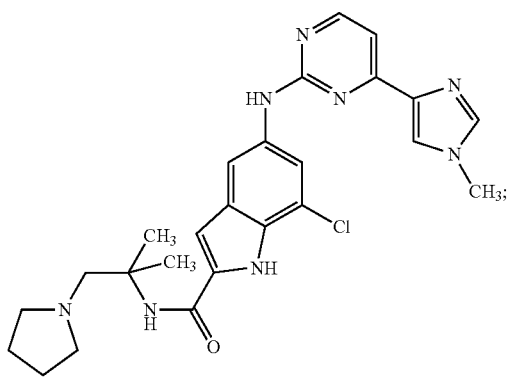
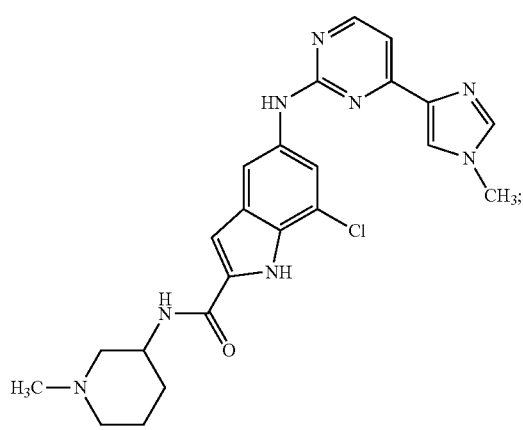
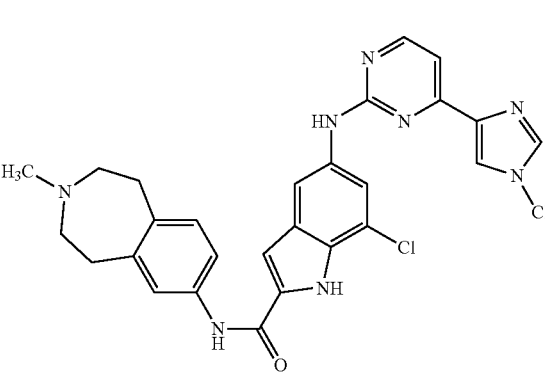
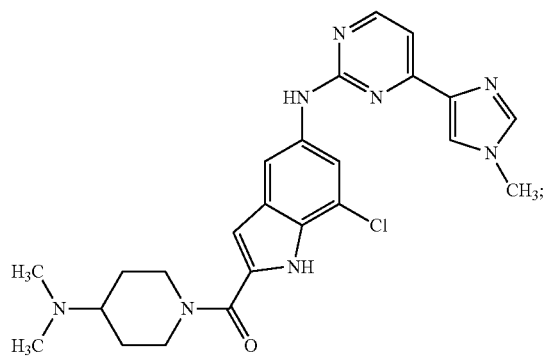
232
-continued
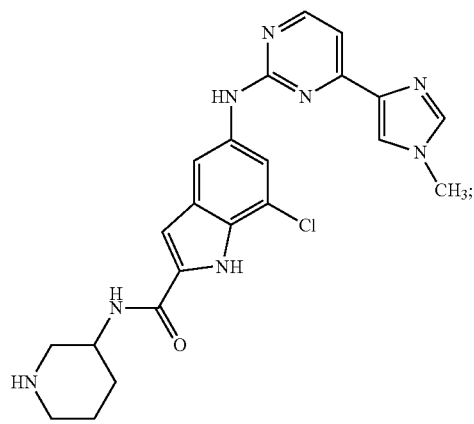
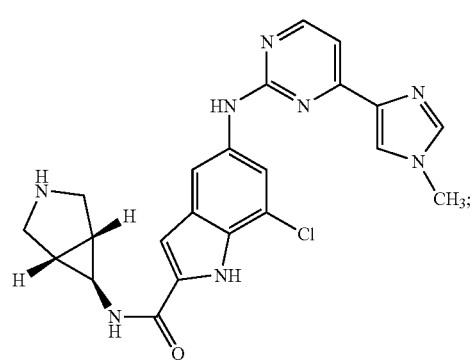
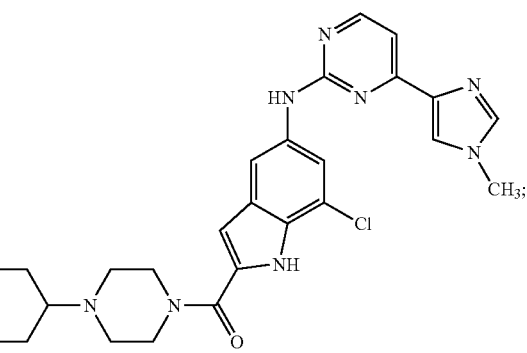
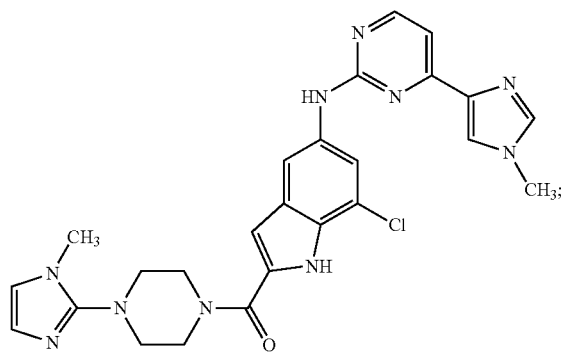

233
-continued
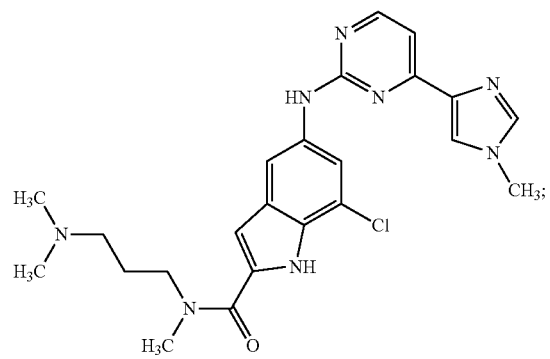
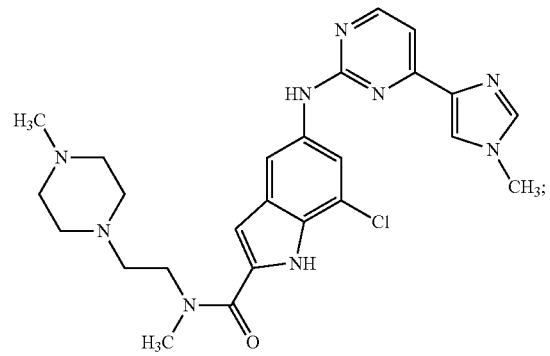
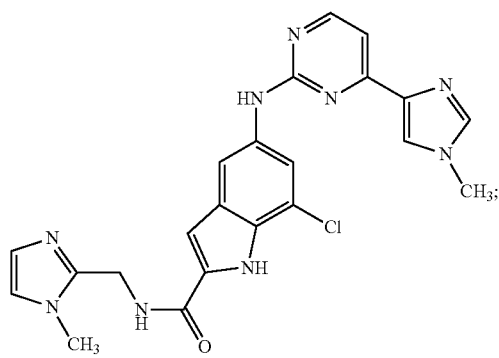
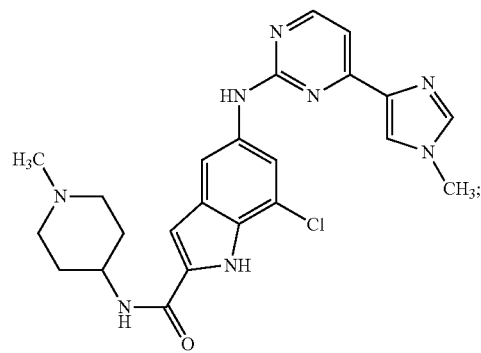
234
-continued
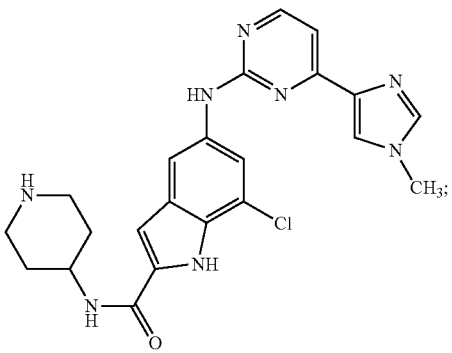
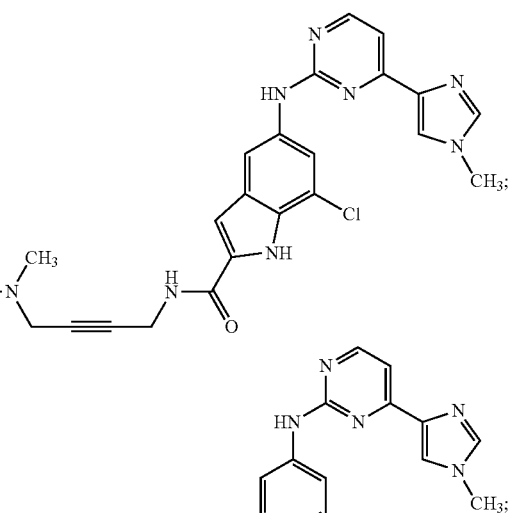
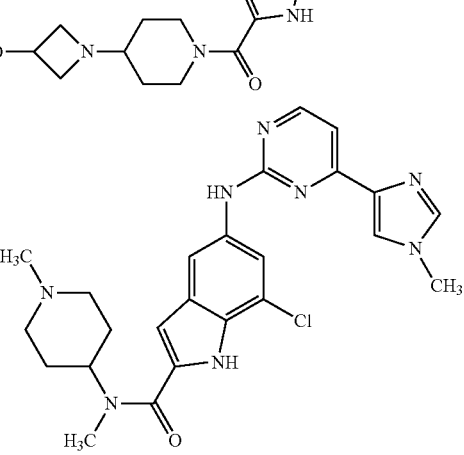
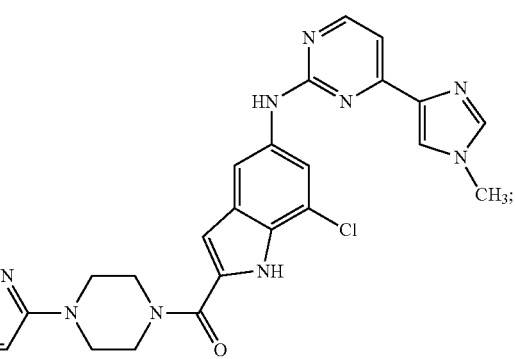

235
-continued
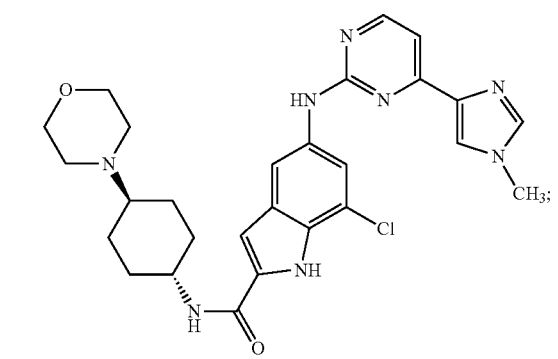
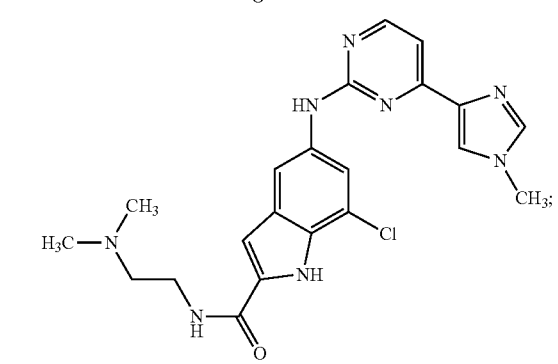
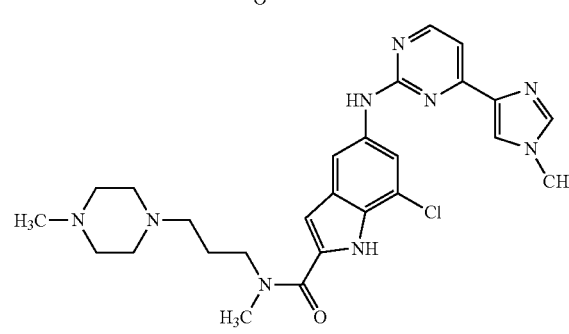
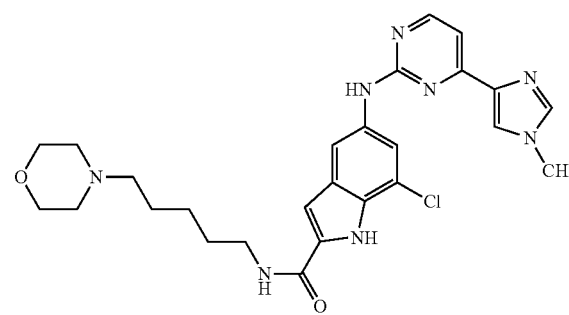
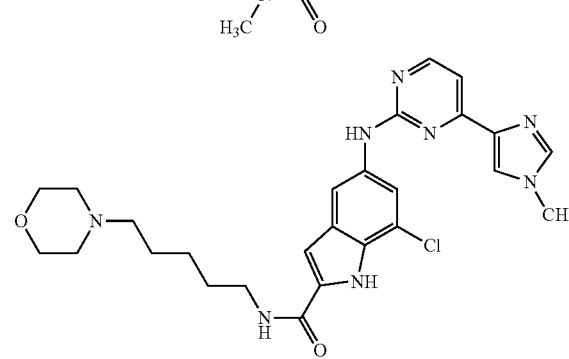
236
-continued
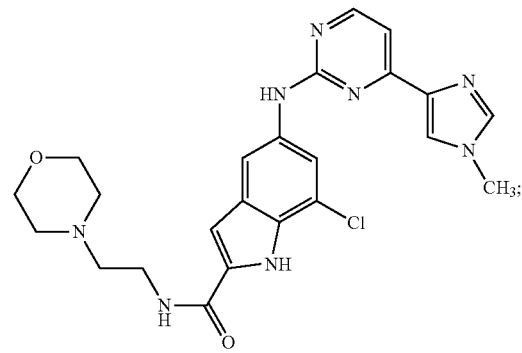
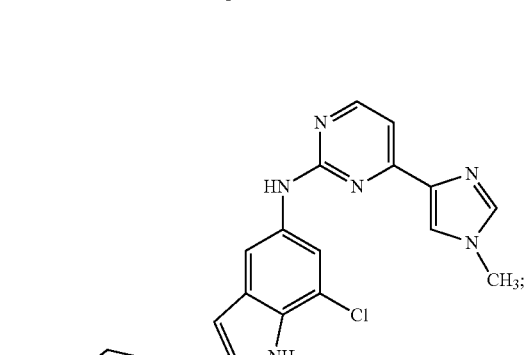
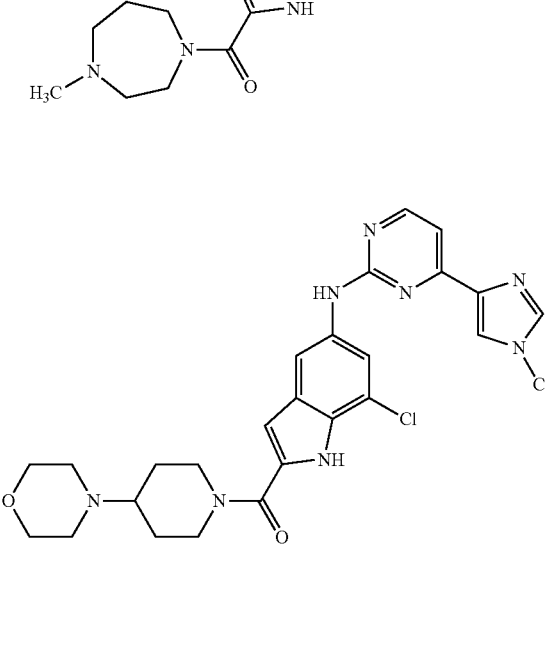

237
-continued
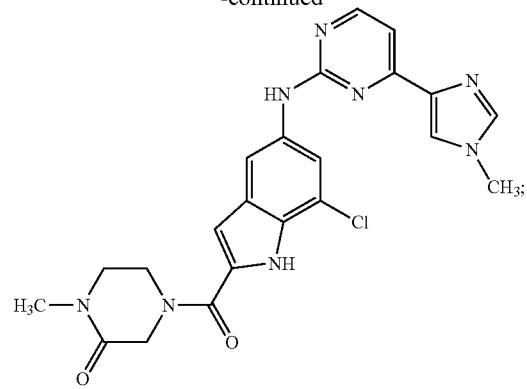
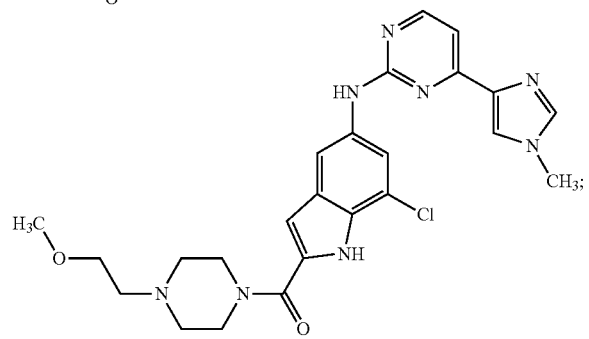
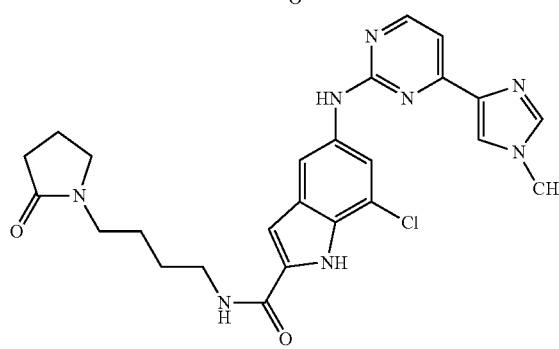
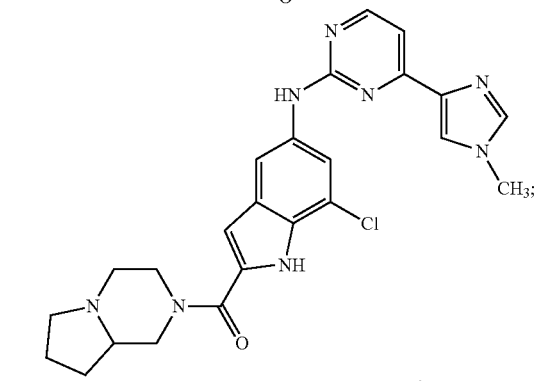
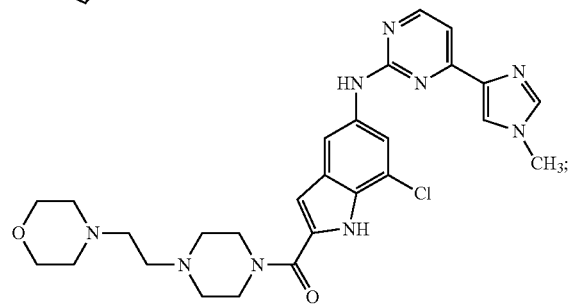
238
-continued
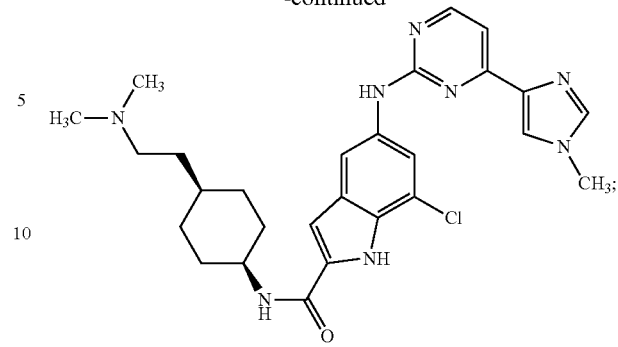
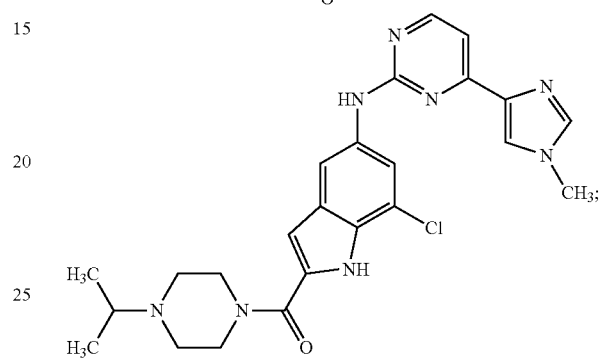
Chiral;
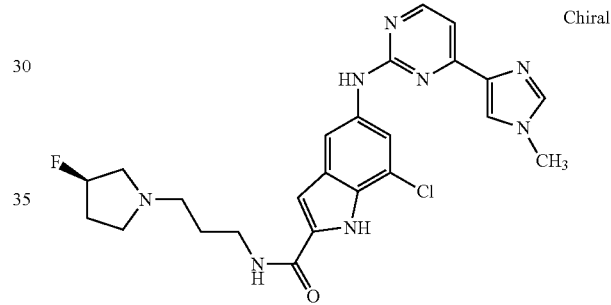
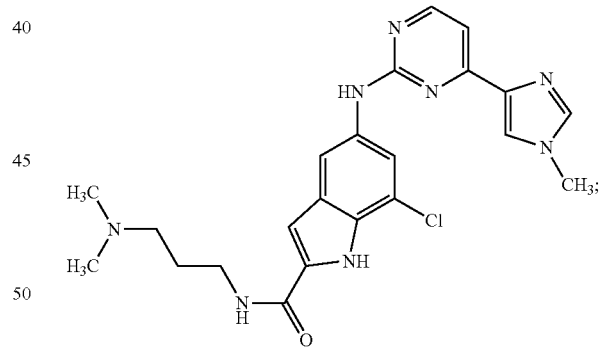
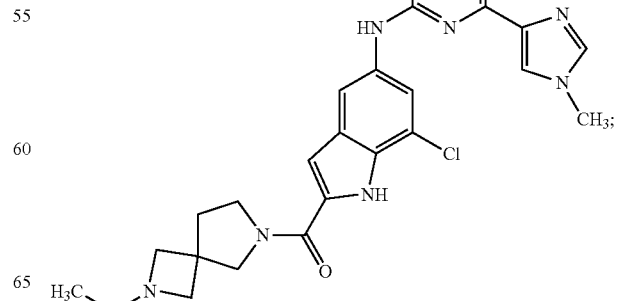

239
-continued
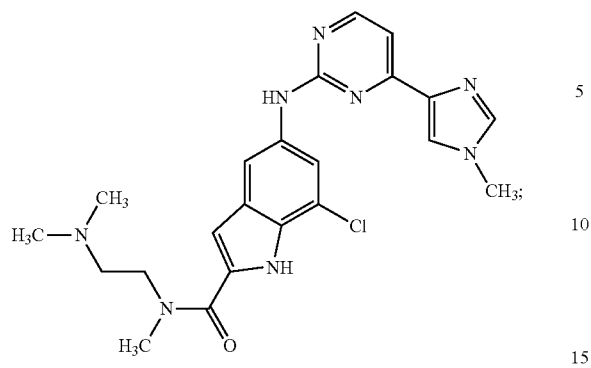
240
-continued
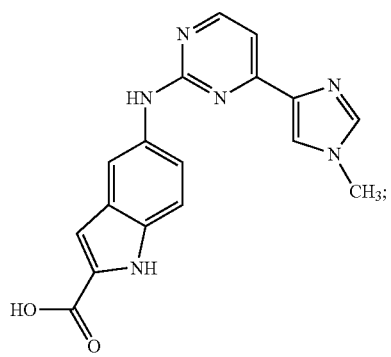
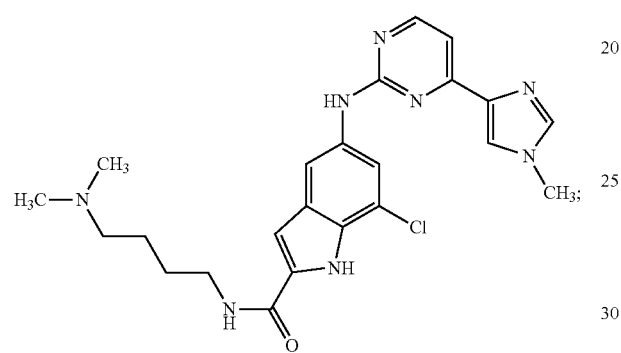
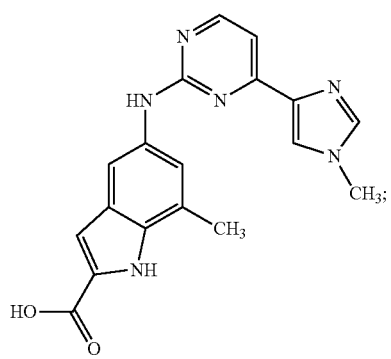
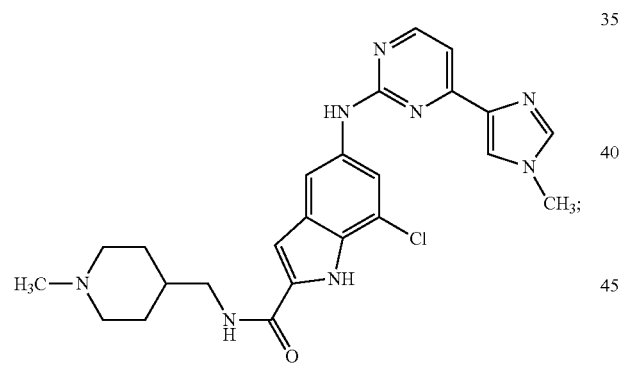
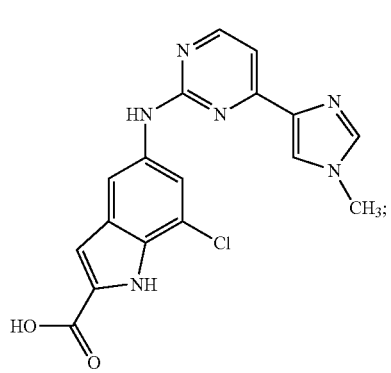
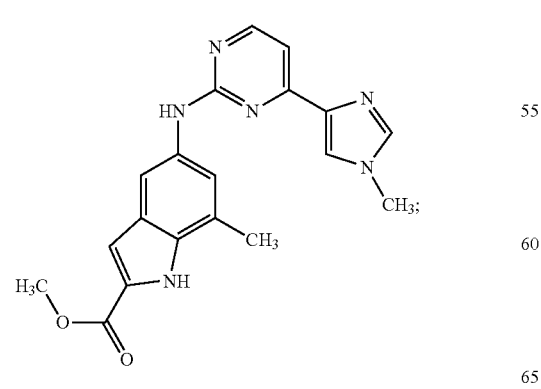

241
-continued
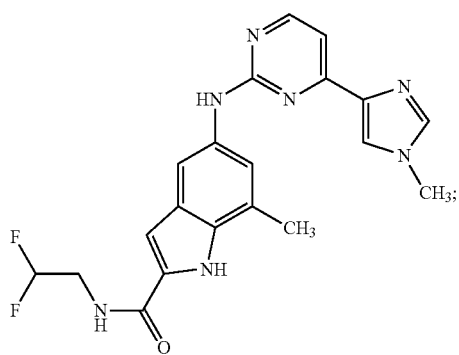
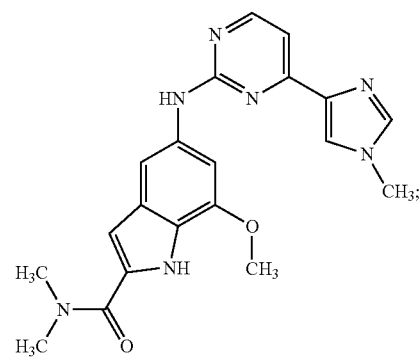
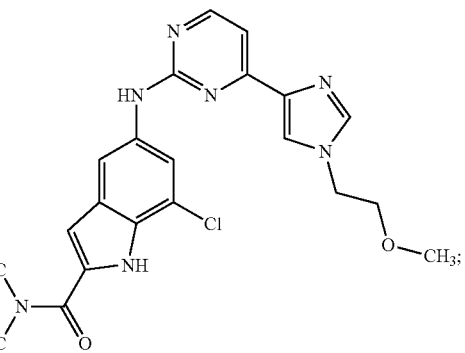
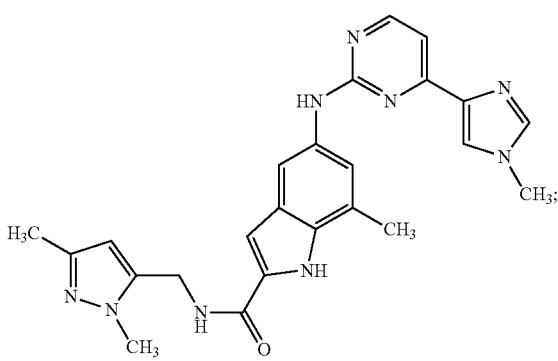
242
-continued
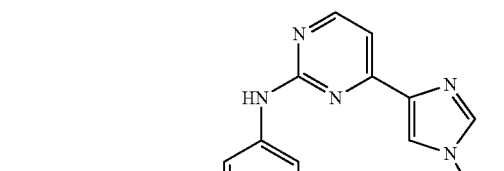
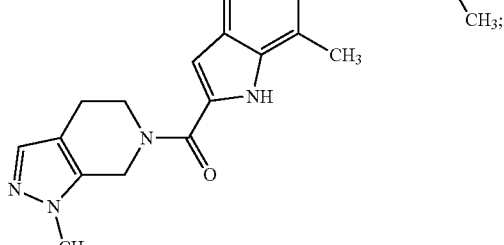
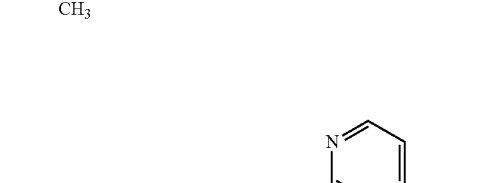
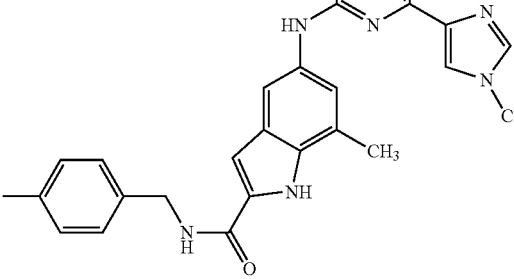
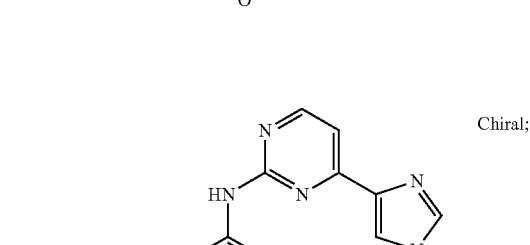
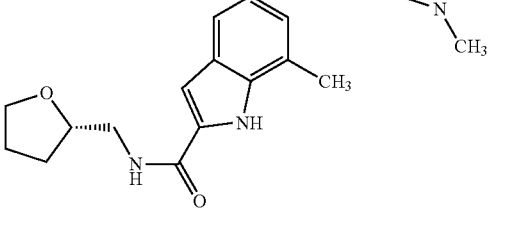

243
-continued
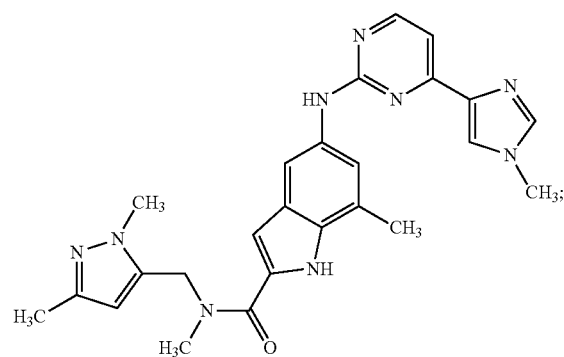
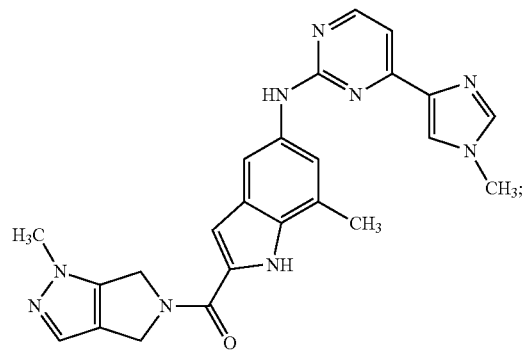
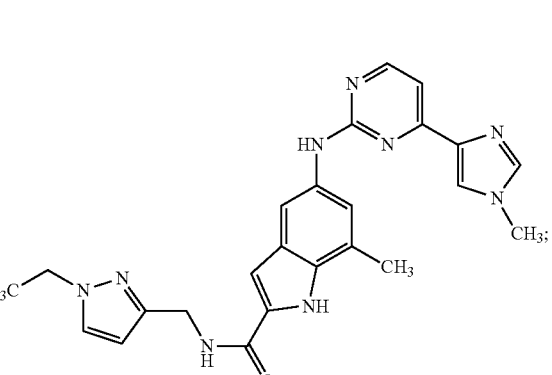
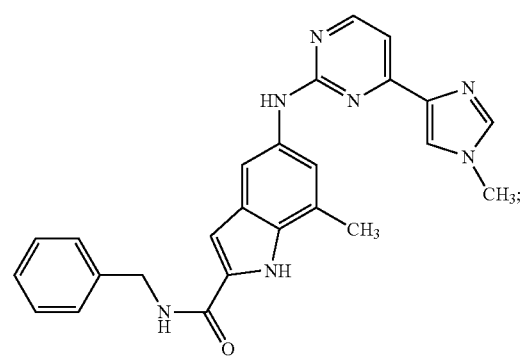
244
-continued
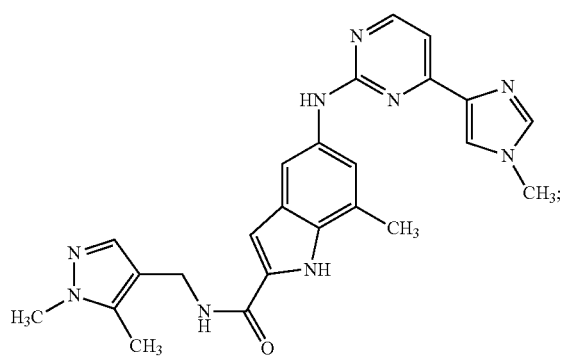
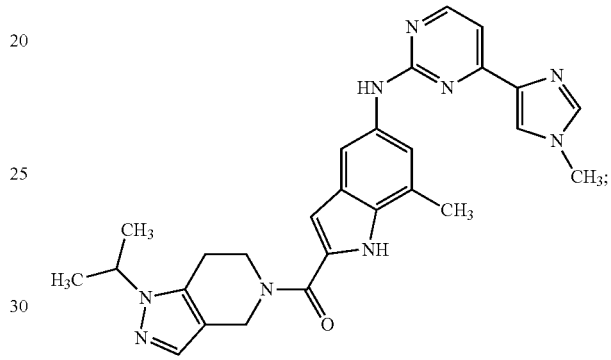
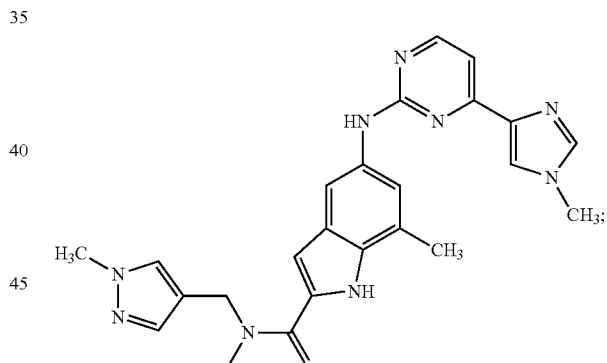
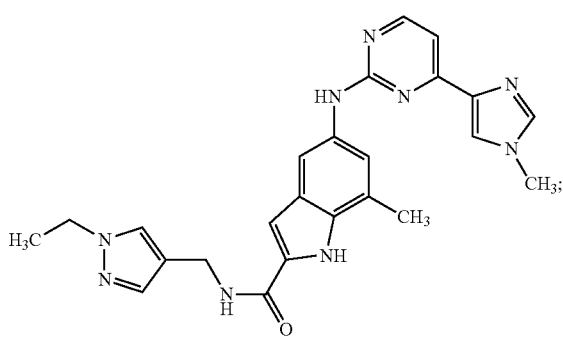

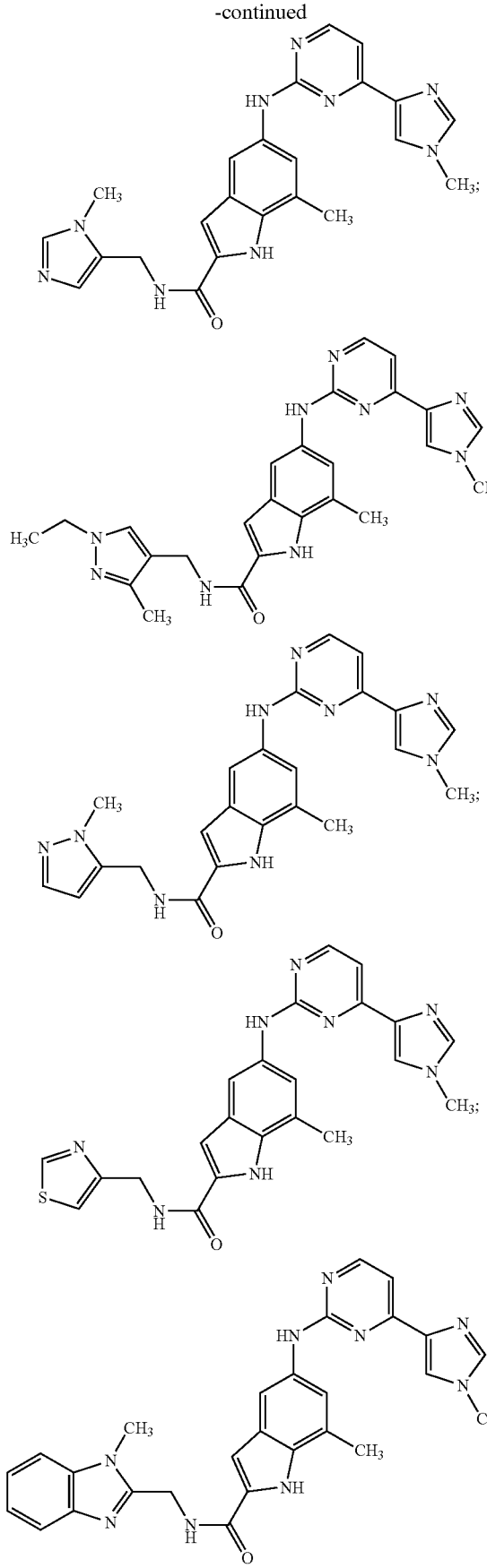
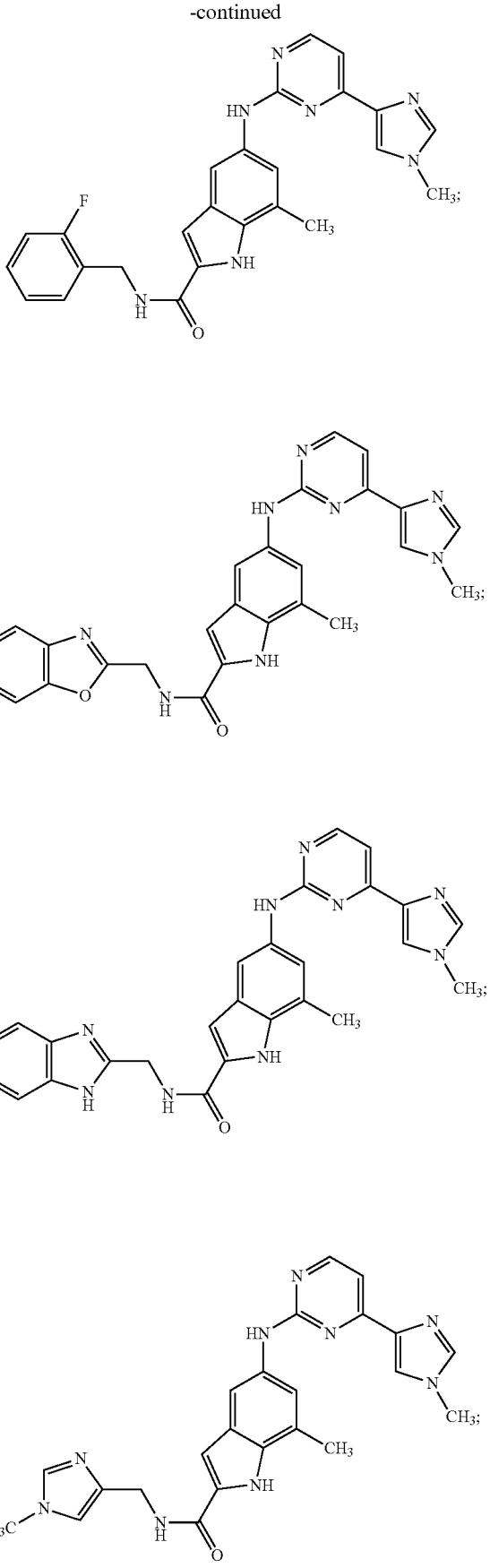

-continued
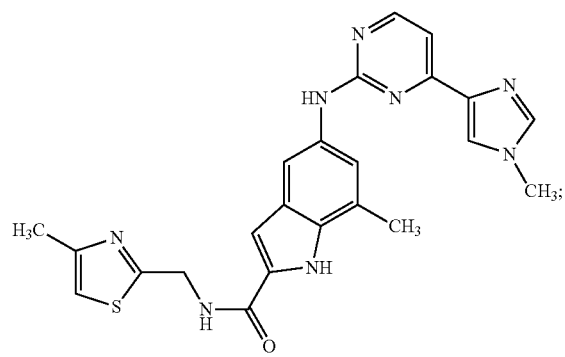
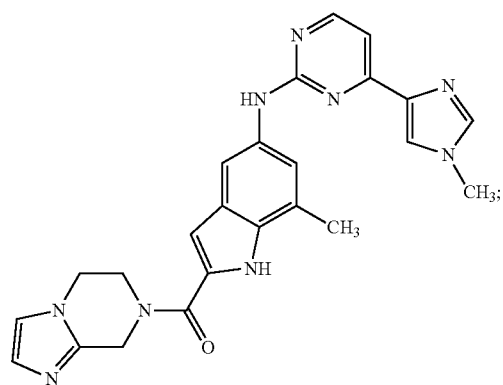
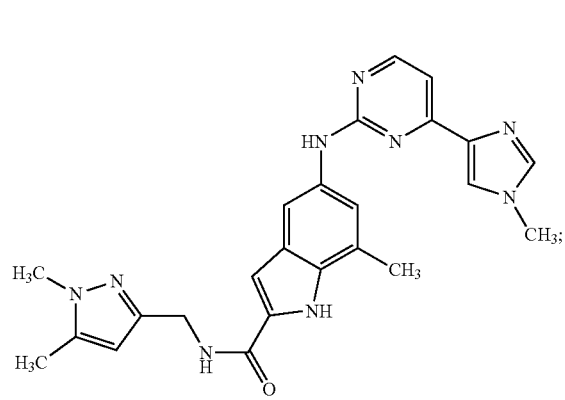
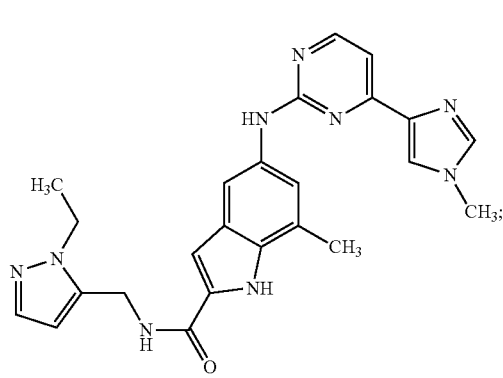
-continued
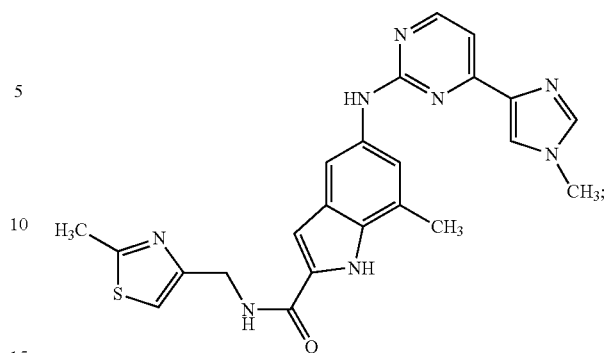
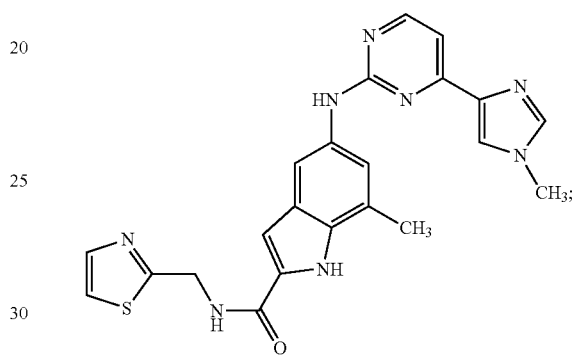
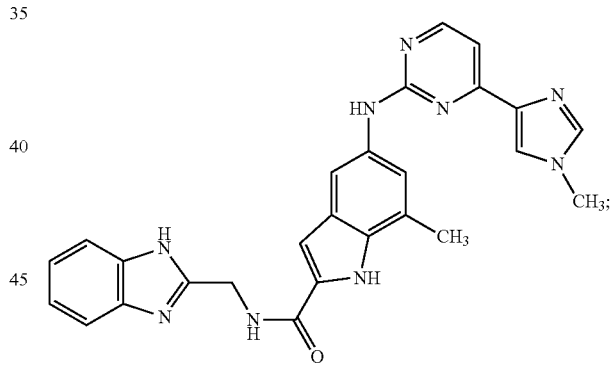
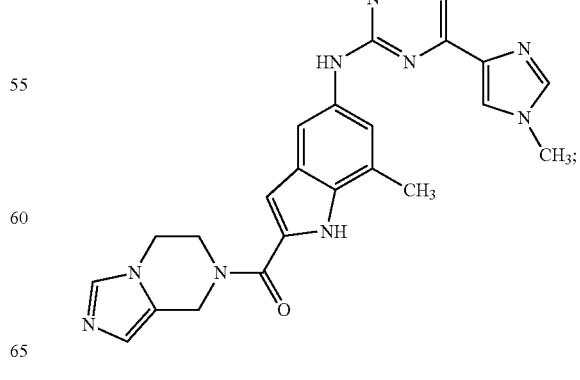

249
-continued
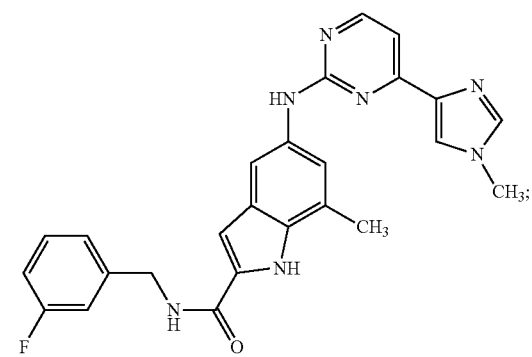
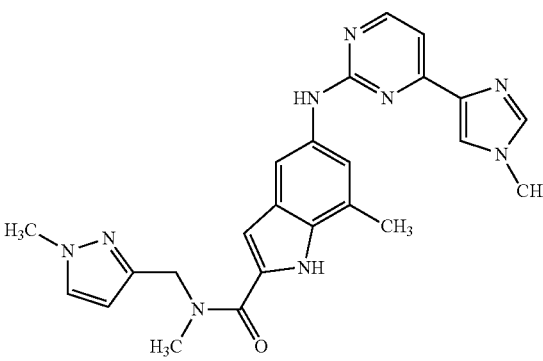
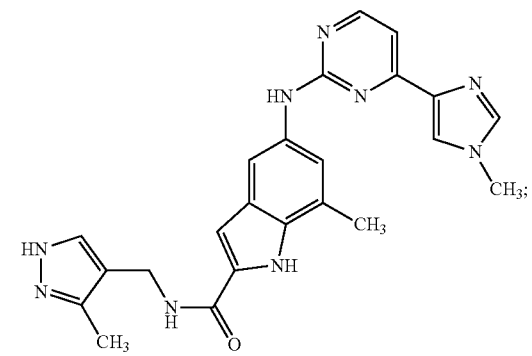
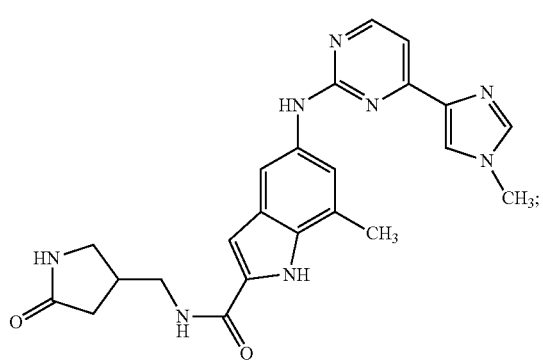
250
-continued
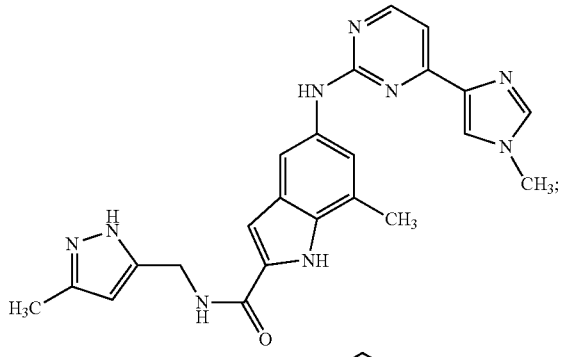
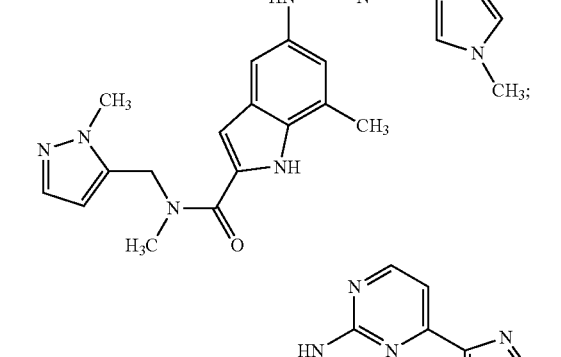
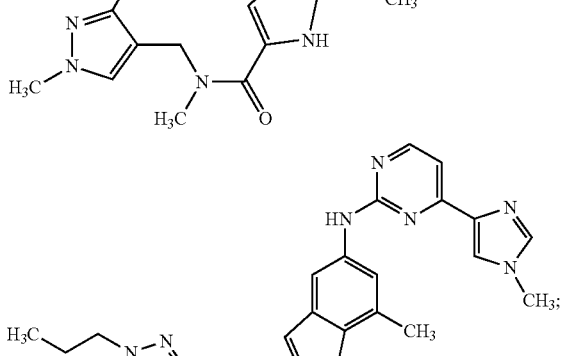
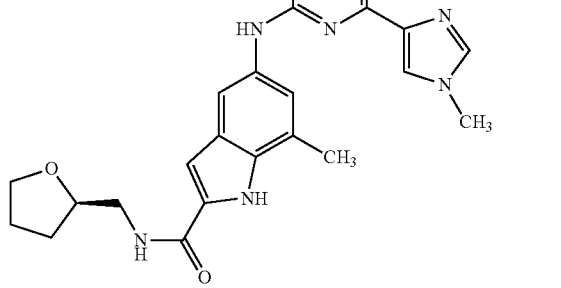
Chiral;
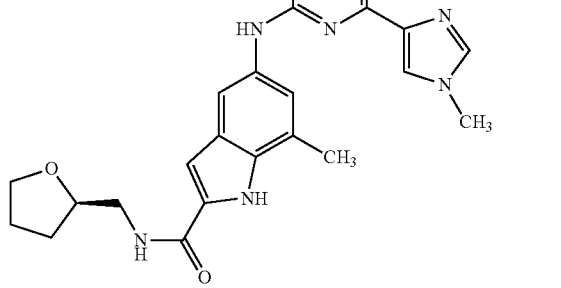

251
-continued
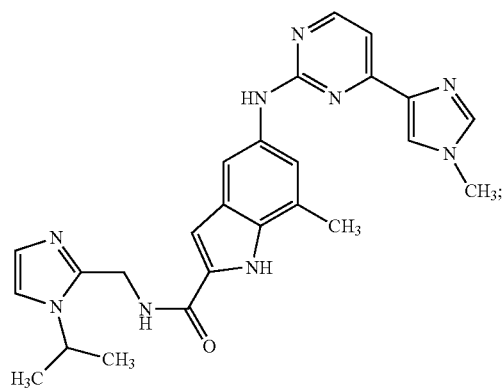
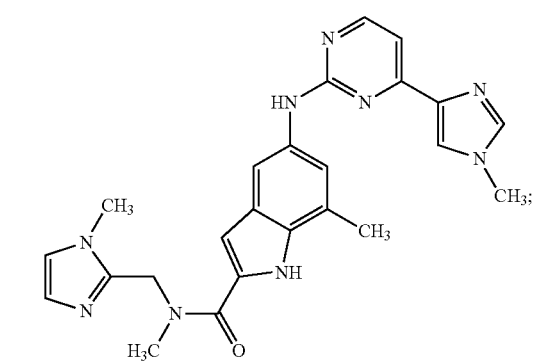
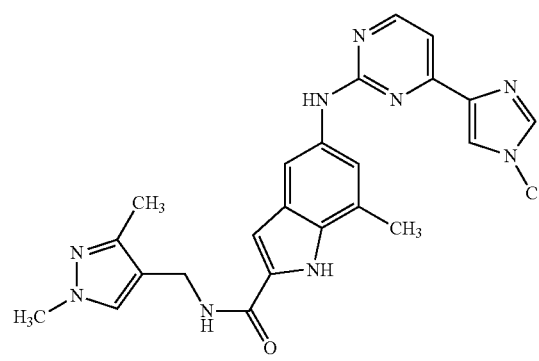
252
-continued
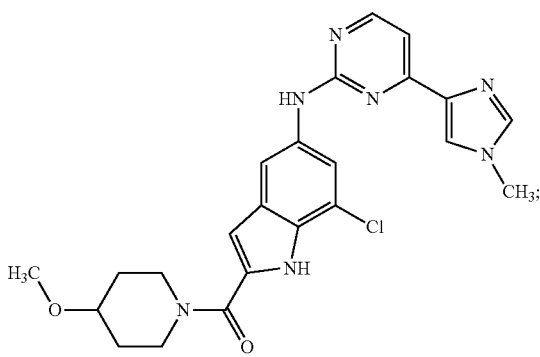
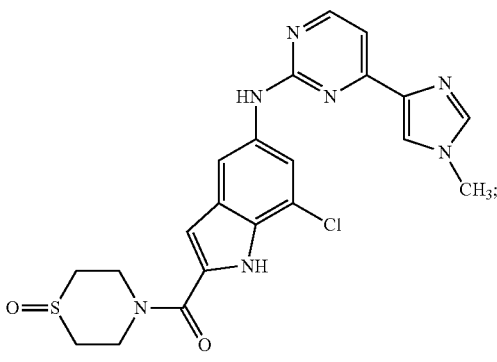
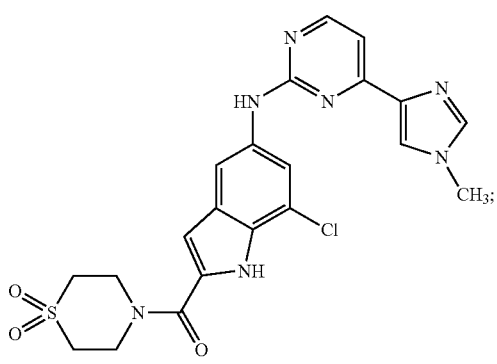
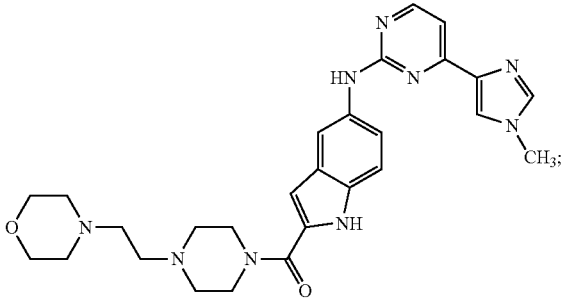

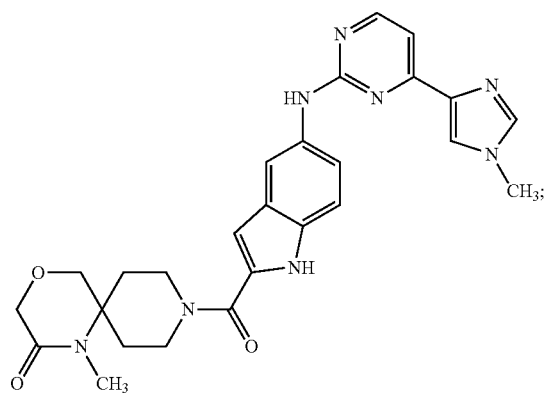
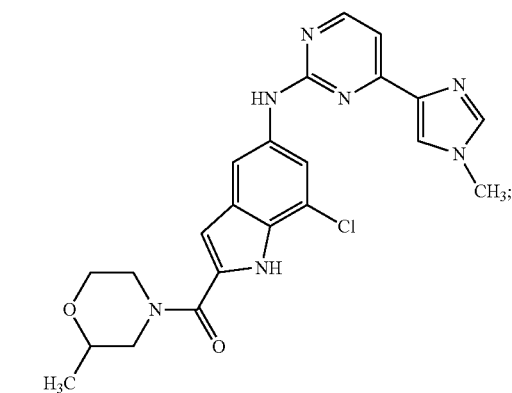
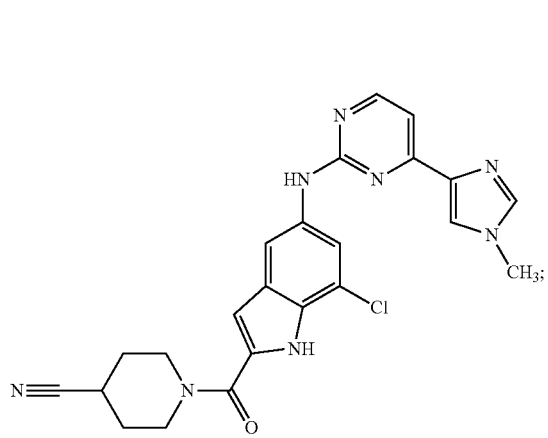
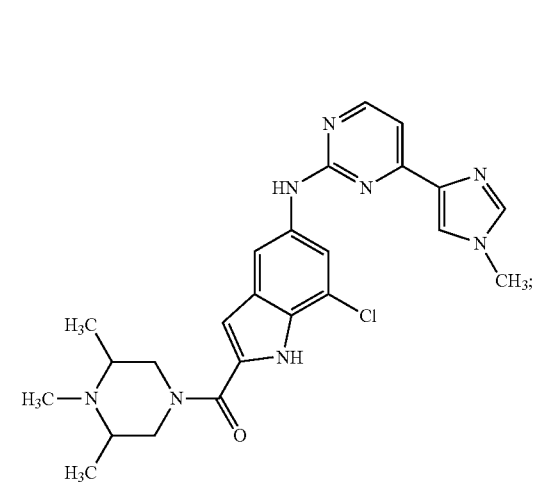
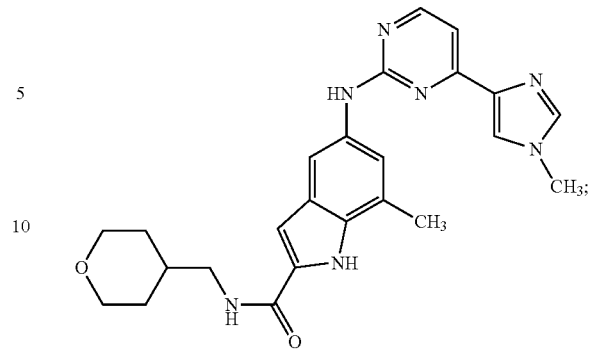
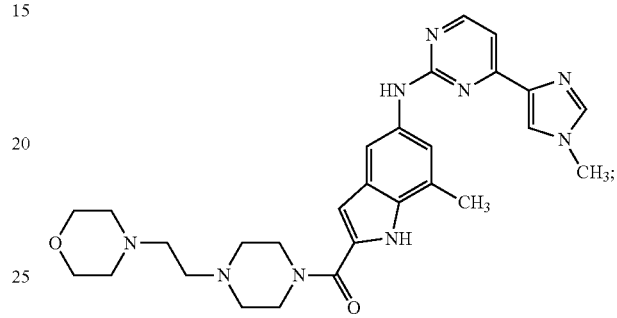
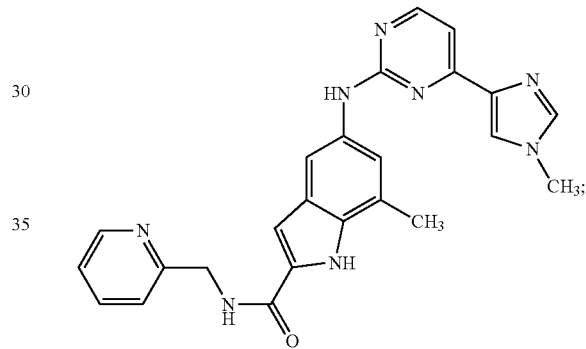
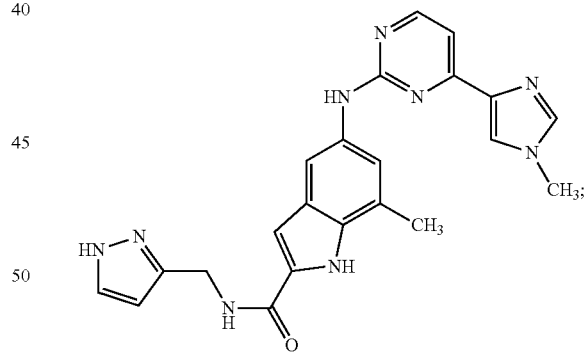
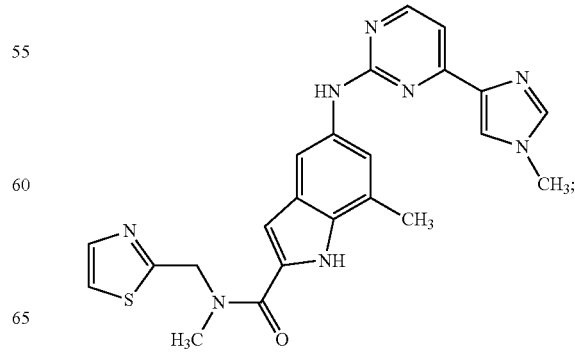

255
-continued
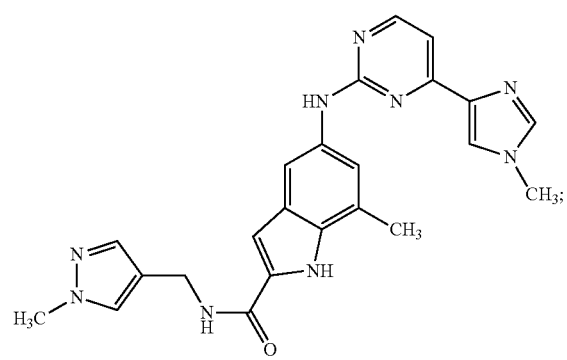
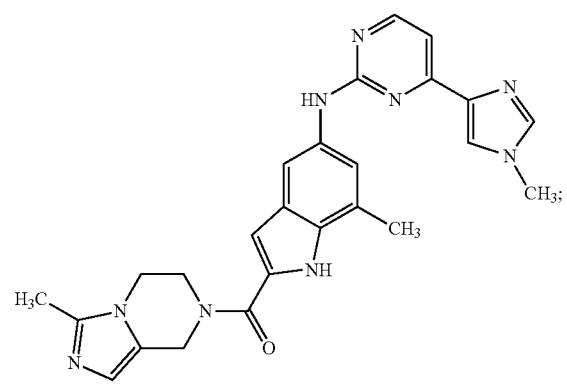
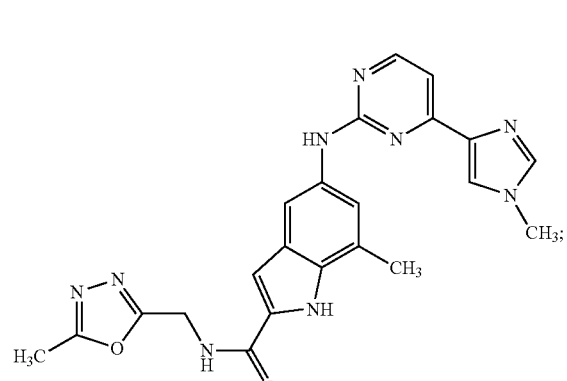
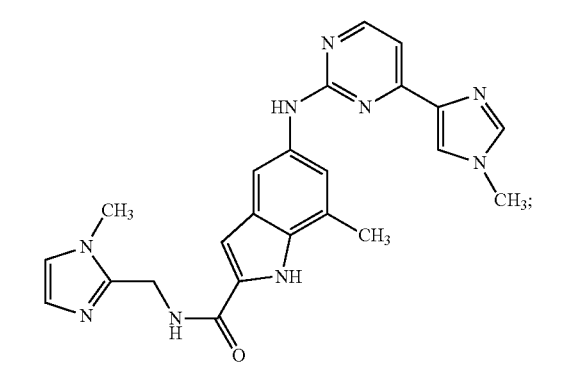
256
-continued
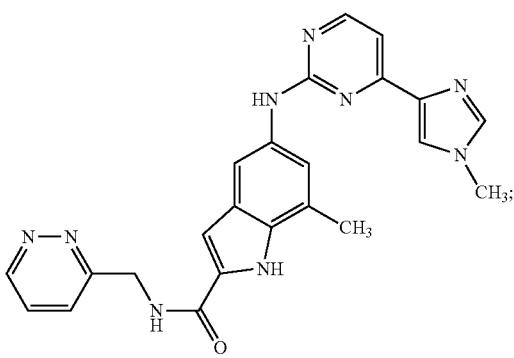
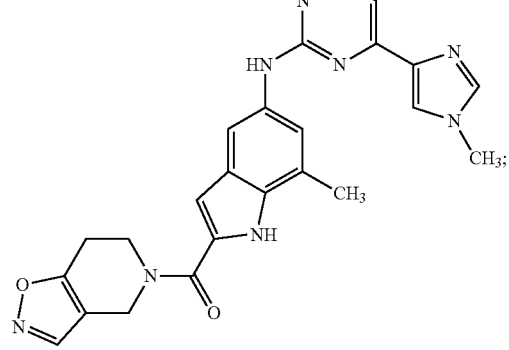

257
-continued
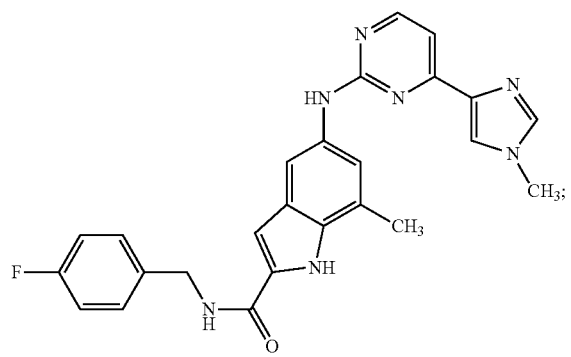
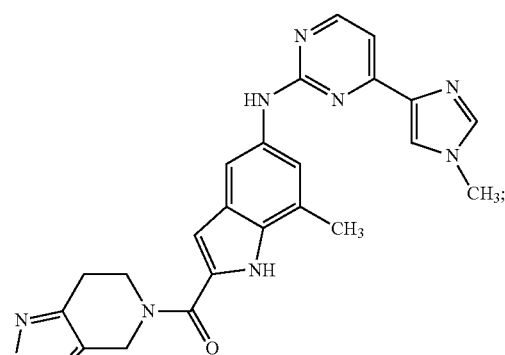
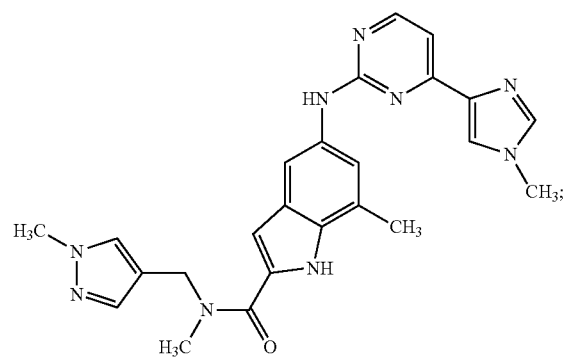
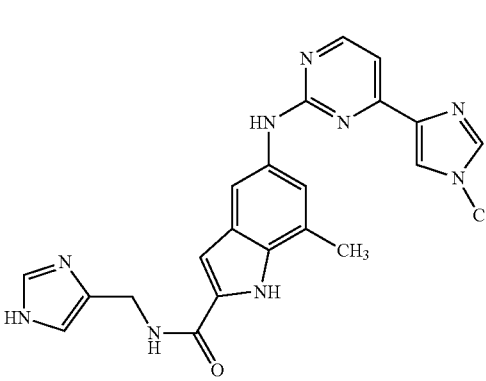
258
-continued
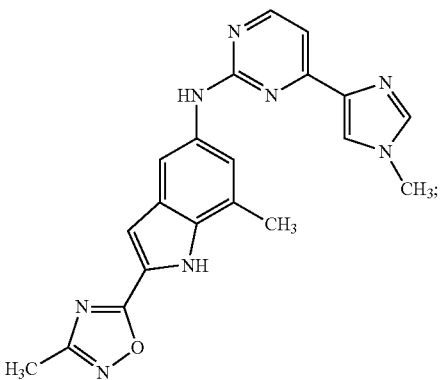
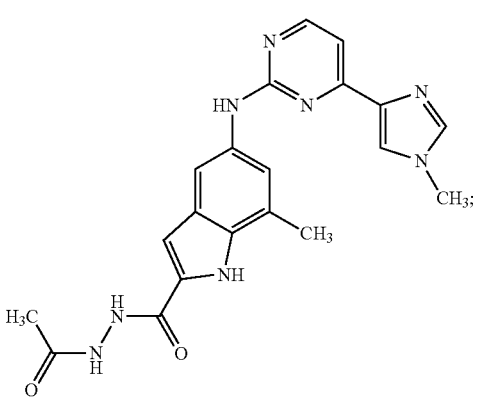
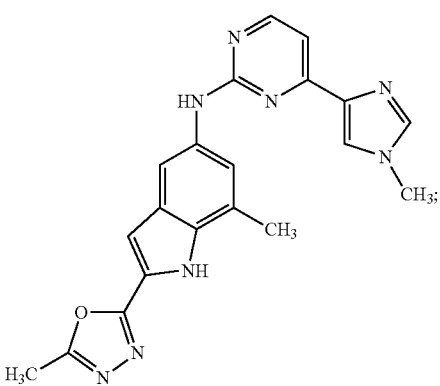
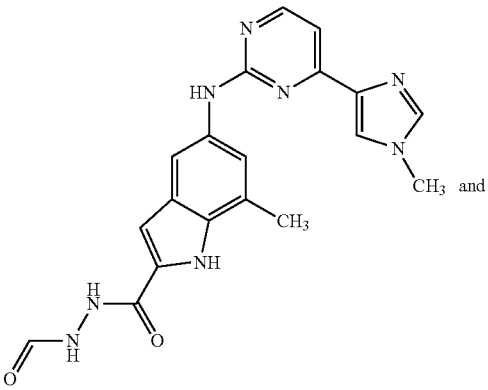
and -continued or a pharmaceutically acceptable salt thereof.

21. A pharmaceutical formulation comprising a compound of formula 1 according to claim 1, or a pharmaceutically acceptable salt thereof.

22. The pharmaceutical formulation of claim 21, in further combination with an active substance selected from anticholinergics, betamimetics, corticosteroids, PDE4-inhibitors, EGFR-inhibitors, LTD4-antagonists, CCR3-inhibitors, iNOS-inhibitors, CRTH2-antagonists, HMG-CoA reductase inhibitors or combinations thereof.

23. A method for treating a disease selected from asthma, COPD, rheumatoid arthritis, allergic rhinitis, adult respiratory distress syndrome, bronchitis, idiopathic thrombocytopenic purpura, and lupus erythematodes, comprising administering a therapeutically effective amount of a compound of formula 1 according to claim 1.

24. The method according to claim 23, wherein the disease is selected from asthma, COPD, allergic rhinitis and rheumatoid arthritis.

25. The method according to claim 24, wherein the disease is asthma.

* * * * *